United States Patent
Chan et al.

(10) Patent No.: US 9,974,799 B2
(45) Date of Patent: May 22, 2018

(54) COMPOSITION COMPRISING XANTHOCERAS SORBIFOLIA EXTRACTS, COMPOUNDS ISOLATED FROM SAME, METHODS FOR PREPARING SAME AND USES THEREOF

(71) Applicant: PACIFIC ARROW LIMITED, Hong Kong (CN)

(72) Inventors: Pui-Kwong Chan, Sugarland, TX (US); May Sung Mak, Hong Kong (CN); Yun Wang, Dunedin (NZ)

(73) Assignee: Pacific Arrow Limited, Hong Kong (CN)

( * ) Notice: Subject to any disclaimer, the term of this patent is extended or adjusted under 35 U.S.C. 154(b) by 0 days. days.

(21) Appl. No.: 14/926,138

(22) Filed: Oct. 29, 2015

(65) Prior Publication Data
US 2016/0101121 A1  Apr. 14, 2016

Related U.S. Application Data

(63) Continuation of application No. 13/718,575, filed on Dec. 18, 2012, now abandoned, which is a continuation of application No. 12/392,795, filed on Feb. 25, 2009, now Pat. No. 8,334,269, which is a continuation of application No. 10/906,303, filed on Feb. 14, 2005, now Pat. No. 7,524,824, which is a continuation-in-part of application No. PCT/US2004/043465, filed on Dec. 23, 2004, which is a continuation-in-part of application No. PCT/US2004/033359, filed on Oct. 8, 2004, said application No. 10/906,303 is a continuation-in-part of application No. 10/471,384, filed as application No. PCT/IB02/04750 on Aug. 28, 2002, now Pat. No. 7,189,420, which is a continuation-in-part of application No. 09/944,805, filed on Aug. 31, 2001, now Pat. No. 6,166,943.

(60) Provisional application No. 60/617,379, filed on Oct. 8, 2004, provisional application No. 60/613,811, filed on Sep. 27, 2004, provisional application No. 60/607,858, filed on Sep. 7, 2004, provisional application No. 60/532,101, filed on Dec. 23, 2003, provisional application No. 60/509,851, filed on Oct. 9, 2003.

(51) Int. Cl.
| | |
|---|---|
| A61K 31/704 | (2006.01) |
| A61K 36/77 | (2006.01) |
| C07H 15/256 | (2006.01) |
| C07J 63/00 | (2006.01) |

(52) U.S. Cl.
CPC .......... *A61K 31/704* (2013.01); *A61K 36/77* (2013.01); *C07H 15/256* (2013.01); *C07J 63/00* (2013.01)

(58) Field of Classification Search
None
See application file for complete search history.

(56) References Cited

U.S. PATENT DOCUMENTS

| | | | |
|---|---|---|---|
| 7,524,824 B2 * | 4/2009 | Chan | A61K 36/77 514/33 |
| 2005/0220910 A1 * | 10/2005 | Chan | A61K 36/77 424/769 |

OTHER PUBLICATIONS

Xiao et al., "Bioactive barrigenol type triterpenoids from the leaves of Xanthoceras sorbifolia Bunge" European Journal of Medicinal Chemistry (2013) vol. 60 pp. 263-270.*
Chen et al., "Studies on the Constituents of Xanthoceras sorbifolia BUNGE. II. Major Sapogenol and a Prosapogenin from the Fruits of Xanthoceras sorbifolia BUNGE" Chemical and Pharmaceutical Bulletin (1984) vol. 32 No. 9 pp. 3378-3383.*

* cited by examiner

*Primary Examiner* — Eric Olson
(74) *Attorney, Agent, or Firm* — Law Offices of Albert Wai-Kit Chan, PLLC

(57) ABSTRACT

This invention provides compositions, methods and process of producing extracts from *Xanthoceras sorbifolia*. The extract comprises alkaloids, coumarins, saccharides, proteins, polysaccharides, glycosides, saponins, tannins, acid, flavonoids and others. The composition can be used for treating cancer, arthritis, rheumatism, poor circulation, arteriosclerosis, Raynaud's syndrome, angina pectoris, cardiac disorder, coronary heart disease, headache, dizziness, kidney disorder, impotence and premature ejaculation; for preventing cerebral aging; for improving memory, cerebral functions; or for curing enuresis, frequent micturition, urinary incontinence, dementia, weak intelligence and Alzheimer's disease, autism, brain trauma, Parkinson's disease or other diseases caused by cerebral dysfunctions, and treating arthritis, rheumatism, poor circulation, arteriosclerosis, Raynaud's syndrome, angina pectoris, cardiac disorder, coronary heart disease, headache, dizziness, kidney disorder. This invention provides compounds comprising at least one sugar, a triterpene, such as Sapogenin, and at least one side chains at Carbon 21 and 22, such as Angeloyl groups. The compounds of the present have various pharmaceutical and therapeutic applications.

19 Claims, 51 Drawing Sheets

Structure of Compound Y

3-O-{β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene.

Structure of Compound Y1

Anticancer activity of Compound Y

Y1 and Y2 activity on Ovarian caner cells

Cell growth activity of fractions of plant extract

Figure 7
Fraction Y
Figure 7A
Compound Y
Figure 7
Y3
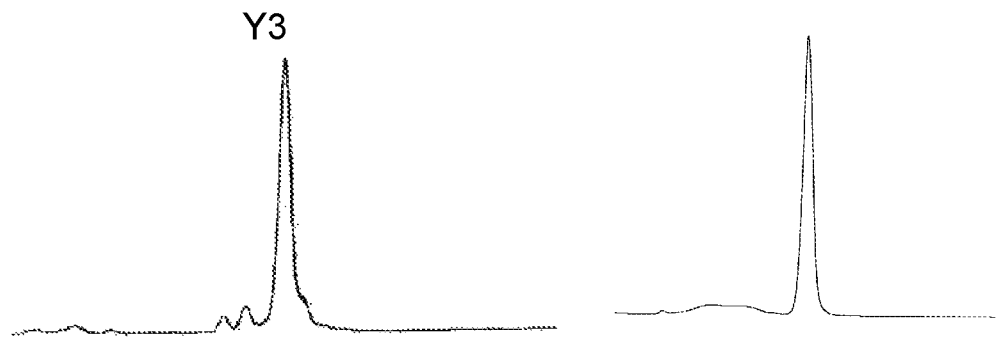
Figure 8
Inhibition Effect of plant extract on Ovarian cancer
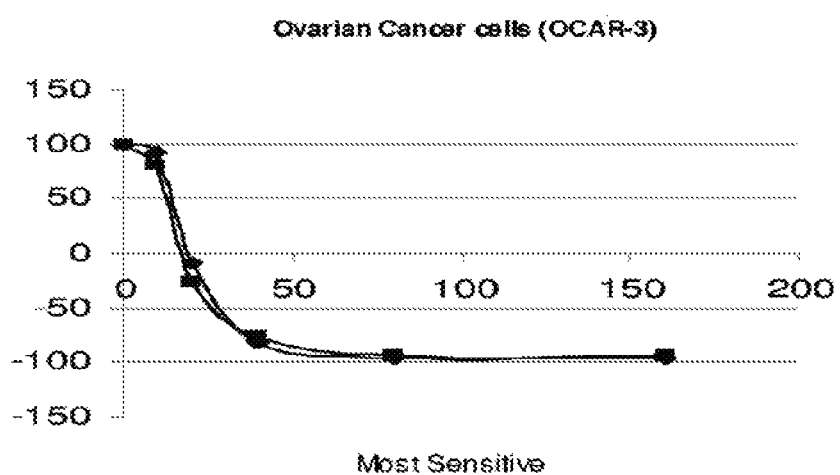

Growth curve of cancer cells after drug treatment

Sensitive

Growth curve of cancer cells after drug treatment

Semi-sensitive

Grwoth curve of cancer cells after drug treatment

Marginal sensitive

Growth curve of cancer cells after drug treatment

Proton NMR of Y

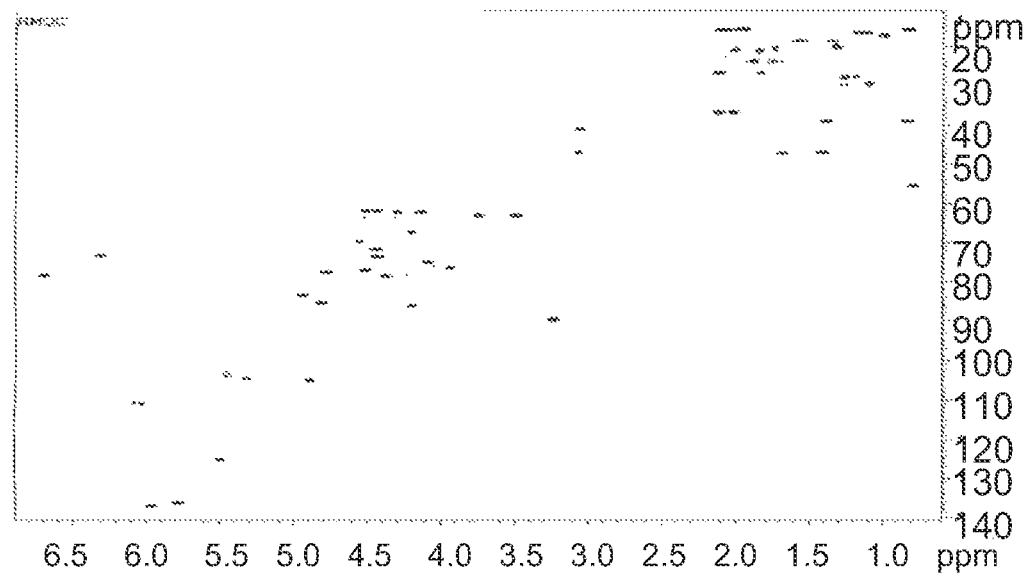
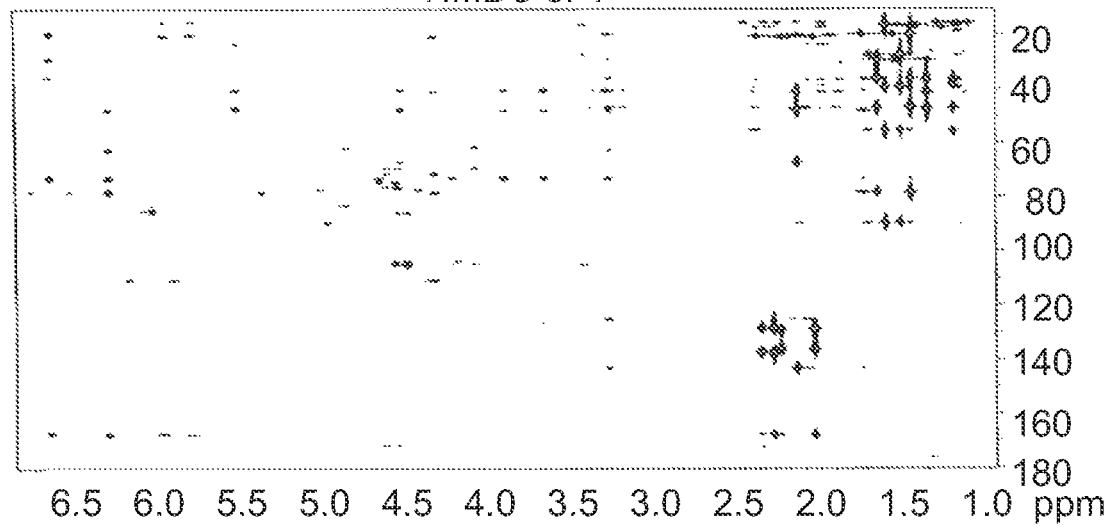

MS-ESI of Y

Proton NMR of Y1

HMQC of Y1

HMBC of Y1

2D NMR (COSY) of Y1

FPLC profile of Plant extract

R1-HNMR

R1-HMQC

R1-HMBC-level 1

R1-COSY

R1-C13-1

O54-HNMR

O54-HMQC

O54-HMBC

Structure of Y1-1

Structure 1

Structure of Y1-2

Structure 2

Figure 33
Structure of Y1-3
Structure 3
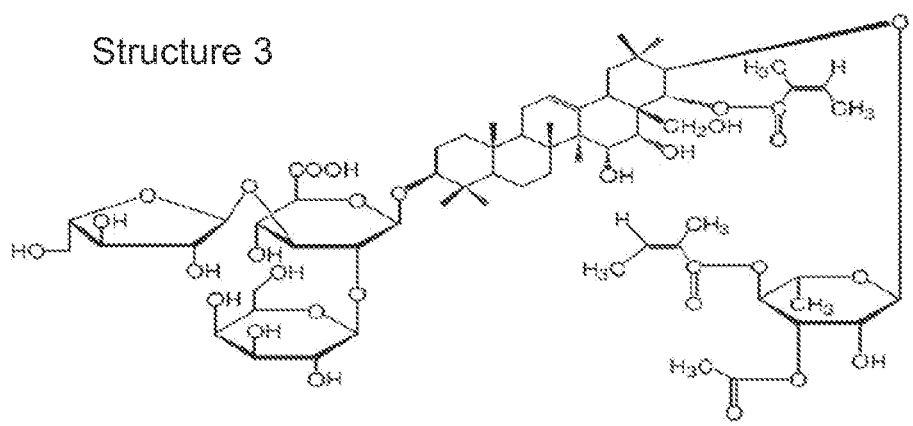
Figure 34
Structure Y1-4
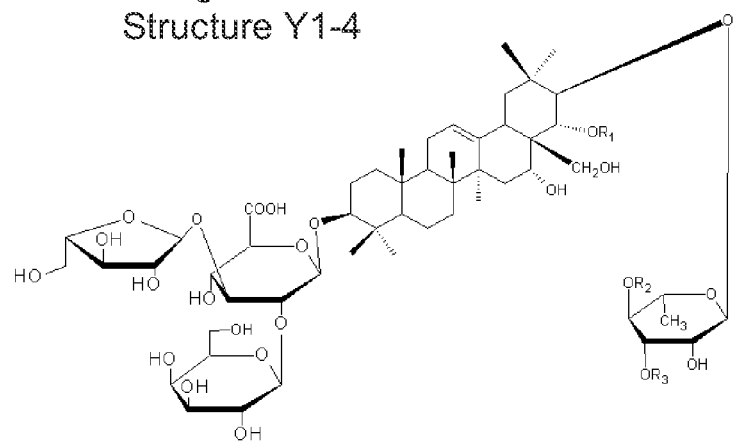
Where R1 = A or B or C
R2 = A or B or C
R3 = A or B or C
A = 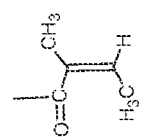
B = 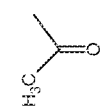
C = H Y-a Y-b

Y-C

Y1-b

Y1-c

Fractionation of # 5962 by FPLC

Effect of Y on cell growth activity

Analysis of fractions #9, 10 and 11 with HPLC (u-bondapak)

Fraction 9    Fraction 10    Fraction 11

(Iso-20)

Re-chromatography of #28 and #34 (from iso-20)

Figure 50
Re-chromatography of #54 (from iso-20)
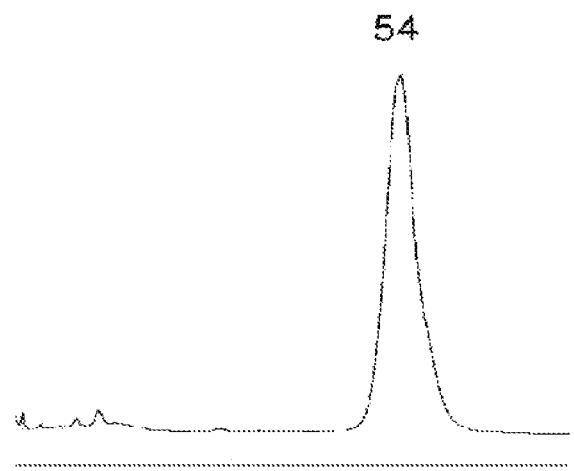
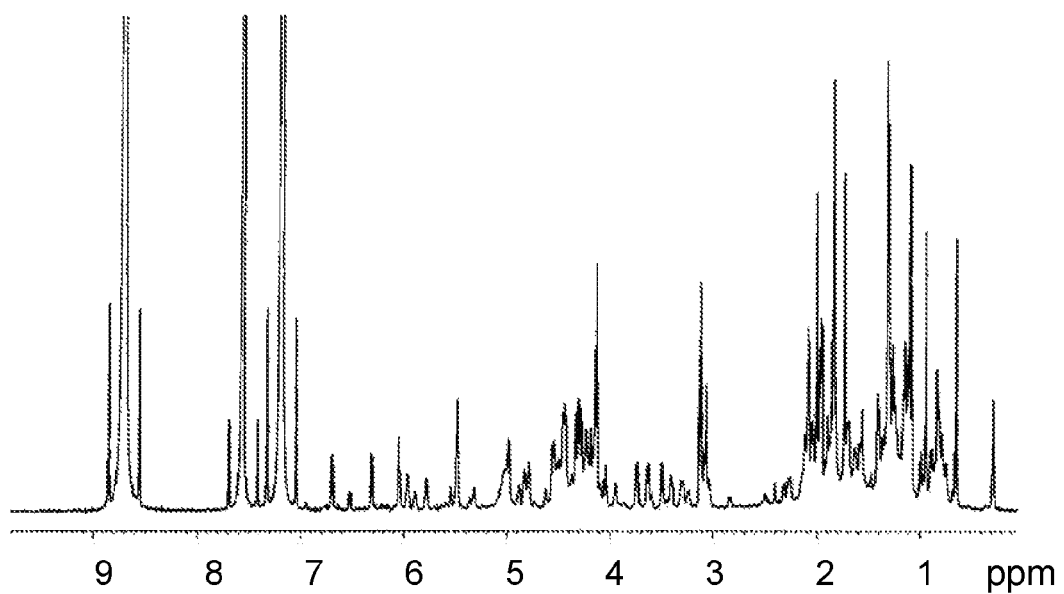
Figure 51
H-NMR of Y2

HMQC of Y2

H-NMR of Y4

HMQC of Y4

O28-HMNR

O28 HMQC

O34-H-NMR

O34-HMQC

Result of urine after 10 days of administration

Plant extract administration aging mice for 9 days

Error frequency in water maze of aging mice for 9 days plant extract injected pentobarbital The result of learning after 3 days injected pentobarbital The result of learning after 3 days injected pentobarbital

Figure 63

Table15A-1 Results of urine volume with water load after FS(X) administration for 25 days

| Groups | Dose mg/kg | Urine volume of all the time phases (hr) after last administration (ml/100g) | | | | | | | |
|---|---|---|---|---|---|---|---|---|---|
| | | 0.25 | 0.5 | 1 | 2 | 3 | 4 | 5 | 6 |
| Control | | 0.24±0.24 | 0.85±0.40 | 2.20±0.48 | 3.89±0.56 | 4.41±0.36 | 4.61±0.57 | 4.48±0.59 | 4.96±0.59 |
| Pituitrin | 0.25ug/kg | 0.04±0.12 * | 0.47±0.36 ** | 1.14±0.52 *** | 1.53±0.46 *** | 2.22±0.71 *** | 2.82±1.19 *** | 3.76±1.44 *** | 4.10±1.40 *** |
| FS(X) | 100 | 0.17±0.22 | 0.68±0.34 | 2.08±0.51 | 3.27±0.39 * | 3.47±0.39 *** | 3.75±0.48 *** | 3.97±0.49 ** | 4.15±0.64 ** |
| | 200 | 0.14±0.23 | 0.60±0.53 | 1.28±0.66 ** | 2.53±0.76 *** | 3.24±0.66 *** | 3.54±0.67 *** | 3.84±0.67 ** | 4.17±0.67 * |
| | 400 | 0.02±0.07 * | 0.23±0.38 ** | 0.61±0.72 *** | 1.42±1.32 *** | 1.66±1.37 *** | 2.11±1.58 *** | 2.67±1.21 *** | 2.89±1.12 *** |
| FS(Y) | 400 | 0.03±0.11 * | 0.37±0.45 * | 0.91±0.62 *** | 1.87±1.12 *** | 2.80±0.98 *** | 3.37±0.99 ** | 3.89±0.78 ** | 3.97±0.74 ** |

*: P<0.05, : P<0.01, *: P<0.001      Student T Test vs Control

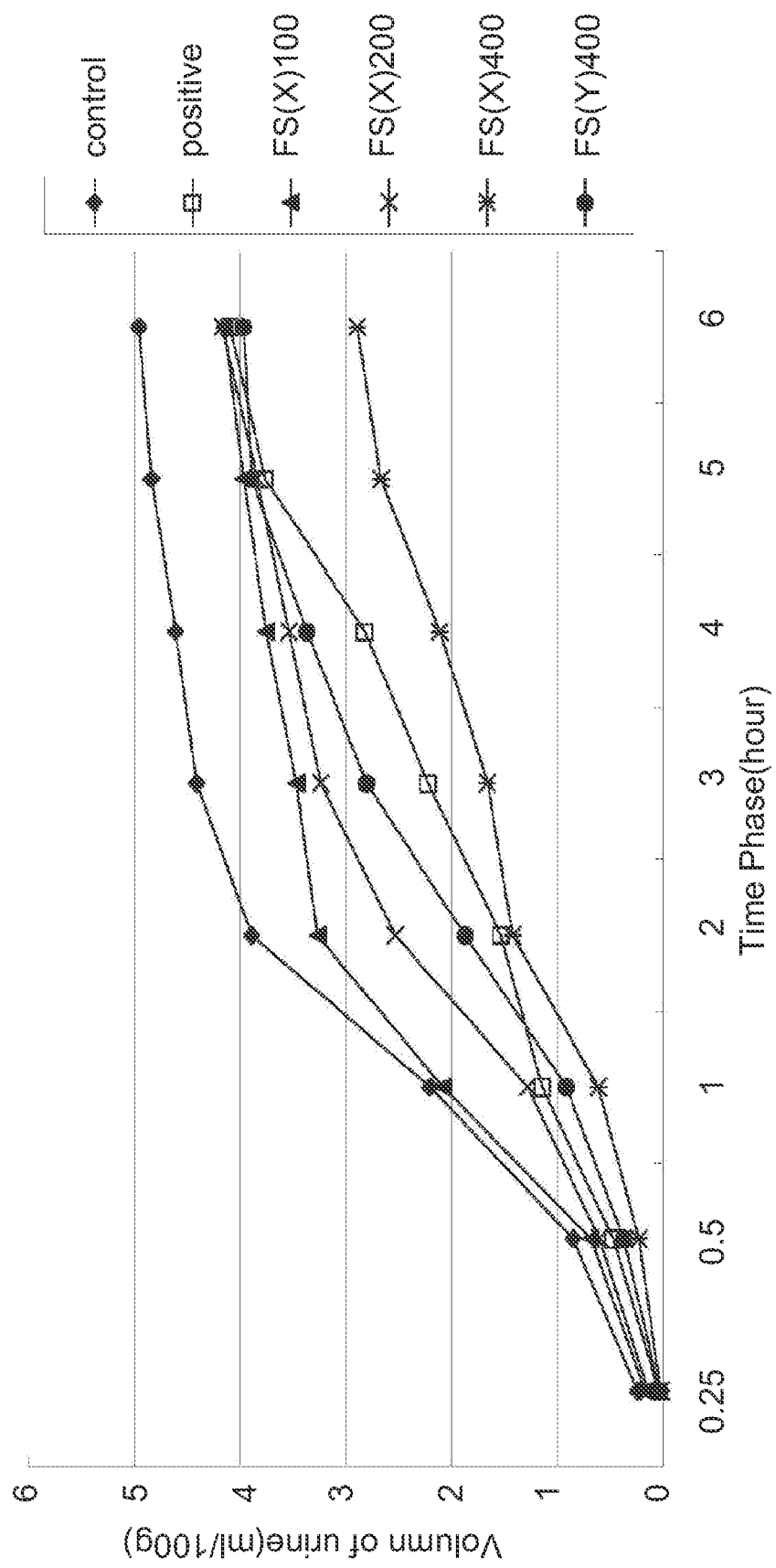

Figure 64

Table 15A-2 Results of discharging urine rate with water load after FS(x) administration for 25 days

| Groups | Dose mg/kg | Discharge urine speed of all the time phases (hr) after last administration (ml · kg⁻¹ · 5min⁻¹) | | | | | | | |
|---|---|---|---|---|---|---|---|---|---|
| | | 0.25 | 0.5 | 1 | 2 | 3 | 4 | 5 | 6 |
| Control | | 0.82±0.80 | 2.01±0.97 | 2.25±0.78 | 1.41±0.61 | 0.43±0.35 | 0.17±0.29 | 0.19±0.25 | 0.10±0.13 |
| Pituitrin | 0.25ug/kg | 0.14±0.40 | 1.43±1.10 | 1.12±0.55 | 0.32±0.42 | 0.58±0.46 | 0.50±0.45 | 0.78±0.49 | 0.28±0.41 |
| | | * | | *** | | | | | |
| FS(X) | 100 | 0.58±0.73 | 1.70±1.22 | 2.33±0.52 | 1.00±0.51 | 0.16±0.24 | 0.23±0.28 | 0.18±0.24 | 0.16±0.29 |
| | 200 | 0.48±0.75 | 1.50±1.25 | 1.14±0.68 | 1.04±0.53 | 0.59±0.35 | 0.25±0.27 | 0.25±0.31 | 0.27±0.24 |
| | | | | ** | | | | | |
| | 400 | 0.08±0.24 | 0.69±1.28 | 0.63±0.91 | 0.68±0.66 | 0.2±0.27 | 0.38±0.35 | 0.47±0.61 | 0.18±0.22 |
| | | * | * | *** | * | | | | |
| FS(Y) | 400 | 0.12±0.37 | 1.11±1.39 | 0.90±0.76 | 0.80±0.52 | 0.78±0.53 | 0.47±0.32 | 0.43±0.36 | 0.06±0.14 |
| | | * | | ** | * | | * | | |

*: $P<0.05$,    : $P<0.01$,    *$P<0.001$    Student T Test vs Control

Figure 65

Table 15A-3. Results of urine specific gravity and pH with water load after FS(X) administration for 25 days

| Groups | Dose | Urine volume ml | Urine index ml/kg | Specific gravity | pH |
|---|---|---|---|---|---|
| Control | | 10.2±1.28 | 49.6±5.94 | 1.009±0.002 | 7.7±0.67 |
| Pituitrin | 0.25ug/kg | 8.04±2.59* | 41.0±13.97 | 1.01±0.002*** | 8.1±0.74 |
| FS(X) | 100 mg/kg | 8.5±1.47* | 41.5±6.36** | 1.01±0.004* | 8.0±0.67 |
| | 200 mg/kg | 8.69±2.30 | 41.7±6.67* | 1.01±0.004* | 8.0±0.82 |
| | 400 mg/kg | 5.93±2.44** | 28.9±11.2** | 1.01±0.003 | 8.2±1.03 |
| FS(Y) | 400 mg/kg | 7.94±1.74*** | 39.7±7.38** | 1.01±0.003 | 7.9±1.01 |

*: $P<0.05$,  : $P<0.01$,  *: $P<0.001$    Student T Test vs Control

Figure 66

Table 15A-4 Concentration of Na+, K+ and Cl- in urine with water load after FS(X) administration for 25 days

| Groups | Dose | Na+ mmol/l | Na+ index mmol/kg | K+ mmol/l | K+ index mmol/kg | Cl- mmol/l | Cl- index mmol/kg |
|---|---|---|---|---|---|---|---|
| Control | | 9.51±2.36 | 0.47±0.10 | 6.67±1.25 | 0.33±0.08 | 12.2±3.22 | 0.6±0.14 |
| Pituitrin | 0.25 ug/kg | 74.8±23.5** | 2.99±1.56** | 22.3±7.82** | 0.86±0.32** | 83.2±26.9** | 3.33±1.60** |
| FS(X) | 100 mg/kg | 16.8±7.38** | 0.71±0.38 | 12.0±5.46*** | 0.49±0.20 | 21.3±10.7* | 0.90±0.52 |
| | 200 mg/kg | 23.6±13.0** | 0.99±0.64* | 18.2±6.30*** | 0.75±0.26** | 30.1±17.2** | 1.25±0.75* |
| | 400 mg/kg | 24.3±11.9** | 0.62±0.30 | 21.8±10.7** | 0.57±0.26* | 28.3±10.1** | 0.80±0.35 |
| FS(Y) | 400 | 16.2±11.4 | 0.67±0.55 | 15.2±5.37** | 0.60±0.25** | 19.6±10.9 | 0.81±0.52 |

*: P<0.05, : P<0.01, *:P<0.001    Student T Test vs Control

Structure of Compound

COMPOSITION COMPRISING XANTHOCERAS SORBIFOLIA EXTRACTS, COMPOUNDS ISOLATED FROM SAME, METHODS FOR PREPARING SAME AND USES THEREOF

CROSS-REFERENCE TO RELATED APPLICATIONS

This application is a continuation of U.S. Ser. No. 13/718,575, Filed Dec. 18, 2012, which is a continuation of U.S. Ser. No. 12/392,795, Filed Feb. 25, 2009, U.S. Pat. No. 8,334,269, issued Dec. 18, 2002, which is a continuation of U.S. Ser. No. 10/906,303, Filed Feb. 14, 2005, U.S. Pat. No. 7,524,824, issued Apr. 28, 2009, which is a Continuation-In-Part application of International Application No. PCT/US04/43465, Filed Dec. 23, 2004, which is a Continuation-In-Part application of PCT/US04/33359, Filed Oct. 8, 2004, which claims benefit of U.S. Ser. Nos. 60/617,379, Filed Oct. 8, 2004, 60/613,811, Filed Sep. 27, 2004, 60/607,858, Filed Sep. 7, 2004, 60/532,101, Filed Dec. 23, 2003, and 60/509,851, Filed Oct. 9, 2003. Furthermore, U.S. Ser. No. 10/906,303, Filed Feb. 14, 2005, is a Continuation-In-Part of U.S. Ser. No. 10/471,384, Filed Sep. 4, 2003, U.S. Pat. No. 7,189,420, issued Mar. 13, 2007, which is a National Stage of Intl App'l No. PCT/IB02/04750, Filed Aug. 28, 2002, which is a continuation-in-part of U.S. Ser. No. 09/944,805, Filed Aug. 31, 2001, U.S. Pat. No. 6,616,943, issued Sep. 9, 2003. The entire contents of these preceding applications are hereby incorporated by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention relates to extracts from a plant called Wenguanguo (*Xanthoceras Sorbifolia* Bunge), their usages and functions, and methods of their preparation.

BACKGROUND OF THE INVENTION

Wenguanguo is a species of the sapindaceae family. Its scientific name is *Xanthoceras sorbifolia* Bunge. Wenguanguo is the common Chinese name; others are Wenguanng-guo, Wenguanmu, Wenguanhua, Xilacedeng and xilasendeng. Goldenhorn and Yellowhorn are its common English names. Wenguanguo is grown in Liaoning, Jilin, Hebei, Shandong, Jiangsu, Henan, Shanxi, Shaanxi, Gansu, Ningxia and Inner Mongolia, China. Its seeds, leaves and flowers are edible and its seeds have been used as a folk medicine to treat enuresis for centuries. Its branches and woods are also used as a folk medicine.

Chinese patent applications CN 1092991A and CN 1092992A discussed the methods for producing a medicine from Wenguanguo kernel powder for curing enuresis and enhancing cerebral functions. Chinese patent CN 1052636C discussed a method for producing a medicine with ethanol extract from the Wenguanguo kernel powder for curing enuresis and enhancing cerebral functions. Journal of Shenyang University of Pharmacy (2001), 18(1), 53-56 disclosed the n-butanol extract from the wood of Wenguanguo, which has anti-inflammatory effect.

United States Patent Application Publication No. 20030096030 discussed the extracts from the husks of Wenguanguo which are Bunkankasaponin A. B. C. D and two sterols for preventing cerebral aging, improving cerebral functions and curing enuresis, frequent micturition, urinary incontinence, dementia, weak intelligence, and increasing the body's ability to resist the activity of glycosuria.

United States Patent Application Publication No. 20030082293 disclosed the extracts Bunkankasaponin A. B. C. D, crude fats, crude protein and sugars from the shell of Wenguanguo.

U.S. Pat. No. 6,616,943, issued on Sep. 9, 2003, discussed the composition comprising Wenguanguo combined extracts and the methods for preparing them and uses thereof. The methods for preparing the combined extract from the husks comprise the following steps: extracting Wenguanguo husks with an organic solvent (e.g. ethanol) to form an organic (e.g. ethanol) extract; removing the organic solvent (e.g. ethanol) from the organic (e.g. ethanol) extract to form aqueous extracts; and drying and sterilizing the aqueous extracts to form the combined extracts. The combined extracts contain saponins, saccharides, proteins and others. The extracts can be used for producing medicines or health foods for preventing cerebral aging, improving memory, improving cerebral functions and curing enuresis, frequent micturition, urinary incontinence, dementia, weak intelligence and Alzheimer's disease, autism, brain trauma, Parkinson's disease and other diseases caused by cerebral dysfunction. The medicines or health foods further comprise Vitamin B, Vitamin D, K, anti-oxidant, *Cordyceps* or its extracts, gingko or its extracts, *Echinacea* or its extracts, Huperzine A, folic acid, amino acids, creatine, fiber supplement or a combination thereof.

Yingjie Chen, Tadahiro Takeda and Yukio Ogihara in Chem. Pharm. Bull 33(4)1387-1394(1985) described a study on the constituent of *Xanthoceras sorbifolia* Bunge. See Section V. Saponins from the Fruits of *Xanthoceras sorbifolia*. Four new saponins were isolated from the fruits of *Xanthoceras sorbifolia* Bunge. The structures of these saponins are bunkankasaponins A, B, C and D:

(1) 22-O-acetyl-21-O-(4-O-acetyl-3-O-angeloyl)-β-D-fucopyranosyl-3-O-[β-D-glucopyranosyl-(1→2)-β-D-glucuronopyranosyl]protoaecigenin (2) 22-O-acetyl-21-O-(3,4-di-O-angeloyl)-β-D-fucopyranosyl-3-O-[β-D-glucopyranosyl-(1→2)-β-D-glucuronopyranosyl]protoaecigenin (3) 28-O-acetyl-21-O-(4-O-acetyl-3-O-angeloyl)-β-D-fucopyranosyl-3-O-[β-D-glucopyranosyl-(1→2)-β-D-glucuronopyranosyl]protoaecigenin (4) 28-O-acetyl-21-O-(3,4-di-O-angeloyl)-β-D-fucopyranosyl-3-O-[β-D-glucopyranosyl-(1→2)-β-D-glucuronopyranosyl]protoaecigenin Yingjie Chen, Tadahiro Takeda and Yukio Ogihara in Chem. Pharm. Bull 33(3)1043-1048(1985) described studies on the constituent of *Xanthoceras sorbifolia* Bunge. See Section IV. Structures of the Miner Prosapogenin. The prosapogenins from the partial hydrilyzate of fruit saponin of *Xanthoceras sorbifolia* were examinated, and are characterized as:

16-O-acetyl-21-O-(3,4-di-O-angeloyl-β-D-fucopyranosyl) protoaecigenin

22-O-acetyl-21-O-(3,4-di-O-angeloyl-β-D-fucopyranosyl) protoaecigenin 3-O-β-D-glucuronopyranoside Yingjie Chen, Tadahiro Takeda and Yukio Ogihara in Chem. Pharm. Bull 33(1)127-134(1985) describe studies on the constituent of *Xanthoceras sorbifolia* Bunge. See Section III. Minor Prosapogenins aponins from the Fruits of *Xanthoceras sorbifolia* Bunge. The structure of 3 minor prosapogenins, obtained by acid hydrolysis of the crude saponin faction, were characterized as:

21-O-(3,4-di-O-angeloyl)-β-D-fucopyranosyltheasapogenol B

21-O-(4-O-acetyl-3-O-angeloyl)-β-D-fucopyranosyltheasapogenol B

21-O-(4-O-acetyl-3-O-angeloyl)-β-D-fucopyranosyl-22-O-acetylprotoaescigenin

Yingjie Chen, Tadahiro Takeda and Yukio Ogihara in Chem. Pharm. Bull 33(4)1387-1394(1985) described a study on the constituent of *Xanthoceras sorbifolia* Bunge. See Section II. Major Sapogenol and prosapogenin from the Fruits of *Xanthoceras sorbifolia*.

Laurence Voutquenne, Cecile Kokougan. Catherine Lavaud, Isabelle Pouny, Marc Litaudon. Triterpenoid saponins and Acylated prosapogenins from Harpullia austro-caledonica. Phytochemistry 59 (2002) 825-832

Zhong Jaing, Jean-francois Gallard, Marie-Therese Adeline, Vincent Dumontet, Mai Van Tri, Thierry Sevenet, and Mary Pais Six Triterpennoid Saponins from Maesa *laxiflora*. J. Nat. Prod. 1999, 62, 873-876

Young Seo, John M. Berger, Jennine Hoch, Kim M Neddermann, Isia Bursuker, Steven W. Mamber and David G. Kingston. A new Triterpene Saponin from *Pittosporum viridiflorum* from the Madagascar Rainforest. J. Nat. Prod. 2002, 65, 65-68

Xiu-Wei Yang, Jing Zhao, Xue-Hui Lui, Chao-Mei Ma, Masao Hattori, and Li He Zhang Anti-HIV-1 Protease Triterpenoid Saponins from the Seeds of *Aesculus chinensis*. J. Nat. Prod. 1999 62, 1510-1513

Yi Lu, Tatsuya Umeda, Akihito Yagi, Kanzo Sakata, Tirthankar Chaudhuri, D. K. Ganguly, Secion Sarma. Triterpenoid Saponins from the roots of the tea plant (*Camellia sinensis* var. Assamica). Phytochchemistry 53 (2000) 941-946

Sandra Apers, Tess E. De Bruyne, Magda Claeys, Arnold J. Viletinck, Luc A. C. Pieters. New acylated triterpenoid saponins from Maesa laceceolata. Phytochemistry 52 (1999) 1121-1131

Ilaria D'Acquarica, Maria Cristina, Di Giovanni, Francesco Gasparrini, Domenico Misiti, Claudio D'Arrigo, Nicolina Fagnano, Decimo Guarnieri, Giovanni Iacono, Giuseppe Bifulco and Raffaele Riccio. Isolation and structure elucidation of four new triterpenoid estersaponins from fruits of the Pittosporumtobira AIT.

Tetrahedron 58 (2002) 10127-10136

Cancer cells are defined by two heritable properties: (1) they reproduce in defiance of normal restraints on cell division; and (2) they invade and colonize territories normally reserved for other cells.

Cancers require mutations of many genes to develop, and they are classified according to the tissue and cell type from which they arise. Cancers arising from epithelial cells are named carcinomas; those arising from connective tissue or muscle cells are named sarcomas. In addition, there are cancers called leukemias, which are derived from hemopaietic cells; and cancers derived from cells of the nervous system.

Cancers originating from different types of cells are, in general, very different diseases. Each cancer has characteristics that reflect its origin. Even when a cancer has metastasized and proliferated out of control, its origins can be traced back to a single, primary tumor. Therefore it is important to develop drugs against target cells with a specified character.

Ovarian cancer is the 5th leading cause of cancer death in women and the leading cause of death from gynecologic. In the United States, females have a 1.4 to 2.5% (1 out of 40-60 women) lifelong chance of developing ovarian cancer. Older women are at highest risk. More than half of the deaths from ovarian cancer occur in women between 55 and 74 years of age and approximately one quarter of ovarian cancer deaths occur in women between 35 and 54 years of age.

Ovarian cancer is disproportionately deadly for a number of reasons. First, symptoms are vague and non-specific, so women and their physicians frequently attribute them to more common conditions. By the time the cancer is diagnosed, the tumor has often spread beyond the ovaries. Also, ovarian cancers shed malignant cells that frequently implant on the uterus, bladder, bowel, and lining of the bowel wall (omentum). These cells can begin forming new tumor growths before cancer is even suspected. Second, because no cost-effective screening test for ovarian cancer exists, more than 50 percent of women with ovarian cancer are diagnosed in the advanced stages of the disease.

This invention provides compounds or compositions extracted from *Xanthoceras Sorbifolia* or synthesized which have substantial potency against ovarian cancer.

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The invention provides a compound comprising the following structure, with the formula of $C_{57}H_{88}O_{23}$ and the name of 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene, also known as Xanifolia-Y This compound was isolated from *Xanthoceras sorbifolia*.

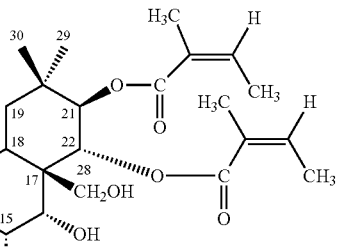
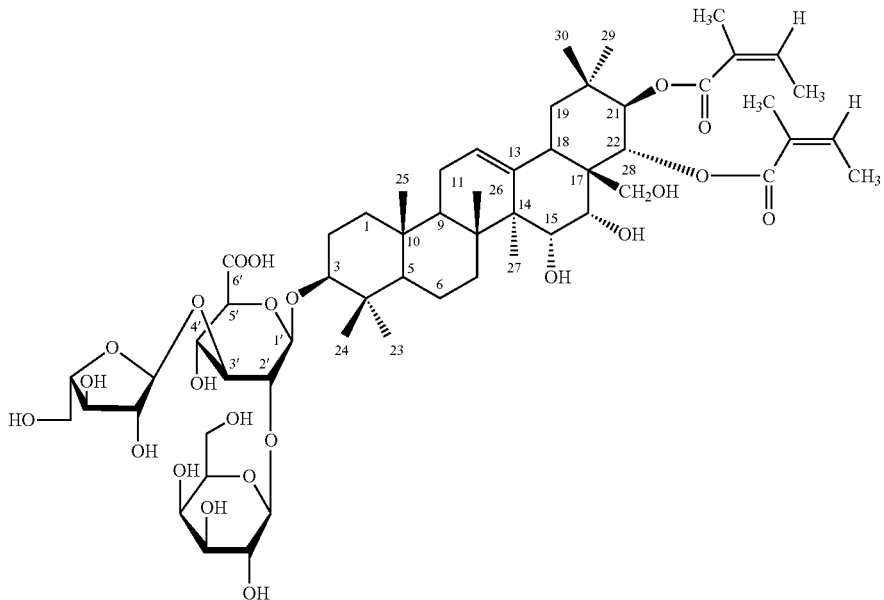

This invention provides a compound comprising the following structure, with the formula of $C_{65}H_{100}O_{27}$ and the name of 3-O-[β-D-galactopyranosyl(12→)]-α-L-arabinofuranosyl (1→3)-β-D-glucuronopyranosyl-21-O-(3,4-diangeloyl)-α-L-rhamnophyranosyl-22-O-acetyl-3β,16α, 21β, 22α, 28-pentahydroxyolean-12-ene, also known as Xanifolia-Y1

The compound Y is purified with procedure as described in this application (FIG. 7A). The purified compound Y shows 10 times higher potency (IC50=1.5 ug/ml) than the original extract (IC50=25 ug/ml) (FIG. 8). The compound Y has a high selectivity toward ovarian cancer (FIG. 9).

The compound Y shows inhibitory activity toward the following human cancer cells (eleven human cancer cell lines were tested in this study) with a higher potency toward ovarian carcinoma (comparison of activities is presented in FIG. 10 and Table 3.1).

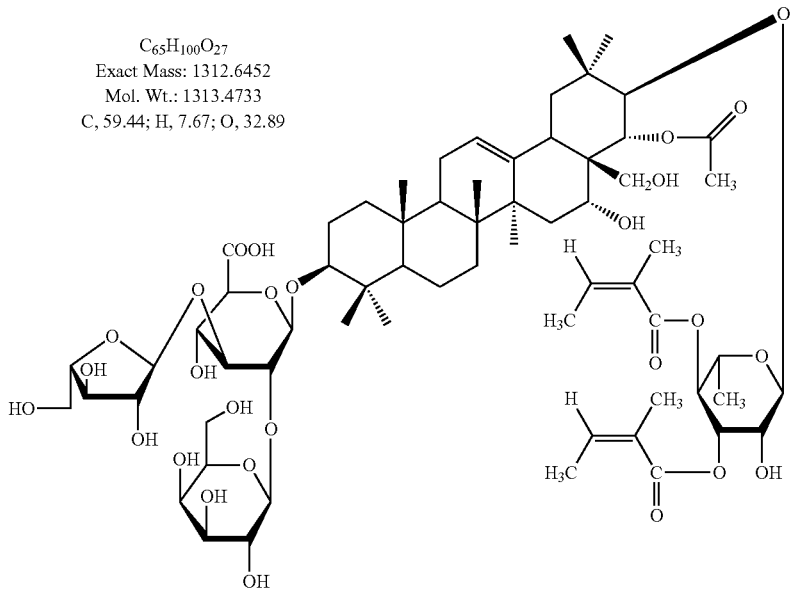

The above compounds (Y and Y1) have anti-cancer effect. They inhibit the growth of human ovarian cancer (FIG. 3, 4).

These compounds (Y and Y1) are two of the active components identified from extracts of *Xanthoceras sorbifolia* by methods of FPLC and HPLC as shown in FIG. 5, 6, 7.

This invention provides the extract of *Xanthoceras Sorbifolia* against cancer growth. The cancer includes, but is not limited to ovary cancer, bladder cancer, prostate cancer, leukocytes cancer, and bone cancer.

The compounds can be isolated from the plant called *Xanthoceras Sorbifolia* or can be synthesized chemically, or extracted from other biological sources.

This invention is related to the use of extracts of Wenguanguo. Extracts from husks, leaves, branches or stems, and fruit-stems, roots and barks of the Wenguanguo can be combined and this invention discloses methods of their preparation.

The extracts contain saponins, saccharides, proteins, glycosides, flavonoids, curmarin extracts, alkaloid extracts, organic acid extracts, tannin and others.

This invention provides the extract of *Xanthoceras Sorbifolia* for preventing cerebral aging; for improving memory; for improving cerebral functions; for curing enuresis, frequent micturition, urinary incontinence, dementia, weak intelligence, Alzheimer's disease, brain trauma, or other diseases caused by cerebral dysfunctions.

Wenguanguo extracts may be used for accelerating the growth of bladder, for suppressing deep sleep, for increasing alertness in a sleeping subject, for modulating the release, breakdown and uptake of Antidieuretic hormone (ADH) and its receptors, for modulating the secretion, breakdown and uptake of Adrenocorticotropic hormone (ACTH) and its receptors, for modulating the release, breakdown and uptake of 5-hydroxytryptamine and its receptors, for modulating the release, breakdown and uptake of Acetycholine (Ach) and its receptors, for modulating the release, breakdown and uptake of Adrenaline (AD) and its receptors, for modulating the release, breakdown and uptake of Dopamine (DA) and its receptors, for modulating the release, breakdown and uptake of Norepinephrine (NE) and its receptors, for preventing sleep paralysis, for modulating the formation, release, breakdown and activity of neuropeptides and their receptors, for curing cancer, including but not limited to breast cancer, leukocyte cancer, liver cancer, ovary cancer, bladder cancer, prostate cancer and brain cancer, and for improving the functions of the lung and the bladder.

This invention provides a compound comprising a sugar, a triterpene or Sapogenin, and side chain at Carbon 21 and/or 22 including Angeloyl groups, operatively linked to form a biologically active compound. In an embodiment, the compound comprises one or more sugars.

This invention provides a salt of the above-described compounds.

This invention provides a pharmaceutical composition comprising an effective amount of the above-described compounds and a pharmaceutically acceptable carrier(s).

This invention provides a method for isolating compounds from *Xanthoceras Sorbifolia* comprising steps of: extracting *Xanthoceras Sorbifolia* powder with an appropriate amount of one or more organic solvents for an appropriate amount of time to form an organic extract; collecting the organic extract; refluxing the organic extract to form a second extract; removing the organic solvent from the second extract; drying and sterilizing the second extract to form a *Xanthoceras Sorbifolia* extract powder; fractionating the extract powder to obtain one or more components of the extract powder; identifying the bioactive components of the extract powder; purifying one or more bioactive components of the extract powder with FPLC to obtain one or more fraction of the bioactive component; and isolating the pure compound with preparative HPLC.

This invention provides a compound having a Structure verified by NMR spectral data derived from proton NMR, Carbon NMR, 2D NMR of the Heteronuclear Multiple Quantum Correlation (HMQC), Heteronuclear Multiple Bond Correlation (HMBC), and COSY, and Mass spectral data derived from WADLI-TOF and ESI-MS.

This invention provides the chemical features of a compound and its derivatives which are effective against cancer.

The compounds or compositions of the present invention regulate the receptors or components of cell such as G-protein receptor, Fas protein, receptor Tyrosine Kinases, Mitogen, mitogen receptor. The compound inhibits cellular pathways include TGF Beta-smad, FGF, TGF-beta and TGF-alphaa, ras-GTPase-MAP kinase, jun-fos, Src-fyn, Jak-Jnk-STAT, BMP, Wnt, myc-cell proliferation, etc. The mutation of cancer cell causes the cell-death program to become inactive, allowing cells to divide indefinitely. The *Xanthoceras Sorbifolia* derived compound and/or composition regulates the components and receptors and re-activates the cell death program.

Abnormal changes in components' activities in pathways cause the cells to fail to stop proliferating so as to form cancer. The pathways include TGF Beta-smad, FGF, TGF-beta and TGF-alphaa, ras-GTPase-MAP kinase, jun-fos, Src-fyn, Jak-Jnk-STAT, BMP, Wnt, myc-cell proliferation, etc. The mutation of cancer cell causes the cell-death program to become inactive, allowing cells to divide indefinitely. The *Xanthoceras Sorbifolia* derived compound and/or composition regulates the components and receptors and re-activates the cell death program.

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the inventive concepts will follow in later sections.

DETAILED DESCRIPTION OF THE FIGURES

Figure 3:
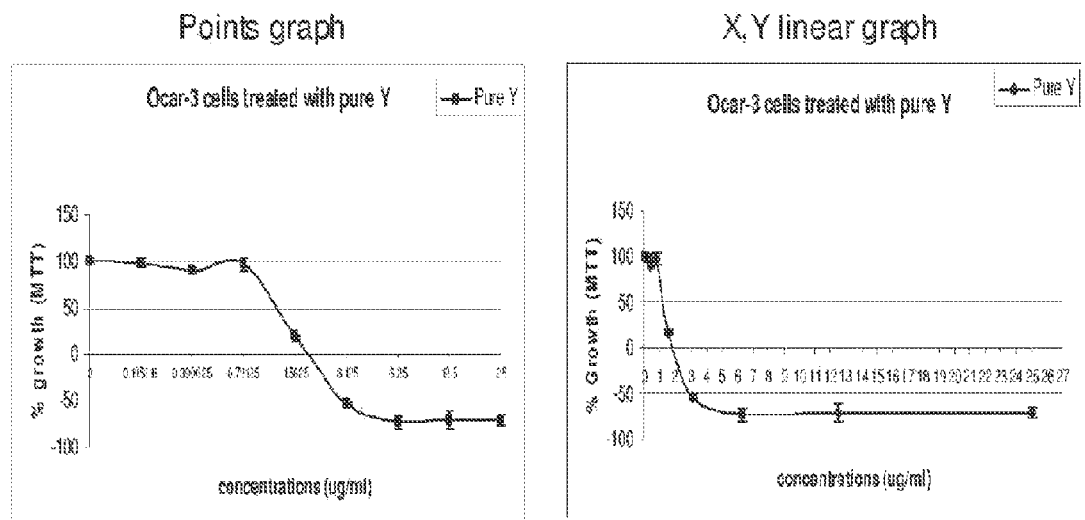

FIG. 3 shows the anticancer activity of purified Compound Y. The periment was performed on ovarian cancer cells (OCAR-3) and the inhibition activity was determined by MTT assay (for details, refer to Experiment 3). Abscissa: Concentration (ug/ml). Ordinate: % Cell Growth. The IC50 is approximately 1 ug/ml. A: Point scale. B: Linear scale.

Figure 4:
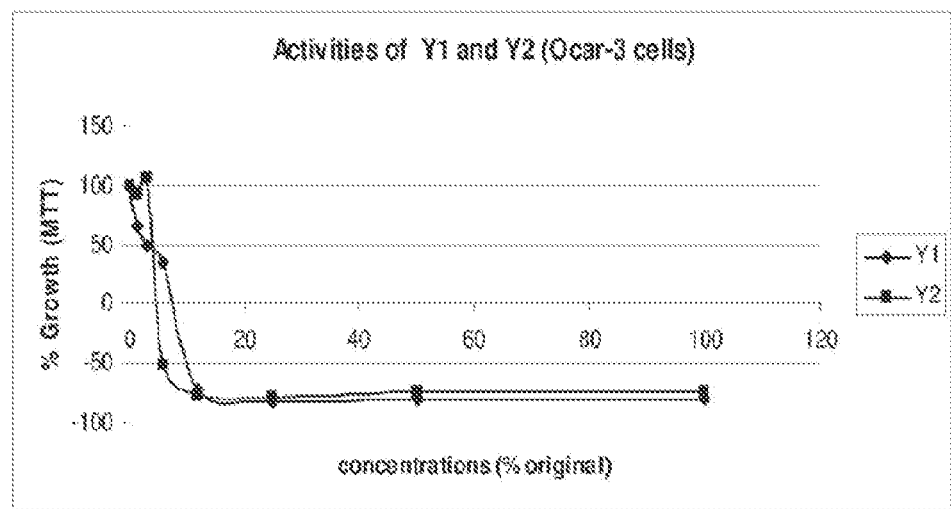

FIG. 4 shows the inhibition of the purified Compound Y1 and Compound Y2 on Ovarian cancer cells' growth.

Figure 5:
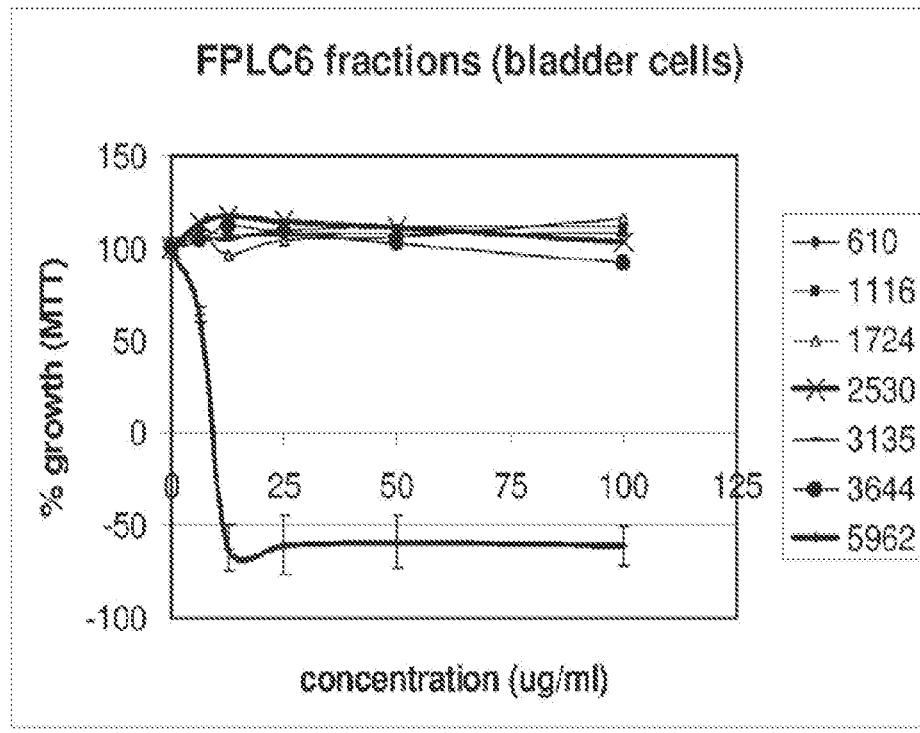
Figure 20:
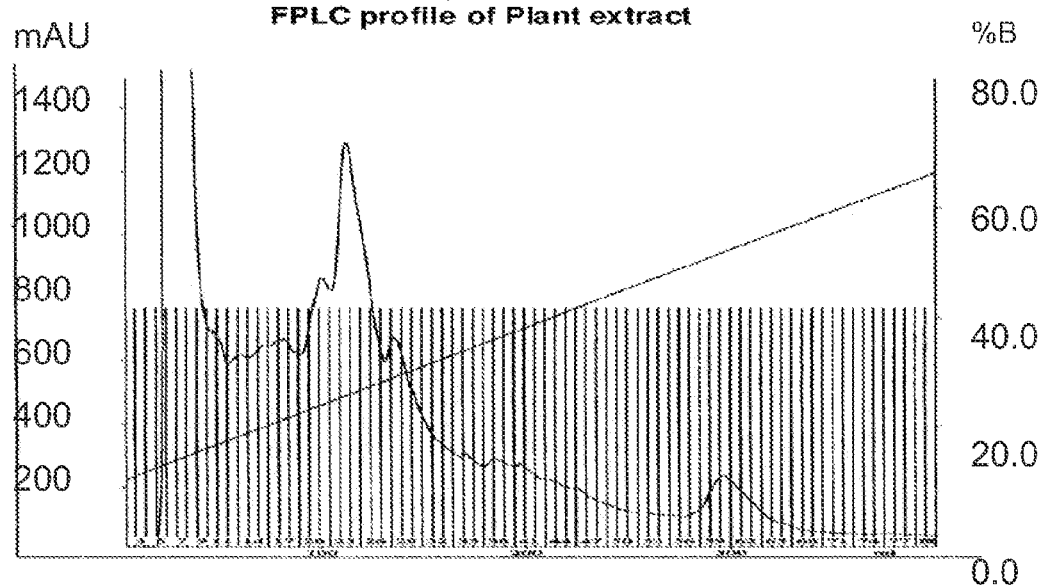

FIG. 5 shows the results of the screening of cell growth activity of fractions obtained after FPLC chromatography. The assay was conducted with bladder cells. The fractions obtained from FPLC as shown in FIG. 20 were used. As shown in this figure, that different components of *Xanthoceras Sorbifolia* extracts cause either growth or inhibition effects on cells. Only fraction 5962 (Fraction Y) causes cell inhibition. Fractions 610 and 1116 cause minor stimulation of cell growth. Abscissa: concentration (ug/ml). Ordinate: % Cell Growth (determined by MTT assay).

Figure 6:
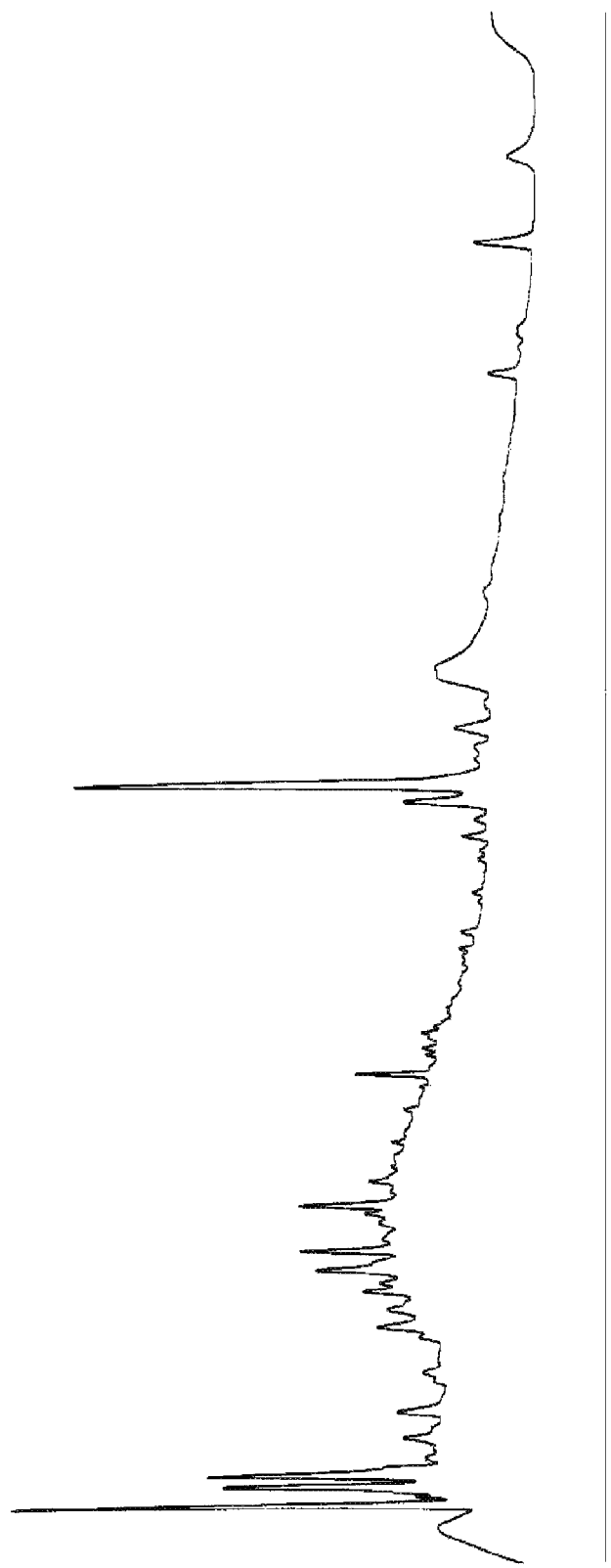

FIG. 6 shows the separation of the components of *Xanthoceras Sorbifolia* extract by HPLC with a μbondapak C18 column. Details of experiment was presented in Experiment 2.

FIG. 7 shows HPLC profile of Fraction Y with 45% Acetonitrile isocratic elution in a preparative C18 column (Delta Pak C18). Under these conditions, fractions Y, Y1 and Y2 are well separated from each other and they are collected individually.

FIG. 7A shows the purity of the collected Compound Y by HPLC using 45% acetonitrile isocratic elution in a preparative C18 column.

FIG. 8 shows the a growth curve of ovarian cancer cells after treatment with the crude extract of *Xanthoceras Sorbifolia* as determined by MTT assay. This is a preliminary study on the sensitivity of extract of *Xanthoceras Sorbifolia* on cancer cell. Cell lines from 11 different human organs were employed. With the crude extract, this figure shows the most sensitive cancer cells are Ovary cancer cells. Activities on other cancer cells were represented in FIGS. 10A-D.

Figure 9:
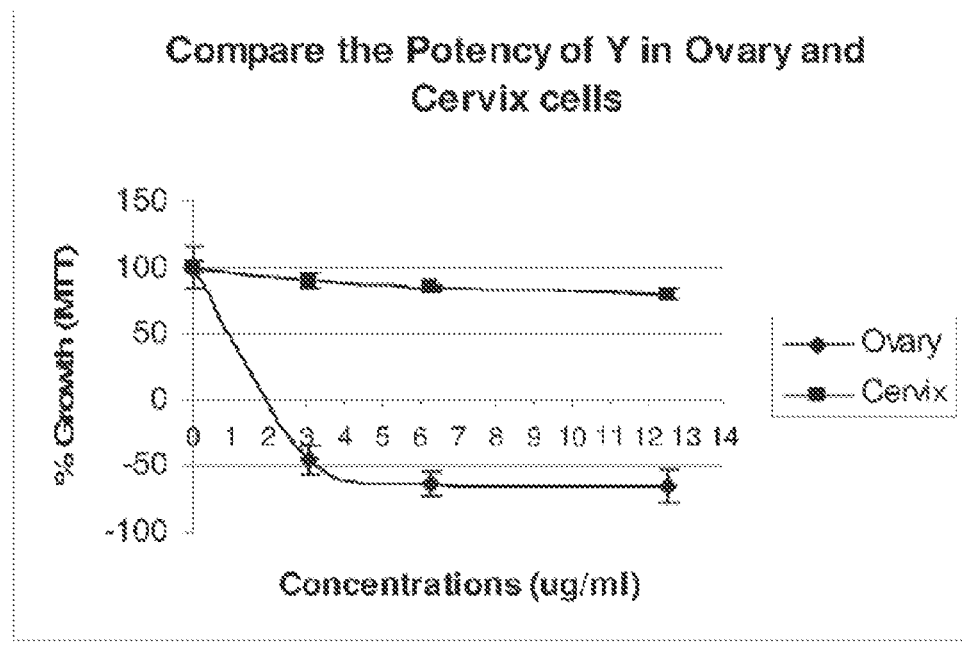
Figure 10A:
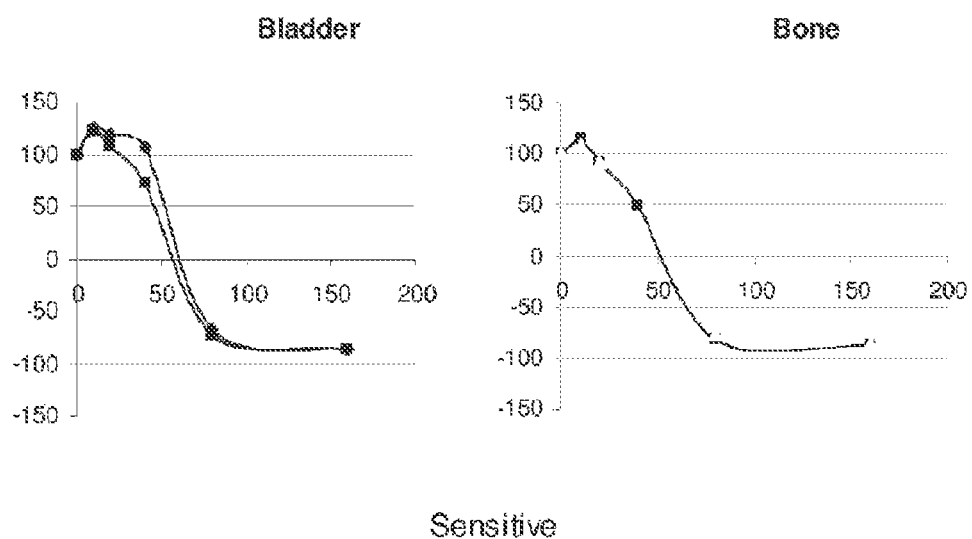
Figure 10B:
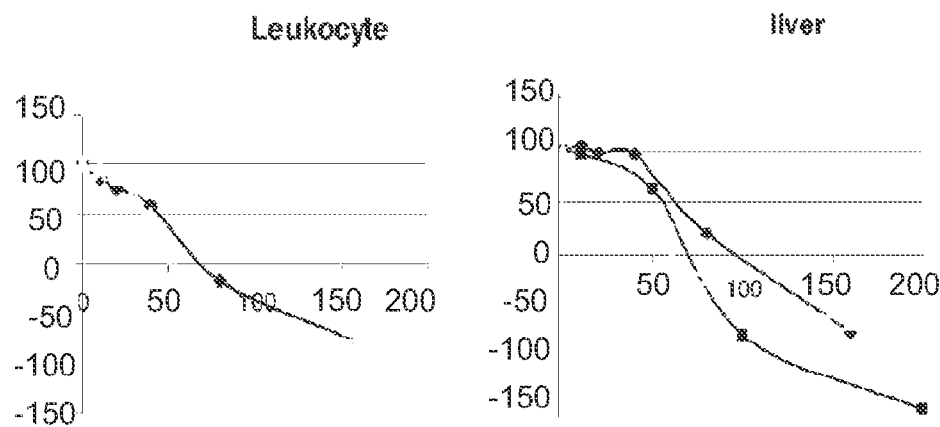
Figure 10C:
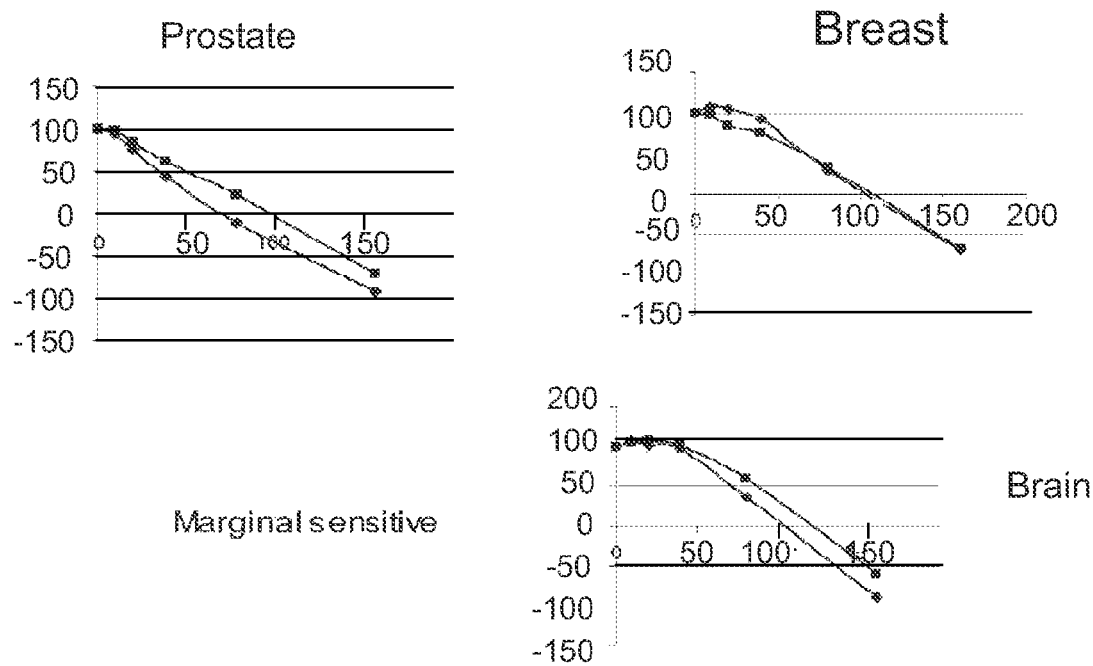
Figure 10D:
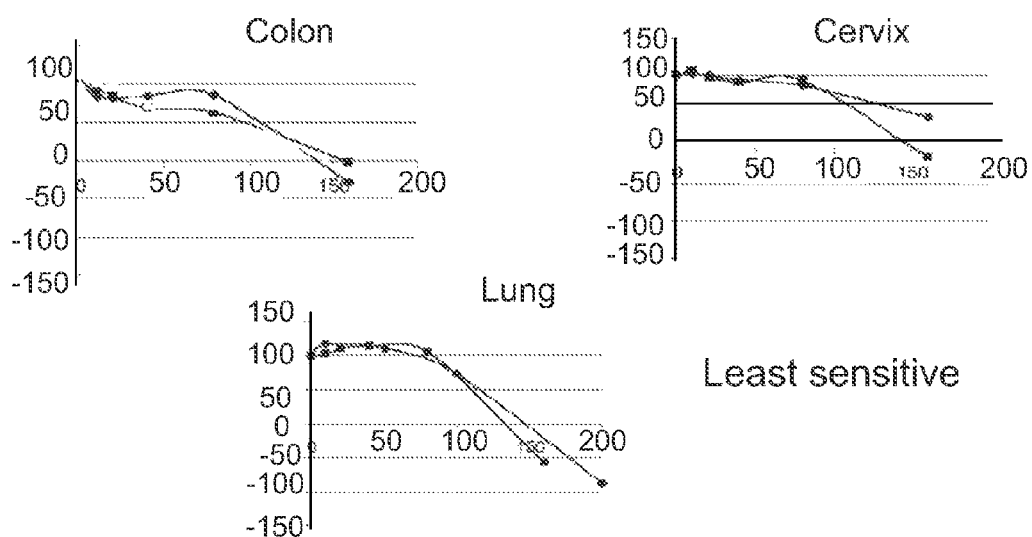

FIG. 9 shows the comparison of potency of Compound Y between ovarian cancer cells and cervical cancer cells. Ovarian cancer cells are much more sensitive to Compound Y than the cervical cancer cells. The IC50 for Compound Y in ovary cells is about 1.5. This result confirms that the activity of compound Y is more selective toward ovary cancer.

FIGS. 10A-D show the growth curves of cancer cells derived from different human organs as determined by MTT assay. After treatment with the extract of *Xanthoceras Sorbifolia*, growth curves of different cell lines were presented and their sensitivities (base on IC50 values) were determined.

10A: Sensitive: bladder and bone.
10B: Semi-sensitive: leukocyte and liver.
10C: Marginal sensitive: prostate, breast and brain.
10D: Least sensitive: colon, cervix and lung.

Figure 11:
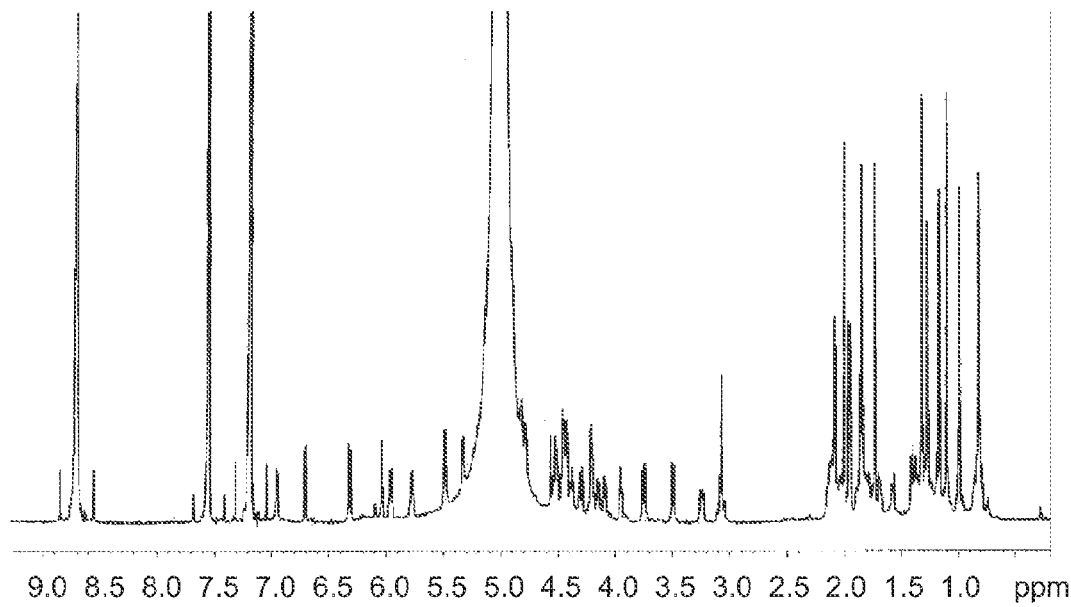

FIG. 11 shows the spectrum of proton NMR of Compound Y.

FIG. 12 shows 2D NMR (HMQC) results of Compound Y. Also see Table 5.2 for the listed chemical shift data.

FIG. 13 shows 2D NMR (HMBC) results of Compound Y. Also see Table 5.3 for the listed chemical shift data.

Figure 14:
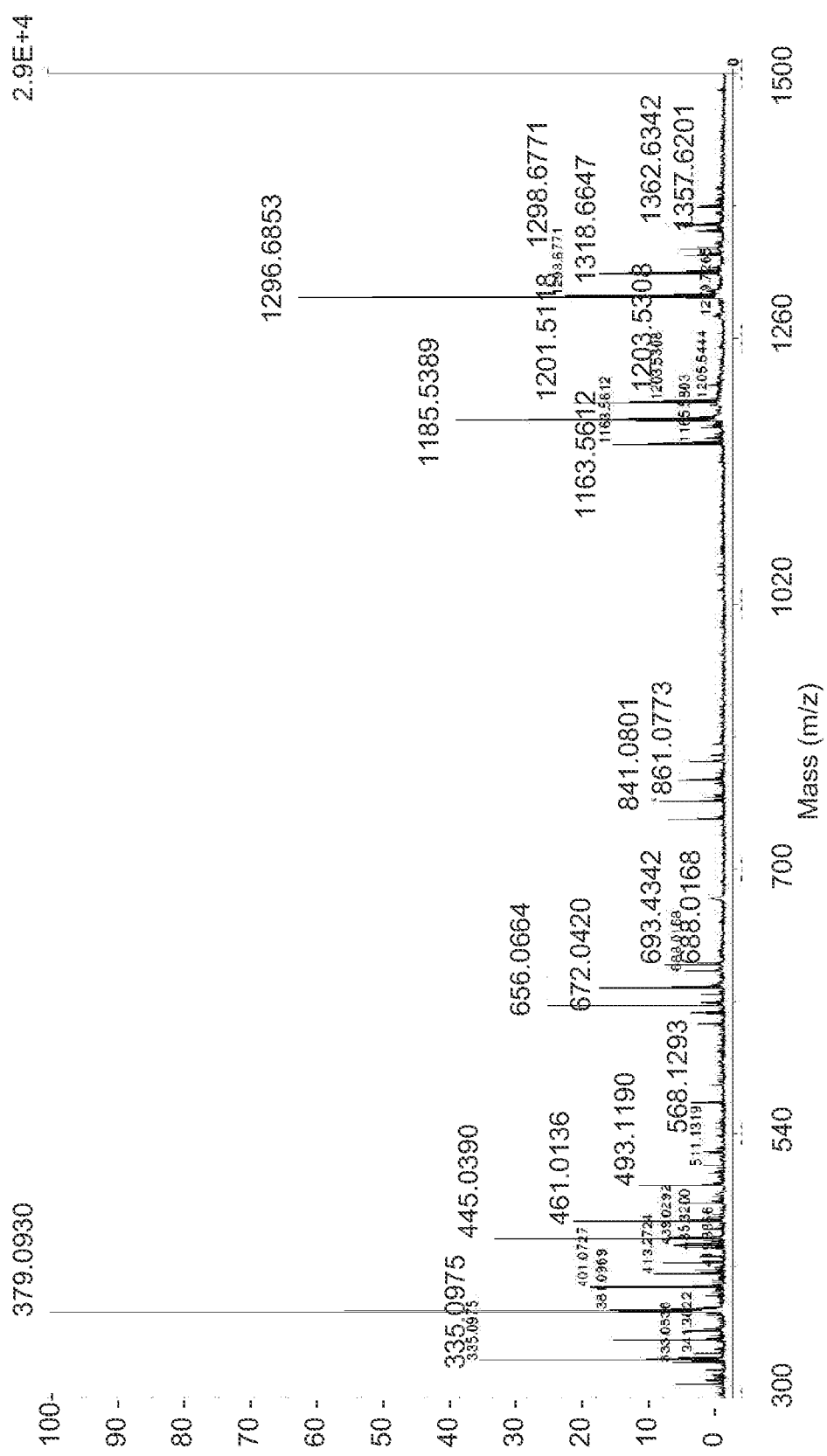

FIG. 14 shows the Mass spectrum of compound Y with MALDI-TOF (high mass): Y+Matrix (CHCA)+Angiotensin 1 "two point calibration".

Figure 15:
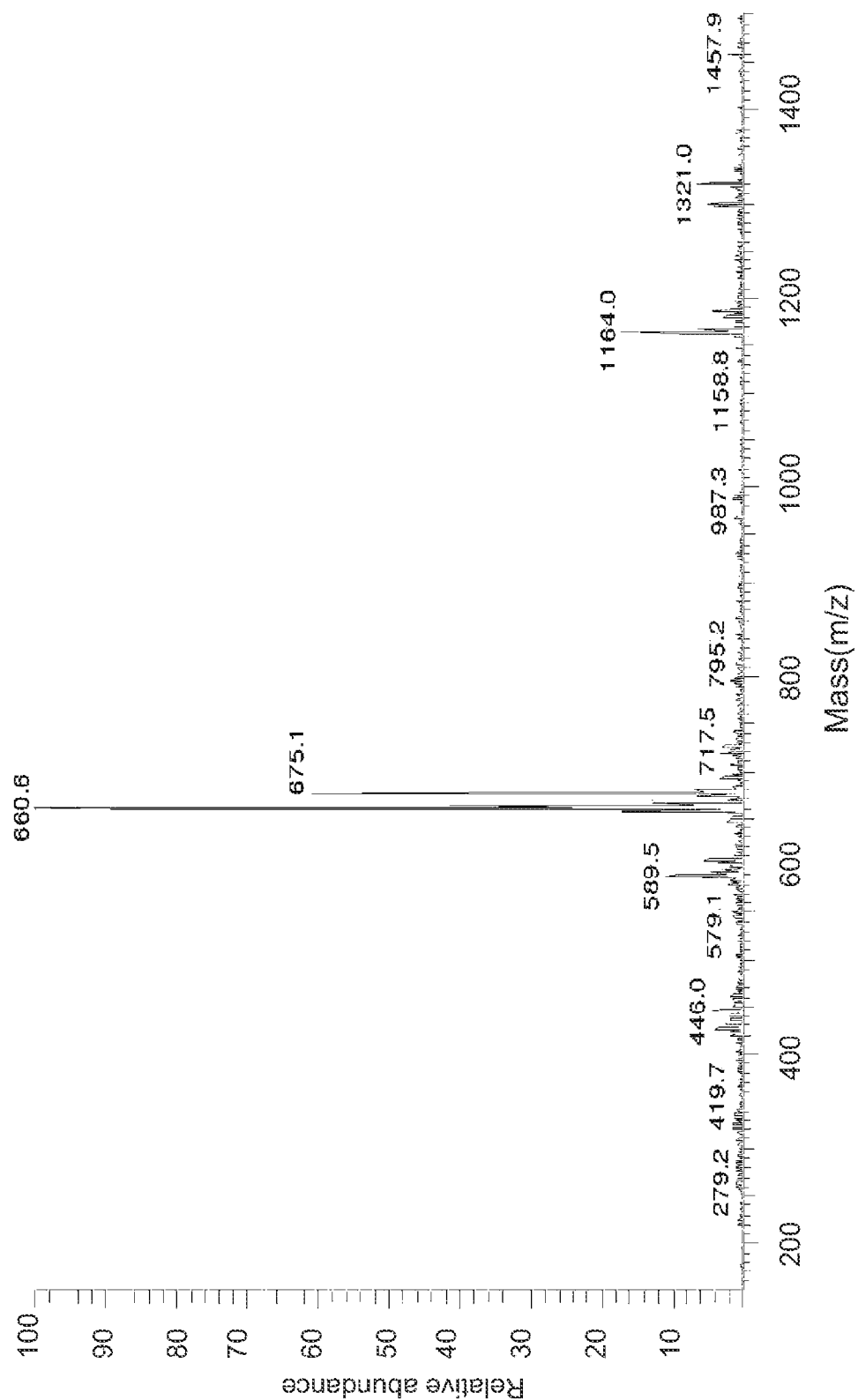

FIG. 15 shows the Mass spectrum of compound Y with ESI-MS.

Figure 16:
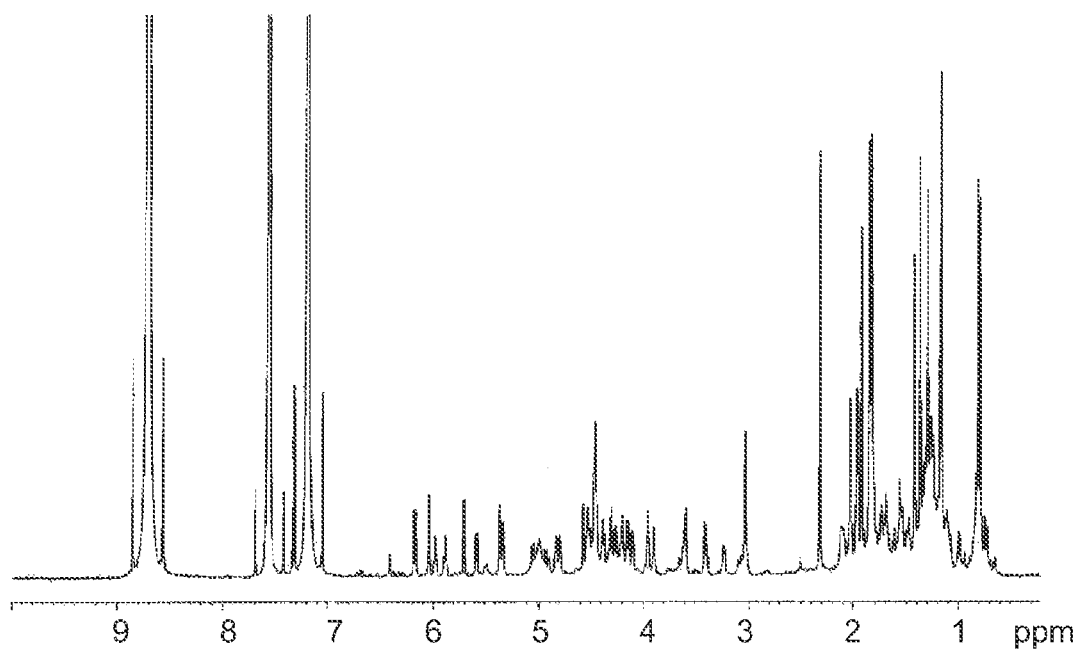

FIG. 16 shows the Proton NMR spectrum of Compound Y1.

Figure 17:
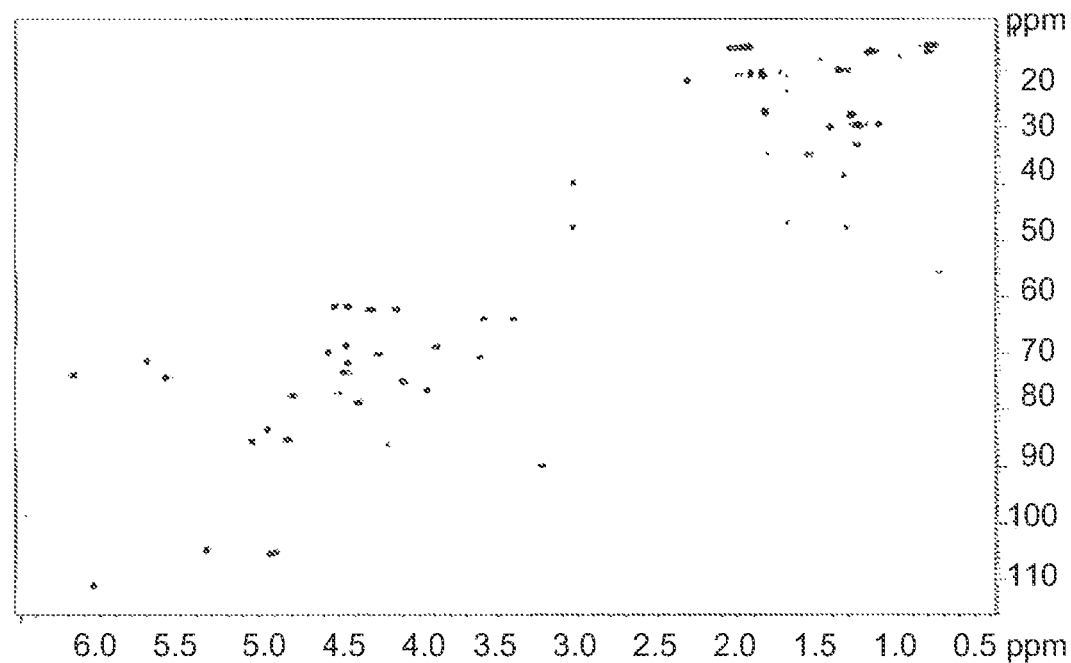

FIG. 17 shows the 2D NMR (HMQC) results of Compound Y1. Also see the chemical shift data from Table 6.2.

Figure 18:
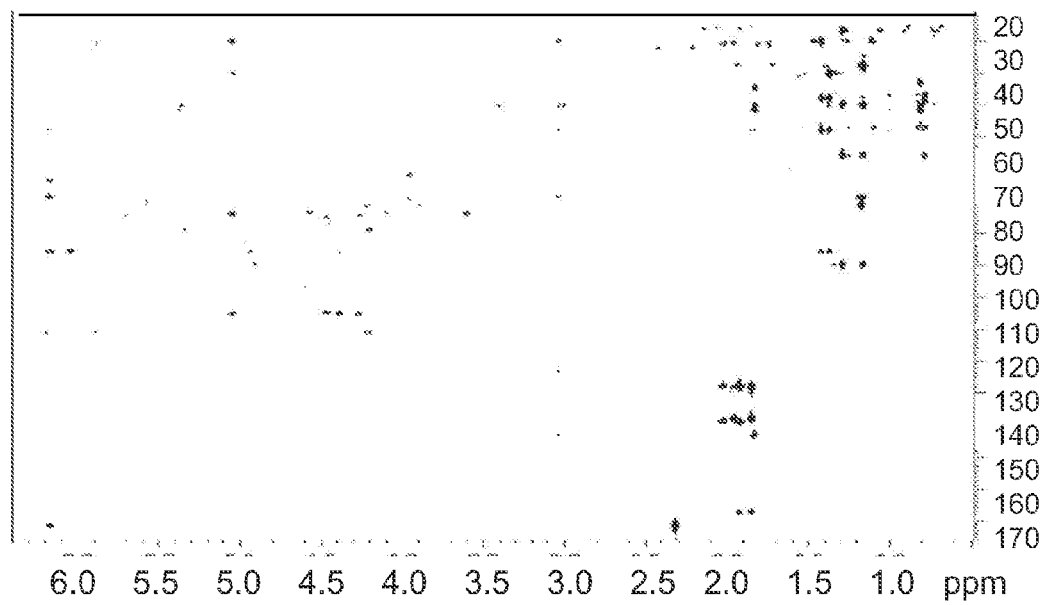

FIG. 18 shows the 2D NMR (HMBC) results of Y1. Also see the chemical shift data from Table 6.3.

Figure 19:
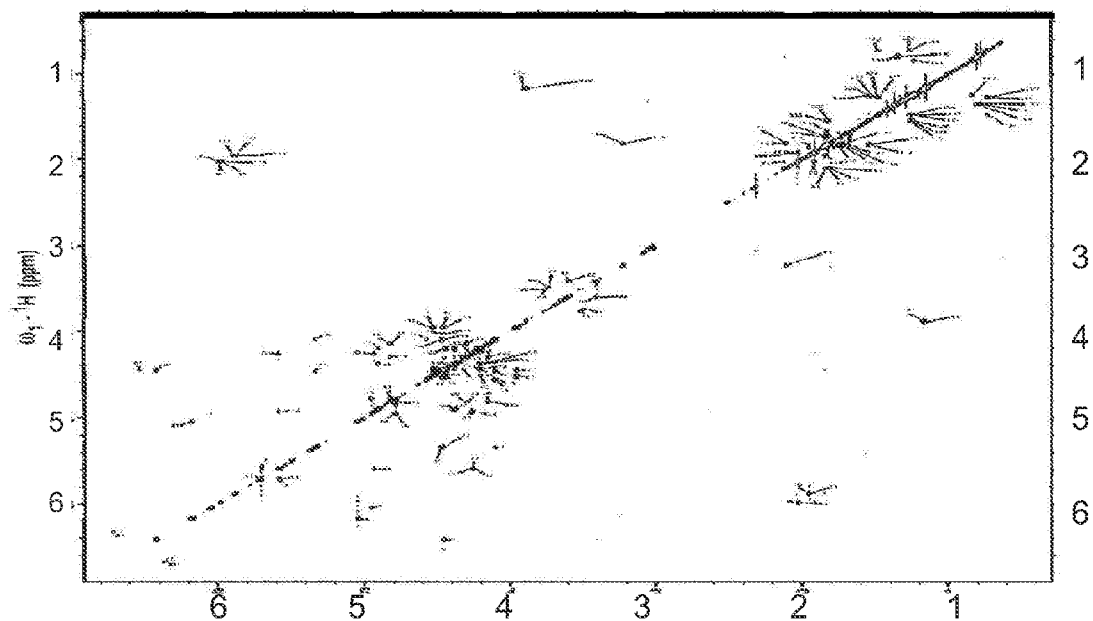

FIG. 19 shows COSY-NMR profile of Y1 with chemical shift data from Table 6.4.

FIG. 20 shows the elution profile of an extract of *Xanthoceras Sorbifolia* in FPLC with 10-80% gradient. Ordinate: Optical density (at 245 nm). Abscissa: Fractions (5 ml/fraction).

Figure 21:
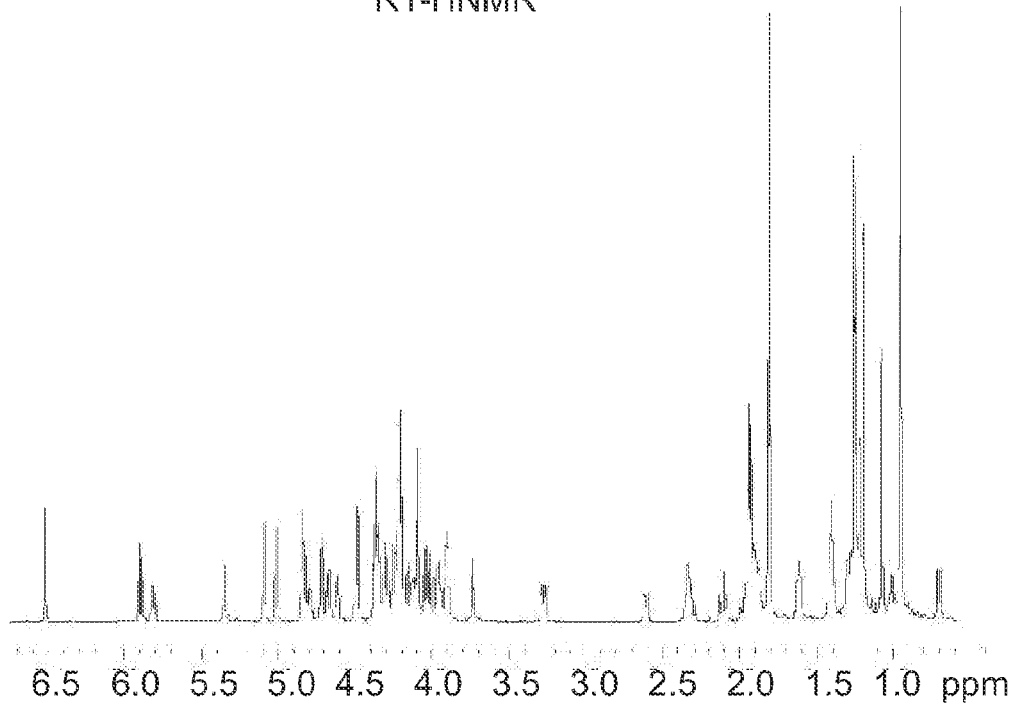

FIG. 21 shows the Proton-NMR spectra of compound R1.

Figure 22:
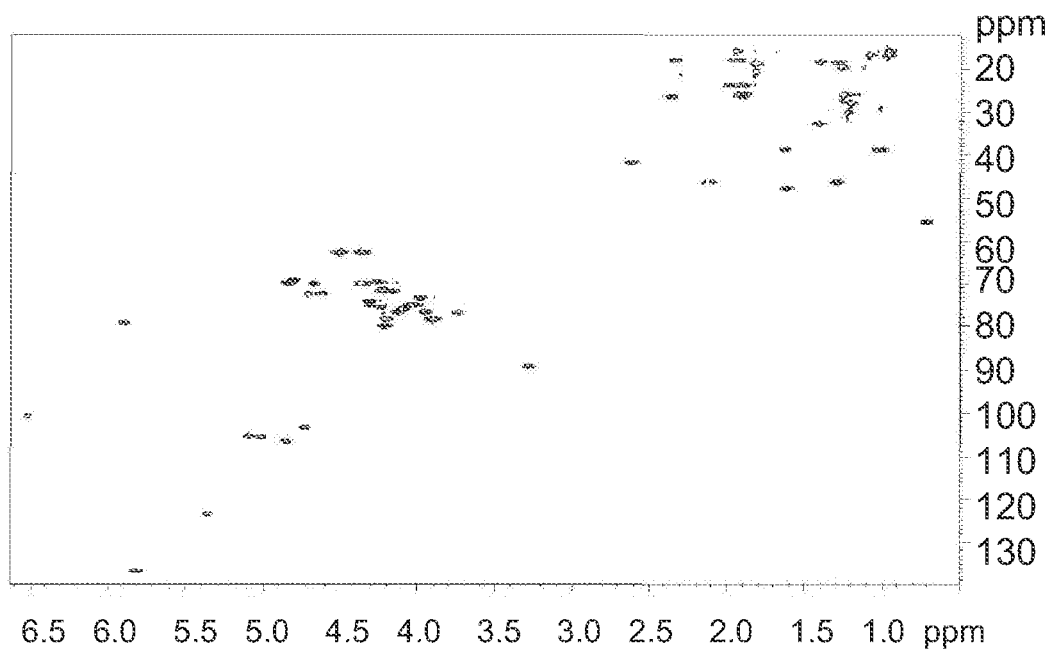

FIG. 22 shows the 2D NMR (HMQC) spectra of compound R1.

Figure 23:
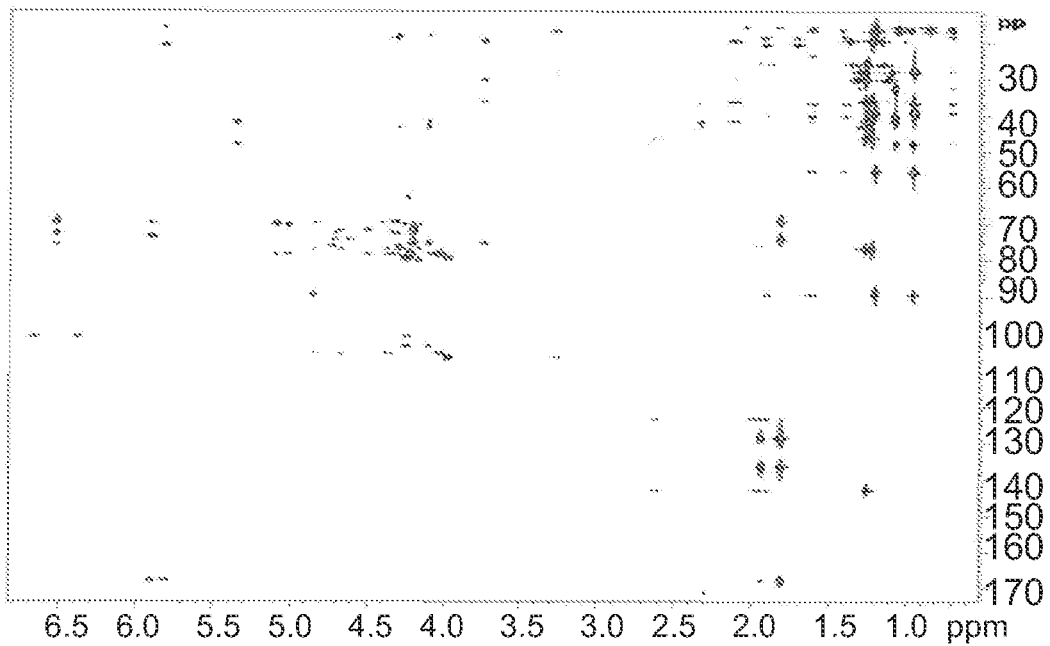

FIG. 23 shows the 2D NMR (HMBC) spectra of compound R1.

Figure 24:
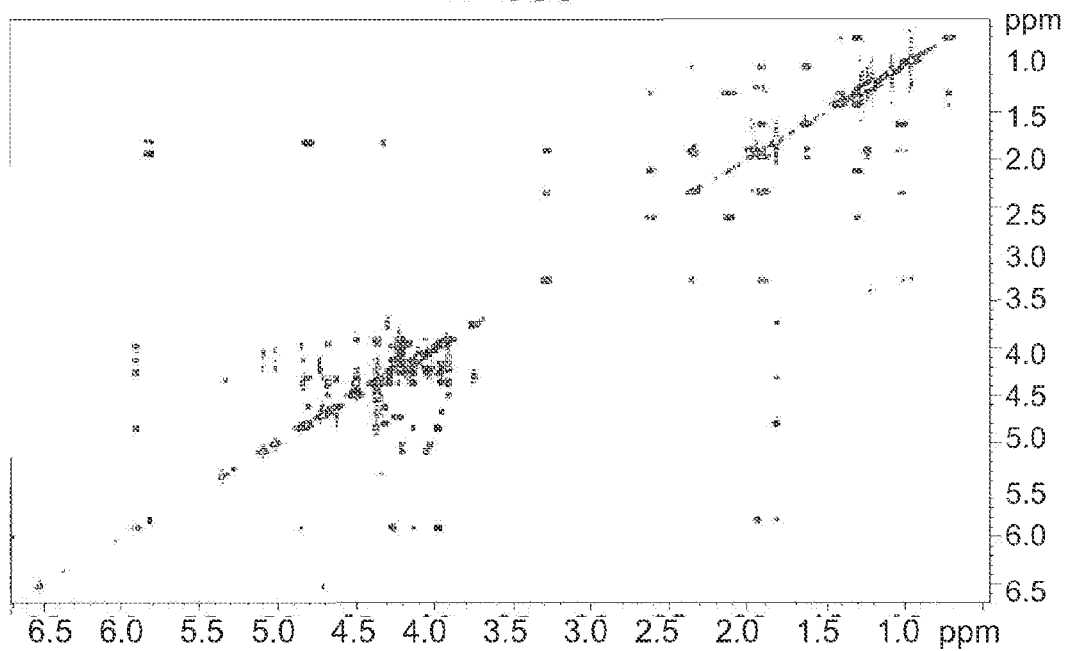

FIG. 24 shows the 2D NMR (COSY) spectra of compound R1.

Figure 25:
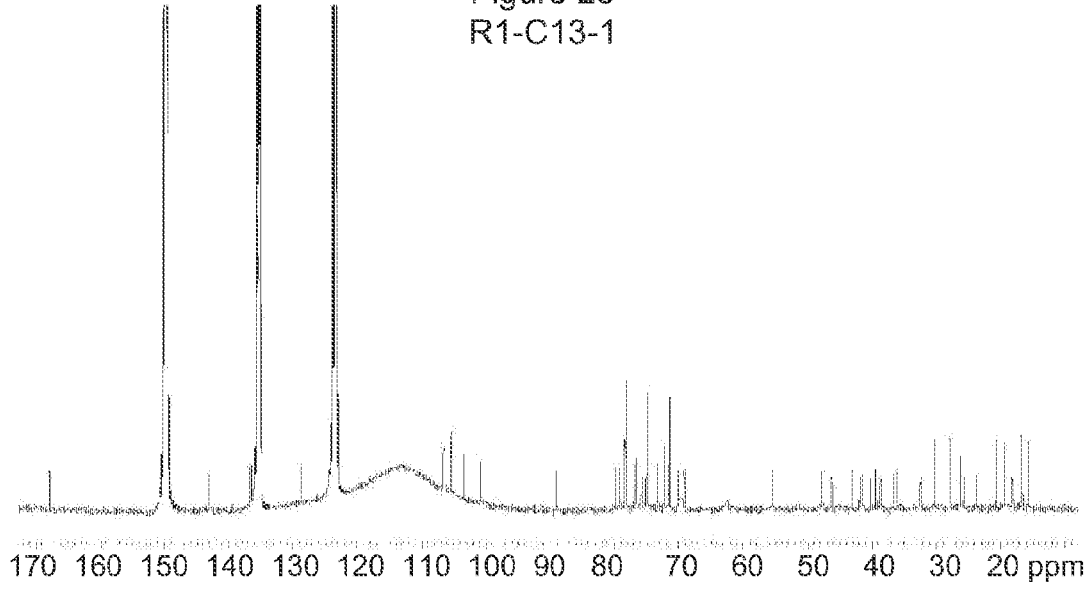

FIG. 25 shows the C13 NMR spectra of compound R1.

Figure 26:
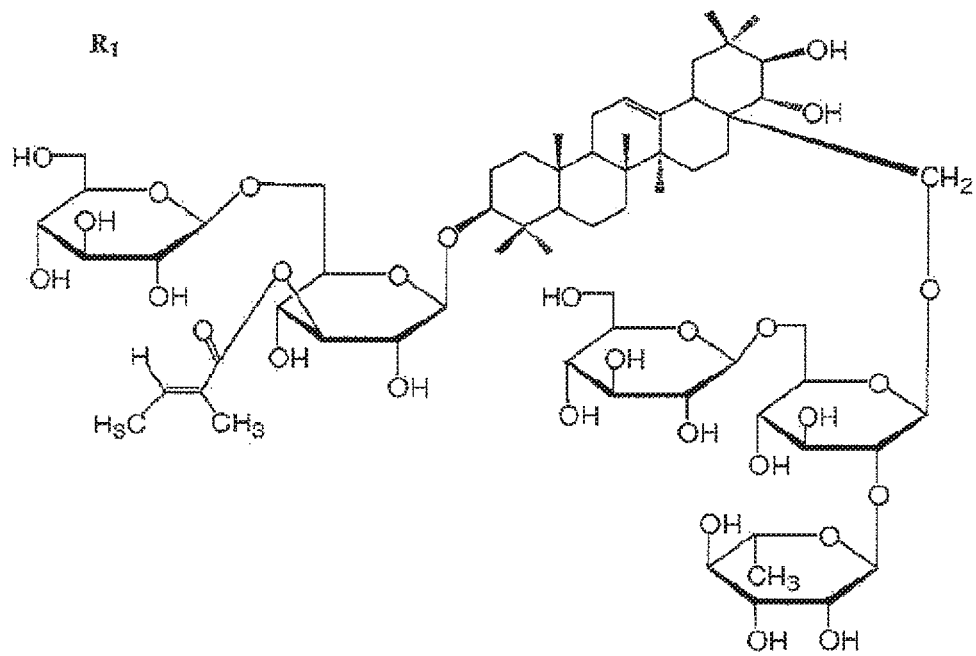
Figure 27:
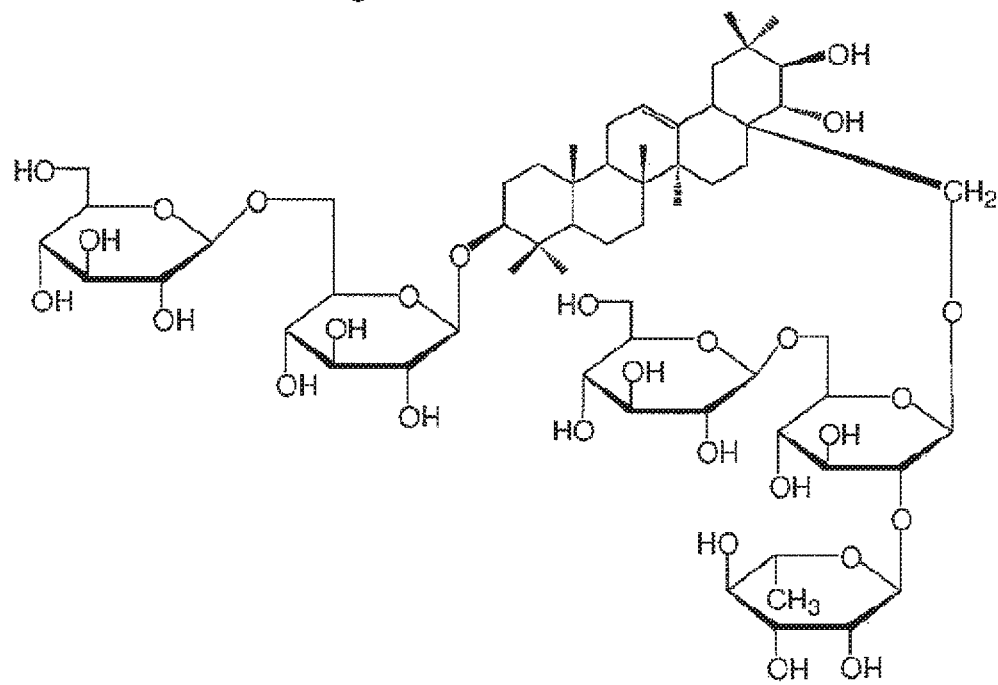

FIG. 26 shows the chemical structure of Compound R1: 3-O-[angeloyl-(1→3)-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β,21β,22α,28-tetrahydroxyolean-12-ene FIG. 27 shows the chemical structure of Compound O54.

Figure 28:
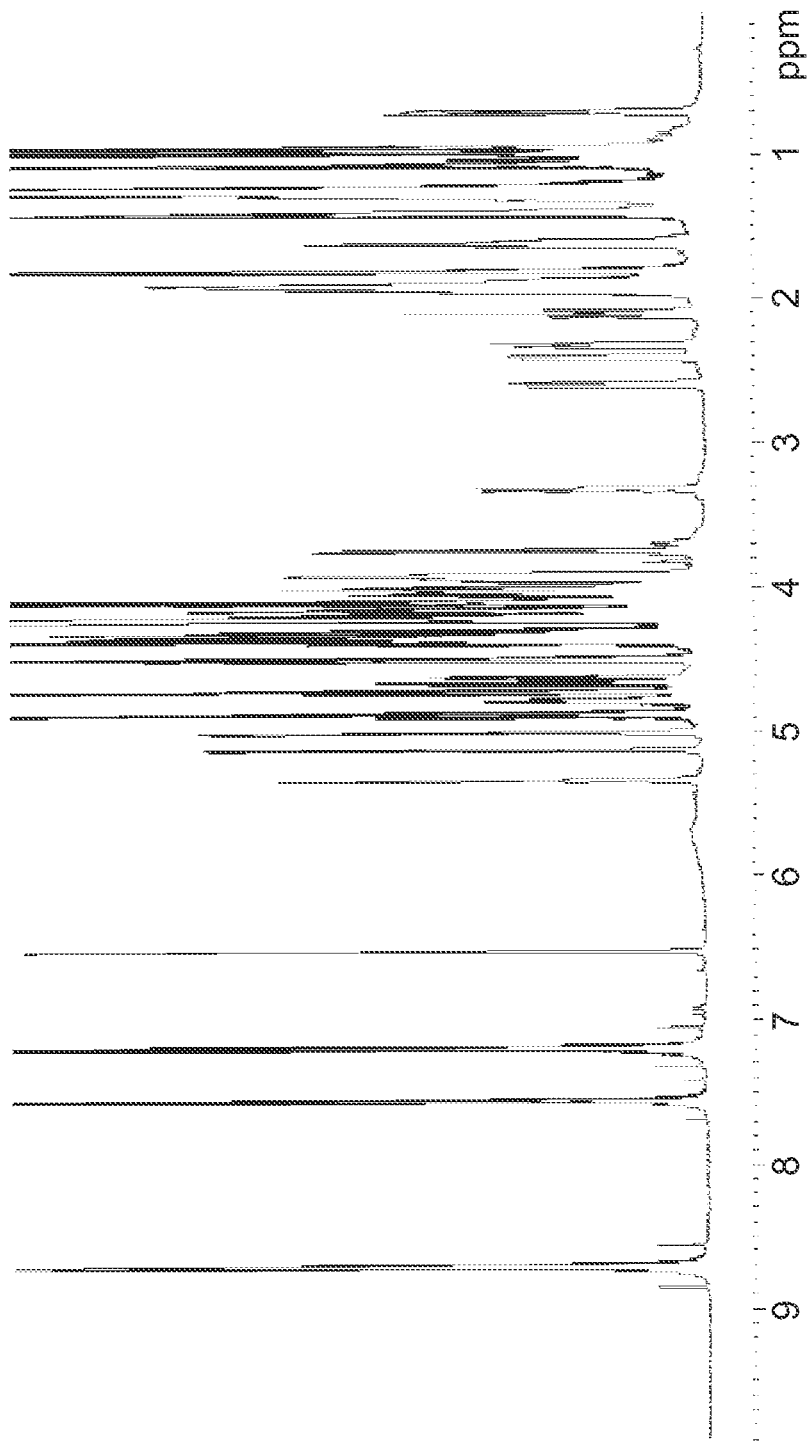

FIG. 28 shows the Proton-NMR spectra of compound O54.

Figure 29:
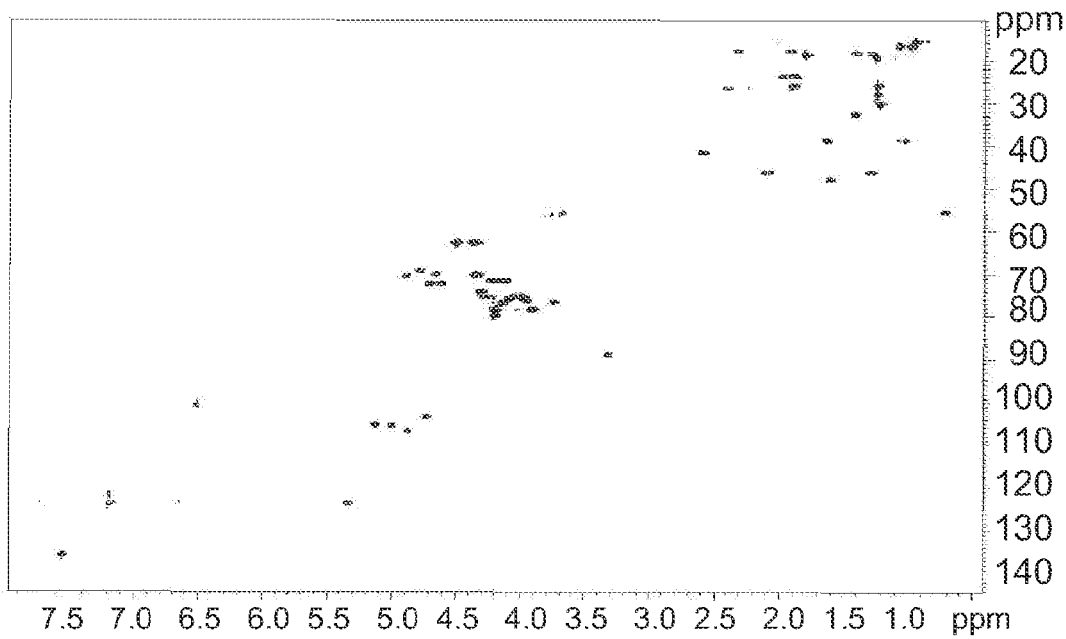

FIG. 29 shows the 2D NMR (HMQC) spectra of compound O54.

Figure 30:
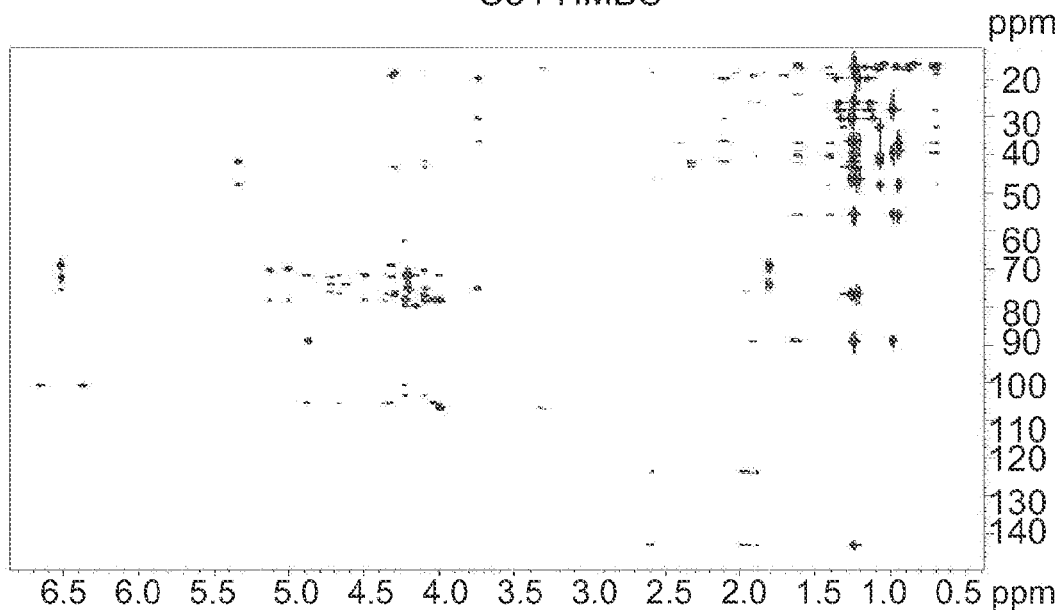

FIG. 30 shows the 2D NMR (HMBC) spectra of compound O54.

Figure 31:
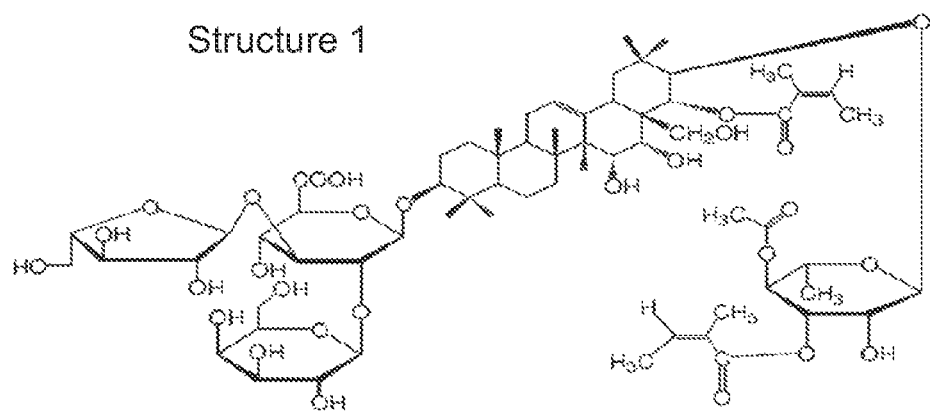

FIG. 31 shows one of the four possible chemical structures of Y1. A: structure Y1-1.

Figure 32:
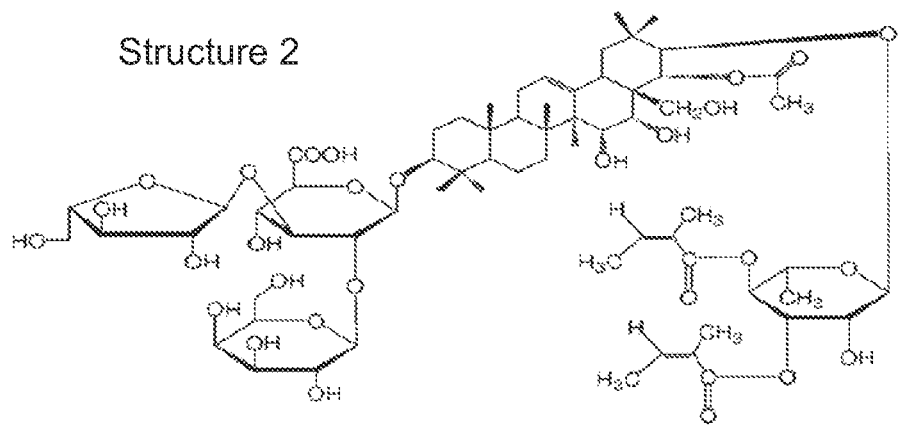

FIG. 32 shows one of the four possible chemical structures of Y1. B: structure Y1-2.

FIG. 33 shows one of the four possible chemical structures of Y1. C: structure Y1-3.

FIG. 34 shows one of the four possible chemical structures of Y1. D: structure Y1-4. R1=A or B or C; R2=A or B or C; R3=A or B or C.

|    | R1 | R2 | R3 |
|----|----|----|----|
| 1  | A  | A  | A  |
| 2  | A  | A  | B  |
| 3  | A  | A  | C  |
| 4  | A  | B  | A  |
| 5  | A  | B  | B  |
| 6  | A  | B  | C  |
| 7  | A  | C  | A  |
| 8  | A  | C  | B  |
| 9  | A  | C  | C  |
| 10 | B  | A  | A  |
| 11 | B  | A  | B  |
| 12 | B  | A  | C  |
| 13 | B  | B  | A  |
| 14 | B  | B  | B  |
| 15 | B  | B  | C  |
| 16 | B  | C  | A  |
| 17 | B  | C  | B  |
| 18 | B  | C  | C  |
| 19 | C  | A  | A  |
| 20 | C  | A  | B  |
| 21 | C  | A  | C  |
| 22 | C  | B  | A  |
| 23 | C  | B  | B  |
| 24 | C  | B  | C  |
| 25 | C  | C  | A  |
| 26 | C  | C  | B  |
| 27 | C  | C  | C  |

Figure 35:
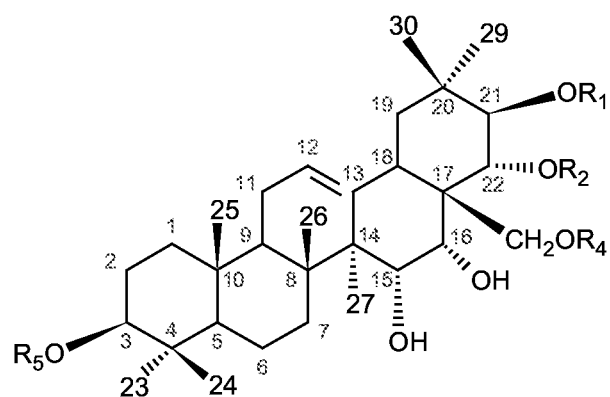

FIG. 35 shows the chemical structure of Y-a.
R5=B or C or S1 (see note 1); R1=A or B or C; R4=B or C; Note 1: A=angeloy, B=acetyl, C=H, S1=chain with one or more sugar such as D-glucose, D-galactose, L-rhamnose, L-arabinose, D-xylose, and alduronic acid such as D-glucuronic acid, D-galacturonic acid and their derivatives.

Figure 36:
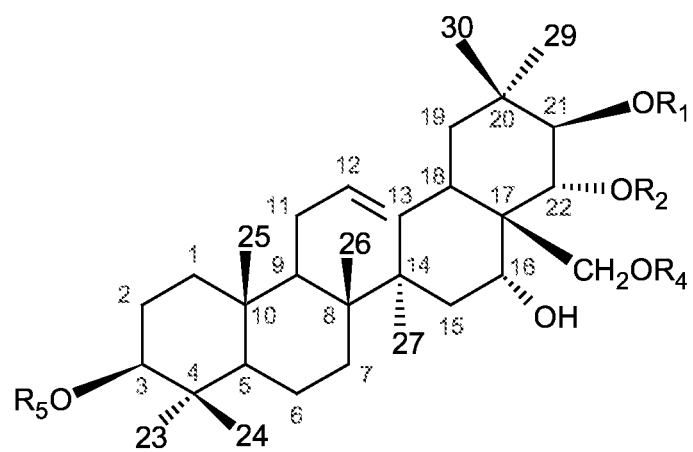

FIG. 36 shows the chemical structure of Y-b.
R5=B or C or S1 (see note 1); R1=A or B or C; R4=B or C; Note 1: A=angeloy, B=acetyl, C=H, S1=chain with one or more sugar such as D-glucose, D-galactose, L-rhamnose, L-arabinose, D-xylose, and alduronic acid such as D-glucuronic acid, D-galacturonic acid and their derivatives.

Figure 37:
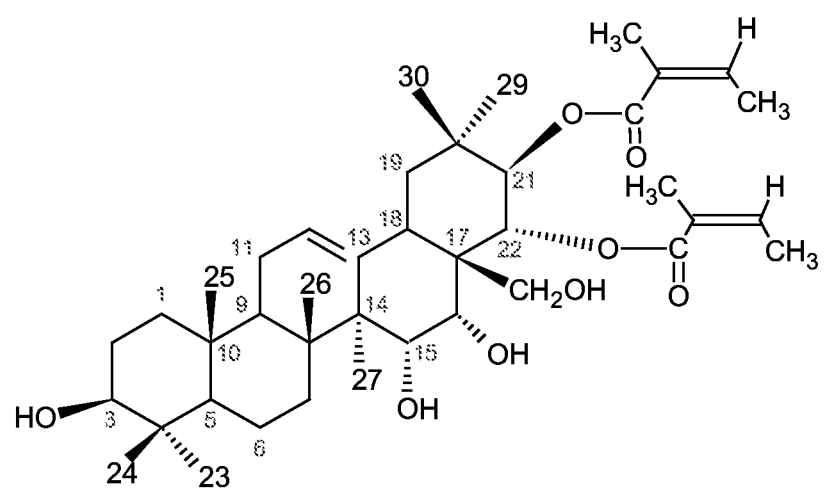

FIG. 37 shows the chemical structure of Y-c.

Figure 38:
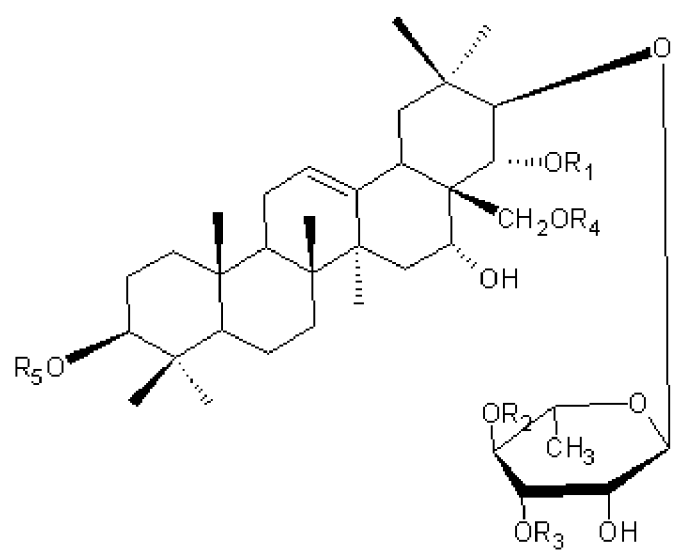

FIG. 38 shows the chemical structure of Y1-a.
R5=B or C or S1 (see note 1); R1=A or B or C; R4=B or C; Note 1: A=angeloy, B=acetyl, C=H, S1=chain with one or more sugar such as D-glucose, D-galactose, L-rhamnose, L-arabinose, D-xylose, and alduronic acid such as D-glucuronic acid, D-galacturonic acid and their derivatives.

Figure 39:
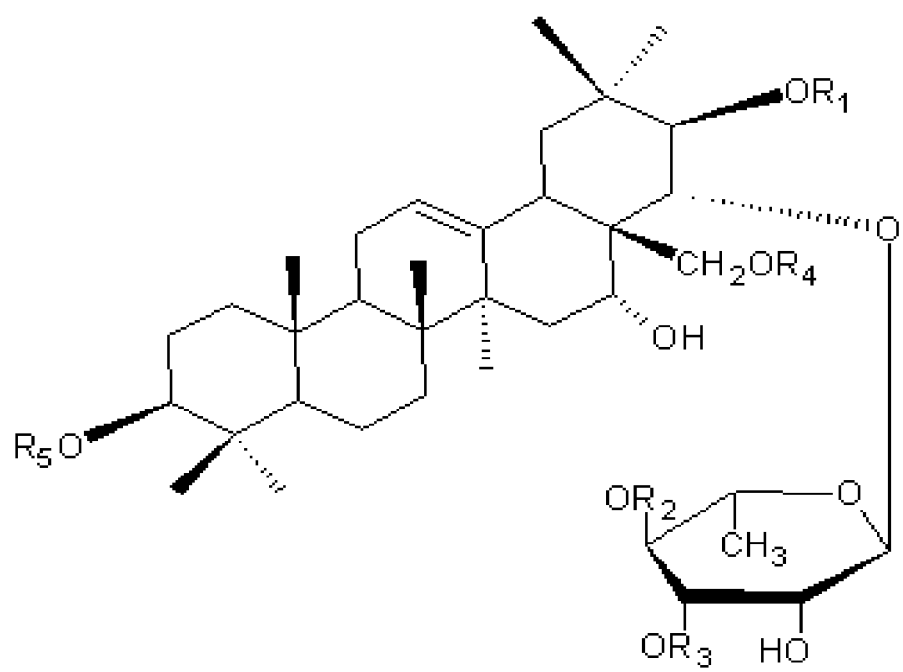

FIG. 39 shows the chemical structure of Y1-b.
R5=B or C or S1 (see note 1); R1=A or B or C; R4=B or C; Note 1: A=angeloy, B=acetyl, C=H, S1=chain with one or more sugar such as D-glucose, D-galactose, L-rhamnose, L-arabinose, D-xylose, and alduronic acid such as D-glucuronic acid, D-galacturonic acid and their derivatives.

Figure 40:
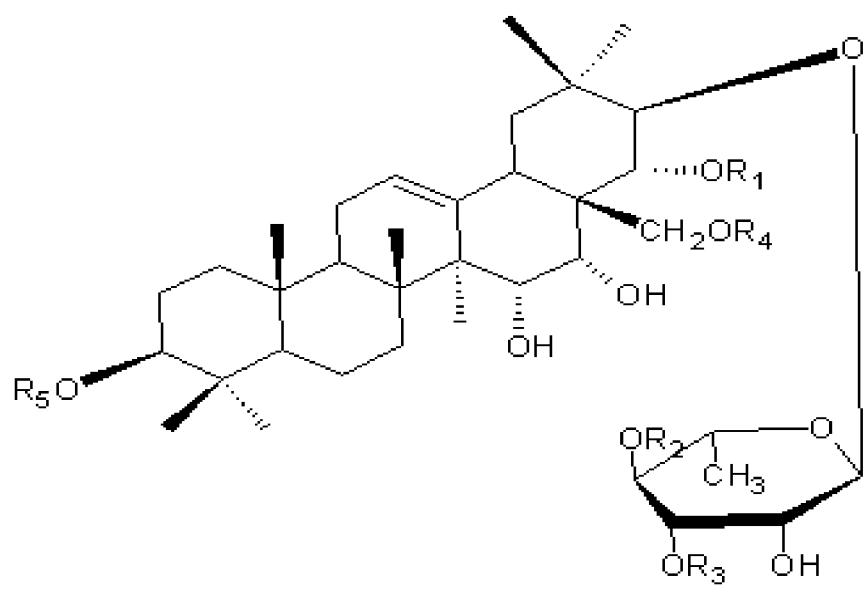

FIG. 40 shows the chemical structure of Y1-c.
R5=B or C or S1 (see note 1); R1=A or B or C; R4=B or C;

Note 1: A=angeloy, B=acetyl, C=H, S1=chain with one or more sugar such as D-glucose, D-galactose, L-rhamnose, L-arabinose, D-xylose, and alduronic acid such as D-glucuronic acid, D-galacturonic acid and their derivatives.

Figure 41:
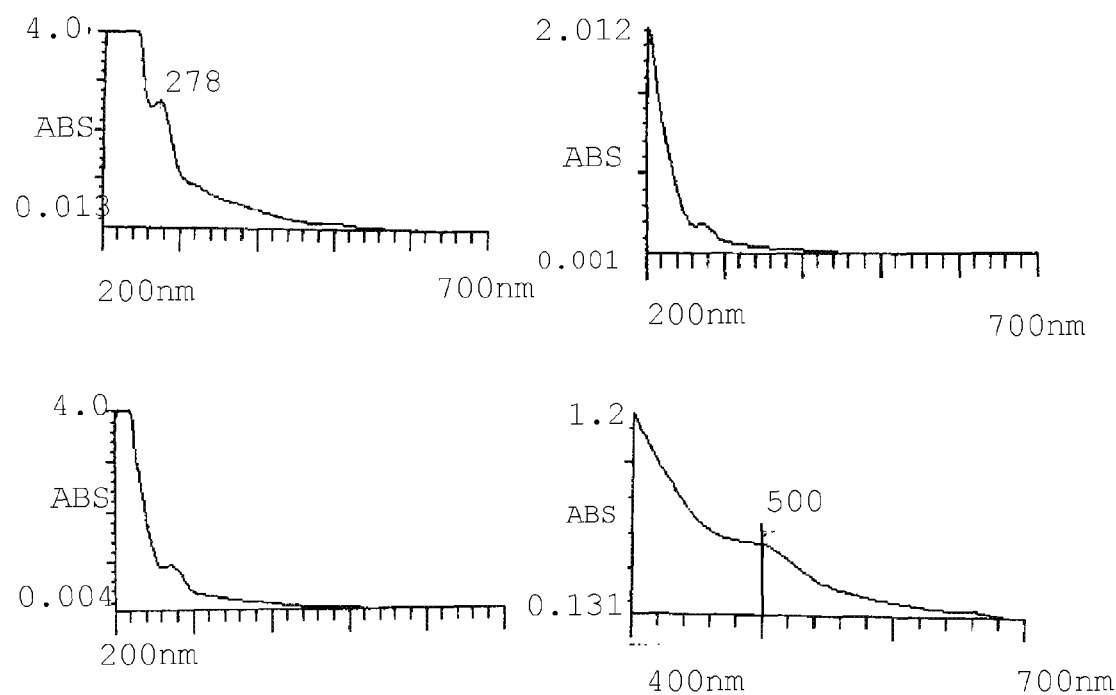

FIG. 41 shows the absorption spectrum of *Xanthoceras Sorbifolia* extract. Abscissa: Wavelength in nm. Ordinate: Optical Density. The extract has three absorption maximum at 207 nm, 278 nm and 500 nm.

Figure 42:
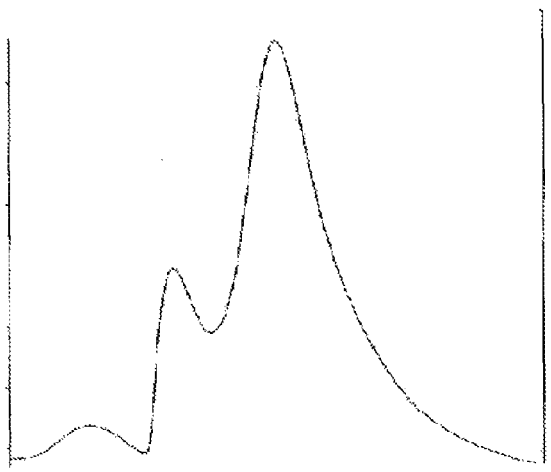

FIG. 42 shows elution profile of Fraction 5962 with 64% acetonitrile isocratic elution. Two major FPLC fractions X and Y are separated. Ordinate: optical density (254 nm). Abscissa: fraction Number (1 ml/fraction).

Figure 43:
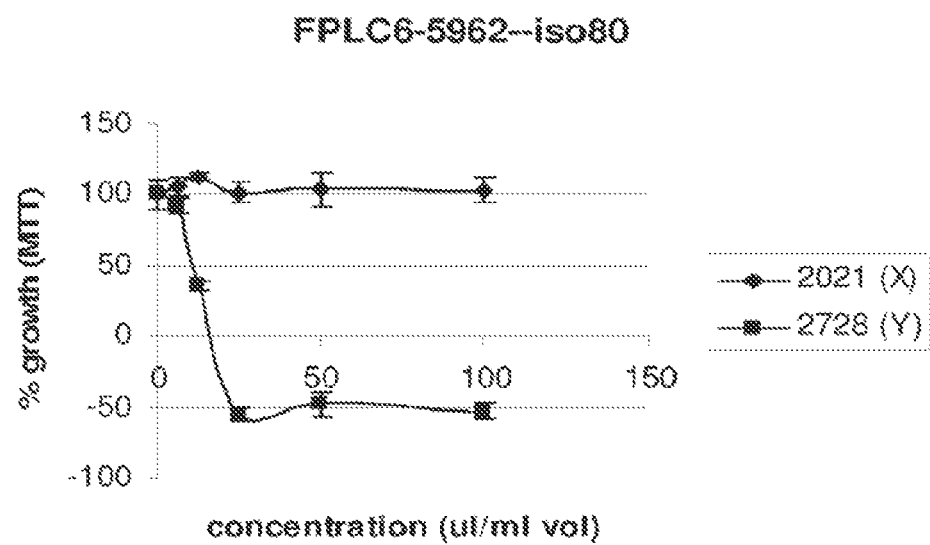

FIG. 43 shows the comparison of inhibition activity in bladder cells by Fractions X (2021) and Y (2728). Only Fraction Y has inhibition activity.

Figure 44:
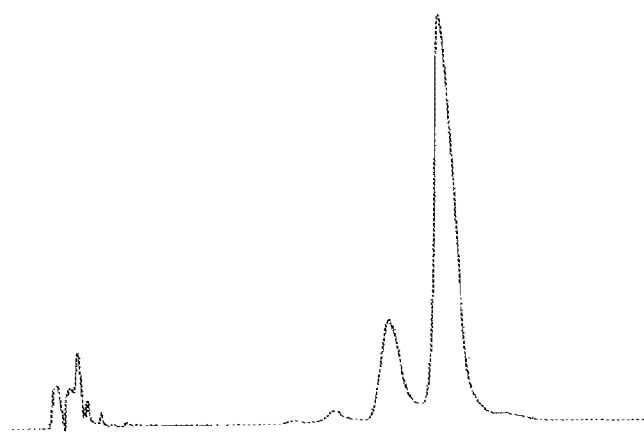

FIG. 44 shows HPLC profile of Fraction Y with 45% Acetonitrile isocratic elution. Two major and 2-3 minor compounds were identified.

Figure 45:
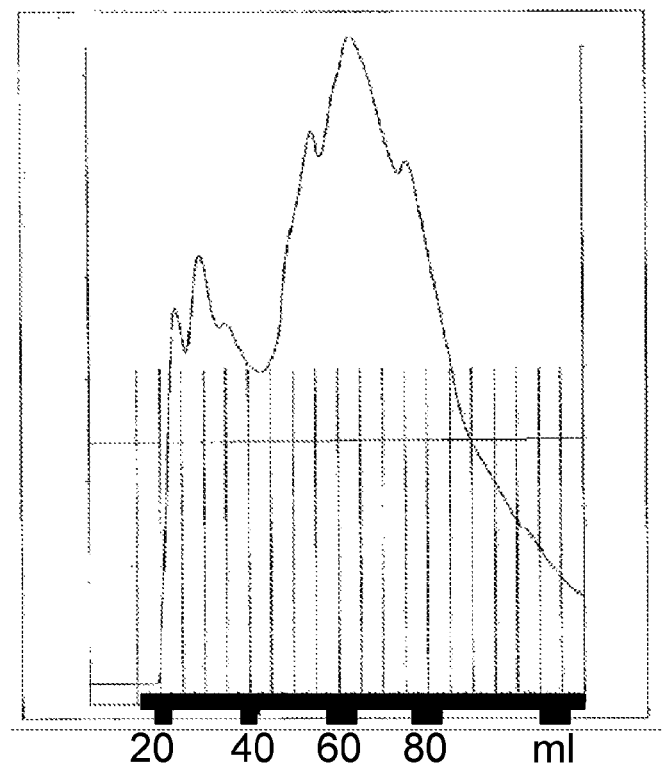

FIG. 45 shows purification of Fraction R from with FPLC.

Figure 46:
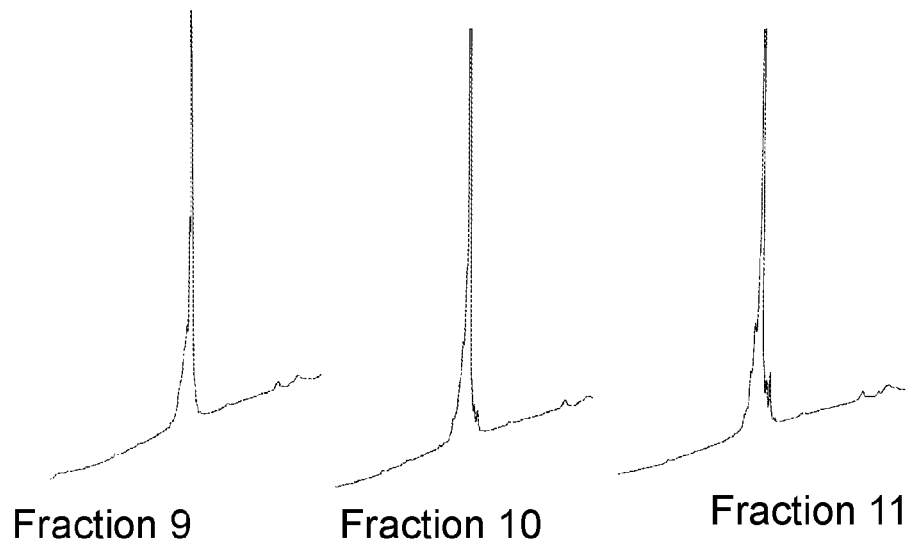

FIG. 46 shows the HPLC analysis of fractions #9, #10 and #11 obtained from FPLC.

Figure 47:
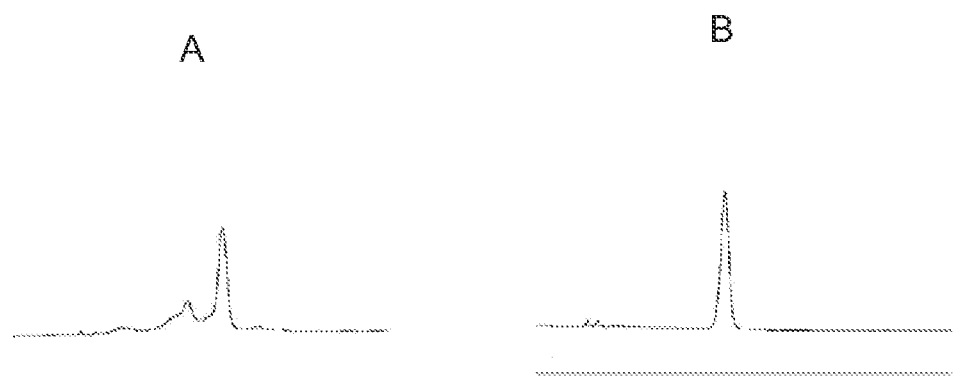

FIG. 47 shows purification of component-R with HPLC (Delta-Pak C18). A: Extract from fraction #10 of FPLC (iso-30) was further separated by HPLC. B: Rechromatogram of the major component under same condition as described in A.

Figure 48:
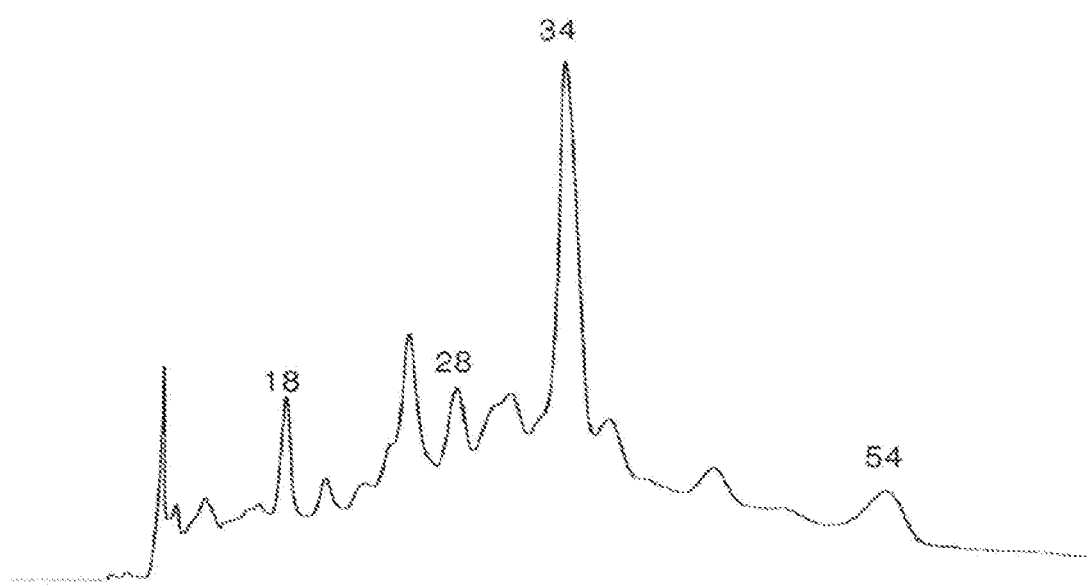

FIG. 48. Fractionation of Fraction-O from FPLC with HPLC with 20% acetonitrile isocratic elution (iso-20).

Figure 49:
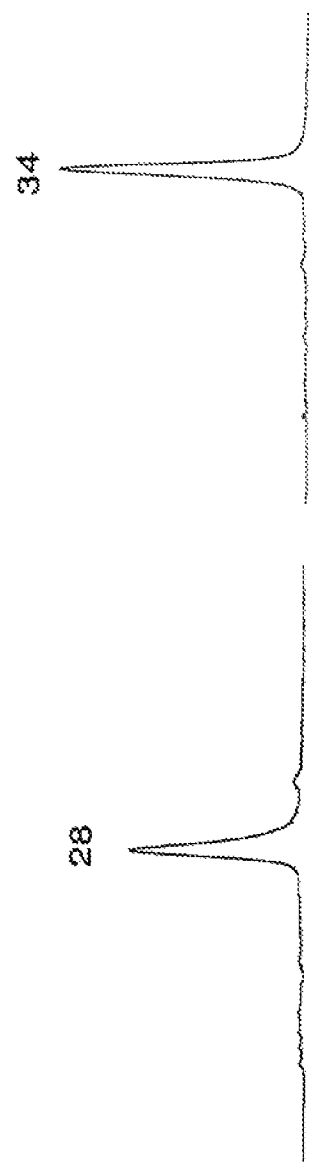

FIG. 49. Rechromatography of O28 and O34 (from iso-20).

FIG. 50. Rechromatography of O54 (from iso-20).

FIG. 51 shows the proton NMR spectrum of Y2.

Figure 52:
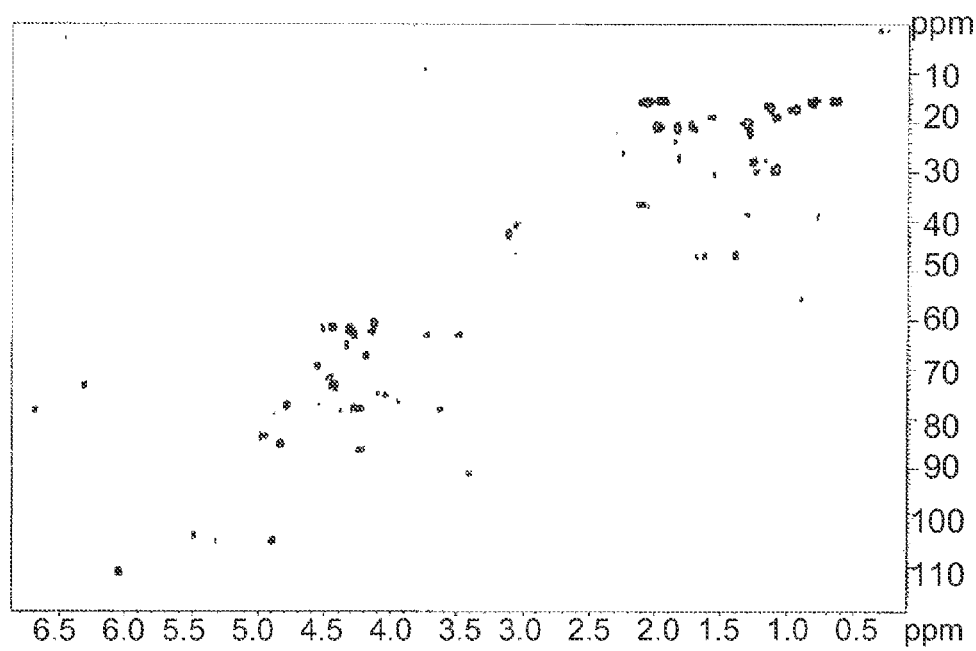

FIG. 52 shows the 2D NMR spectrum of Y2 (HMQC).

Figure 53:
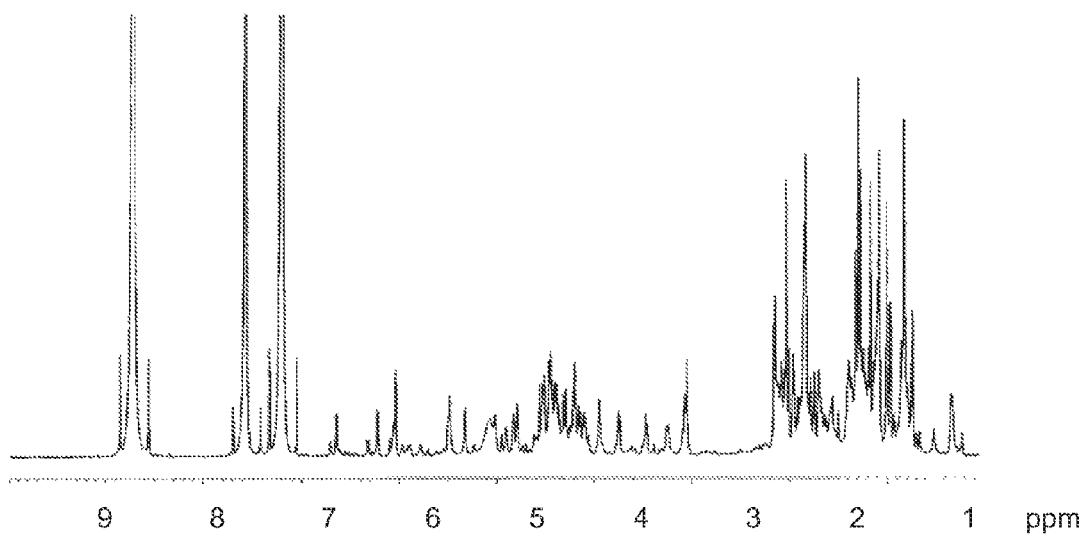

FIG. 53 shows the proton NMR spectrum of Y4.

Figure 54:
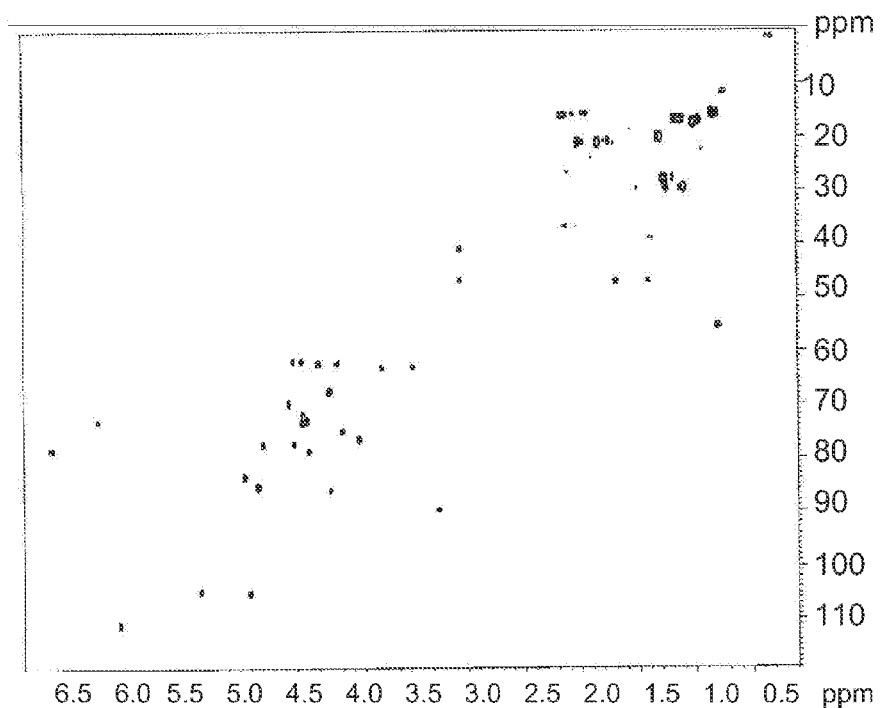

FIG. 54 shows the 2D NMR (HMQC) spectrum of Y4.

Figure 55:
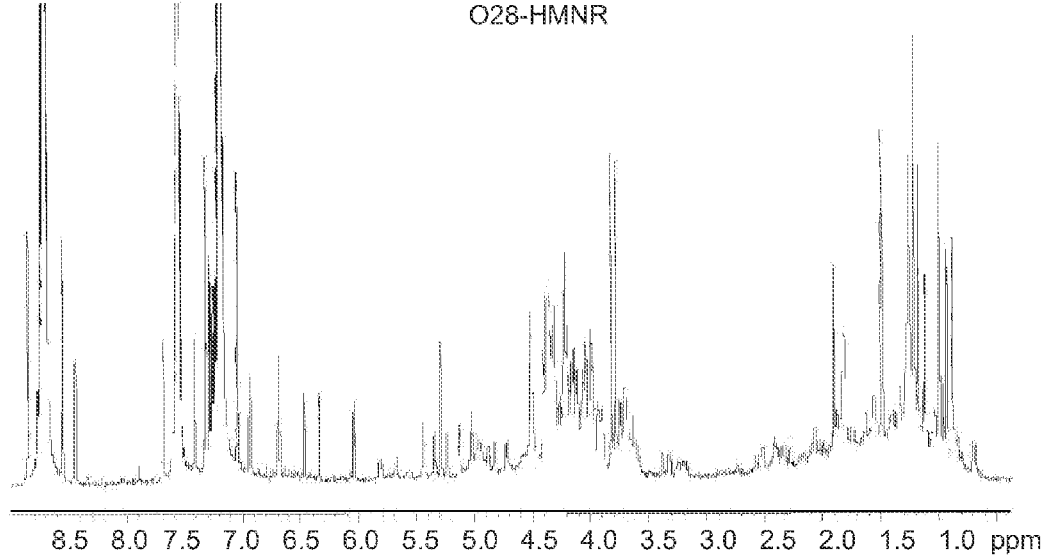

FIG. 55 shows the proton NMR spectrum of O28.

Figure 56:
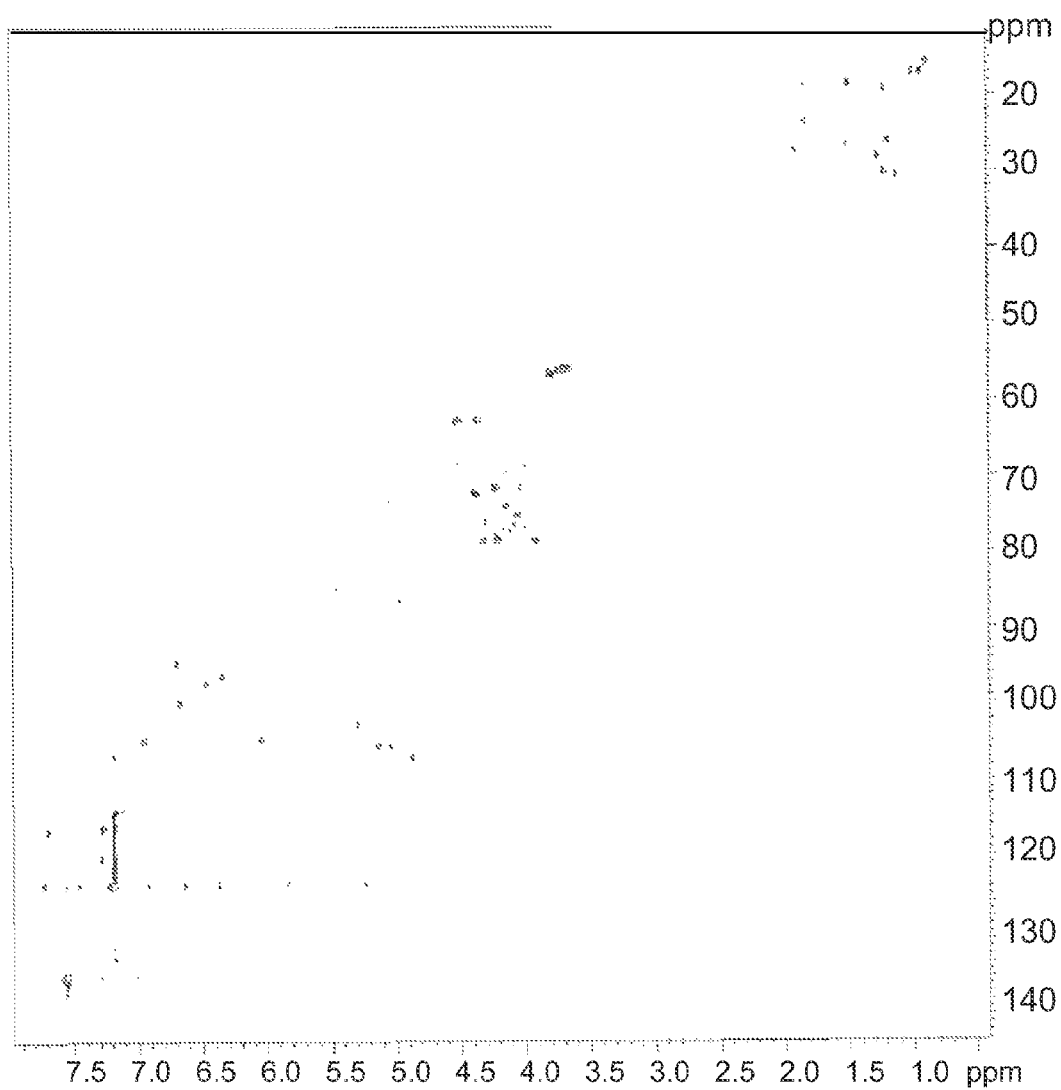

FIG. 56 shows the 2D NMR (HMQC).

Figure 57:
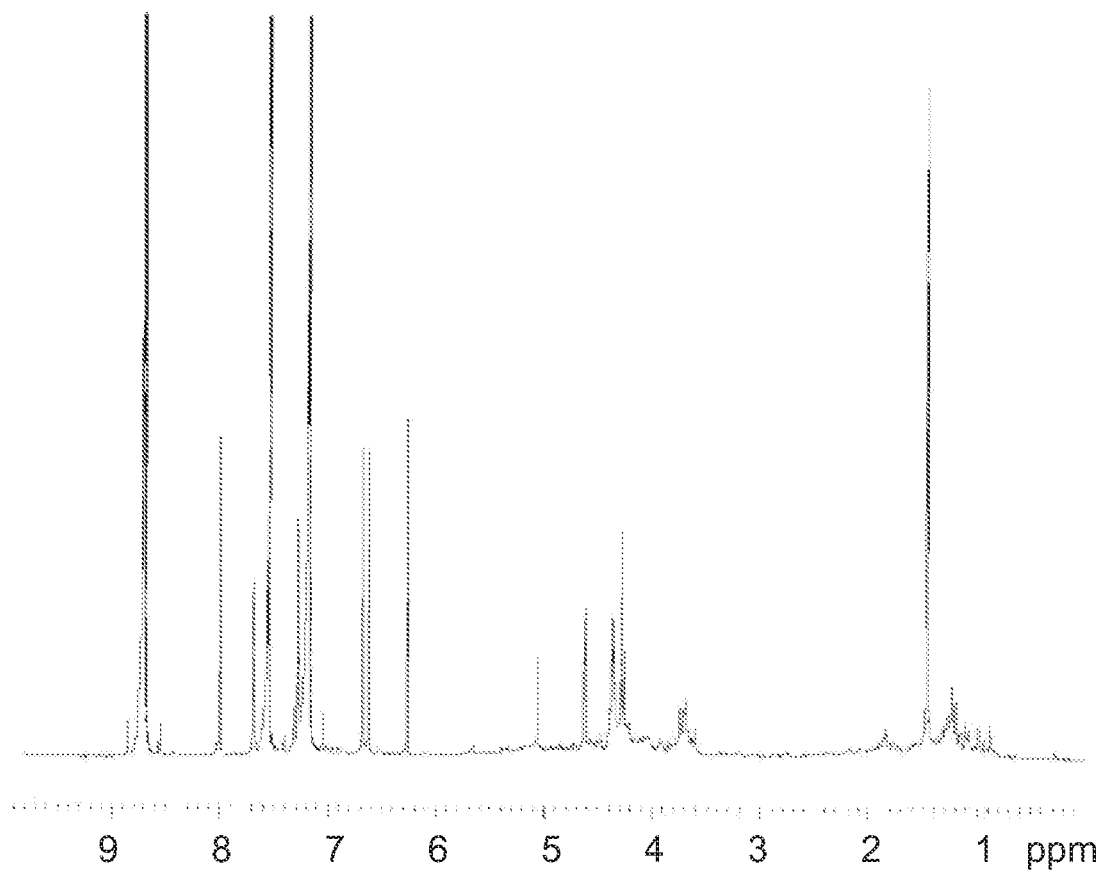

FIG. 57 shows the proton NMR spectrum of O34.

Figure 58:
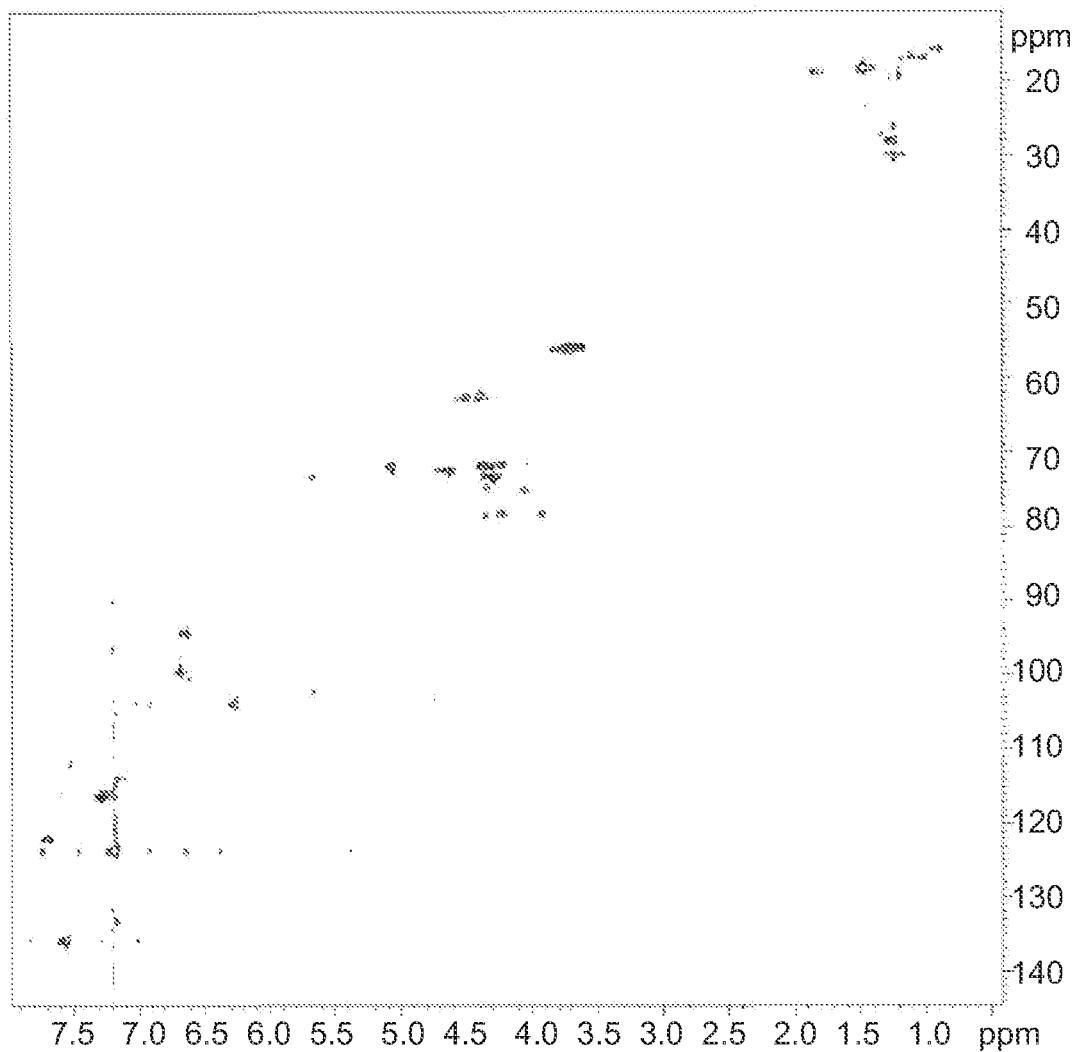

FIG. 58 shows the 2D NMR (HMQC) spectrum of O34.

Figure 59:
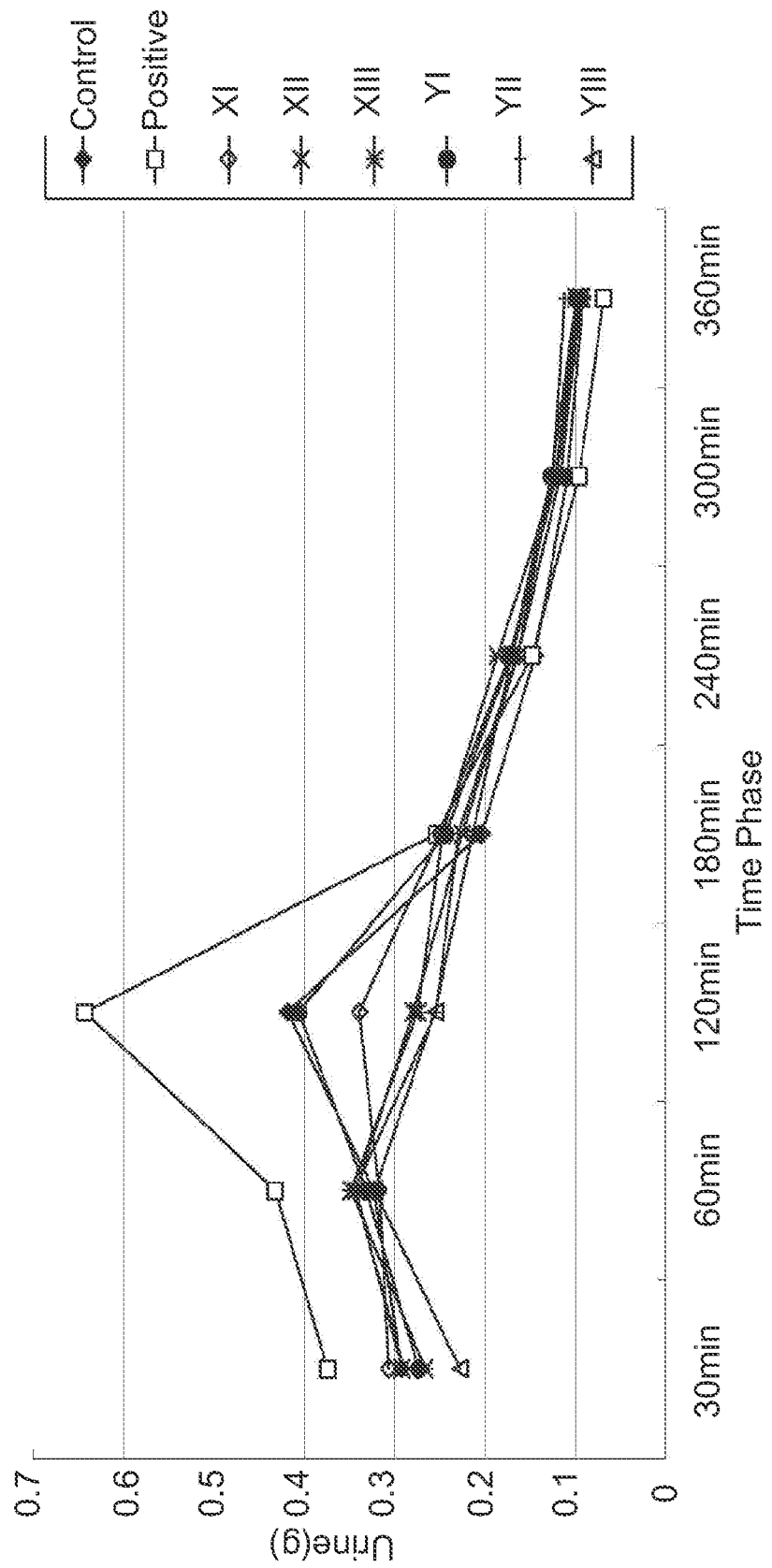

FIG. 59 shows the effects of the extract X and Y on the quantity of urine in mice after 10 days of administration of X and Y.

FIGS. 60(*a*) and (*b*) show the water maze learning effect of plant extract administration of aging mice for 9 days.

Figure 61A:
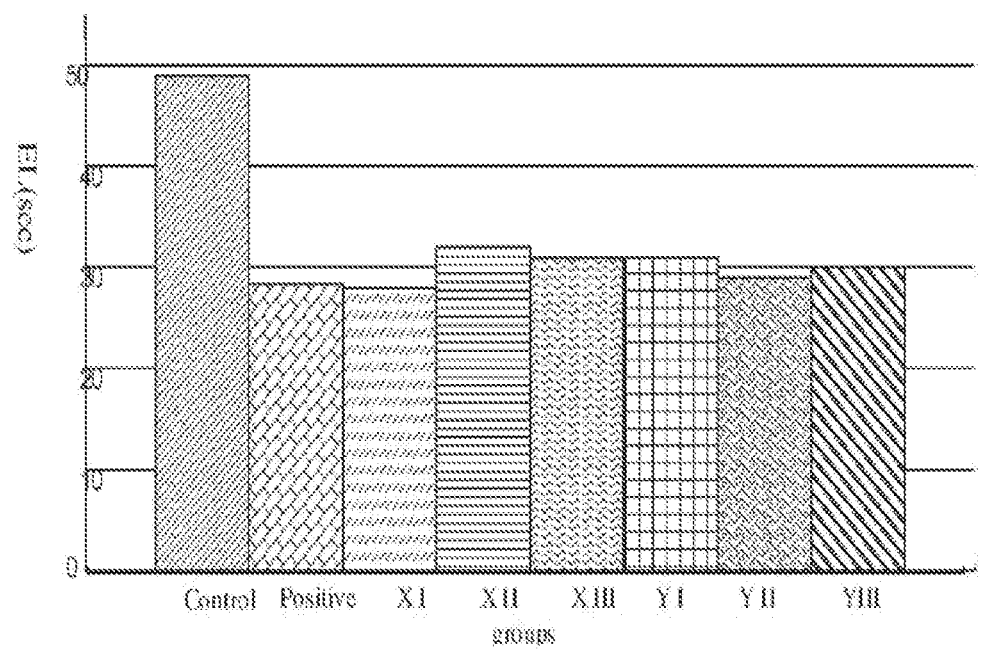
Figure 61B:
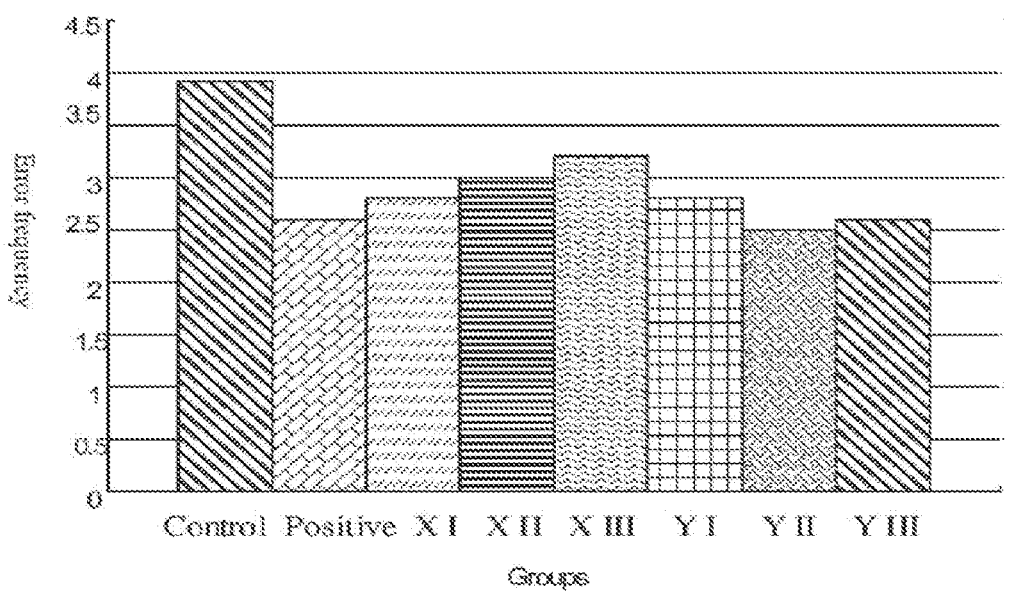

FIGS. 61(*a*) and (*b*) show the result of water maze learning of 3 days injected pentobarbital.

Figure 62:
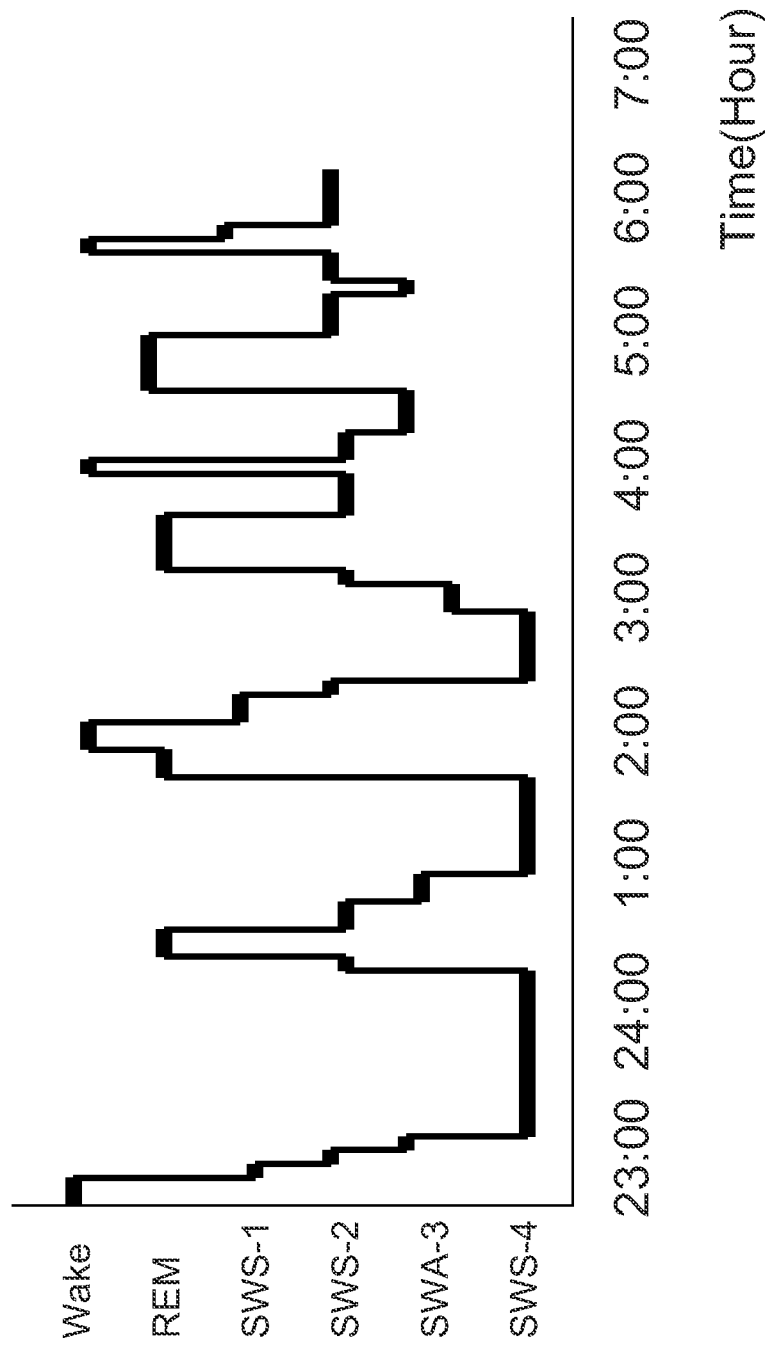

FIG. 62 shows the sleep cycle of a typical person.

FIG. 63. Table 15A-1 shows results of urine volume with water load after administration extract for 25 days. FIG. 63A shows the urine volume with water load after administration of FS(X) and FS(Y) extract for 25 days.

Figure 64A:
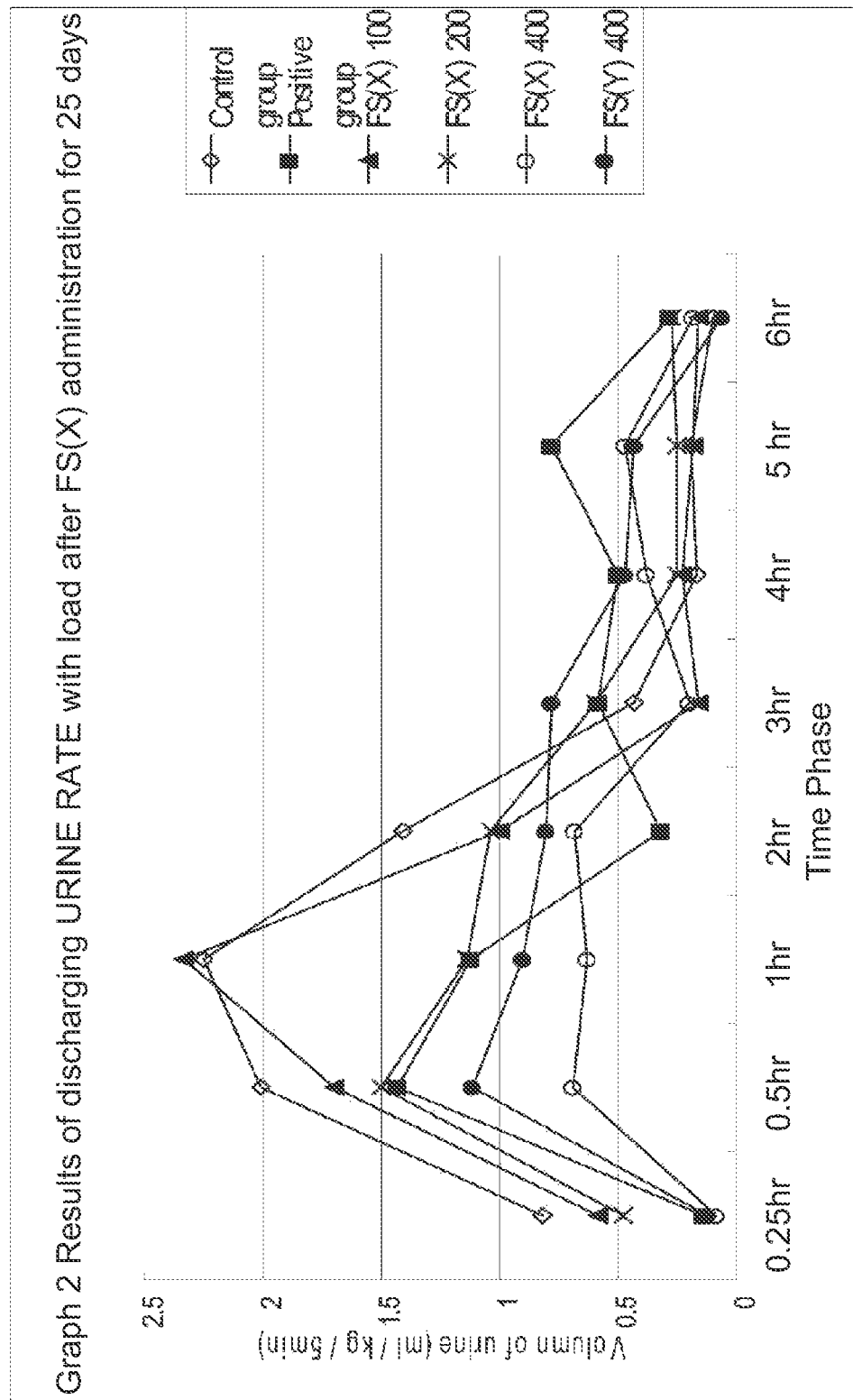

FIG. 64. Table 15A-2 shows results of discharging urine speed with water load after administration extract for 25 days. FIG. 64A shows the discharging urine speed with water load after administration of FS(X) and FS(Y) extract for 25 days.

FIG. 65. Table 15A-3 shows results of urine specific gravity and pH with water load after administration extract for 25 days.

FIG. 66. Table 15A-4 shows concentration of Na+, K+ and Cl− in urine with water load after administration extract for 25 days.

Figure 67:
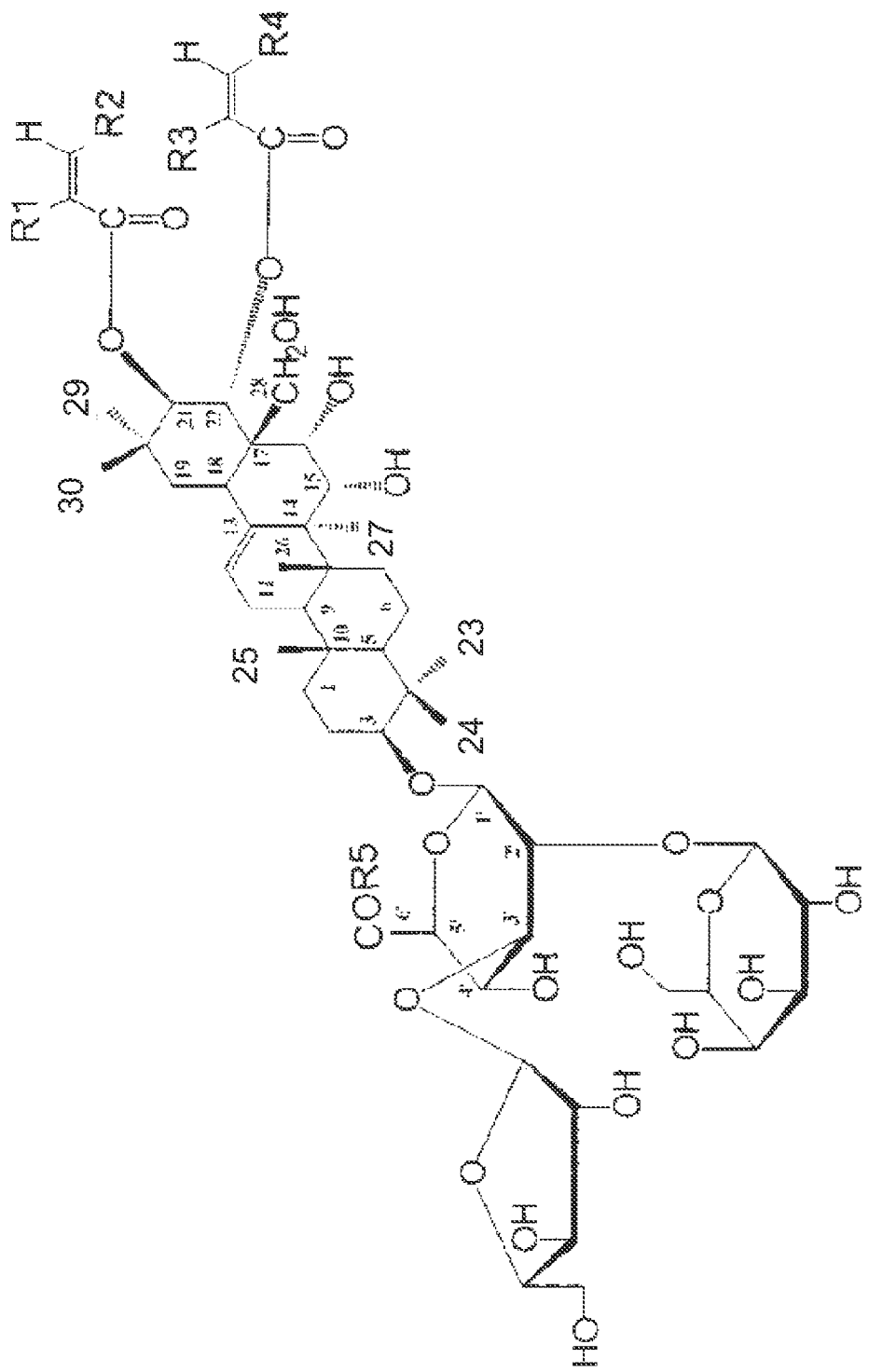
Figure 68:
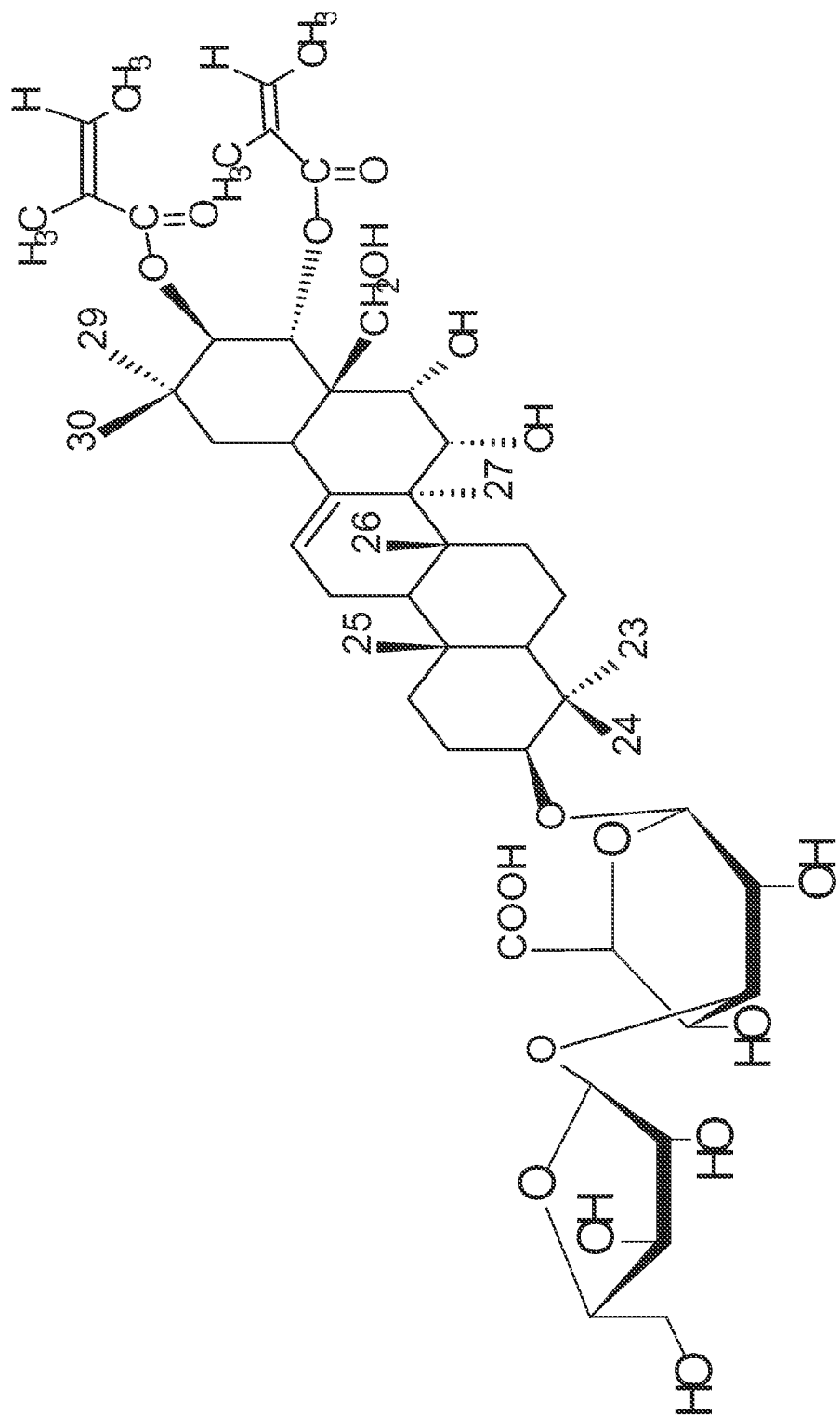
Figure 69:
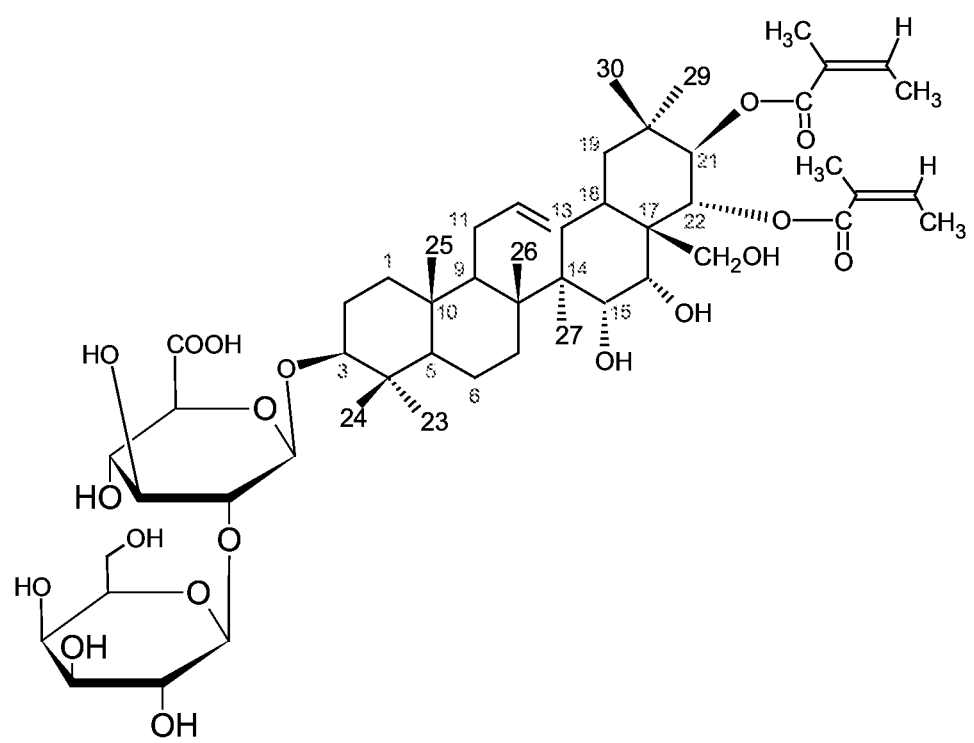
Figure 70:
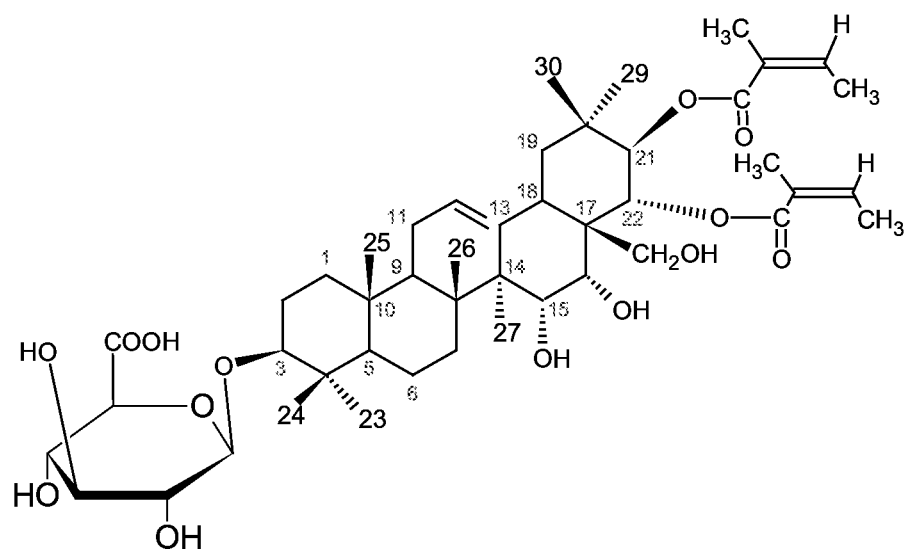
Figure 71:
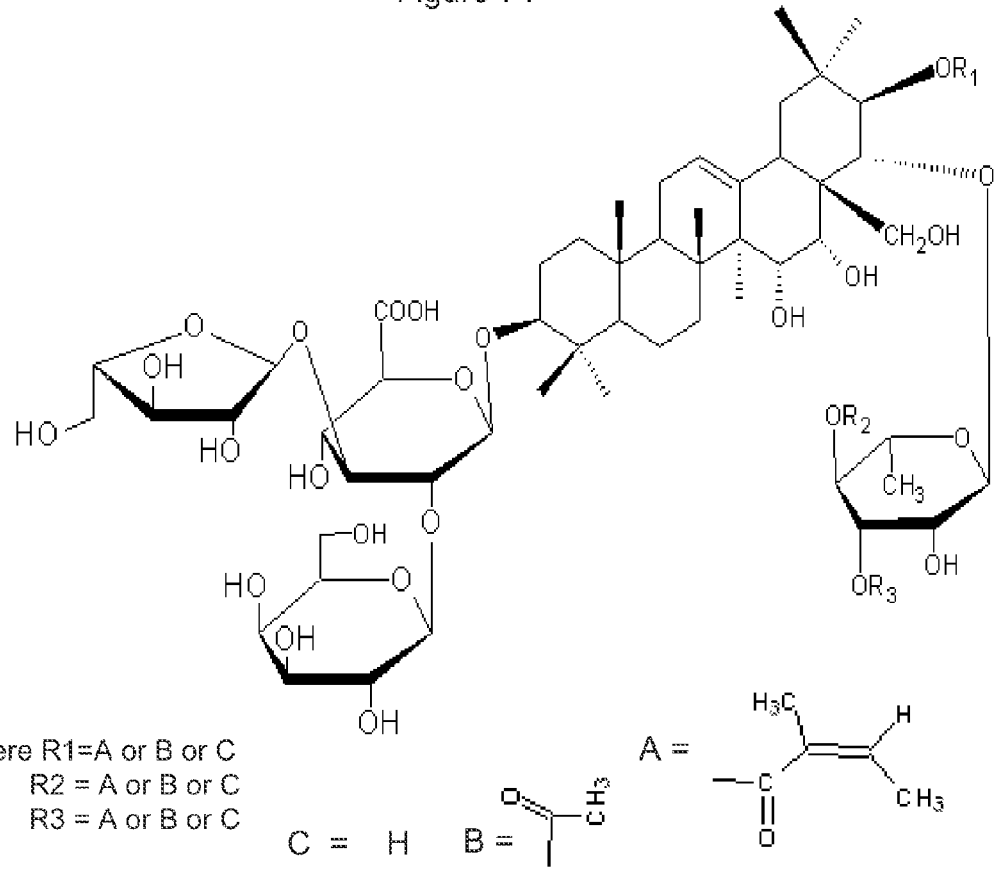

FIG. 67 shows the structure of the compound.
FIG. 68 shows the structure of the compound.
FIG. 69 shows the structure of the compound.
FIG. 70 shows the structure of the compound.
FIG. 71 shows the structure of the compound.

DETAILED DESCRIPTION OF THE INVENTION

The invention provides a compound comprising the following structure, with the formula of $C_{57}H_{88}O_{23}$ and the name of 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene, also known as Xanifolia-Y This compound was isolated from *Xanthoceras sorbifolia*

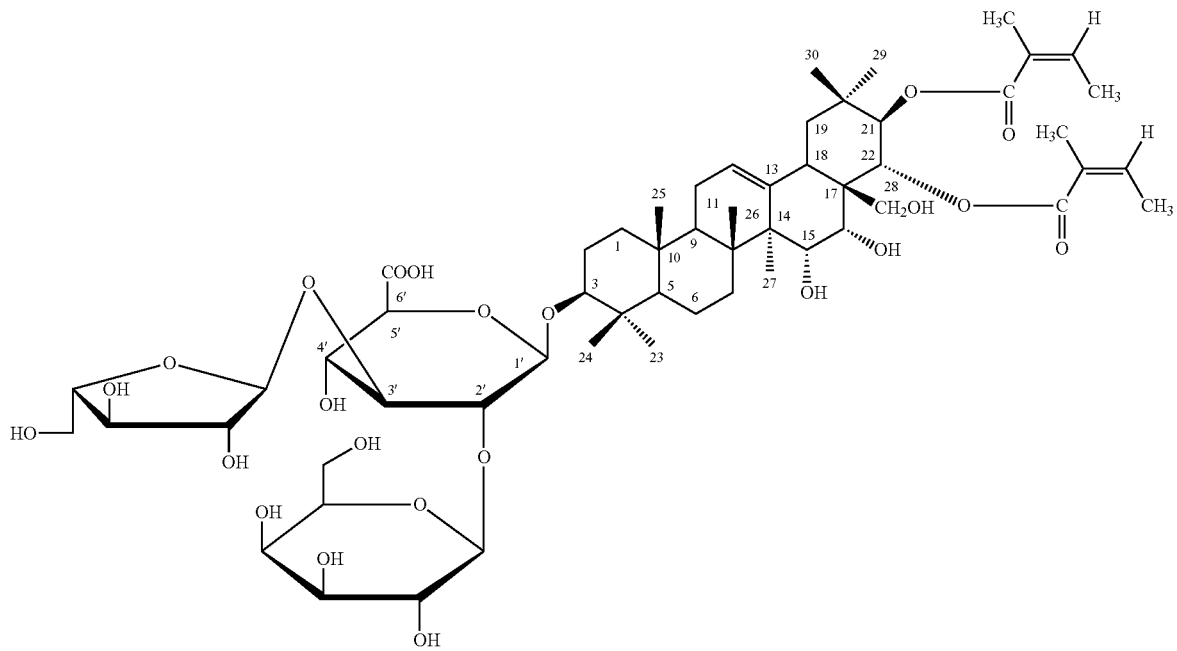

This compound belongs to saponins consist of a triterpene, sugar moiety and angeloyl groups links to the backbone. The angeloyl groups linked to the C21 and C22 positions. This compound has the anti-cancer activity.

The assignment of this structure is supported by the spectral data (1 D H-NMR, C-NMR, 2D NMR (HMBC, HMQC, COSY), and MS (MALDI-TOF, EMS). Accordingly, this compound has the characteristic property as shown in FIGS. 11-15 or Table 5.1.

This invention provides another compound comprising the following structure, with the formula of $C_{65}H_{100}O_{27}$ and the name of 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β,16α, 21β, 22α, 28-pentahydroxyolean-12-ene, also known as Xanifolia-Y1

TABLE 3.1

IC50 values of *Xanthoceras Sorbifolia* Extract Determined in Different Cancer Cells

| Cancer cells from different organs | IC50 determined by MTT assay (ug/ml) |
|---|---|
| Ovary (most sensitive) | 15-15 |
| Bladder (sensitive) | 45-50 |
| Bone | 40-55 |
| Prostate | 40-50 |
| Leukocyte | 45-50 |
| Liver (marginal sensitive) | 45-65 |
| Breast | 65 |
| Brain | 70-85 |
| Colon (least sensitive) | 90 |
| Cervix | 115 |
| Lung | 110 |

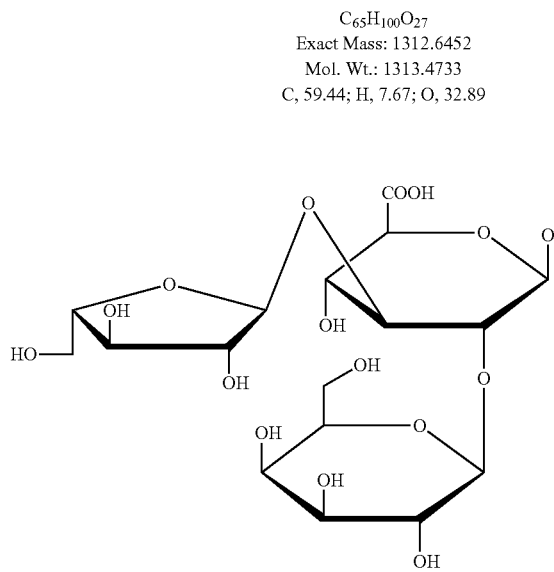

$C_{65}H_{100}O_{27}$
Exact Mass: 1312.6452
Mol. Wt.: 1313.4733
C, 59.44; H, 7.67; O, 32.89

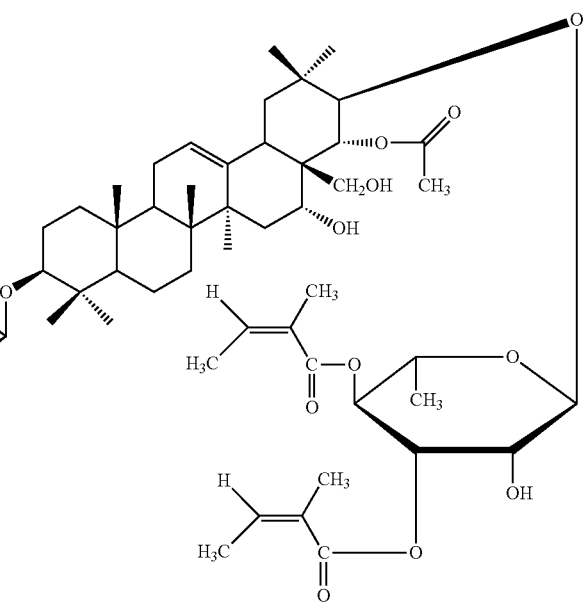

This compound belongs to saponins consist of a triterpene, sugar moiety connected to the backbone. A sugar that linked to the C21 position has two angeloyl groups attached. This compound has anti-cancer activity.

The assignment of this structure is supported by the spectral data (1 D H-NMR, C-NMR, 2D NMR (HMBC, HMQC, COSY), and MS (MALDI-TOF, EMS). Accordingly, this compound has the characteristic property as shown in FIGS. 16-19 or Table 6.1.

This invention provides evidence to show that the extract of *Xanthoceras Sorbifolia* contains anticancer activity. The experiments for determining the anti-cancer activity employed human cells lines derived from eleven human organs (HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain) and OVCAR-3 (ovary)). Among the 11 cell lines studies, their sensitivity toward *Xanthoceras Sorbifolia* extract can be divided into four groups: (A) most sensitive: Ovary (FIG. 8); (B) Sensitive: bladder, bone, prostate, and leukocyte, (C) marginal sensitive: liver, breast, and brain; and (D) lease sensitive: colon, cervix, and lung. (FIG. 10A-D). Their IC50 values are listed in Table 3.1.

In order to identify the active compounds of *Xanthoceras Sorbifolia*, the extract from *Xanthoceras Sorbifolia* were separated by chromatography comprising FPLC (Fast Protein Liquid Chromatography) and HPLC (High Preferment Liquid Chromatography). Multiple fractions were obtained by FPLC procedures (FIG. 20) and HPLC (FIG. 6).

Analysis of the components of *Xanthoceras Sorbifolia* by HPLC shows that the extract comprises 26 identifiable fractions (named a to z) as shown in FIG. 6.

Anti-cancer activities of these fractions were determined by the MTT assay. Only fraction Ys has the anti-cancer activity (FIG. 5). Fraction Ys were further separated into 4 components (FIG. 7). The compounds Y and Y1 are the active components currently isolated from *Xanthoceras Sorbifolia* as shown in FIG. 3-4.

The invention tested the inhibition effects of ovarian cancer cells with the MTT assay, and the compound Y shows 10 times higher potency (IC50=1.5 ug/ml) (FIG. 3) than the original crude extract as shown in FIG. 8 (IC50=25 ug/ml).

The selectivity of compound Y was tested, and it has been found that compound Y has a much higher potency toward ovarian cancer cells as compared to the cervical cancer cells (FIG. 9).

The compounds Y1 and Y2 have anti-cancer activity as shown in FIG. 4.

This invention provides the detail isolation procedures for the active compounds of the present invention.

This invention provides the spectral data evidence (1D H-NMR, C-NMR, 2D NMR (HMBC, HMQC, COSY), and MS (MALDI-TOF, ESI-MS) in supporting the assigned structures.

This invention provides a salt of the above-described compounds.

This invention provides a composition comprising the above-described compounds and a suitable carrier.

This invention provides a pharmaceutical composition comprising an effective amount of the above-described compounds and a pharmaceutically acceptable carrier.

This invention provides an anti-ovarian cancer agents and composition comprising the above-described composition.

This invention provides the compositions against cancer growth. The cancer includes, but is not limited to bladder cancer, bone cancer, and ovary cancer.

This invention provides a composition comprising the above compounds and their derivatives for inhibition of tumour growth.

The following methods and materials were used in the examples and/or experiments described in this application.
Cells.

Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain) and OVCAR-3 (ovary). Cells were grown in culture medium (HeLa-S3, DU145, MCF-7, Hep-G2 and T98G in MEN (Earle's salts); HTB-9, H460, K562, OVCAR-3 in RPMI-1640; HCT-116, U2OS in McCoy-5A) supplemented with 10% fetal calf serum, glutamine and antibiotics in a 5% CO2 humidified incubator at 37° C.
MTT Assay.

The procedure for MTT assay followed the method described in (Carmichael et al., 1987) with only minor modifications. Cells were seeded into a 96-wells plate at concentrations of 10,000/well (HTB-9, HeLa, H460, HCT116, T98G, OVCAR-3), 15,000/well (DU145, MCF-7, HepG2, U2OS), or 40,000/well (K562), for 24 hours before drug-treatment. Cells were then exposed to drugs for 48 hours (72 hours for HepG2, U2OS, and 96 hours for MCF-7). After the drug-treatment, MTT (0.5 mg/ml) was added to cultures for an hour. The formation of formazan (product of the reduction of tetrazolium by viable cells) was dissolved with DMSO and the O.D. at 490 nm was measured by an ELISA reader. The MTT level of cells before drug-treatment was also measured (T0). The % cell-growth (% G) is calculated as:

$$\% \ G = (TD-T0/TC-T0) \times 100 \qquad (1),$$

where TC or TD represent O.D. readings of control or drug-treated cells. When T0>TD, then the cytotoxicity (LC) expressed as % of the control is calculated as:

$$\% \ LC = (TD-T0/T0) \times 100 \qquad (2).$$

In addition to the compounds Y and Y1, other compounds from the extract including R1 and O54, were also purified and the structure were determined by 1D H-NMR, C13-NMR, 2D NMR (HMQC, HMBC, COSY); MS (MALDI-TOF).

The Structure of Compound R1 shown below and in FIG. 26, has a chemical formula of $C_{65}H_{106}O_{29}$ and chemical name of
3-O-[angeloyl-(1→3)-β-D-glucopyranosyl-(1→6)]-β-D-glucopyranosyl-28-O-[α-L-rhamnopyranosyl-(1→2)β-D-glucopyranosyl-(1→6)β-D-glucopyranosyl-3β, 21β, 22α, 28-tetrahydroxyolean-12-ene, also known as Xanifolia-R1.

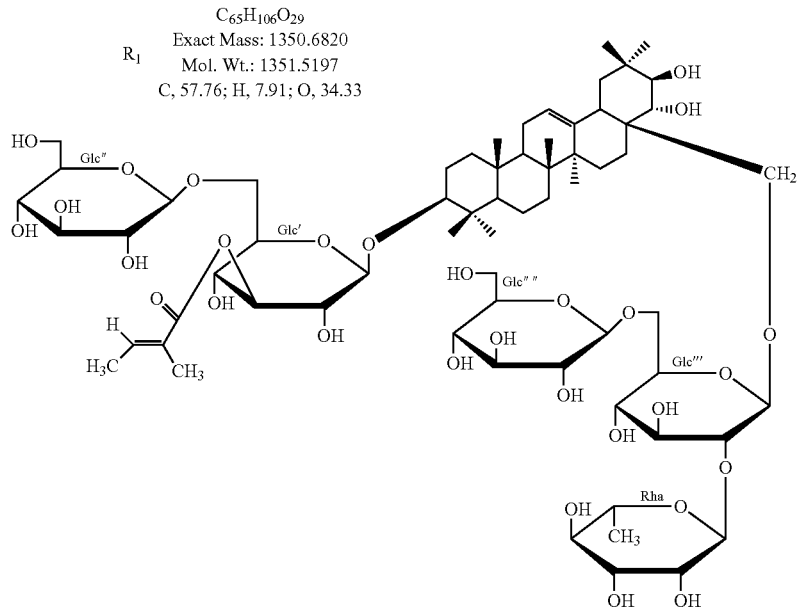

The assignment of this structure is supported by the spectral data (1 D H-NMR, C-NMR, 2D NMR (HMBC, HMQC, COSY), and MS (MALDI-TOF, EMS). Accordingly, this compound has the characteristic property as shown in FIGS. 21-25 or Table 8.1
Compound-O54

This invention provides a compound O54 with formula of $C_{60}H_{100}O_{28}$ and the structure was determined by 1D NMR, 2D NMR, MS).

The Structure of Compound O54 (also shown in FIG. 27):

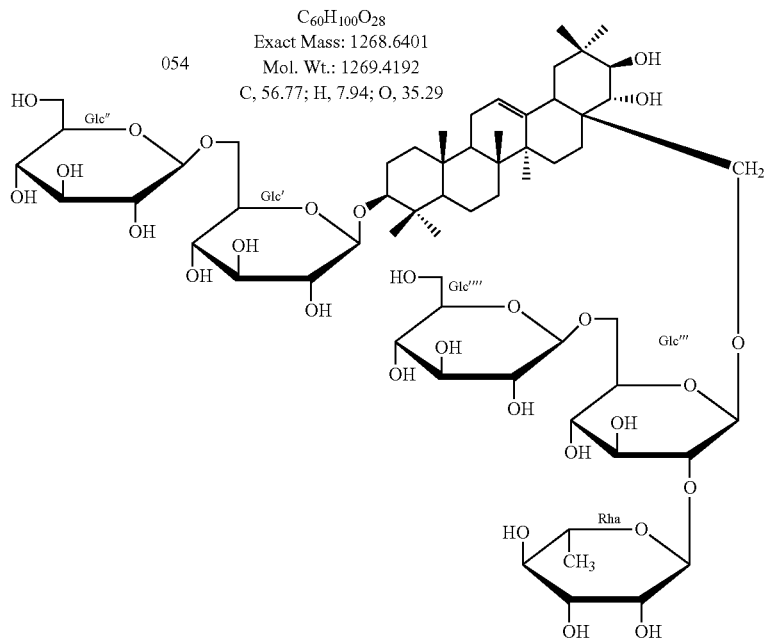

The name of Compound O54 is The chemical name of compound-O54 is: 3-O-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene The assignment of this structure is supported by the spectral data (1 D H-NMR, 2D NMR (HMBC, HMQC). Accordingly, this compound has the characteristic property as shown in FIGS. 28-30 and table 9.1.

In other embodiments, the structures of the compounds are as follows:
Structure 1 as shown in FIG. 31
Structure 2 as shown in FIG. 32
Structure 3 as shown in FIG. 33
Structure 4 as shown in FIG. 34
Structure Y-a as shown in FIG. 35
Structure Y-b as shown in FIG. 36
Structure Y-c as shown in FIG. 37
Structure Y1-a as shown in FIG. 38
Structure Y1-b as shown in FIG. 39
Structure Y1-c as shown in FIG. 40

This invention provides a compound comprising a sugar, a triterpene or Sapogenin, and a side chain at Carbon 21 and 22 or Angeloyl groups. In an embodiment, the compound comprises two or more sugars.

This invention provides a salt of the above-described compounds.

This invention provides a composition comprising the above-described compounds and a suitable carrier.

This invention provides a pharmaceutical composition comprising an effective amount of the above-described compounds and a pharmaceutically acceptable carrier.

This invention provides an anti-ovarian cancer agents and composition comprising the above-described composition.

This invention provides the compositions against cancer growth. The cancer includes, but is not limited to bladder cancer, bone cancer, and ovary cancer.

This invention provides composition comprising the above compounds and their derivatives to inhibit tumour growth.

This invention provides composition comprising the above compounds and their derivatives to cure human immunodeficiency virus (HIV) or Severe Acute Respiratory Syndrome (SARS) or flux disease or inhibit virus activities.

This invention provides medicine or health food for improving the sensory stretch receptor in the bladder wall, inhibiting AChE or use as an anti-inflammatory agent.

This invention provides a method for preventing cerebral aging, improving memory, improving cerebral functions and curing enuresis, frequent micturition, urinary incontinence, dementia, weak intelligence and Alzheimer's disease, autism, brain trauma, Parkinson's disease and other diseases caused by cerebral dysfunctions, and treating arthritis, rheumatism, poor circulation, arteriosclerosis, Raynaud's syndrome, angina pectoris, cardiac disorder, coronary heart disease, headache, dizziness, kidney disorder and treating impotence and premature ejaculation.

This invention provide methods for inhibiting tumor cell growth or to treat patients with HIV or SARS, or inhibit virus activities, or for preventing cerebral aging, improving memory, improving cerebral functions and curing enuresis, frequent micturition, urinary incontinence, dementia, weak intelligence and Alzheimer's disease, autism, brain trauma, Parkinson's disease and other diseases caused by cerebral dysfunctions, and treating arthritis, rheumatism, poor circulation, arteriosclerosis, Raynaud's syndrome, angina pectoris, cardiac disorder, coronary heart disease, headache, dizziness, kidney disorder and treating impotence and premature ejaculation. comprising contacting an amount of the compound is a triterpene or sapongenin with any two of angeloyl group or tigloyl group or senecioyl group or their combinations attach to carbon 21 and 22, or any two of angeloyl group or tigloyl group or senecioyl group or their combinations attached to a sugar moiety which bonds to carbon 21 or 22.

Wenguanguo is a species of the sapindaceae family. Its scientific name is *Xanthoceras sorbifolia* Bunge. Wenguanguo is the common Chinese name; others are Wenguannguo, Wenguanmu, Wenguanhua, and Xilacedeng. This plant can grow up to 8 meters in height. It features odd pinnately compound leaf, eraceme with white flowers, capsules with thick and woody husks. Wenguanguo is grown in Liaoning, Jilin, Hebei, Shandong, Jiangsu, Henan, Shanxi, Shaanxi, Gansu, Ningxia and Inner Mongolia, China. Its seeds are edible and have been used as a folk medicine to treat enuresis for centuries. Its branches and woods are also used as a folk medicine.

This invention is a further description of the extracts from Wenguanguo, their uses and methods for preparation. This invention provides the extracts that can prevent enuresis by improving patients' cerebral functions so that patients can be more aware of the signals sent from the bladder and wake up from deep sleep. When the bladder is full of urine, the smooth muscle of the bladder is extended, which produces a signal up to the cerebral cortex and cerebellum through the pelvic nerve and the sacral spinal cord. The response of the cerebral cortex and cerebellum to the signal is to make the bladder sustain contracted but the sphincter relaxed. The urine is then discharged. When the bladder is filled with urine via the urethra during sleep, the detrusor stretches, allowing the bladder to expand. As the bladder starts to accumulate urine, it will stimulate the stretch receptors in the bladder that will generate signals continually to the brain according to the amount of urine accumulated in the bladder. When the bladder is full enough with urine, then the intra-vesicle has accumulated enough pressure for the brain to recognize and wake the person to urinate. If the signal is not strong enough to wake the sleeping person or blocked due to impairment of cerebral function, then enuresis occurs. This particular plant extract can cure enuresis by improving cerebral functions.

The sensory stretch receptors are located within the bladder wall and help with assessing the degree of bladder fullness. This information is transmitted up to the spinal cord and then via the spinothalamic tracts to the central nervous system. The extracts of Wenguanguo make the central nervous system more aware of the signal.

When the bladder becomes contracted under stress and nervousness, the capacity of the urinary bladder will be reduced and then the frequent micturition occurs. The extracts of Wenguanguo can relax the bladder for storing more urine.

The capacity of the urinary bladder is reduced because of aging, and this may even happen to middle-aged people. They suffer from experience of early detrusor contraction due to a sense of urgency to empty the bladder at low urine level. The extracts of Wenguanguo can help relax the detrusor and therefore the bladder capacity increases and urinary frequency decreases.

Patients with detrusor overactivity, detrusor instability, detrusor hyper-reflexia or uninhibited bladder have early, forceful detrusor contractions before the bladder is full. This creates urgency and frequency urinary discharge. The extract of Wenguanguo relaxes the patient's detrusor. The bladder becomes stable and can store a full amount of urine.

The smooth muscle of the urinary bladder has two functions: When the bladder is relaxed, the urine is stored. When it is contracted, the urine will be discharged. The sensory stretch receptors are located within the bladder wall to assess the bladder's fullness. This information is transmitted up the spinal cord via the spinothalamic tracts to the nervous system. The brain generates inhibitory signals when detrusor relaxation is desired. But the brain generates excitatory signal when detrusor contraction is desired. The extracts of Wenguanguo can relax the bladder tissue by inhibiting Acetylcholinesterase, AchE. The inhibiting effect can be maintained for a long period of time. The extracts of Wenguanguo are a good AChE inhibitor that can cure the diseases caused by deficiency of Acetylcholine, ACh.

Antidiuretic hormone (ADH) is stored in the posterior pituitary gland in the brain. It is the primary regulator of body water. ADH acts on the kidneys to increase or decrease total body water. This has an effect on the volume of urine generated by the kidney. The release of ADH is controlled by the cells of osmoreceptors and baroreceptors. Osmoreceptors are the specialized cell hypothalamus. These cells sense the concentration of particles in the blood. When the concentration of particles is higher, more ADH will be released by the pituitary. This stimulates retention of water to dilute body fluids. When the concentration is lower, less ADH will be released by the pituitary. Baroreceptors are located in the right atria and great veins and carotid sinus the specialized area in the heart that sense blood volume and blood pressure. The heart will generate signals to the hypothalamus and pituitary to release more ADH when blood volume or blood pressure is low and vice versa. The extracts of Wenguanguo can regulate the release of ADH which will reduce the volume of urine produced by the body.

This invention relates to the flavone extracts from Wenguanguo husks and fruit-stems, and methods of their preparation. The methods for preparing the extracts from Wenguanguo husks and fruit-stems comprise the following steps: extracting Wenguanguo powder made from husk and fruit-stem with ethanol 3-4 times to form an ethanol extract; removing the ethanol from the ethanol extract to form an aqueous extracts; drying the aqueous extracts to form the flavone extracts that is yellow powder.

This invention provides a composition comprising extracts from husks and fruit-stems which are flavonols, flavanols, dihydroflavonols, phenoloids, and others.

This invention relates to the crude flavone extracts from Wenguanguo leaves that includes a water-soluble flavone extracts and a water-insoluble flavone extract and methods of their preparation. The methods for preparing the extracts from Wenguanguo leaves comprise the following steps: extracting Wenguanguo powder made from the leaves with ethanol for 3 times to form an ethanol extract; concentrating the ethanol extract to form a concentrated condensed extracts; extracting the concentrated extract with hot water to from an aqueous extracts and a water-insoluble extract; drying the aqueous extracts and the water-insoluble extract to form a water-soluble flavone extracts and a water-insoluble flavone extract. This invention provides a composition comprising the crude extracts from leaf which are flavonols, flavanols, dihydroflavonols, phenoloids and others.

This invention relates to the flavone extracts from Wenguanguo branches or stems and methods of their preparation. The methods for preparing the extract from branches or stem comprise the following steps: extracting Wenguanguo powder made from the branches or stems with ethanol for 4 times to form an ethanol extract; removing the ethanol from the ethanol extract to form an aqueous extracts; drying the aqueous extracts to form flavone extracts which is a yellowish powder.

This invention provides a composition comprising extracts from Wenguanguo branches and stems which are flavonols, flavanols, dihydroflavonols, phenoloids and others.

This invention relates to the flavone extracts from Wenguanguo kernels and methods of their preparation. The methods for preparing the extract from kernels comprise the following steps: removing oil by pressing the kernels to form kernel cakes; grinding and extracting the kernel cakes with n-hexane to from n-hexane extract; removing the n-hexane from the n-hexane extract and drying them to form the kernel powder; extracting the kernel powder with ethanol to form an ethanol extract; removing the ethanol from the ethanol extract to form an aqueous extract; drying the aqueous extracts to form a flavone extracts that is a yellow powder.

This invention provides a composition comprising extracts from kernel which are flavonols, flavanols, dihydroflavonols, proteins, phenoloids, and others.

This invention relates to the flavone extract from Wenguanguo root, and methods of their preparation. The methods for preparing the flavone extract from Wenguanguo root comprise the following steps: extracting Wenguanguo powder made from root with ethanol 3-4 times to form an ethanol extract; removing the ethanol from the ethanol extract to form an aqueous extract; drying the aqueous extracts to form the flavone extracts which is a yellow powder.

This invention provides a composition comprising extracts from roots of Wenguanguo which are flavonols, flavanols, dihydroflavonols, phenoloids and others.

This invention relates to the flavone extracts from Wenguanguo barks, and methods of their preparation. The methods for preparing the bark extracts from Wenguanguo barks comprise the following steps: extracting Wenguanguo powder made from the barks with ethanol 3-4 times to form an ethanol extract; removing the ethanol from the ethanol extract to form an aqueous extract; drying the aqueous extracts to form the flavone extracts which is a yellowish powder.

This invention provides an extract composition from Wenguanguo barks comprising flavonols, flavanols, dihydroflavonols, phenoloids and others.

This invention is related to the combined extracts from Wenguanguo husks or fruit-stems and method of their preparation. The methods for preparing the extract from the husks or fruit-stems comprise the following steps: extracting Wenguanguo powder made from the husks or fruit-stems with an organic solvent (ethanol, methanol and others) to form an organic extract; removing the organic solvent from the organic extract to from an aqueous extracts; drying and sterilizing the aqueous extracts to form the combined extracts.

This invention provides a composition comprising the combined extracts from the husks or fruit-stems of the Wenguanguo. The combined extracts comprise saponins, saccharides, proteins and others.

This invention is related to the combined extracts from Wenguanguo leaves and method of their preparation. The methods for preparing the extracts from the leaves comprise the following steps: extracting Wenguanguo powder made from leaves with an organic solvent (ethanol, methanol and others) to form an organic extract; removing the organic solvent from the second extract to an aqueous extract; extracting the aqueous extract with ether and water to form an second aqueous extract; extracting the second aqueous extract with n-butanol to form a n-butanol extract; removing the n-butanol from the n-butanol extract to form a third aqueous extract; drying and sterilizing the third aqueous extract to form the combined extracts.

This invention provides a composition comprising the organic extracts from the leaves of the Wenguanguo. The organic extracts comprise saponins, saccharides, proteins and others.

This invention is related to the combined extracts from Wenguanguo branches or stems and method of their preparation. The methods for preparing the extracts from the branches or stems comprise the following steps: extracting Wenguanguo powder made from the branches or stems with an organic solvent (ethanol, methanol and others) to form an organic extract; removing the organic solvent from the second extract to an aqueous extract; drying and sterilizing the aqueous extracts to form the combined extracts.

This invention provides a composition comprising the organic extracts from the branches, and stems and of the Wenguanguo. The organic extracts comprise saponins, saccharides, proteins and others.

This invention is related to the combined extracts from Wenguanguo kernels and method of their preparation. The methods for preparing the extracts from Wenguanguo kernels comprise the following steps: removing oil by pressing the kernels to form kernel cakes; grinding and extracting the kernel cakes with n-hexane to from n-hexane extract; removing the n-hexane from the n-hexane extract and drying them to form the kernel powder; extracting the kernel powder with an organic solvent (ethanol, methanol and others) to form an organic extract; removing the organic solvent from the second extract to an aqueous extract; drying and sterilizing the aqueous extracts to form the combined extracts.

This invention provides a composition comprising the organic extracts from the kernels of the Wenguanguo. The combined extracts comprise saponins, saccharides, proteins and others.

This invention is related to the combined extracts from Wenguanguo roots and method of their preparation. The methods for preparing the extracts from Wenguanguo roots comprise the following steps: extracting Wenguanguo powder made from the roots with an organic solvent (ethanol, methanol and others) to form an organic extract; removing the organic solvent from the organic extract to from an aqueous extracts; drying and sterilizing the aqueous extracts to form the combined extracts.

This invention provides a composition comprising the combined extracts from the roots of the Wenguanguo. The combined extracts comprise saponins, saccharides, proteins and others.

This invention is related to the combined extracts from Wenguanguo barks and method of their preparation. The methods for preparing the extracts from the barks of Wenguanguo comprise the following steps: extracting Wenguanguo powder made from the barks with an organic solvent (ethanol, methanol and others) to form an organic extract; removing the organic solvent from the organic extract to from an aqueous extract; drying and sterilizing the aqueous extracts to form the combined extracts.

This invention provides a composition comprising the combined extracts from the barks of the Wenguanguo. The combined extracts comprise saponins, saccharides, proteins and others.

This invention provides the crude saponins from the husks or fruit-stems or seed's shell of Wenguanguo. The methods for preparing the crude saponins from Wenguanguo husks or fruit-stems comprise the following steps: extracting Wenguanguo powder of the husks or fruit-stems with an organic solvent (ethanol, methanol and others) at ratio of 1:2 for 4-5 times, 20-35 hours for each time to form an organic extract;

collect and reflux the organic extract 2-3 times at 80° C. to form second extracts; resolve the second extracts in water to form an aqueous solution; extract the aqueous solution by n-butanol to form a n-butanol extracts; chromatograph the n-butanol extracts to form the crude saponins. The crude extract comprises saponins.

This invention provides the crude saponins from the leaves of Wenguanguo and method for their preparation. The methods for preparing the crude saponins from the leaves comprise the following steps: extracting Wenguanguo powder of the leaves with an organic solvent (ethanol, methanol and others) at ratio of 1:2, 4-5 times, 20-35 hours each time to form an organic extract; collect and reflux the organic extract 2-3 times at 80° C. to form a second extract; resolve the second extracts in water to form an aqueous solution; extract the aqueous solution by n-butanol to form a n-butanol extracts; chromatograph the n-butanol extracts to form the crude saponins. The crude extract comprises saponins.

This invention provides the crude saponins from the branches and stems of Wenguanguo. The methods for preparing the crude saponins from the branches or stems comprise the following steps: extracting Wenguanguo powder of the branches or stems with an organic solvent (ethanol, methanol and others) at ratio of 1:2, 4-5 times, 20-35 hours each time to form an organic extract; collect and reflux the organic extract 2-3 times at 80° C. to form second extracts; resolve the second extracts in water to form an aqueous solution; extract the aqueous solution by n-butanol to form a n-butanol extracts; chromatograph the n-butanol extracts to form the crude saponins. The crude extract comprises saponins.

This invention provides the crude saponins from the kernels of Wenguanguo. The methods for preparing the crude saponins from Wenguanguo kernels comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with an organic solvent (ethanol, methanol and others) at ratio of 1:2, 4-5 times, 20-35 hours each time to form an organic extract; collect and reflux the organic extract for 2-3 times at 80° C. to form second extracts; resolve the second extracts in water to form an aqueous solution; Extract the aqueous solution by n-butanol to form a n-butanol extracts; chromatograph the n-butanol extracts to form the crude saponins. The crude extracts comprise saponins.

This invention provides the crude saponins from the roots of Wenguanguo and method for their preparation. The methods for preparing the crude saponins from Wenguanguo roots comprise the following steps: extracting Wenguanguo powder of the roots with an organic solvent (ethanol, methanol and others) at ratio of 1:2, 4-5 times, 20-35 hours each time to form an organic extract; collect and reflux the organic extract 2-3 times at 80° C. to form second extracts; resolve the second extracts in water to form an aqueous solution; extract the aqueous solution by n-butanol to form a n-butanol extracts; chromatograph the n-butanol extracts to form the crude saponins. The crude extracts contain saponins.

This invention provides the crude saponins from the barks of Wenguanguo and method for their preparation. The methods for preparing the crude saponins from the barks comprise the following steps: extracting Wenguanguo powder of the barks with an organic solvent (ethanol, methanol and others) at a ratio of 1:2, 4-5 times, 20-35 hours each time to form an organic extract; collect and reflux the organic extract 2-3 times at 80° C. to form second extracts; resolve the second extracts in water to form an aqueous solution; extract the aqueous solution by n-butanol to form a n-butanol extracts; chromatograph the n-butanol extracts to form the crude saponins. The crude extracts comprise saponins.

This invention provides a process of producing a coumarin extract from the husks or fruit-stems of Wenguanguo and their applications. The methods for preparing the coumarin extracts from husks or fruit-stems of Wenguanguo comprise the following steps: extracting Wenguanguo powder of the husks or fruit-stems with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extracts from the husks or fruit-stems of Wenguanguo. The extract comprises coumarins, coumaric glycosides and others.

This invention provides a process of producing a coumarin extract from the leaves of Wenguanguo and their applications. The methods for preparing the coumarin extracts from leaves of Wenguanguo comprise the following steps: extracting Wenguanguo powder of the leaves with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extracts from the leaves of Wenguanguo. The extract comprises coumarins, coumaric glycosides and others.

This invention provides a process of producing a coumarin extract from the branches and stems of Wenguanguo and their applications. The methods for preparing the coumarin extract from the branches or stems of Wenguanguo comprise the following steps: extracting Wenguanguo powder branches or stems with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the extract comprising crude coumarins.

This invention provides a composition comprising the coumarin extracts from the branches and stems of Wenguanguo. The extract comprises coumarins, coumaric glycosides, saccharides, proteins and others.

This invention provides the crude saponins from the leaves of Wenguanguo and method for their preparation. The methods for preparing the crude saponins from the leaves comprise the following steps: extracting Wenguanguo powder of the leaves with an organic solvent (ethanol, methanol and others) at ratio of 1:2, 4-5 times, 20-35 hours each time to form an organic extract; collect and reflux the organic extract 2-3 times at 80° C. to form a second extract; resolve the second extracts in water to form an aqueous solution; extract the aqueous solution by n-butanol to form a n-butanol extracts; chromatograph the n-butanol extracts to form the crude saponins. The crude extract comprises saponins.

This invention provides the crude saponins from the branches and stems of Wenguanguo. The methods for preparing the crude saponins from the branches or stems comprise the following steps: extracting Wenguanguo powder of the branches or stems with an organic solvent (ethanol, methanol and others) at ratio of 1:2, 4-5 times, 20-35 hours each time to form an organic extract; collect and reflux the organic extract 2-3 times at 80° C. to form second extracts; resolve the second extracts in water to form an aqueous solution; extract the aqueous solution by n-butanol to form a n-butanol extracts; chromatograph the n-butanol extracts to form the crude saponins. The crude extract comprises saponins.

This invention provides the crude saponins from the kernels of Wenguanguo. The methods for preparing the crude saponins from Wenguanguo kernels comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with an organic solvent (ethanol, methanol and others) at ratio of 1:2, 4-5 times, 20-35 hours each time to form an organic extract; collect and reflux the organic extract for 2-3 times at 80° C. to form second extracts; resolve the second extracts in water to form an aqueous solution; Extract the aqueous solution by n-butanol to form a n-butanol extracts; chromatograph the n-butanol extracts to form the crude saponins. The crude extracts comprise saponins.

This invention provides the crude saponins from the roots of Wenguanguo and method for their preparation. The methods for preparing the crude saponins from Wenguanguo roots comprise the following steps: extracting Wenguanguo powder of the roots with an organic solvent (ethanol, methanol and others) at ratio of 1:2, 4-5 times, 20-35 hours each time to form an organic extract; collect and reflux the organic extract 2-3 times at 80° C. to form second extracts; resolve the second extracts in water to form an aqueous solution; extract the aqueous solution by n-butanol to form a n-butanol extracts; chromatograph the n-butanol extracts to form the crude saponins. The crude extracts contain saponins.

This invention provides the crude saponins from the barks of Wenguanguo and method for their preparation. The methods for preparing the crude saponins from the barks comprise the following steps: extracting Wenguanguo powder of the barks with an organic solvent (ethanol, methanol and others) at a ratio of 1:2, 4-5 times, 20-35 hours each time to form an organic extract; collect and reflux the organic extract 2-3 times at 80° C. to form second extracts; resolve the second extracts in water to form an aqueous solution; extract the aqueous solution by n-butanol to form a n-butanol extracts; chromatograph the n-butanol extracts to form the crude saponins. The crude extracts comprise saponins.

This invention provides a process of producing a coumarin extract from the husks or fruit-stems of Wenguanguo and their applications. The methods for preparing the coumarin extracts from husks or fruit-stems of Wenguanguo comprise the following steps: extracting Wenguanguo powder of the husks or fruit-stems with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extracts from the husks or fruit-stems of Wenguanguo. The extract comprises coumarins, coumaric glycosides and others.

This invention provides a process of producing a coumarin extract from the leaves of Wenguanguo and their applications. The methods for preparing the coumarin extracts from leaves of Wenguanguo comprise the following steps: extracting Wenguanguo powder of the leaves with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extracts from the leaves of Wenguanguo. The extract comprises coumarins, coumaric glycosides and others.

This invention provides a process of producing a coumarin extract from the branches and stems of Wenguanguo and their applications. The methods for preparing the coumarin extract from the branches or stems of Wenguanguo comprise the following steps: extracting Wenguanguo powder branches or stems with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the extract comprising crude coumarins.

This invention provides a composition comprising the coumarin extracts from the branches and stems of Wenguanguo. The extract comprises coumarins, coumaric glycosides, saccharides, proteins and others.

This invention provides a process of producing a coumarin extract from the kernels of Wenguanguo and their applications. The methods for preparing the coumarin extracts from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and drying them to form the kernel powder; extracting the kernel powder with 0.5% NaOH solution to form an aqueous extract; collect and extract the aqueous extract by ether to form an ether extract; neutralizing the ether extract with HCL to form a neutralized ether extract; concentrate and acidize the neutralized ether extract to form the coumarin extract.

This invention provides a composition comprising the coumarin extracts from the kernels of Wenguanguo. The extract comprises coumarins, coumaric glycosides and others.

This invention provides a process of producing a coumarin extract from the roots of Wenguanguo and their applications. The methods for preparing the coumarin extract from roots of Wenguanguo comprise the following steps: extracting Wenguanguo powder of the root with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extracts from the roots of Wenguanguo. The extract comprises coumarins, coumaric glycosides and others.

This invention provides a process of producing a coumarin extract from the barks of Wenguanguo and their applications. The methods for preparing the coumarin extract from barks of Wenguanguo comprise the following steps: extracting Wenguanguo powder of the bark with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extract from the barks of Wenguanguo. The extract comprises coumarins, coumaric glycosides and others.

This invention provides a process of producing an aqueous extract from the husks or fruit-stems of Wenguanguo and their applications. The method for preparing the water extracts from the husks or fruit-stems of Wenguanguo comprise the following steps: extracting Wenguanguo powder of the husk or fruit-stem with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extract from the husks or fruit-stems of Wenguanguo The aqueous extract comprises sugars, polysaccharides, glycosides, saponins, tannins and others.

This invention provides a process of producing an aqueous extract from the leaves of Wenguanguo and their applications. The method for preparing the water extracts from the leaves of Wenguanguo comprise the following steps: extracting Wenguanguo powder of the leaves with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extract from leaves of Wenguanguo. The aqueous extract comprises sugars, polysaccharides, glycosides, saponins, tannins and others.

This invention provides a process of producing an aqueous extract from the branches or stems of Wenguanguo and their applications. The method for preparing the water extracts from branches or stems of Wenguanguo comprise the following steps: extracting the Wenguanguo powder of the branches or stems with water at room temperature for 24 hours to form an aqueous extract; cooking the aqueous extract at 60-70° C. for 1-2 hours to form a second water extract; filtering the second water extract to from a filtered extract; concentrating the filtered extract to form the aqueous extract.

This invention provides a composition comprising the aqueous extract from the branches or stems of Wenguanguo. The aqueous extract comprises sugars, polysaccharides, glycosides, saponins, tannins and others.

This invention provides a process of producing an aqueous extract from the kernels of Wenguanguo and their applications. The method for preparing the water extracts from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extract from kernels of Wenguanguo. The aqueous extract comprises sugars, polysaccharides, glycosides, saponins, tannins and others.

This invention provides a process of producing an aqueous extract from the roots of Wenguanguo and their applications. The method for preparing the water extracts from the roots of Wenguanguo comprises the following steps: extracting Wenguanguo powder of the roots with water at room temperature for 24 hours to form an aqueous extract; cooking the aqueous extract at 60-70° C. for 1-2 hours to form a second water extract; filtering the second water extract to from a filtered extract; concentrating the filtered extract to form the aqueous extract.

This invention provides a composition comprising the aqueous extract from the roots of Wenguanguo The aqueous extract comprises sugars, polysaccharides, glycosides, saponins, tannins and others.

This invention provides a process of producing an aqueous extract from the barks of Wenguanguo and their applications. The method for preparing the water extracts from the barks of Wenguanguo comprise the following steps: extracting Wenguanguo powder of the barks with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extracts from the barks of Wenguanguo The aqueous extract comprises sugars, polysaccharides, glycosides, saponins, tannins and others.

This invention provides a process of producing an alkaloid extract from the husks of Wenguanguo and their applications. The methods for preparing the alkaloid extracts from the husks and fruit-stems of Wenguanguo comprising the following steps: extracting Wenguanguo powder of the husks or fruit-stems with water at a ratio of 1:6, 3-4 times, 10-15 hours each time to form an aqueous extract; collect and alkalify the aqueous extract with NaOH to form a alkalified aqueous extract with pH 10-12; extract the alkalified aqueous extract by toluol to form a toluol extract; the toluol extract flows through 2% of dicarboxyl solution with pH 5-7 to form a dicarboxyl solution; concentrate the dicarboxyl solution with decompression a to form crude alkaloids.

This invention provides a composition comprising the alkaloid extract from the husks or fruit-stems of Wenguanguo. The extract comprises alkaloids and others.

This invention provides a process of producing an alkaloid extract from the leaves of Wenguanguo and their applications. The methods for preparing the alkaloid extract from the leaves of Wenguanguo comprise the following steps: extracting Wenguanguo powder of the leaves with water at a ratio of 1:6, 3-4 times, 10-15 hours each time to form an aqueous extract; collecting and alkalifying the aqueous extract with NaOH to form a alkalified aqueous extract with pH 10-12; extracting the alkalified aqueous extract by toluol to form a toluol extract; flow the toluol extract through 2% of dicarboxyl solution with pH 5-7 to form a dicarboxyl solution; concentrate the dicarboxyl solution with decompression to form the alkaloid extract.

This invention provides a composition comprising the alkaloid extract from the leaves of Wenguanguo. The extract comprises alkaloids and others.

This invention provides a process of producing an alkaloid extract from the branches and stems of Wenguanguo and their applications. The methods for preparing the extracts containing alkaloids from branches or stems of Wenguanguo comprising the following steps: extracting Wenguanguo powder of the branches or stems with water at ratio of 1:6, 3-4 times, 10-15 hours each time to form an aqueous extract; collect and alkalify the aqueous extract with NaOH to form a alkalified aqueous extract with pH 10-12; extracting the alkalified aqueous extract by toluol to form a toluol extract; flow the toluol extract through 2% of dicarboxyl solution with pH 5-7 to form a dicarboxyl solution; concentrate the dicarboxyl solution with decompression to form the alkaloid extract.

This invention provides a composition comprising the extract containing crude alkaloids from the branches or stems of Wenguanguo. The extract comprises alkaloids and others.

This invention provides a process of producing an alkaloid extract from the kernels of Wenguanguo and their applications. The methods for preparing the alkaloid extract from kernels of Wenguanguo comprise the following steps: removing oil by pressing the kernels to form kernel cakes; grounding and extracting the kernel cakes with n-hexane to from n-hexane extract; removing the n-hexane from the n-hexane extract and dry them to form the kernel powder; extracting the kernel powder with water at ratio of 1:6 for 3-4 times, 10-15 hours for each time to form an aqueous extract; collect and alkalify the aqueous extract with NaOH to form a alkalified aqueous extract with pH 10-12; extract the alkalified aqueous extract by toluol to form a toluol extract; the toluol extract flows through 2% of dicarboxyl solution with pH 5-7 to form a dicarboxyl solution; concentrate the dicarboxyl solution with decompression to form the alkaloid extract.

This invention provides a composition comprising the alkaloid extract from the kernels of Wenguanguo. The extract comprises alkaloids and others.

This invention provides a process of producing an alkaloid extract from the roots of Wenguanguo and their applications. The methods for preparing the alkaloid extract from the roots of Wenguanguo comprise the following steps: extracting Wenguanguo powder of the Wenguanguo roots with water at a ratio of 1:6, 3-4 times, 10-15 hours each time to form an aqueous extract; collecting and alkalifying the aqueous extract with NaOH to form a alkalified aqueous extract with pH 10-12; extracting the alkalified aqueous extract by toluol to form a toluol extract; flow the toluol extract through 2% of dicarboxyl solution with pH 5-7 to form a dicarboxyl solution; concentrate the dicarboxyl solution with decompression a to form crude alkaloids.

This invention provides a composition comprising the alkaloid extract from the roots of Wenguanguo. The extract comprises alkaloids and others.

This invention provides a process of producing an alkaloid extract from the barks of Wenguanguo and their applications. The methods for preparing the alkaloid extract from the barks of Wenguanguo comprise the following steps: extracting Wenguanguo powder of the barks with water at ratio of 1:6, 3-4 times, 10-15 hours each time to form an aqueous extract; collect and alkalify the aqueous extract with NaOH to form a alkalified aqueous extract with pH 10-12; extract the alkalified aqueous extract by toluol to form a toluol extract; flow the toluol extract through 2% of dicarboxyl solution with pH 5-7 to form a dicarboxyl solution; concentrate the dicarboxyl solution with decompression a to form crude alkaloids.

This invention provides a composition comprising the alkaloid extract from the barks of Wenguanguo. The extract comprises alkaloids and others.

This invention provides a process of producing extract containing organic acids from husks and fruit-stems and their applications. The methods for preparing the extracts containing organic acids from the husks or fruit-stems of Wenguanguo comprise the following steps: extract Wenguanguo powder of the husks and or fruit-stems with 10% HCL to form an acid solution; extract the acid solution by an organic solvent (ether or benzol) to form organic extract; extract the organic extract by 5-10% NaHCO3 solution to form a $NaHCO^3$ extract; acidize and filter the NaHCO3 extract to form a deposit matter; extract the deposit matter by an organic solvent to form the second organic extract; remove the organic solvent from the second extract to form crude organic acid.

This invention provides a composition comprising crude organic acids from the husks of Wenguanguo. The extract comprising aromatic organic acids, fatty organic acids, terpenoid organic acids and others This invention provides a process of producing extract contains organic acids from leaf and their applications. The methods for preparing the extracts containing organic acids from the leaves of Wenguanguo comprise the following steps: extract Wenguanguo powder of the leaves with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the extract comprising crude organic acids extract from the leaves of Wenguanguo. The extract comprises aromatic organic acids, fatty organic acids, terpenoid organic acids and others.

This invention provides a process of producing extract contains organic acids from branches and stems and their applications. The methods for preparing the extracts comprising organic acids from the branches or stems of Wenguanguo comprise the following steps: extract Wenguanguo powder of the branches or stems with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the crude organic acids extract from the branches and stems of Wenguanguo. The extract comprises aromatic organic acids, fatty organic acids, terpenoid organic acids and others.

This invention provides a process of producing extract comprise organic acids from kernels and their applications. The methods for preparing the extracts comprising organic acids from the kernels of Wenguanguo comprise the following steps: removing oil by pressing the kernels to form kernel cakes; grounding and extracting the kernel cakes with n-hexane to from n-hexane extract; removing the n-hexane from the n-hexane extract and dry them to form the kernel powder; extracting the kernel powder with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising crude organic acids extract from the kernels of Wenguanguo. The extract comprises aromatic organic acids, fatty organic acids, terpenoid organic acids and others.

This invention provides a process of producing extract contains organic acids from the roots of Wenguanguo and their applications. The methods for preparing the extracts containing organic acids from the roots of Wenguanguo comprise the following steps: extract Wenguanguo powder of the roots with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the extract comprising crude organic acids from the roots of Wenguanguo. The extract comprises aromatic organic acids, fatty organic acids, terpenoid organic acids and others.

This invention provides a process of producing extract comprising organic acids from barks of Wenguanguo and their applications. The methods for preparing the extracts containing organic acids from the barks of Wenguanguo comprise the following steps: extract Wenguanguo powder of the bark with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the extract comprising crude organic acids from the barks of Wenguanguo. The extract comprises aromatic organic acids, fatty organic acids, terpenoid organic acids and others.

This invention provides two methods of producing a tannin extract from Wenguanguo husks and fruit-stems and its usage. The first method for preparing the tannin extract from the husks or fruit-stems of Wenguanguo comprises the following steps: extracting Wenguanguo powder of husks and or fruit-stems with 95% ethanol to form an ethanol extract; concentrate the ethanol extract with decompression a to form the tannin extract. The second method for preparing the tannin extracts from the husks and or fruit-stems of Wenguanguo comprise the following steps: extracting Wenguanguo powder of the husks and or fruit-stems with a solvent of acetone-water at ratio of 1:1 for 2-7 days to form an acetone-water extract; removing acetone from the acetone-water extract at 50° C. to form a concentrated extract; filtering the concentrated extract to form a filtered extract; extract the filtered extract with ether to form an aqueous extract; extracting the aqueous extract with ethyl acetate and n-butanol to form ethyl acetate and n-butanol extract comprising tannins.

This invention provides a composition comprising the tannin extracts from the husks or fruit-stems of Wenguanguo. The extracts are comprised of tannins and others.

This invention provides two methods of producing a tannin extract from Wenguanguo leaves and its usage. The first method for preparing the tannin extract from the leaves of Wenguanguo comprise the following steps: extracting Wenguanguo powder of the leaves with 95% ethanol to form an ethanol extract; concentrate the ethanol extract with decompression a to form the tannin extract.

The second method for preparing the tannin extract from the leaves of Wenguanguo comprise the following steps: extracting Wenguanguo powder of the leaves with a solvent of acetone-water at ratio of 1:1 for 2-7 days to form an acetone-water extract; removing acetone from the acetone-water extract at 50° C. to form a concentrated extract; filtering the concentrated extract to form a filtered extract; extract the filtered extract with ether to form an aqueous extract; extracting the aqueous extract with ethyl acetate and n-butanol to form ethyl acetate and n-butanol extract containing tannins.

This invention provides a composition comprising the tannin extract from the leaves of Wenguanguo. The extract comprises tannins and others.

This invention provides two methods of producing tannin extract from Wenguanguo branches and stems and its usage. The first method for preparing the extracts comprising tannins from branches or stems of Wenguanguo comprise the following steps: extracting Wenguanguo powder of branches or stems with 95% ethanol to form an ethanol extract; concentrate the ethanol extract with decompression a to form the tannin extract.

The second method for preparing the tannin extract from the branches or stems of Wenguanguo comprise the following steps: extracting Wenguanguo powder of the branches or stems and with a solvent of acetone-water at ratio of 1:1 for 2-7 days to form an acetone-water extract; removing acetone from the acetone-water extract at 50° C. to form a concentrated extract; filtering the concentrated extract to form a filtered extract; extract the filtered extract with ether to form an aqueous extract; extracting the aqueous extract with ethyl acetate and n-butanol to form ethyl acetate and n-butanol extract comprising tannins. This invention provides a composition comprising the tannin extract from the branch or stem of Wenguanguo. The extract comprises tannins and others.

This invention provides two methods of producing tannin extract from Wenguanguo kernels and its usage. The first method for preparing the tannin extract from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with 95% ethanol to form an ethanol extract; concentrating the ethanol extract with decompression to form the extract comprising tannins.

The second method for preparing the extracts containing tannins from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with a solvent of acetone-water at ratio of 1:1 for 2-7 days to form an acetone-water extract; removing acetone from the acetone-water extract at 50° C. to form a concentrated extract; filtering the concentrated extract to form a filtered extract; extracting the filtered extract with ether to form an aqueous extract; extracting the aqueous extract with ethyl acetate and n-butanol to form ethyl acetate and n-butanol extract containing tannins.

This invention provides a composition comprising the tannin extract from kernels of Wenguanguo. The extract comprises tannins and others.

This invention provides two methods of producing tannin extract from Wenguanguo roots and its usage. The first method for preparing the tannin extract from the roots of Wenguanguo comprises the following steps: extracting Wenguanguo powder of roots with 95% ethanol to form an ethanol extract; concentrating the ethanol extract with decompression to form the tannin extract. The method-2 for preparing the tannin extract from the root of Wenguanguo comprises the following steps: extracting Wenguanguo powder of the root with a solvent of acetone-water at a ratio of 1:1 for 2-7 days to form an acetone-water extract; removing acetone from the acetone-water extract at 50° C. to form a concentrated extract; filtering the concentrated extract to form a filtered extract; extracting the filtered extract with ether to form an aqueous extract; extracting the aqueous extract with ethyl acetate and n-butanol to form ethyl acetate and n-butanol extract comprising tannins.

This invention provides a composition comprising the tannin extracts from the roots of Wenguanguo. The extracts comprise tannins and others.

This invention provides two methods of producing tannin extract from Wenguanguo barks and its usage. The method-1 for preparing the tannin extract from the barks of Wenguanguo comprises the following steps: extracting Wenguanguo powder of barks with 95% ethanol to form an ethanol extract; concentrating the ethanol extract with decompression to form the tannin extract. The second method for preparing the tannin extract from the barks of Wenguanguo comprising the following steps: extracting Wenguanguo powder of the barks with a solvent of acetone-water at ratio of 1:1 for 2-7 days to form an acetone-water extract; removing acetone from the acetone-water extract at 50° C. to form a concentrated extract; filtering the concentrated extract to form a filtered extract; extracting the filtered extract with ether to form an aqueous extract; extracting the aqueous extract with ethyl acetate and n-butanol to form ethyl acetate and n-butanol extract comprising tannins.

This invention provides a composition comprising the tannin extracts from the barks of Wenguanguo. The extracts comprise tannins and others.

This invention provides a method for preventing cerebral aging, improving memory, improving cerebral functions and curing enuresis, frequent micturition, urinary incontinence, dementia, weak intelligence and Alzheimer's disease, autism, brain trauma, Parkinson's disease and other diseases caused by cerebral dysfunctions, and treating arthritis, rheumatism, poor circulation, arteriosclerosis, Raynaud's syndrome, angina pectoris, cardiac disorder, coronary heart disease, headache, dizziness, kidney disorder and treating impotence and premature ejaculation.

According to the theory of traditional Chinese medicine, enuresis, frequent micturition and urinary incontinence are caused by "deficiency in kidney ("shen")". Therefore, they are treated by using Chinese herbs which can tone the kidney, such as *Ginseng Bajitian, Roucongrong Duzhong* and *Cordyceps*. These tonifying herbs can strengthen function of the kidney and regulate water metabolism of human's body through the "kidney pathway" that will help with curing the enuresis, frequent micturition and urinary incontinence.

The Wenguanguo extracts of the present invention can also be used to treat the enuresis, frequent micturition and urinary incontinence. However, the Wenguanguo extracts cure the enuresis, frequent micturition and urinary incontinence through the "bladder pathway" to regulate water metabolism of human's body and urination. The Wenguanguo extracts of the present invention stimulate the growth of the bladder. See FIG. 10A. The Wenguanguo extracts of the present invention increase the capacity of bladder and function of bladder controlling the urination. See Experiment 15 and Experiment 15A. In another aspect of the present invention, Wenguanguo extracts, when used with the "kidney pathway" herbs to treat the enuresis, frequent micturition and urinary incontinence, will strengthen both the pathways of kidney and bladder, and then will produce better treatment results.

This invention provides the medicines or health foods which further comprise Vitamin B, Vitamin D, Vitamin K, grape seed extract and other antioxidants, *Cordyceps* or its extract, gingko or its extract, *Panax ginseng* and *P. quinquefolium* or their extracts, Huangpi (*Clausena lansium*) or its extracts, *Echinacea* or its extract, St John's Wort (*Hypericum perforatum*) or its extract, Gegen (*Pueraria lobata*) or its extract, Tianma (*Gastrodia elata*) or its extract, *Armillariella mellea* or its extract, Danshen (*Salvia miltiorrhiza*) or its extract, Sanqi (*Panax notoginsen*) or its extract, Monascus or Honqu (Red yeast rice), Huanqi (*Hedysarum polybotrys*) or its extract, Dihuang (*Rehmannia glutinosa*) or its extract, Danggui (*Angelica sinensis*), Yuanzhi (*Polygala tenuifoila*) or its extract, Lingzhi (*Ganoderma* spp.) or its extracts, Fuling (*Poria cocos*) or its extract, enokitake (*Flammulina velutipes*) or its extract, Gan Cao (*Glycyrrhiza uralensis* Fisch) or its extract, Huperzine A, Lacithin, Metrifonate, Nocetile, folic acid, amino acids, creatine, fiber supplement, or any combination thereof.

This invention provides a process of producing a coumarin extract from the kernels of Wenguanguo and their applications. The methods for preparing the coumarin extracts from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and drying them to form the kernel powder; extracting the kernel powder with 0.5% NaOH solution to form an aqueous extract; collect and extract the aqueous extract by ether to form an ether extract; neutralizing the ether extract with HCL to form a neutralized ether extract; concentrate and acidize the neutralized ether extract to form the coumarin extract.

This invention provides a composition comprising the coumarin extracts from the kernels of Wenguanguo. The extract comprises coumarins, coumaric glycosides and others.

This invention provides a process of producing a coumarin extract from the roots of Wenguanguo and their applications. The methods for preparing the coumarin extract from roots of Wenguanguo comprise the following steps: extracting Wenguanguo powder of the root with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extracts from the roots of Wenguanguo. The extract comprises coumarins, coumaric glycosides and others.

This invention provides a process of producing a coumarin extract from the barks of Wenguanguo and their applications. The methods for preparing the coumarin extract from barks of Wenguanguo comprise the following steps: extracting Wenguanguo powder of the bark with 0.5% NaOH solution to form an aqueous extract; collect and extract the aqueous extract by ether to form a ether extract; neutralize the ether extract with HCL to form a neutralized ether extract; concentrate and acidize the neutralized ether extract to form the coumarin extract.

This invention provides a composition comprising the coumarin extract from the barks of Wenguanguo. The extract comprises coumarins, coumaric glycosides and others.

This invention provides a process of producing an aqueous extract from the husks or fruit-stems of Wenguanguo and their applications. The method for preparing the water extracts from the husks or fruit-stems of Wenguanguo comprise the following steps: extracting Wenguanguo powder of the husk or fruit-stem with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extract from the husks or fruit-stems of Wenguanguo The aqueous extract comprises sugars, polysaccharides, glycosides, saponins, tannins and others.

This invention provides a process of producing an aqueous extract from the leaves of Wenguanguo and their applications. The method for preparing the water extracts from the leaves of Wenguanguo comprise the following steps: extracting Wenguanguo powder of the leaves with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extract from leaves of Wenguanguo. The aqueous extract comprises sugars, polysaccharides, glycosides, saponins, tannins and others.

This invention provides a process of producing an aqueous extract from the branches or stems of Wenguanguo and their applications. The method for preparing the water extracts from branches or stems of Wenguanguo comprise the following steps: extracting the Wenguanguo powder of the branches or stems with water at room temperature for 24 hours to form an aqueous extract; cooking the aqueous extract at 60-70° C. for 1-2 hours to form a second water extract; filtering the second water extract to from a filtered extract; concentrating the filtered extract to form the aqueous extract.

This invention provides a composition comprising the aqueous extract from the branches or stems of Wenguanguo. The aqueous extract comprises sugars, polysaccharides, glycosides, saponins, tannins and others.

This invention provides a process of producing an aqueous extract from the kernels of Wenguanguo and their applications. The method for preparing the water extracts from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extract from kernels of Wenguanguo. The aqueous extract comprises sugars, polysaccharides, glycosides, saponins, tannins and others.

This invention provides a process of producing an aqueous extract from the roots of Wenguanguo and their applications. The method for preparing the water extracts from the roots of Wenguanguo comprises the following steps: extracting Wenguanguo powder of the roots with water at room temperature for 24 hours to form an aqueous extract; cooking the aqueous extract at 60-70° C. for 1-2 hours to form a second water extract; filtering the second water extract to from a filtered extract; concentrating the filtered extract to form the aqueous extract.

This invention provides a composition comprising the aqueous extract from the roots of Wenguanguo The aqueous extract comprises sugars, polysaccharides, glycosides, saponins, tannins and others.

This invention provides a process of producing an aqueous extract from the barks of Wenguanguo and their applications. The method for preparing the water extracts from the barks of Wenguanguo comprise the following steps: extracting Wenguanguo powder of the barks with water at room temperature for 24 hours to form an aqueous extract; cooking the aqueous extract at 60-70° C. for 1-2 hours to form a second water extract; filtering the second water extract to from a filtered extract; concentrate the filtered extract to form the aqueous extract.

This invention provides a composition comprising the aqueous extracts from the barks of Wenguanguo The aqueous extract comprises sugars, polysaccharides, glycosides, saponins, tannins and others.

This invention provides a process of producing an alkaloid extract from the husks of Wenguanguo and their applications. The methods for preparing the alkaloid extracts from the husks and fruit-stems of Wenguanguo comprising the following steps: extracting Wenguanguo powder of the husks or fruit-stems with water at a ratio of 1:6, 3-4 times, 10-15 hours each time to form an aqueous extract; collect and alkalify the aqueous extract with NaOH to form a alkalified aqueous extract with pH 10-12; extract the alkalified aqueous extract by toluol to form a toluol extract; the toluol extract flows through 2% of dicarboxyl solution with pH 5-7 to form a dicarboxyl solution; concentrate the dicarboxyl solution with decompression a to form crude alkaloids.

This invention provides a composition comprising the alkaloid extract from the husks or fruit-stems of Wenguanguo. The extract comprises alkaloids and others.

This invention provides a process of producing an alkaloid extract from the leaves of Wenguanguo and their applications. The methods for preparing the alkaloid extract from the leaves of Wenguanguo comprise the following steps: extracting Wenguanguo powder of the leaves with water at a ratio of 1:6, 3-4 times, 10-15 hours each time to form an aqueous extract; collecting and alkalifying the aqueous extract with NaOH to form a alkalified aqueous extract with pH 10-12; extracting the alkalified aqueous extract by toluol to form a toluol extract; flow the toluol extract through 2% of dicarboxyl solution with pH 5-7 to form a dicarboxyl solution; concentrate the dicarboxyl solution with decompression to form the alkaloid extract.

This invention provides a composition comprising the alkaloid extract from the leaves of Wenguanguo. The extract comprises alkaloids and others.

This invention provides a process of producing an alkaloid extract from the branches and stems of Wenguanguo and their applications. The methods for preparing the extracts containing alkaloids from branches or stems of Wenguanguo comprising the following steps: extracting Wenguanguo powder of the branches or stems with water at ratio of 1:6, 3-4 times, 10-15 hours each time to form an aqueous extract; collect and alkalify the aqueous extract with NaOH to form a alkalified aqueous extract with pH 10-12; extracting the alkalified aqueous extract by toluol to form a toluol extract; flow the toluol extract through 2% of dicarboxyl solution with pH 5-7 to form a dicarboxyl solution; concentrate the dicarboxyl solution with decompression to form the alkaloid extract.

This invention provides a composition comprising the extract containing crude alkaloids from the branches or stems of Wenguanguo. The extract comprises alkaloids and others.

This invention provides a process of producing an alkaloid extract from the kernels of Wenguanguo and their applications. The methods for preparing the alkaloid extract from kernels of Wenguanguo comprise the following steps: removing oil by pressing the kernels to form kernel cakes; grounding and extracting the kernel cakes with n-hexane to from n-hexane extract; removing the n-hexane from the n-hexane extract and dry them to form the kernel powder; extracting the kernel powder with water at ratio of 1:6 for 3-4 times, 10-15 hours for each time to form an aqueous extract; collect and alkalify the aqueous extract with NaOH to form a alkalified aqueous extract with pH 10-12; extract the alkalified aqueous extract by toluol to form a toluol extract; the toluol extract flows through 2% of dicarboxyl solution with pH 5-7 to form a dicarboxyl solution; concentrate the dicarboxyl solution with decompression to form the alkaloid extract.

This invention provides a composition comprising the alkaloid extract from the kernels of Wenguanguo. The extract comprises alkaloids and others.

This invention provides a process of producing an alkaloid extract from the roots of Wenguanguo and their applications. The methods for preparing the alkaloid extract from the roots of Wenguanguo comprise the following steps: extracting Wenguanguo powder of the Wenguanguo roots with water at a ratio of 1:6, 3-4 times, 10-15 hours each time to form an aqueous extract; collecting and alkalifying the aqueous extract with NaOH to form a alkalified aqueous extract with pH 10-12; extracting the alkalified aqueous extract by toluol to form a toluol extract; flow the toluol extract through 2% of dicarboxyl solution with pH 5-7 to form a dicarboxyl solution; concentrate the dicarboxyl solution with decompression a to form crude alkaloids.

This invention provides a composition comprising the alkaloid extract from the roots of Wenguanguo. The extract comprises alkaloids and others.

This invention provides a process of producing an alkaloid extract from the barks of Wenguanguo and their applications. The methods for preparing the alkaloid extract from the barks of Wenguanguo comprise the following steps: extracting Wenguanguo powder of the barks with water at ratio of 1:6, 3-4 times, 10-15 hours each time to form an aqueous extract; collect and alkalify the aqueous extract with NaOH to form a alkalified aqueous extract with pH 10-12; extract the alkalified aqueous extract by toluol to form a toluol extract; flow the toluol extract through 2% of dicarboxyl solution with pH 5-7 to form a dicarboxyl solution; concentrate the dicarboxyl solution with decompression a to form crude alkaloids.

This invention provides a composition comprising the alkaloid extract from the barks of Wenguanguo. The extract comprises alkaloids and others.

This invention provides a process of producing extract containing organic acids from husks and fruit-stems and their applications. The methods for preparing the extracts containing organic acids from the husks or fruit-stems of Wenguanguo comprise the following steps: extract Wenguanguo powder of the husks and or fruit-stems with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising crude organic acids from the husks of Wenguanguo. The extract comprising aromatic organic acids, fatty organic acids, terpenoid organic acids and others This invention provides a process of producing extract contains organic acids from leaf and their applications. The methods for preparing the extracts containing organic acids from the leaves of Wenguanguo comprise the following steps: extract Wenguanguo powder of the leaves with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the extract comprising crude organic acids extract from the leaves of Wenguanguo. The extract comprises aromatic organic acids, fatty organic acids, terpenoid organic acids and others.

This invention provides a process of producing extract contains organic acids from branches and stems and their applications. The methods for preparing the extracts comprising organic acids from the branches or stems of Wenguanguo comprise the following steps: extract Wenguanguo powder of the branches or stems with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the crude organic acids extract from the branches and stems of Wenguanguo. The extract comprises aromatic organic acids, fatty organic acids, terpenoid organic acids and others.

This invention provides a process of producing extract comprise organic acids from kernels and their applications. The methods for preparing the extracts comprising organic acids from the kernels of Wenguanguo comprise the following steps: removing oil by pressing the kernels to form kernel cakes; grounding and extracting the kernel cakes with n-hexane to from n-hexane extract; removing the n-hexane from the n-hexane extract and dry them to form the kernel powder; extracting the kernel powder with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising crude organic acids extract from the kernels of Wenguanguo. The extract comprises aromatic organic acids, fatty organic acids, terpenoid organic acids and others.

This invention provides a process of producing extract contains organic acids from the roots of Wenguanguo and their applications. The methods for preparing the extracts containing organic acids from the roots of Wenguanguo comprise the following steps: extract Wenguanguo powder of the roots with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the extract comprising crude organic acids from the roots of Wenguanguo. The extract comprises aromatic organic acids, fatty organic acids, terpenoid organic acids and others.

This invention provides a process of producing extract comprising organic acids from barks of Wenguanguo and their applications. The methods for preparing the extracts containing organic acids from the barks of Wenguanguo comprise the following steps: extract Wenguanguo powder of the bark with 10% HCL to form an acid solution; extract the acid solution by an organic solvent (ether or benzol) to form organic extract; extract the organic extract by 5-10% $NaHCO_3$ solution to form a $NaHCO_3$ extract; acidize and filter the $NaHCO_3$ extract to form a deposit matter; extract the deposit matter by an organic solvent to form the second organic extract; remove the organic solvent from the second extract to form crude organic acid.

This invention provides a composition comprising the extract comprising crude organic acids from the barks of Wenguanguo. The extract comprises aromatic organic acids, fatty organic acids, terpenoid organic acids and others.

This invention provides two methods of producing a tannin extract from Wenguanguo husks and fruit-stems and its usage. The first method for preparing the tannin extract from the husks or fruit-stems of Wenguanguo comprises the following steps: extracting Wenguanguo powder of husks and or fruit-stems with 95% ethanol to form an ethanol extract; concentrate the ethanol extract with decompression a to form the tannin extract. The second method for preparing the tannin extracts from the husks and or fruit-stems of Wenguanguo comprise the following steps: extracting Wenguanguo powder of the husks and or fruit-stems with a solvent of acetone-water at ratio of 1:1 for 2-7 days to form an acetone-water extract; removing acetone from the acetone-water extract at 50° C. to form a concentrated extract; filtering the concentrated extract to form a filtered extract; extract the filtered extract with ether to form an aqueous extract; extracting the aqueous extract with ethyl acetate and n-butanol to form ethyl acetate and n-butanol extract comprising tannins.

This invention provides a composition comprising the tannin extracts from the husks or fruit-stems of Wenguanguo. The extracts are comprised of tannins and others.

This invention provides two methods of producing a tannin extract from Wenguanguo leaves and its usage. The first method for preparing the tannin extract from the leaves of Wenguanguo comprise the following steps: extracting Wenguanguo powder of the leaves with 95% ethanol to form an ethanol extract; concentrate the ethanol extract with decompression a to form the tannin extract.

The second method for preparing the tannin extract from the leaves of Wenguanguo comprise the following steps: extracting Wenguanguo powder of the leaves with a solvent of acetone-water at ratio of 1:1 for 2-7 days to form an acetone-water extract; removing acetone from the acetone-water extract at 50° C. to form a concentrated extract; filtering the concentrated extract to form a filtered extract; extract the filtered extract with ether to form an aqueous extract; extracting the aqueous extract with ethyl acetate and n-butanol to form ethyl acetate and n-butanol extract containing tannins.

This invention provides a composition comprising the tannin extract from the leaves of Wenguanguo. The extract comprises tannins and others.

This invention provides two methods of producing tannin extract from Wenguanguo branches and stems and its usage. The first method for preparing the extracts comprising tannins from branches or stems of Wenguanguo comprise the following steps: extracting Wenguanguo powder of branches or stems with 95% ethanol to form an ethanol extract; concentrate the ethanol extract with decompression a to form the tannin extract.

The second method for preparing the tannin extract from the branches or stems of Wenguanguo comprise the following steps: extracting Wenguanguo powder of the branches or stems and with a solvent of acetone-water at ratio of 1:1 for 2-7 days to form an acetone-water extract; removing acetone from the acetone-water extract at 50° C. to form a concentrated extract; filtering the concentrated extract to form a filtered extract; extract the filtered extract with ether to form an aqueous extract; extracting the aqueous extract with ethyl acetate and n-butanol to form ethyl acetate and n-butanol extract comprising tannins. This invention provides a composition comprising the tannin extract from the branch or stem of Wenguanguo. The extract comprises tannins and others.

This invention provides two methods of producing tannin extract from Wenguanguo kernels and its usage. The first method for preparing the tannin extract from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with 95% ethanol to form an ethanol extract; concentrating the ethanol extract with decompression to form the extract comprising tannins.

The second method for preparing the extracts containing tannins from the kernels of Wenguanguo comprise the following steps: removing oil by pressing the kernels to form kernel cakes; grinding and extracting the kernel cakes with n-hexane to from n-hexane extract; removing the n-hexane from the n-hexane extract and dry them to form the kernel powder; extracting the kernel powder with a solvent of acetone-water at ratio of 1:1 for 2-7 days to form an acetone-water extract; removing acetone from the acetone-water extract at 50° C. to form a concentrated extract; filtering the concentrated extract to form a filtered extract; extracting the filtered extract with ether to form an aqueous extract; extracting the aqueous extract with ethyl acetate and n-butanol to form ethyl acetate and n-butanol extract containing tannins.

This invention provides a composition comprising the tannin extract from kernels of Wenguanguo. The extract comprises tannins and others.

This invention provides two methods of producing tannin extract from Wenguanguo roots and its usage. The first method for preparing the tannin extract from the roots of Wenguanguo comprises the following steps: extracting Wenguanguo powder of roots with 95% ethanol to form an ethanol extract; concentrating the ethanol extract with decompression to form the tannin extract. The method-2 for preparing the tannin extract from the root of Wenguanguo comprises the following steps: extracting Wenguanguo powder of the root with a solvent of acetone-water at a ratio of 1:1 for 2-7 days to form an acetone-water extract; removing acetone from the acetone-water extract at 50° C. to form a concentrated extract; filtering the concentrated extract to form a filtered extract; extracting the filtered extract with ether to form an aqueous extract; extracting the aqueous extract with ethyl acetate and n-butanol to form ethyl acetate and n-butanol extract comprising tannins.

This invention provides a composition comprising the tannin extracts from the roots of Wenguanguo. The extracts comprise tannins and others.

This invention provides two methods of producing tannin extract from Wenguanguo barks and its usage. The method-1 for preparing the tannin extract from the barks of Wenguanguo comprises the following steps: extracting Wenguanguo powder of barks with 95% ethanol to form an ethanol extract; concentrating the ethanol extract with decompression to form the tannin extract. The second method for preparing the tannin extract from the barks of Wenguanguo comprising the following steps: extracting Wenguanguo powder of the barks with a solvent of acetone-water at ratio of 1:1 for 2-7 days to form an acetone-water extract; removing acetone from the acetone-water extract at 50° C. to form a concentrated extract; filtering the concentrated extract to form a filtered extract; extracting the filtered extract with ether to form an aqueous extract; extracting the aqueous extract with ethyl acetate and n-butanol to form ethyl acetate and n-butanol extract comprising tannins.

This invention provides a composition comprising the tannin extracts from the barks of Wenguanguo. The extracts comprise tannins and others.

This invention provides a method for preventing cerebral aging, improving memory, improving cerebral functions and curing enuresis, frequent micturition, urinary incontinence, dementia, weak intelligence and Alzheimer's disease, autism, brain trauma, Parkinson's disease and other diseases caused by cerebral dysfunctions, and treating arthritis, rheumatism, poor circulation, arteriosclerosis, Raynaud's syndrome, angina pectoris, cardiac disorder, coronary heart disease, headache, dizziness, kidney disorder and treating impotence and premature ejaculation.

According to the theory of traditional Chinese medicine, enuresis, frequent micturition and urinary incontinence are caused by "deficiency in kidney ("shen")". Therefore, they are treated by using Chinese herbs which can tone the kidney, such as *Ginseng Bajitian, Roucongrong Duzhong* and *Cordyceps*. These tonifying herbs can strengthen function of the kidney and regulate water metabolism of human's body through the "kidney pathway" that will help with curing the enuresis, frequent micturition and urinary incontinence.

The Wenguanguo extracts of the present invention can also be used to treat the enuresis, frequent micturition and urinary incontinence. However, the Wenguanguo extracts cure the enuresis, frequent micturition and urinary incontinence through the "bladder pathway" to regulate water metabolism of human's body and urination. The Wenguanguo extracts of the present invention stimulate the growth of the bladder. See FIG. 10A. The Wenguanguo extracts of the present invention increase the capacity of bladder and function of bladder controlling the urination. See Experiment 15 and Experiment 15A. In another aspect of the present invention, Wenguanguo extracts, when used with the "kidney pathway" herbs to treat the enuresis, frequent micturition and urinary incontinence, will strengthen both the pathways of kidney and bladder, and then will produce better treatment results.

This invention provides the medicines or health foods which further comprise Vitamin B, Vitamin D, Vitamin K, grape seed extract and other antioxidants, *Cordyceps* or its extract, gingko or its extract, *Panax ginseng* and *P. quinquefolium* or their extracts, Huangpi (*Clausena lansium*) or its extracts, *Echinacea* or its extract, St John's Wort (*Hypericum perforatum*) or its extract, Gegen (*Pueraria lobata*) or its extract, Tianma (*Gastrodia elata*) or its extract, *Armillariella mellea* or its extract, Danshen (*Salvia miltiorrhiza*) or its extract, Sanqi (*Panax notoginsen*) or its extract, Monascus or Honqu (Red yeast rice), Huanqi (*Hedysarum polybotrys*) or its extract, Dihuang (*Rehmannia glutinosa*) or its extract, Danggui (*Angelica sinensis*), Yuanzhi (*Polygala tenuifoila*) or its extract, Lingzhi (*Ganoderma* spp.) or its extracts, Fuling (Poria *cocos*) or its extract, enokitake (*Flammulina velutipes*) or its extract, Gan Cao (*Glycyrrhiza uralensis* Fisch) or its extract, Huperzine A, Lacithin, Metrifonate, Nocetile, folic acid, amino acids, creatine, fiber supplement, or any combination thereof.

There are many different periods of sleep a person goes through. These include Slow-Wave-Sleep 1 (SWS 1), Slow-Wave-Sleep 2 (SWS 2), Slow-Wave-Sleep 3 (SWS 3) Slow-Wave-Sleep 4 (SWS 4) and Rapid Eye Movement (REM). SWS 1 and SWS 2 are both periods of light sleep where it is relatively easy to wake someone up. Light sleep is usually more frequent in the second half of sleep. SWS 3 and SWS 4 are both periods of deep sleep, where it is difficult to wake the sleeper. Deep sleep is more frequent in the first half of sleep and each period will get shorter each time afterward. REM is a period of sleep in which people have their most vivid dreams. The wave patterns are similar to the patterns in which a person is awake. However, it is difficult to wake someone up who is in this state of sleep. The sleep cycle of a typical person can be described as follows: SWS1, SWS2, SWS3, SWS4, SWS3, SWS2, REM, SWS1, SWS2, SWS3, SWS4, SWS3, SWS2, REM. (See FIG. 62)

However, the above sequence may not be in a fixed order. The sleep status may shift from SWS 4 to SWS1 or wake up because the body turns from one side to the other. It may shift to the SWS2 status after the movement. The interval between two REM is about 90 min. For healthy people, SWS1 will occupy about 5% of sleep, SWS2 will occupy about 50% of sleep, SWS3 will occupy about 10% of sleep, SWS4 will occupy about 10% of sleep and REM will occupy about 25% of sleep. Since a person in SWS1 and SWS2 can easily be woken, a healthy person has enough opportunities to wake up to urinate. However if a person's sleeping status is mostly in SWS4, he has less chance of waking up when the bladder is full. It is difficult for him to break through the barriers of deep sleep. Then enuresis occurs. This invention relates to a plant extract, including Wenguanguo, for preventing enuresis.

This invention provides the extract of Wenguanguo for inhibiting the uptake of 5-hydroxytryptamine (5HT) in a subject.

5-HT controls and modulates a sleep factor that sustains and increases deep sleep. Inhibiting the uptake of 5HT will decrease deep sleep. People who spend too much time in SWS 3 and SWS 4 are unable to awaken from their sleep when their bladder is full because their sleep is too deep. This is the reason that enuresis often occurs during SWS 3 and SWS 4.

This invention provides the extract of Wenguanguo for increasing the activity of Dopamine in a subject thereby making the central nerve system of said subject alert.

This invention provides the extract of Wenguanguo for increasing the secretion of antidiuretic hormone (ADH) in a subject, which reduces urine in said subject.

This invention provides the extract of Wenguanguo for modulating the release, breakdown and uptake of Acetylcholine (Ach) and its receptors in a subject. The said extracts of this invention inhibits the deep sleep created by 5HT and increase REM sleep.

This invention provides the extract of Wenguanguo for preventing sleep paralysis in a subject.

This invention provides the extract of Wenguanguo for providing alertness to a sleeping subject.

This invention provides the extract for helping the growth of the bladder and sphincter.

An immature bladder and sphincter cannot control the process and action of urination. By accelerating the growth of the bladder and the sphincter, this problem will be overcome, and enuresis will not occur.

This invention provides the extract of Wenguanguo against cancer growth. The cancer includes, but is not limited to bladder cancer, cervix cancer, prostate cancer, lung cancer, breast cancer, leukocytes cancer, colon cancer, liver cancer, bone cancer, skin cancer, brain cancer, and ovary cancer This invention provides the extract of Wenguanguo inhibit tumor activities.

This invention provides the pathways interacted by compounds isolated from *Xanthoceras Sorbifolia*. In an embodiment, a compound has the formula $C_{57}H_{88}O_{23}$ and the chemical name 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene, designated herein as "Structure Y", and derivative compounds which are effective against cancer. In another embodiment, the compounds of the present invention comprise the chemical structures designated herein as "Structure Y1", "Structure R1", "Structure 1 to 4", "Structure Y-a to Y-c" and "Structure Y1-a to Y1-c", "Structure Y1-1 to Y1-4" and their derivatives. See FIG. 31-40.

They regulate the receptors or components of cells. The compounds can be isolated from the plant called *Xanthoceras Sorbifolia* or can be synthesized.

Figure 1:
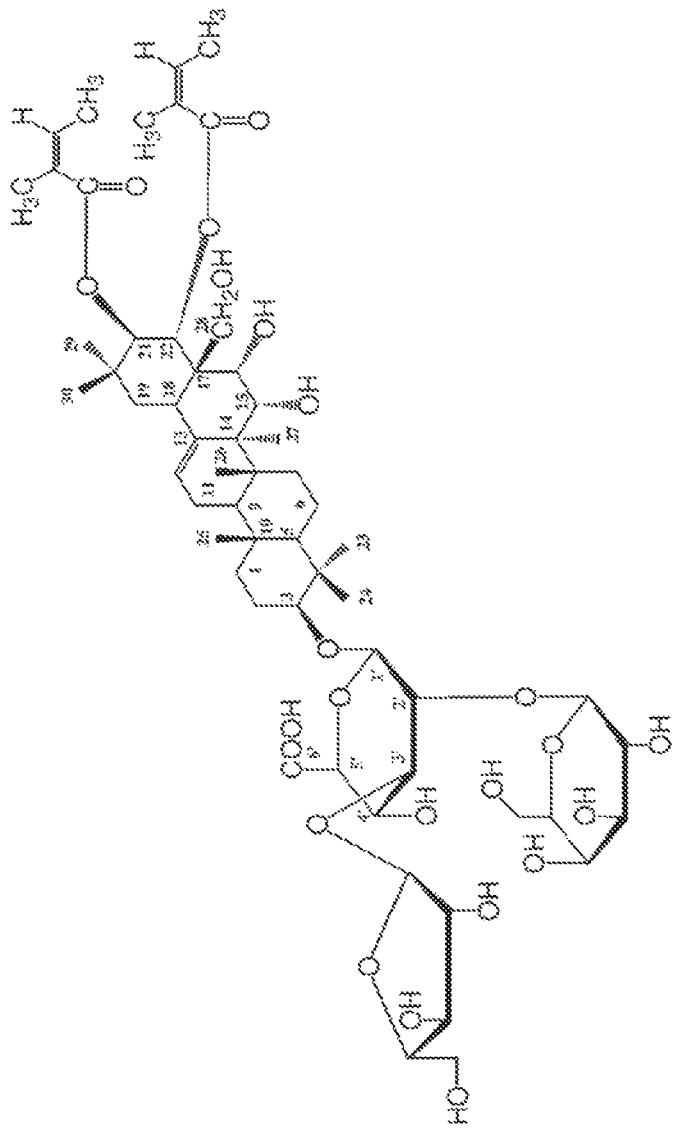
FIG. 1 shows the structure Compound Y with the formula of $C_{57}H_{88}O_{23}$ and the chemical name of 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene.

The compounds of the present invention have structures as shown below: Structure Y (also shown in FIG. 1)

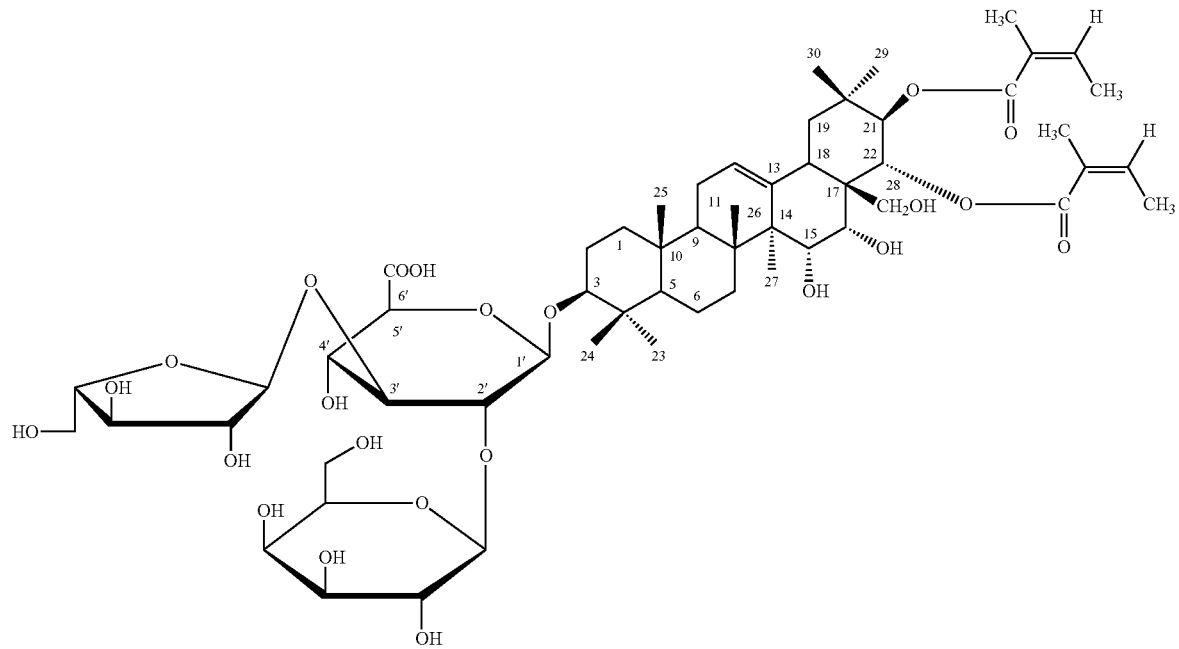

Figure 2:
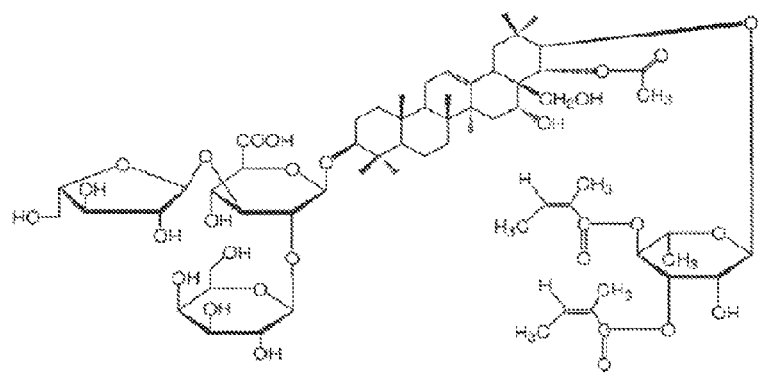
FIG. 2 shows the structure of Compound Y1 with the formula of $C_{65}H_{100}O_{27}$ and the chemical name of 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β,16α, 21β, 22α, 28-pentahydroxyolean-12-ene.

3-O-[β-D-galactopyranosyl(1→2)]-α-L-arabinofuranosyl (1→3)-β-D-glucuronopyranosyl-21,22-O-diangeloyl-3β, 15α, 16α, 21β, 22α, 28-hexahydroxyolean-12-ene Structure 1 as shown in FIG. 31
Structure 2 as shown in FIG. 32
Structure 3 as shown in FIG. 33
Structure 4 as shown in FIG. 34
Structure Y-a as shown in FIG. 35
Structure Y-b as shown in FIG. 36
Structure Y-c as shown in FIG. 37
Structure Y1 (also shown in FIG. 2).

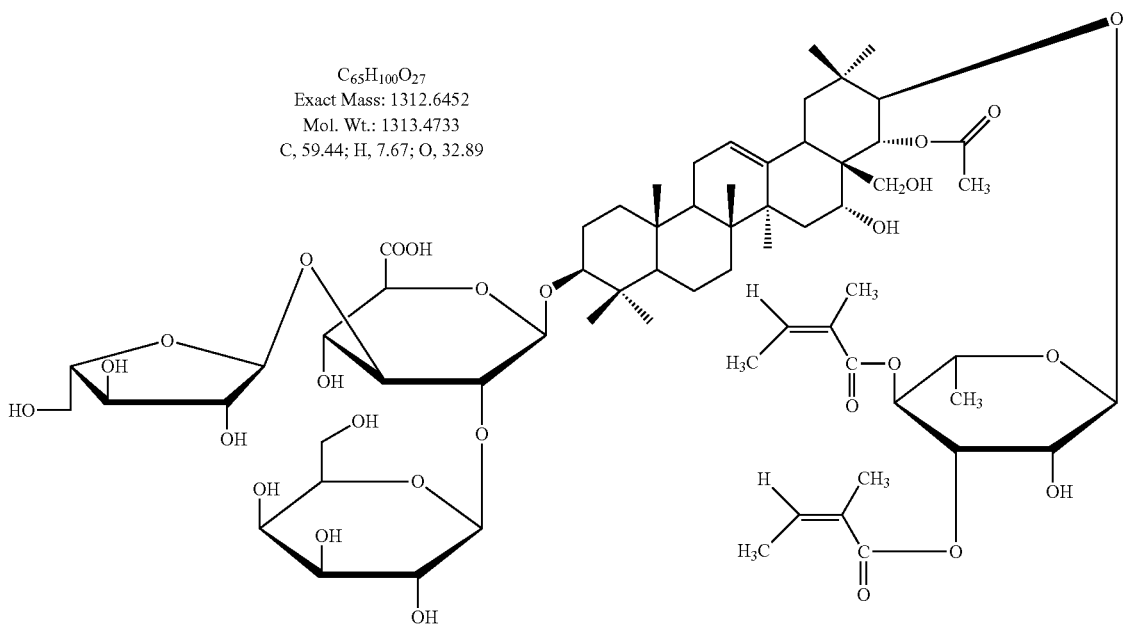

3-O-[β-D-galactopyranosyl(1→2)]-α-L-arabinofuranosyl (1→3)-β-D-glucuronopyranosyl-21-O-(3,4-diangeloyl)-α-L-rhamnophyranosyl-22-O-acetyl-3β,16α, 21β, 22α, 28-pentahydroxyolean-12-ene Structure Y1-a as shown in FIG. 38
Structure Y1-b as shown in FIG. 39
Structure Y1-c as shown in FIG. 40.

This invention further provides a compound comprising the following structure:

Structure R1: 3-O-[angeloyl-(1→3)-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene This invention further provides a compound comprising the following structure:

The structure of compound O54 is presented in the following figure.

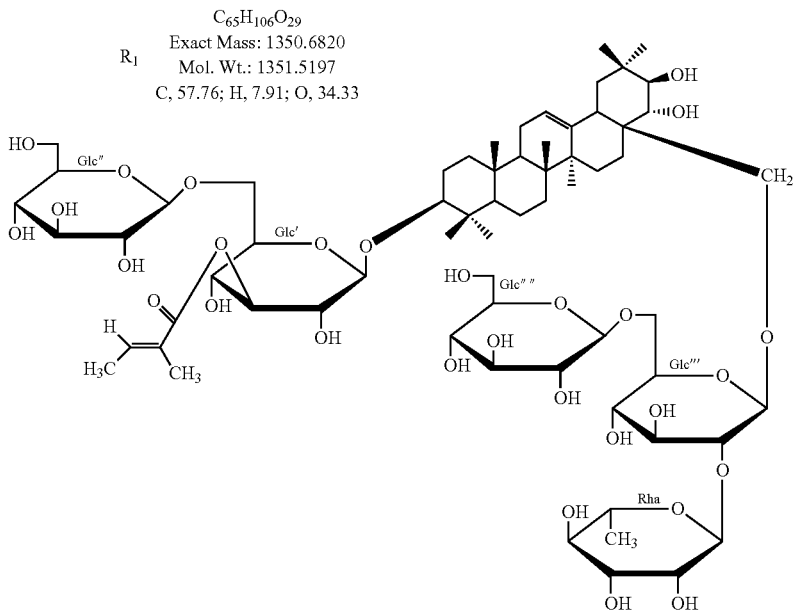

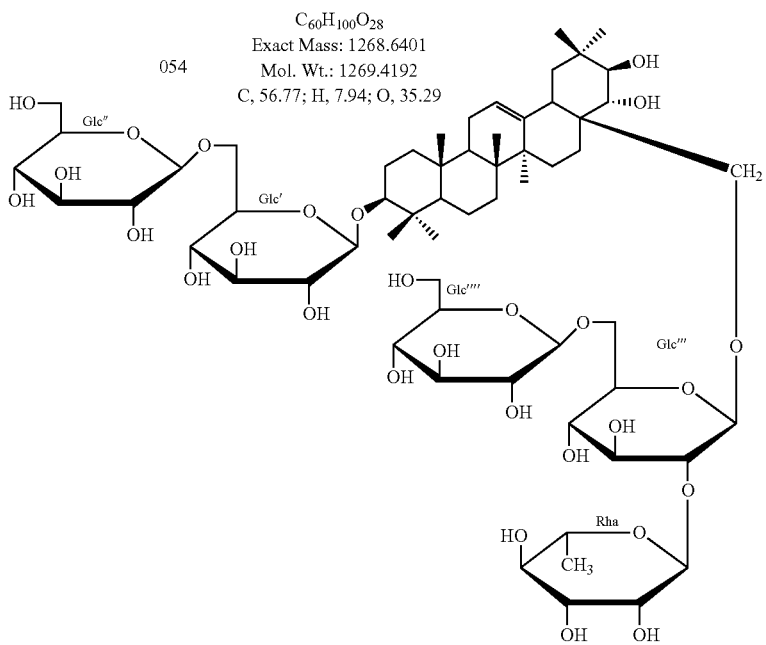

The chemical name of compound-O54 is:

O54:3-O-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene There are many components and pathways monitoring cell proliferation.

The *Xanthoceras Sorbifolia* compound or its derivatives work in the Wnt (Wingless-type MMTV integration site family member) signaling pathway. The Wnt signaling pathway is evolutionarily conserved and controls many events during the embryogenesis. This pathway regulates cell morphology, proliferation, motility and as well as cell apoptosis. It also plays an important role during tumorigenesis. The Wnt pathway has also been observed as inappropriately activated in several different types of cancers in humans.

In the nucleus, the target genes for Wnt signaling are normally kept silent by an inhibitory complex of gene regulatory proteins, e.g. the Groucho corepressor protein bound to the gene regulatory protein LEF-I/TCF. In the absence of a Wnt signal, some β-cartenin is bound to the cytosolic tail of cadherin proteins, and any cytosolic β-cartenin that becomes bound by the APC-axin-GSK-3β will trigger its ubiquitylation and degradation in proteasomes. The result is the decrease of intracellular amount of β-cartenin. However, when the Wnt binding to Frizzled (a seven transmembrane receptor) and LRP (Low density lipoprotein Receptor) activates Dishevelled (a cytoplasmic signaling protein) by a mechanism, this leads to the inactivation of GSK-β3 in the degradation complex by a mechanism which requires casein kinase I, as well as casein kinase II. The activity of the multiprotein complex of β-catenin-axin-adenomatous-polyposis coli (APC)-glycogen synthase kinase (GSK)-3β, which targets β-catenin by phosphorylation for degradation by the proteasome, is then inhibited by Dsh/Dvl (Dishevelled, dsh homolog 1). This then inhibits priming of β-catenin, and indirectly prevents the GSK-3β phosphorylation of β-catenin. When stimulated by Wnt, Dvl recruits the GSK-3 binding protein, GBP, to the multiprotein complex of β-catenin-axin-adenomatous-polyposis coli (APC)-glycogen synthase kinase (GSK)-3β. GBP then titrates GSK-β from axin, and in this way, phosphorylation of β-catenin is inhibited. Then, axin is sequestrated by LRP at the cell membrane. The result of all of this is an accumulation of cytosolic β-catenin. In the nucleus, β-catenin binds to LEF-I/TCF, displaces Groucho, and acts a co-activator to stimulate the transcription of Wnt target genes.

*Xanthoceras Sorbifolia* compositions regulate the components related to Wnt pathways or its receptors, thereby stopping the proliferation of cancer cells.

The compound or its derivatives work in the Mitogens, Ras and a MAP (Mitogen activation protein) kinase pathway. Mitogens stimulate cell division. The binding of mitogens to cell-surface receptors leads to the activation of Ras and a MAP kinase cascade. One effect of this pathway is the increased production of the gene regulatory protein Myc. Myc increases the transcription of several genes, including the gene encoding cyclin D and a subunit of the SCF ubiquitin ligase. The resulting increase in $G_1$-Cdk and $G_1$/S-Cdk activities promotes Rb phosphyorylation and activation of the gene regulatory protein E2F, resulting in S-phase entry, in which $G_1$-Cdk activity initiates Rb phosphorylation, in turn inactivating Rb and freeing E2F to activate the transcription of S-phase genes including the genes for a $G_1$/S-cyclin (cyclin E) and S-cyclin (cyclin A). The resulting appearance of $G_1$/S-Cdk and S-Cdk further enhances Rb phosphorylation, forming a positive feedback loop, and the E2F acts back to stimulate the transcription of its own gene, forming another positive feedback loop. Myc may also promote E2F activity directly by stimulating the transcription of the E2F gene. The result is the increased transcription of genes entry into S phase. However if this pathway is overactive, it will cause cancer cell growth.

Compounds or compositions derived from the plant *Xanthoceras Sorbifolia* regulate the Ras-MAP kinase cascade so that the pathway is not overactive.

The compound or its derivatives work in Ras-dependent or Myc pathway. Sometimes the mutation of amino acid in Ras causes the protein to become permanently overactive, stimulating the Ras-dependent signal pathways overactive in absence of mitogenic stimulation. Similarly, mutations that cause an overexpression of Myc promote excessive cell growth, which in turn promotes the development of cancer.

Compounds or compositions derived from the plant *Xanthoceras Sorbifolia* regulate the components of the Ras-dependent or Myc pathway to make sure it is not overactive.

The compound or its derivatives reactivate the abnormal cell checkpoint mechanism. Inside the cell, there is a checkpoint mechanism which detects abnormal mitogenic stimulation and causes abnormally overactive cells to go into apoptosis. However this mechanism is not active in cancer cells due to mutations in the genes that encode essential components of the checkpoint responses. If the mutation happens in the checkpoint mechanism, the cancer cell will grow and divide endlessly.

Compounds or compositions derived from the plant *Xanthoceras Sorbifolia* reactivate the checkpoint mechanism to stop the cancer cell growth.

The compound or its derivatives affect the extracellular growth signaling pathways. The extracellular growth factors that stimulate cell growth are bound to receptors on the cell surface and activate intracellular signaling pathways. It activates the enzyme PI3-kinase, which promotes protein synthesis, at least partly through the activation of EIF4e and phosphorylated S6 kinase, resulting in increased mRNA translation and then a stimulation of cell growth.

Compounds or compositions derived from the plant *Xanthoceras Sorbifolia* regulate the components or receptor relate to extracellular growth. It binds the receptor of ovarian cancer cells so as to stop the cancer cell growth.

Compounds or compositions derived from the plant *Xanthoceras Sorbifolia* regulate the components relating to Ras and MAP Kinase, which ceases ovarian cancer cell growth.

The compound or its derivatives affect the intracellular mechanism. Cell division is also controlled by an intracellular mechanism that can limit cell proliferation. In normal cells, the Myc protein acts in the nucleus as a signal for cell proliferation. Large quantities of Myc can cause the cell to proliferate in excess and form a tumor.

Compounds or compositions derived from the plant *Xanthoceras Sorbifolia* regulate the components or receptor of the Myc cell's proliferation to stop the tumor cells from dividing.

The compound or its derivatives affect the TGF-alpha signaling pathway. TGF-alpha is produced by keratincytes, macrophages, hepatocytes, and platelets. Its synthesis is stimulated by the infection by viruses. TGF-Alpha induces the long term proliferation of murine and chicken immature hematopoietic progenitor cell such as BFU-E without causing differentiation. It also induces the terminal differentiation of BFU-Ecell into erythrocytes. TGF-Alpha stimulates the proliferation of cultured endothelial cells. It plays an importance role in the vascularisation of tumor tissues.

Compounds or compositions derived from the plant *Xanthoceras Sorbifolia* regulate the components or receptor of TGF-alpha to suppress ovarian cancer and bladder cancer cell growth.

The compound or its derivative compounds affect the TGF-beta signaling pathway. TGF-beta regulates growth and proliferation of cells, blocking growth of many cell types. There are two TGF-beta receptors: Type 1 and Type 2. They are serine-threonine kinases that signal through the SMAD (Protein named after the first two identified, Sma in *C. elegans* and Mad in *Drosophila*) family of transcriptional regulators. The TGF-beta pathway and mutation in SMADs are associated with cancer in humans.

Compounds or compositions derived from the plant *Xanthoceras Sorbifolia* regulate the components or receptor of TGF-beta to suppress the ovarian cancer and bladder cancer cell growth.

The compound or its derivatives reactivate the cell functions which are damaged by DNA viruses. DNA tumor viruses cause cancer by interfering with cell cycle control Rb protein and the p53 protein. Mutation in p53 gene will allow cancer cells to survive and proliferate despite DNA damage. The papillomanius uses the proteins E6 and E7 to release the p53 and Rb respectively. This action activates mutated cells, allowing them to survive and then divide and accumulate. The accumulation of damaged cells can lead to cancer.

Compounds or compositions derived from the plant *Xanthoceras Sorbifolia* regulate the proteins E6 and E7 and release the proteins Rb and p53, which will prevent abnormal cells from dividing. It also regulates or reacts with the protein, causing the cancer cells to die.

The compound or its derivatives affect the p53 signaling pathway. p53 helps multi-cellular organisms cope safely with DNA damage and other stressful cellular events, stopping cell proliferation in circumstances where it would be dangerous. Cancer cells tend to contain large quantities of mutant p53 protein, suggesting that the genetic accidents they undergo or the stresses of growth in an inappropriate environment created the signals that normally activate the p53 protein. Thus, the loss of p53 activity can be extremely dangerous in relation to cancer because it allows mutant cells to continue through the cell cycle. It also allows them to escape apoptosis. So, if their DNA is damaged, some cells will die but the cells which survive will carry on dividing without pausing to repair the damage. This may cause the cells to die, or they could survive and proliferate with a corrupted genome, which could lead to loss of both tumor suppressor genes and the activation of oncogenes, for example by gene amplification. Gene amplification could enable cells to develop resistance against therapeutic drugs.

Compounds or compositions derived from the plant *Xanthoceras Sorbifolia* regulate the components and receptor of the p53 pathway, which stops the cancer cells from dividing.

The compound or its derivatives affect the cell suicide signaling pathway. All cells with a nucleus contain various inactive procaspases, awaiting a signal before destroying the cell. Each suicide protease is made as an inactive proenzyme called procaspase. It is usually activated by proteolytic cleavage by another member of the caspase family. Two of the cleaved fragments come together to form the active part of the caspase, and the active enzyme is thought to be a tetramer of two of these two parts. Each activated caspase molecule can cleave many procaspase molecules, which in turn activates more molecules. Through a chain reaction or cascade, this leads to the explosive action of a large number of procaspase molecules. Then, some of the activated procaspases cleave a number of key proteins in the cell, including specific cytosolic proteins and nuclear-lamins leading to the controlled death of the cell.

Activating the death receptor on the outside of the cell can also trigger inactive procaspases. For example, killer lymphocytes can cause apoptosis by producing the protein Fas on the surface of the targeted cell. These clusters of Fas protein then recruit intracellular adaptor proteins that bind and aggregate procaspase-8 molecules. These then cleave and activate one another. The activated caspase-8 molecules then activate downstream procaspases to induce apoptosis.

However in cancer cells, the signal to destroy the cell is blocked, due to gene mutation. This means that the cancer cells continue to divide, thereby causing a tumor.

Compounds or compositions derived from the plant *Xanthoceras Sorbifolia* unblock the suicide signals, allowing cancer cells to destroy themselves. Structure showed in FIG. 67.

This invention provides a method for inhibiting tumor cell growth comprising contacting an amount of the above-described compound, wherein R1, R2, R3, R4 are short aliphatic chain and R5 contains an oxyl group; and a pharmaceutically acceptable carrier effective to inhibit growth of said tumor cells.

This invention provides a method for inhibiting tumor cell growth comprising contacting an amount of the above-described compounds.

This invention provides a method for inhibiting tumor cell growth comprising contacting an amount of the compound comprising: a sugar; a triterpene or Sapogenin; side chain at Carbon 21 and 22 or Angeloyl groups, operatively linked form the compound; and a pharmaceutically acceptable carrier.

Structure showed in FIG. 67.

This invention provides a method for inhibiting tumor cell growth in a subject comprising administering to the above-described subject, wherein R1, R2, R3, R4 are short aliphatic chain and R5 contains an oxyl group; effective to inhibit growth of said tumor cells and a pharmaceutically acceptable carrier.

This invention provides a method of for inhibiting tumor cell wherein R1=R2=R3=R4=CH3 and R5 contains an oxyl bond.

This invention provides a method for inhibiting tumor cell growth comprising contacting an amount of the above-described compounds.

This invention provides a compound consist of a triterpene or sapongenin, sugar moiety connected to the backbone. A sugar was linked the C21 position where two angeloyl groups were attached. This compound has the anti-cancer activity This invention provides a method for inhibiting tumor cell growth comprising contacting an amount of the compound is a triterpene or sapongenin with any two of angeloyl group or tigloyl group or senecioyl group or their combinations attach to carbon 21 and 22, or any two of angloyl group or tigloyl group or senecioyl group or their combinations attached to a sugar moiety which bonds to carbon 21 or 22.

The structures of this invention or its derivative can be synthesis or from biological sources.

This invention will be better understood from the examples which follow. However, one skilled in the art will readily appreciate that the specific methods and results discussed are merely illustrative of the invention as described more fully in the claims which follow thereafter.

EXPERIMENTAL DETAILS

Experiment 1: Herb Extraction (a) extracting *Xanthoceras Sorbifolia* powder of husks or branches or stems or leaves or kernels or roots or barks with organic solvent at ratio of 1:2 for 4-5 times for 20-35 hours for each time to form an organic extract; (b) collecting the organic extract; (c) refluxing the organic extract for 2-3 times at 80° C. to form second extracts; (d) removing the organic solvent from the second extract; and (e) Drying and sterilizing the extract to form a *Xanthoceras Sorbifolia* extract powder.

Experiment 2: Analysis of *Xanthoceras Sorbifolia* Extract Components by HPLC Chromatography Methods HPLC. A C-18 reverse phase μbondapak column (Water P/N 27324) was equilibrated with 10% acetonitrile, 0.005%

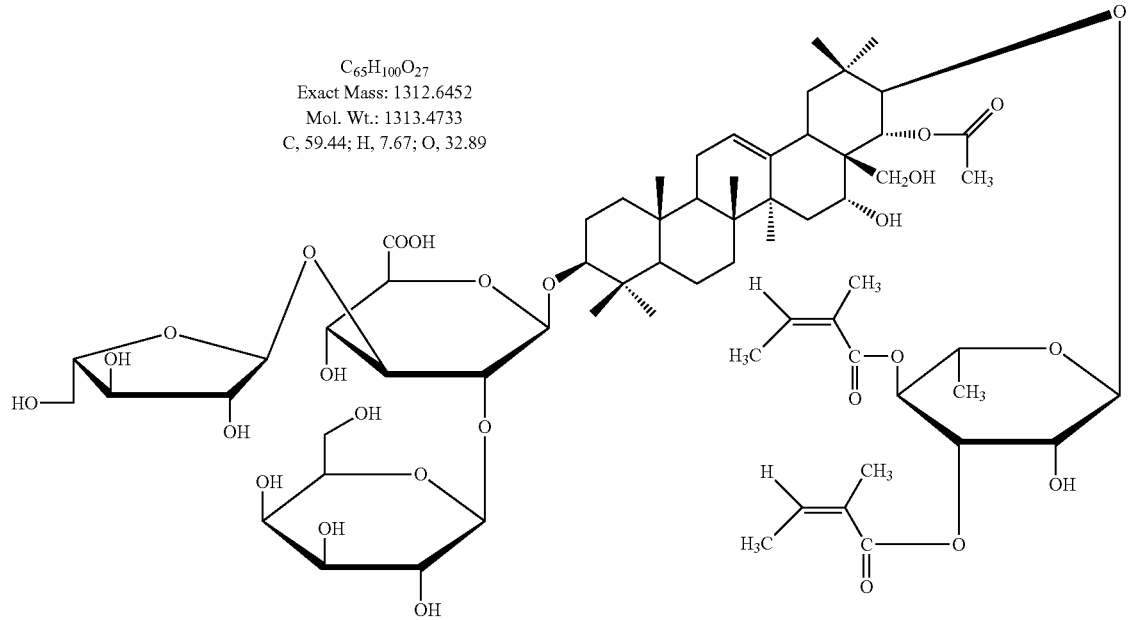

$C_{65}H_{100}O_{27}$
Exact Mass: 1312.6452
Mol. Wt.: 1313.4733
C, 59.44; H, 7.67; O, 32.89

Trifluoroacetic acid (equilibration solution). An extract of *Xanthoceras Sorbifolia* prepared using the methods of the present invention was dissolved in equilibration solution (1 mg/ml) before being applied onto the column. 20 ug of samples was applied into column. Elution conditions: Fractions were eluted (flow rate 0.5 ml/min.) with acetonitrile (concentration gradient from 10% to 80% in 70 min) and then remains at 80% for 10 min (70-80 min). The acetonitrile concentration then decreased to 10% (80-85 min) and remained at 10% for 25 min (85-110 min). The fractions were monitored at 207 nm and recorded in chart with a chart speed of 0.25 cm/min and with a OD full scale of 0.128.

Instruments. Waters Model 510 Solvent Delivery System; Waters 484 tunable Absorbance Detector; Waters 745/745B Data Module Absorbance analysis. The absorption profile of *Xanthoceras Sorbifolia* extract at various wavelengths was determined. An extract of *Xanthoceras Sorbifolia* of the present invention was dissolved in 10% acetonitrile/TFA and scanned at 200-700 nm with a spectrophotometer [Spectronic Ins. Model Gene Sys2].

Results

HPLC. About 60-70 peaks can be accounted for in the profile. Among them four are major peaks, 10 are medium size and the rest are small fractions. The major peaks are labelled with a to z following increased concentration of acetonitrile elution. See FIG. 6.

Absorption maximum. Three absorption maximum were identified for *Xanthoceras Sorbifolia* plant extract; 207 nm, 278 nm and 500 nm. See FIG. 41.

Experiment 3: Screening of Cytotoxicity of *Xanthoceras Sorbifolia* Extract with Cancer Cells Derived from Different Human Organs Using MTT Assay Methods and Materials Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain) and OVCAR-3 (ovary). Cells were grown in culture medium (HeLa-S3, DU145, MCF-7, HepG2 and T98G in MEN (Earle's salts); HTB-9, H460, K562, OVCAR-3 in RPMI-1640; HCT-116, U2OS in McCoy-5A) supplemented with 10% fetal calf serum, glutamine and antibiotics in a 5% CO2 humidified incubator at 37° C.

MTT assay. The procedure for MTT assay followed the method described in (Carmichael et al., 1987) with only minor modifications. Cells were seeded into a 96-wells plate at concentrations of 10,000/well (HTB-9, HeLa, H460, HCT116, T98G, OVCAR-3), 15,000/well (DU145, MCF-7, HepG2, U2OS), or 40,000/well (K562), for 24 hours before drug-treatment. Cells were then exposed to drugs for 48 hours (72 hours for HepG2, U2OS, and 96 hours for MCF-7). After the drug-treatment, MTT (0.5 mg/ml) was added to cultures for an hour. The formation of formazan (product of the reduction of tetrazolium by viable cells) was dissolved with DMSO and the O.D. at 490 nm was measured by an ELISA reader [Dynatech. Model MR700]. The MTT level of cells before drug-treatment was also measured (T0). The % cell-growth (% G) is calculated as:

% $G=(TD-T0/TC-T0) \times 100$ (1)

where TC or TD represent O.D. readings of control or drug-treated cells. When T0>TD, then the cytotoxicity (LC) expressed as % of the control is calculated as:

% $LC=(TD-T0/T0) \times 100$.

Results. Among the 10 cell lines studies, their sensitivity toward *Xanthoceras Sorbifolia* extract can be divided into four groups (most sensitive: Ovary. Sensitive: bladder, bone, prostate, and leukocyte, marginal sensitive: liver, breast, and brain; and lease sensitive: colon, cervix, and lung) (FIG. 8, 10A-D). Their IC50 values are listed in Table 3.1.

TABLE 3.1

IC50 values of *Xanthoceras Sorbifolia* Extract Determined in Different Cancer Cells

| Cancer cells from different organs | IC50 determined by MTT assay (ug/ml) |
|---|---|
| Ovary (most sensitive) | 15-15 |
| Bladder (sensitive) | 45-50 |
| Bone | 40-55 |
| Prostate | 40-50 |
| Leukocyte | 45-50 |
| Liver (marginal sensitive) | 45-65 |
| Breast | 65 |
| Brain | 70-85 |
| Colon (least sensitive) | 90 |
| Cervix | 115 |
| Lung | 110 |

*Xanthoceras Sorbifolia* plant extract stimulate cell growth of bladder, bone and lung cells. See FIGS. 10A, 10D.

To invest Among these cell line studied, it was found that low concentrations of the igate the growth and inhibition components of the *Xanthoceras Sorbifolia* plant extract, the plant extract was fractionated. FIG. 5 shows the results of the screening of cell growth activity of fractions obtained after FPLC chromatography. The assay was conducted with bladder cells. The fractions obtained from FPLC as shown in FIG. 20 were used. As shown in this figure, that different components of *Xanthoceras Sorbifolia* extracts cause either growth or inhibition effects on cells. Only fraction 5962 (Fraction Y) causes cell inhibition. Fractions 610 and 1116 cause minor stimulation of cell growth. Abscissa: concentration (ug/ml). Ordinate: % Cell Growth (determined by MTT assay).

Experiment 4: Purification of Inhibition Components in the *Xanthoceras Sorbifolia* Extract (A) Fractionation of *Xanthoceras Sorbifolia* Extracts Components with FPLC.

Methods

Column. Octadecyl functionalized silica gel; column dimension: 2 cm×28 cm; equilibrated with 10% acetonitrile-0.005% TFA.

Sample loading: 1-2 ml, concentration: 100 mg/ml in 10% acetonitrile/TFA.

Gradient elution: 10-80% acetonitrile in a total volume of 500 ml.

Monitor absorption wavelength: at 254 nm.

Fraction Collector: 5 ml/fractions (collect from 10% to 72% acetonitrile, total 90 fractions)

Instrument: AKTA-FPLC, P920 pump; Monitor UPC-900; Frac-900.

Results.

The elution profile shows 4-5 broad fractions. See FIG. 20. These fractions were analyzed with HPLC. Specific components, i.e., a-z as specified in FIG. 6, are then assigned in the FPLC fractions.

FPLC fractions are grouped into 7 pools and analyzed for cell growth activity with bladder cells with MTT assay. It was found only one pool (#5962) contains inhibition activity. See FIG. 5.

(B) Fractionation of Fraction #5962 with FPLC by a C18 Open Column with 64% Acetonitrile Isocratic Elution Methods Column.

Octadecyl-functionalized silica gel; 50 ml; 2 cm×28 cm; equilibrated with 64% acetonitrile-0.005% TFA.

Sample loading: 0.2 ml, with concentration: 1-2 mg/ml in 65% acetonitrile/TFA.

Elution: 64% acetonitrile isocratic.

Monitor absorption wavelength: at 254 nm.

Fraction Collector: 1 ml fraction (collect the first 90 fractions)

Instrument: AKTA-FPLC, P920 pump; Monitor UPC-900; Frac-900.

Results.

Fraction 5962 was further separated with an open ODS-C18 column using isocratic 64% acetonitrile elution. Two major fractions, i.e., X and Y, were collected. See FIG. 42. MTT assay showed that only the Y fraction has the inhibition activity. See FIG. 43.

(C) Analysis of Fraction Y with HPLC

Methods

Column.

Waters µ-bondapak C18 (3.9 mm×300 cm).

Elution: 35% or 45% isocratic elution.

Flow rate: 0.5 ml/min; monitored at 207 nm with O.D. Scale of 0.128; chart speed: 0.25 cm/min.

Results.

On 45% isocratic analysis, Three fractions of Y were obtained (FIG. 44). (D) Final Isolation of Active Y Component with Preparative HPLC.

Methods

Column: A preparative HPLC column (Waters Delta Pak C18-300A);

Elution: 45% acetonitrile isocratic elution with flow rate of 1 ml/min.

Monitor at 207 nm;

Fractions (designated as Y1, Y2, etc.) were collected and lyophilized.

Results.

Final separation of Y fractions was achieved by HPLC with a preparative column (FIG. 7). These fractions (compound Y1, Y2, Y3 and Y4) including the major fraction Y3 (designated as compound Y) were collected. Re-chromatography of the Compound Y showed a single peak in HPLC with a C18 reverse phase column. See FIG. 7A.

(E) Appearance and Solubility.

The pure Compound Y is amorphous white powder, soluble in aqueous alcohol (methanol, ethanol), 50% acetonitrile and 100% pyridine.

(F) Inhibition analysis of Compound Y with MTT assay.

Inhibition analysis of Compound Y was determined with MTT assay. The results indicated that (a) Compound Y has activity against ovarian cancer cells (OCAR-3) with IC50 value of 1.5 ug/ml which is 10-15 times more potent than the unpurified extract. See FIG. 3; and FIG. 8.

(b) Compound Y maintains its selectivity against ovarian cancer cells versus cervical cancer cells (HeLa). See FIG. 9.

Experiment 5: Determination of the Chemical Structure of Compound Y of *Xanthoceras Sorbifolia* Extract Methods NMR Analysis.

The pure compound Y of *Xanthoceras Sorbifolia* were dissolved in pyridine-D5 with 0.05% v/v TMS. All NMR spectra were acquired using a Bruker Avance 600 MHz NMR spectrometer with a QXI probe ($^1H/^{13}C/^{15}N/^{31}P$) at 298 K. The numbers of scans for 1D $^1H$ spectra were 16 to 128, depending on the sample concentration. 2D HMQC spectra were recorded with spectral widths of 6000×24,000 Hz and data points of 2024×256 for $t_2$ and $t_1$ dimensions, respectively. The numbers of scans were 4 to 128. 2D HMBC were acquired with spectral widths of 6000×30,000 Hz and data points of 2024×512 for $t_2$ and $t_1$ dimensions, respectively. The numbers of scans were 64. The 2D data were zero-filled in $t_1$ dimension to double the data points, multiplied by cosine-square-bell window functions in both $t_1$ and $t_2$ dimensions, and Fourier-transformed using software XWIN-NMR. The final real matrix sizes of these 2D spectra are 2048×256 and 2048×512 data points (F2×F1) for HMQC and HMBC, respectively.

Mass Spectral Analysis.

The mass of samples was analyzed by (A) MALDI-TOF Mass Spectrometry and by (B) ESI-MS Mass spectrometry. (A) Samples for MALDI-TOF were first dissolved in acetonitrile, then mixed with the matrix CHCA (Alpha-cyano-4-hydroxycinnamic acid, 10 mg CHCA/mL in 50:50 water/acetonitrile and 0.1% TFA in final concentration). The molecular weight was determined by the high resolution mass spectroscope analysis with standards. (B) For ESI, the sample was analyzed with LCQ DECA XP Plus machine made by Thermo Finnigan. It is ionized with ESI source and the solvent for the compound is acetonitrile.

Results.

The profile of the proton NMR is presented in FIG. 11. The 2D NMR profiles of HMQC and HMBC are shown in FIGS. 12 and 13, respectively.

Table 5.1 summarizes the 2D NMR chemical shift data and shows the assignment of functional groups derived from these chemical shifts. Based on these data and analysis, the structure of compound Y is assigned and shown below.

Structure of Compound Y:

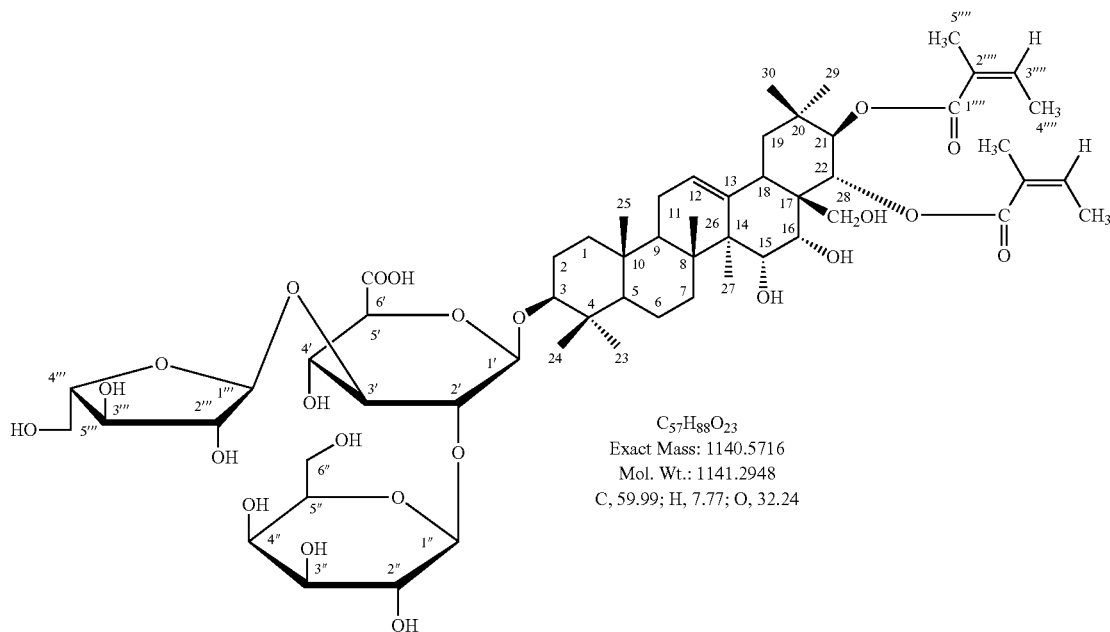

The chemical name of compound Y is: 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene.

TABLE 5.1

$^{13}$C and $^1$H NMR Data for Compound Y (in Pyridine-$d_5$)$^a$

| Position | C | H | Key HMBC correlations |
|---|---|---|---|
| 1 | 38.7 | 0.83, 1.40 | C-3, C-5, C-9 |
| 2 | 26.4 | 1.81, 2.14 | — |
| 3 | 89.6 | 3.25, 1H, dd, 12.0/4.0 Hz | C-23, C-24, GlcA C-1' |
| 4 | 39.4 | — | |
| 5 | 55.3 | 0.78 | — |
| 6 | 18.5 | 1.55, 1.59 | C-8, C-10 |
| 7 | 36.5 | 2.00, 2.10 | C-5, C-9 |
| 8 | 41.2 | — | |
| 9 | 47.0 | 3.06 | C-7, C-8, C-12, C-14, C-26 |
| 10 | 37.2 | — | |
| 11 | 23.7 | 1.74, 1.89 | — |
| 12 | 125.2 | 5.49, 1H, br s | C-9, C-11, C-14, C-18 |
| 13 | 143.4 | — | |
| 14 | 47.5 | — | |
| 15 | 67.3 | 4.21 | C-8, C-27 |
| 16 | 73.6 | 4.45 | C-14, C-15, C-18 |
| 17 | 48.3 | — | |
| 18 | 40.8 | 3.07 | C-12, C-13, C-14, C-16, C-19, C-20, C-28, |
| 19 | 46.8 | 1.41, 1.69 | — |
| 20 | 36.2 | — | |
| 21 | 79.3 | 6.71, 1H, d, 10 Hz | C-20, C-22, C-29, C-30, 21-O-Ang C-1'''' |
| 22 | 73.5 | 6.32, 1H, d, 10 Hz | C-16, C-17, C-21, C-28, 22-O-Ang C-1'''' |
| 23 | 27.7 | 1.26, 3H, s | C-3, C-4, C-5, C-24 |
| 24 | 16.5 | 1.16, 3H, s | C-3, C-4, C-5, C-23 |
| 25 | 16.0 | 0.81, 3H, s | C-1, C-5, C-9, C-10 |
| 26 | 17.3 | 0.99, 3H, s | C-7, C-8, C-9, C-14 |
| 27 | 21.0 | 1.85, 3H, s | C-8, C-13, C-14, C-15 |
| 28 | 62.9 | 3.50, 1H, d, 11.0 Hz, 3.76, 1H, d, 11.0 Hz, | C-16, C-17, C-18, C-22 |
| 29 | 29.2 | 1.09, 3H, s | C-19, C-20, C-21, C-30 |
| 30 | 20.0 | 1.32, 3H, s | C-19, C-20, C-21, C-29 |

TABLE 5.1-continued $^{13}$C and $^1$H NMR Data for Compound Y (in Pyridine-$d_5$)$^a$

| Position | C | H | Key HMBC correlations |
|---|---|---|---|
| GlcA | | | |
| 1' | 104.9 | 4.89, 1H, d, 7.8 Hz | C-3 |
| 2' | 79.1 | 4.38 | GlcA C-1', C-3', Gal C-1'' |
| 3' | 86.1 | 4.20 | GlcA C-2', C-4', Ara C-1''' |
| 4' | 71.5 | 4.42 | GlcA C-3', C-5', C-6' |
| 5' | 78.0 | 4.52 | GlcA C-4', C-6' |
| 6' | 171.9 | — | — |
| Gal | | | |
| 1'' | 104.6 | 5.32, 1H, d, 7.7 Hz | GlcA C-2' |
| 2'' | 73.6 | 4.42 | Gal C-1'', C-3'' |
| 3'' | 74.9 | 4.10 | Gal C-2'' |
| 4'' | 69.5 | 4.56 | Gal C-2'', C-3'' |
| 5'' | 76.4 | 3.94 | Gal C-4'', C-6'' |
| 6'' | 61.6 | 4.43, 4.52 | Gal C-4'', C-5'' |
| Ara-f | | | |
| 1''' | 110.6 | 6.03, 1H, br s | GlcA C-3', Ara C-2''', C-4''' |
| 2''' | 83.4 | 4.94 | Ara C-3''' |
| 3''' | 78.3 | 4.78 | Ara C-2''' |
| 4''' | 85.2 | 4.82 | Ara C-5''' |
| 5''' | 62.2 | 4.12, 4.28 | Ara C-3''' |
| 21-O-Ang | | | |
| 1'''' | 167.7 | — | — |
| 2'''' | 129.6 | — | — |
| 3'''' | 137.2 | 5.96, 1H, dq, 7.0/1.5 Hz | Ang C-1'''', C-4'''', C-5'''' |
| 4'''' | 15.5 | 2.10, 3H, dq, 7.0/1.5 Hz | Ang C-2'''', C-3'''' |
| 5'''' | 20.8 | 2.00, 3H, s | Ang C-1'''', C-2'''', C-3'''' |
| 22-O-Ang | | | |
| 1'''' | 167.9 | — | — |
| 2'''' | 129.8 | — | — |
| 3'''' | 136.3 | 5.78, 1H, dq, 7.0/1.5 Hz | Ang C-1'''', C-4'''', C-5'''' |
| 4'''' | 15.5 | 1.93, 3H, dq, 7.0/1.5 Hz | Ang C-2'''', C-3'''' |
| 5'''' | 20.5 | 1.74, 3H, s | Ang C-1'''', C-2'''', C-3'''' |

$^a$The data were assigned based on HMQC and HMBC correlations.

FIGS. 14 and 15 show the mass spectrum of Compound Y as determined by MALDI-TOF and ESI-MS techniques. Based on these data, the mass of compound Y is 1140.57 which agrees with the theoretical mass of the compound Y.

Conclusion

The active compound Y isolated from extract of *Xanthoceras Sorbifolia* is a triterpenoid saponins with three sugars and biangeloyl groups attached to the C21 and C22 positions of the backbone. The formula of Y is $C_{57}H_{88}O_{23}$, and the chemical name of Compound Y is: 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene.

Experiment 6: Determination of the Chemical Structure of Compound Y1 of *Xanthoceras Sorbifolia* Extract Methods The method for NMR and MS analysis for compound Y1 are same as described in Experiment 5.

Results.

The profile of the H-NMR of Y1 is presented in FIG. 16. The 2D NMR profiles of HMQC, HMBC and COSY are shown in FIGS. 17, 18 and 19, respectively.

Table 6.1 summarizes the 1D and 2D NMR chemical shift data and shows the assignment of functional groups derived from these chemical shifts.

TABLE 6.1

$^{13}C$ and $^1H$ NMR Data for Compound Y1 (in Pyridine-$d_5$)$^a$

| Position | C | H |
|---|---|---|
| 1 | 38.6 | 0.85, 1.33 |
| 2 | 26.3 | 1.86, 2.10 |
| 3 | 89.7 | 3.25, 1H, dd |
| 4 | 39.5 | — |
| 5 | 55.5 | 0.75 |
| 6 | 18.3 | 1.40, 1.43 |
| 7 | 33.1 | 1.20, 1.50 |
| 8 | 40.0 | — |
| 9 | 46.7 | 1.69 |
| 10 | 36.5 | — |
| 11 | 22.5 | 2.30 |
| 12 | 123.6 | 5.36, 1H, br s |
| 13 | 143.5 | — |
| 14 | 41.8 | — |
| 15 | 34.7 | 1.53, 1.73 |
| 16 | 68.5 | 4.45 |
| 17 | 48.2 | — |
| 18 | 39.9 | 3.04 |
| 19 | 47.6 | 1.30, 3.05 |
| 20 | 36.7 | — |
| 21 | 85.3 | 5.05, 1H, d |
| 22 | 73.8 | 6.17, 1H, d |
| 23 | 27.7 | 1.29, 3H, s |
| 24 | 16.5 | 1.16, 3H, s |
| 25 | 15.5 | 0.81, 3H, s |
| 26 | 17.1 | 0.82, 3H, s |
| 27 | 20.6 | 1.83, 3H, s |
| 28 | 63.7 | 3.42, 1H, d, 3.60, 1H, d |
| 29 | 29.9 | 1.42, 3H, s |
| 30 | 19.9 | 1.37, 3H, s |

TABLE 6.1-continued $^{13}C$ and $^1H$ NMR Data for Compound Y1 (in Pyridine-$d_5$)$^a$

| Position | C | H |
|---|---|---|
| GlcA | | |
| 1 | 105.0 | 4.88, 1H, d |
| 2 | 79.0 | 4.37 |
| 3 | 86.0 | 4.20 |
| 4 | 71.6 | 4.43 |
| 5 | 78.0 | 4.50 |
| 6 | 171.8 | — |
| Gal | | |
| 1 | 104.5 | 5.31, 1H, d |
| 2 | 73.5 | 4.43 |
| 3 | 74.9 | 4.10 |
| 4 | 69.5 | 4.57 |
| 5 | 76.3 | 3.95 |
| 6 | 61.1 | 4.44, 4.53 |
| Ara-f | | |
| 1 | 110.9 | 6.04. 1H, br s |
| 2 | 83.3 | 4.95 |
| 3 | 78.3 | 4.78 |
| 4 | 85.2 | 4.82 |
| 5 | 62.0 | 4.13, 4.31 |
| 21-O-Rha | | |
| 1 | 105.1 | 4.92, 1H, d |
| 2 | 70.5 | 4.25 |
| 3 | 74.0 | 5.59 |
| 4 | 71.5 | 5.70 |
| 5 | 68.5 | 3.89 |
| 6 | 17.6 | 1.18, 3H, d |
| Rh-3-Ang | | |
| 1 | 167.2 | — |
| 2 | 127.9 | — |
| 3 | 138.7 | 5.92, 1 H, q |
| 4 | 15.7 | 2.02, 3H, d |
| 5 | 20.6 | 1.92, 3H, s |
| Rh-4-Ang | | |
| 1 | 167.2 | — |
| 2 | 128.0 | — |
| 3 | 137.9 | 5.87, 1 H, q |
| 4 | 15.5 | 1.96, 3H, d |
| 5 | 19.8 | 1.85, 3H, s |
| 22-O-Ac | | |
| 1 | 171.4 | — |
| 2 | 21.8 | 2.31, 3H, s |

Based on these data and analysis, the structure of compound Y1 is assigned and shown below.

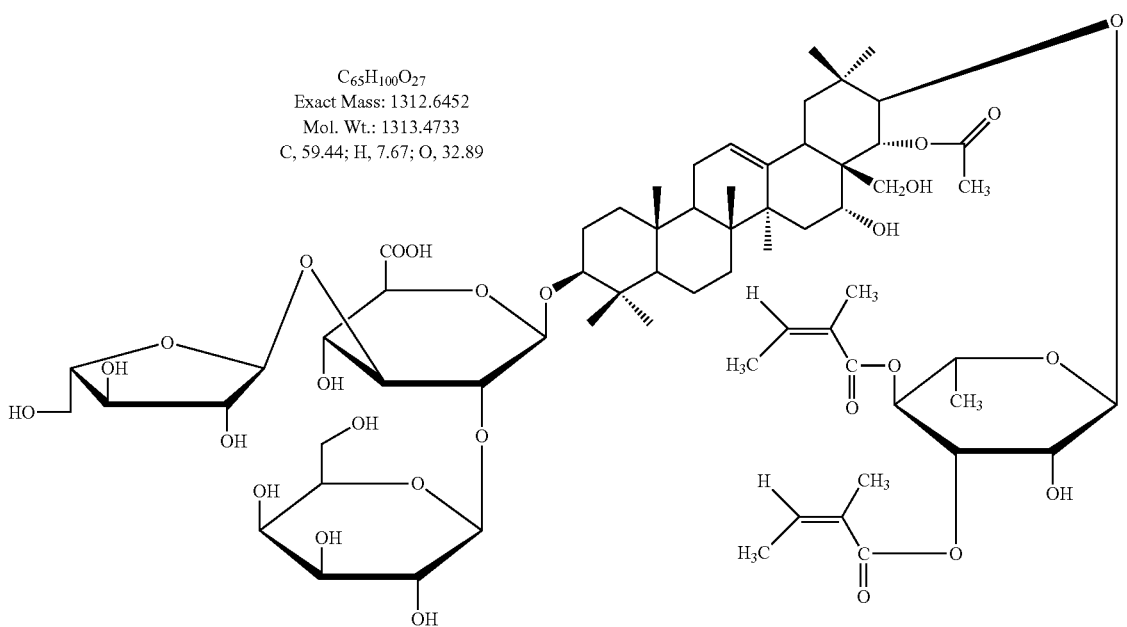

The chemical name of Y1 is: 3-O-[β-D-galactopyranosyl (1→2)]-α-L-arabinofuranosyl(1→3)-β-D-glucuronopyranosyl-21-O-(3,4-diangeloyl)-α-L-rhamnophyranosyl-22-O-acetyl-3β,16α, 21β, 22α, 28-pentahydroxyolean-12-ene.
Conclusion.

Based on the chemical shift analysis, the active compound Y1 isolated from extract of *Xanthoceras Sorbifolia* is a triterpenoid saponins with four sugars and biangeloyl groups attached to the sugar moiety. The formula of Y1 is C65H100O27, Results of Y2 Analysis
The profile of the proton NMR of Y2 is presented in FIG. 51.
The profiles of 2D NMR (HMQC) of Y2 is presented in FIG. 52.
Results of Y4 analysis
The profile of the proton NMR of Y4 is presented in FIG. 53.
The profiles of 2D NMR (HMQC) of Y4 is presented in FIG. 54.

Experiment 7: Acid and Alkaline and Enzyme Hydrolysis of Compound Y

Removal of Sugars from Compound Y.
Acid Hydrolysis of compound Y generates a compound with the following structure, designated herein as Y-c: (FIG. 37).

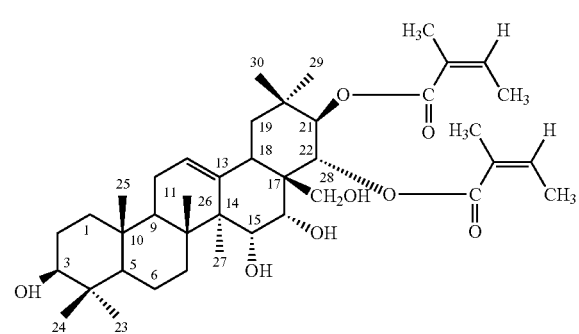

Methods:
5 mg of compound Y is dissolved in 3 ml of MeOH and then treated with 3 ml of 3N HCl. Hydrolysis of saponins will be conducted under reflux for 4 hr. After hydrolysis, the solution will be neutralized with 5% $Na_2CO_3$ and extracted with Ethyl acetate three times to afford an aqueous layer and an organic layer, containing sugars and aglycon, respectively. Aglycon from the organic layer will be further purified on Silica gel chromatography in ($CHCl_3$: MeOH, 1:9) or with C18 ODS HPLC chromatography. About 2 mg of compound with the above structure Y-c can be obtained.
Method reference: Essentials of Carbohydrate Chemistry. By John F. Robyt, (Springer, 1998).
Partial Removal of Sugars from Compound Y.
The linkage of oligosaccharide can be cleaved by partial acid hydrolysis and by specific enzyme hydrolysis. For example, the 1→4 linkage of arabinofuranosyl can be removed by α-amylase. Other enzymes such as β-amylase, isoamylase, glucose oxidase, mannanse and pullulanase can be used to cleave individual saccharide in saponins.
Compound Structure showed in FIG. 70.
Compound structure showed in FIG. 69.
Compound Structure showed in FIG. 68.

Experiment 8 Purification of Component R from *Xanthoceras Sorbifolia* Extract (A) Fractionation of *Xanthoceras Sorbifolia* extracts components with FPLC. Methods
Column: Octadecyl functionalized silica gel; column dimension: 2 cm×28 cm; equilibrated with 10% acetonitrile-0.005% TFA.
Sample loading: volume: 1-2 ml, concentration: 100 mg/ml in 10% acetonitrile/TFA.
Gradient elution: 10-80% acetonitrile in a total volume of 500 ml.
Monitored at 254 nm.
Fraction Collector: 5 ml/fraction.
Instrument: AKTA-FPLC, P920 pump; Monitor UPC-900; Frac-900.

Results

The elution profile shows 4-5 broad fractions (FIG. 20). These fractions were analyzed with HPLC. By comparison with the profiles of the original sample, specific component, in this case the R component, is identified and then collected for further purification.

Fractionation of R with FPLC with 30% Acetonitrile Isocratic Elution Methods

Column: Octadecyl-functionalized silica gel; column dimemsion: 2 cm×28 cm; equilibrated with 30% acetonitrile-0.005% TFA.
Sample loading: 0.2 ml, with concentration: 1-2 mg/ml.
Elution: 30% acetonitrile isocratic. Monitor absorption wavelength: at 254 nm.
Fraction Collector: 5 ml/fraction.
Instrument: AKTA-FPLC, P920 pump; Monitor UPC-900; Frac-900.
Results Fraction No. 39-41 from gradient elution of FPLC were pooled and further purified with an open ODS-C18 column with isocratic 30% acetonitrile elution. Six identifiable fractions in two groups were collected. See FIG. 45. Fractions 6-13 were further characterized with HPLC.

Analysis and Isolation of R with HPLC
Methods

Column: Waters μ-bondapak C18 (3.9×300 nm) and Waters DeltaPak C18 (7.8 mm×30 cm).
Elution: Gradient (10-80%) and 30% isocratic elution.
Flow rate: 0.5 ml/min; monitored at 207 nm; with attenuation 0.128; chart speed: 0.25 cm/min.
Results On HPLC gradient elution analysis, Fractions #9-11 contain a major component with a few minor components. See FIG. 46. These components were further separated into 4-5 components with the 30% acetonitrile isocratic elution in a DeltaPak column. The fraction designated herein as "R1", is the major component. See FIG. 47A. The pure R1 was subsequently collected from the column elution. See FIG. 47B.

Appearance and Solubility.

The pure R1 is amorphous white powder, soluble in aqueous alcohol (methanol, ethanol), 50% acetonitrile and 100% pyridine.

Determination of the chemical structure of R1 isolated from *Xanthoceras Sorbifolia* Extract Methods The NMR and MS Analysis of R1 are same as those described in Experiment 5.
Results The proton NMR profile of pure R1 is presented in FIG. 21. The 2D NMR (HMQC) spectra of R1 are presented in FIG. 22. The 2D NMR (HMBC) spectra of R1 are presented in FIG. 23. The 2D COSY spectrum is presented in FIG. 24. The Carbon 13 NMR spectrum is presented in FIG. 25.

Based on all the data presented above, Table 8.1 summarizes the results of the structural analysis and the assignment of the functional groups of compound R1.

TABLE 8.1

$^{13}$C and $^1$H NMR Data for R1 (in Pyridine-d$_5$)$^a$

| Position | C | H | Key HMBC correlations |
|---|---|---|---|
| 1 | 38.6 | 1.01, 1.63 | C-3, C-25 |
| 2 | 26.4 | 1.89, 2.33 | C-3 |
| 3 | 89.1 | 3.26, 1H, dd, 12.0/4.2 Hz | C-23, C-24, Glc' C-1 |
| 4 | 39.2 | — | — |
| 5 | 55.5 | 0.69, 1H, d, 11.4 Hz | C-4, C-6, C-7, C-9, C-10, C-23, C-24, C-25 |
| 6 | 18.3 | 1.30, 1.39 | C-5, C-8, C-10 |
| 7 | 32.5 | 1.41 | C-6, C-26 |
| 8 | 40.1 | — | — |
| 9 | 47.7 | 1.61 | C-1, C-5, C-8, C-10, C-11, C-14, C-25, C-26 |
| 10 | 36.7 | — | — |
| 11 | 23.7 | 1.90, 2.00 | C-8, C-12, C-14 |
| 12 | 123.5 | 5.35, 1H, br s | C-9, C-14, C-18 |
| 13 | 142.9 | — | — |
| 14 | 41.9 | — | — |
| 15 | 25.7 | 1.88, 1.90 | — |
| 16 | 18.0 | 1.95, 2.29 | C-14, C-17, C-18 |
| 17 | 43.1 | — | — |
| 18 | 41.6 | 2.60, dd, 12.0/2.4 Hz | C-19 |
| 19 | 46.3 | 1.28, 2.11 | C-18, C-20, C-29, C-30 |
| 20 | 36.1 | — | — |
| 21 | 76.5 | 3.73, 1H, d, 9.6 Hz | C-20, C-22, C-29, C-30 |
| 22 | 75.1 | 4.31, 1H, d, 9.6 Hz | C-16, C-17, C-21 |
| 23 | 27.9 | 1.20, 3H, s | C-3, C-4, C-5, C-24 |
| 24 | 16.6 | 0.95, 3H, s | C-3, C-4, C-5, C-23 |
| 25 | 15.7 | 0.95, 3H, s | C-1, C-5, C-9, C-10 |
| 26 | 16.7 | 1.07, 3H, s | C-7, C-8, C-9, C-14 |
| 27 | 26.1 | 1.25, 3H, s | C-8, C-13, C-14 |
| 28 | 75.8 | 4.10, 2H, br s | C-16, C-17, C-18, C-22, Glc''' C-1 |
| 29 | 30.2 | 1.22, 3H, s | C-19, C-20, C-21, C-30 |
| 30 | 19.5 | 1.26, 3H, s | C-19, C-20, C-21, C-29 |
| 3-Glc' | | | |
| 1 | 106.5 | 4.84, 1H, d, 7.2 Hz | C-3, Glc' C-5 |
| 2 | 73.2 | 3.99 | — |
| 3 | 79.1 | 5.90, 1H, t, 9.6 Hz | Ang C-1, Glc' C-2, C-4 |
| 4 | 69.4 | 4.26 | Glc' C-6 |
| 5 | 76.4 | 3.95 | Glc' C-1, C-3 |
| 6 | 69.8 | 4.40, 4.83 | Glc' C-4, Glc'' C-1 |
| Ang | | | |
| 1 | 167.9 | — | — |
| 2 | 128.7 | — | — |
| 3 | 136.7 | 5.80, 1H, ddd, 6.6/0.6 Hz | Ang C-1, C-4, C-5 |
| 4 | 15.7 | 1.93, 3H, dd, 6.6/0.6 Hz | Ang C-2, C-3 |
| 5 | 20.6 | 1.81, 3H, s | Ang C-1, C-2, C-3 |
| Glc'' | | | |
| 1 | 105.4 | 5.09, 1H, d, 7.8 Hz | Glc' C-6, Glc'' C-5 |
| 2 | 74.9 | 4.05 | Glc'' C-1 |
| 3 | 78.2$^b$ | 4.22 | Glc'' C-5 |
| 4 | 71.4$^c$ | 4.24 | Glc'' C-6 |
| 5 | 78.3$^d$ | 3.90 | — |
| 6 | 62.4$^e$ | 4.40, 4.51 | Glc'' C-4 |
| 28-Glc''' | | | |
| 1 | 103.5 | 4.72, 1H, d, 7.2 Hz | C-28 |
| 2 | 75.3 | 4.22 | Glc''' C-1, C-3, Rha C-1 |
| 3 | 79.8 | 4.25 | — |
| 4 | 71.6 | 4.20 | — |
| 5 | 76.6 | 4.13 | Glc''' C-3 |
| 6 | 70.0 | 4.67, 2H, d, 10 Hz | Glc'''' C-1, Glc''' C-4, C-5 |
| Rha | | | |
| 1 | 100.7 | 6.52, 1H, br s | Glc''' C-2, Rha C-3, C-5 |
| 2 | 72.3$^f$ | 4.70, d, 3.0 Hz | Rha C-4 |
| 3 | 72.3$^f$ | 4.63, dd, | Rha C-2 |
| 4 | 74.1 | 4.35 | Rha C-2, C-5 |
| 5 | 69.1 | 4.79 | — |
| 6 | 18.7 | 1.82, 3H, d, 6.6 Hz | Rha C-4, C-5 |
| Glc'''' | | | |
| 1 | 105.5 | 5.01, 1H, d, 7.8 Hz | Glc''' C-6, Glc'''' C-5 |
| 2 | 74.9 | 4.05 | Glc'''' C-1 |
| 3 | 78.2$^b$ | 4.22 | Glc'''' C-5 |
| 4 | 71.4$^c$ | 4.24 | Glc'''' C-6 |
| 5 | 78.3$^d$ | 3.90 | — |
| 6 | 62.5$^e$ | 4.40, 4.51 | Glc'''' C-4 |

$^a$The data were assigned based on COSY, HMQC and HMBC correlations.
$^{b,c,d,f}$The data with the same labels in each column were overlapped.
$^e$The data with the same labels in each column may be interchanged.

Conclusion

Based on the chemical shift analysis, the compound R1 isolated from extract of *Xanthoceras Sorbifolia* is a triterpenoid saponins with five sugars and one angeloyl group attached to the sugar moiety. The chemical structure of R1 is:

$C_{65}H_{106}O_{29}$
Exact Mass: 1350.6820
R1  Mol. Wt.: 1351.5197
C, 57.76; H, 7.91; O, 34.33

The formula of compound R1 is $C_{65}H_{106}O_{29}$, and the chemical name of R1 is: 3-O-[angeloyl-(1→3)-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene Experiment 9

Purification of Component-O from *Xanthoceras Sorbifolia* Extract
(A) Fractionation of *Xanthoceras Sorbifolia* Extracts Components with FPLC
Methods:
Column: Octadecyl functionalized silica gel; column dimension: 2 cm×28 cm; equilibrated with 10% acetonitrile-0.005% TFA.
Sample loading: 1-2 ml, concentration: 100 mg/ml in 10% acetonitrile/TFA.
Gradient elution: 10-80% acetonitrile in a total volume of 500 ml.
Monitor absorption wavelength: at 254 nm.
Fraction Collector: 5 ml/fraction.
Instrument: AKTA-FPLC, P920 pump; Monitor UPC-900; Frac-900.
Results.
The elution profile shows 4-5 broad fractions (FIG. 20). These fractions were analyzed with HPLC. By comparison with the profiles of the original sample, specific component, in this case the component-O, is identified (#28-30) and were collected for further purification.
(B) Purification of Component-O with HPLC with 20% Acetonitrile Isocratic Elution.
Methods.
Column: A preparative HPLC column (Waters Delta Pak C18-300A);
Samples: Fraction #28-30 from the gradient elution of FPLC were pooled and applied into the HPLC.
Elution: 20% acetonitrile isocratic with flow rate of 1 ml/min. Fractions were collected. Monitored at 207 nm; Fractions of interested were collected and lyophilized.
Results.
Sixteen identifiable fractions were observed in the elution profiles (FIG. 48). Fractions 28, 34 and 54 were further characterized with HPLC using same condition (FIGS. 49 and 50). As show in these figures, a single peak elution of fractions 28, 34 and 54 was obtained, indicating that they are homogeneous fractions (pure). These purified components are named as Compound O28, O34 and O54, respectively.
Appearance and solubility: The purified O-23 and O-34 are light yellow amorphous powder, soluble in aqueous alcohol (methanol, ethanol), 50% acetonitrile and 100% pyridine. The purified O-54 is white amorphous powder, soluble in aqueous alcohol (methanol, ethanol), 50% acetonitrile and 100% pyridine.
(C) Structure Analysis of Compound-O54.
Methods:
The NMR and MS analysis of O54 are same as those described in Experiment 5.
Results
The profile of the proton NMR of compound-O54 is presented in FIG. 28. The 2D NMR (HMQC) spectra of O54 is presented in FIG. 29. The 2D NMR (HMBC) spectra of O54 are presented in FIG. 30.
Based on all the data presented above, Table 9.1 summarizes the results of the structural analysis and the assignment of the functional groups of compound-O54.

TABLE 9.1

$^{13}C$ and $^1H$ NMR data for O54 (in Pyridine-$d_5$)$^a$

| Position | C | H | Key HMBC correlations |
|---|---|---|---|
| 1 | 38.6 | 1.03, 1.60 | C-3, C-25 |
| 2 | 26.3 | 1.90, 2.40 | C-3 |
| 3 | 89.1 | 3.30, 1H, dd, 12.0/4.8 Hz | C-23, C-24, Glc' C-1 |
| 4 | 39.3 | — | |
| 5 | 55.6 | 0.70, 1H, d, 12.0 Hz | C-4, C-6, C-7, C-9, C-10, C-23, C-24, C-25 |
| 6 | 18.5 | 1.30, 1.40 | C-5, C-8, C-10 |
| 7 | 32.5 | 1.40 | C-6, C-26 |
| 8 | 40.2 | — | — |

TABLE 9.1-continued

<sup>13</sup>C and <sup>1</sup>H NMR data for 054 (in Pyridine-d$_5$)$^a$

| Position | C | H | Key HMBC correlations |
|---|---|---|---|
| 9 | 47.8 | 1.59 | C-1, C-5, C-8, C-10, C-11, C-14, C-25, C-26 |
| 10 | 36.6 | — | — |
| 11 | 23.6 | 1.90, 1.95 | C-8, C-12, C-14 |
| 12 | 123.5 | 5.34, 1H, br s | C-9, C-14, C-18 |
| 13 | 142.8 | — | — |
| 14 | 41.9 | — | — |
| 15 | 25.8 | 1.90 | — |
| 16 | 18.1 | 1.90, 2.31 | C-14, C-17, C-18 |
| 17 | 43.2 | — | — |
| 18 | 41.7 | 2.58, dd, 13.2/2.0 Hz | C-19 |
| 19 | 46.5 | 1.28, 2.08 (t, 1H, t, 13.2 Hz) | C-18, C-20, C-29, C-30 |
| 20 | 36.2 | — | — |
| 21 | 76.6 | 3.73, 1H, d, 10.2 Hz | C-20, C-22, C-29, C-30 |
| 22 | 75.1 | 4.31, 1H, d, 10.2 Hz | C-16, C-17, C-21 |
| 23 | 27.9 | 1.22, 3H, s | C-3, C-4, C-5, C-24 |
| 24 | 16.8 | 0.98, 3H, s | C-3, C-4, C-5, C-23 |
| 25 | 15.8 | 0.95, 3H, s | C-1, C-5, C-9, C-10 |
| 26 | 16.9 | 1.07, 3H, s | C-7, C-8, C-9, C-14 |
| 27 | 26.1 | 1.26, 3H, s | C-8, C-13, C-14 |
| 28 | 75.9 | 4.10, 2H, br s | C-16, C-17, C-18, C-22, Glc''' C-1 |
| 29 | 30.1 | 1.24, 3H, s | C-19, C-20, C-21, C-30 |
| 30 | 19.6 | 1.26, 3H, s | C-19, C-20, C-21, C-29 |
| 3-Glc' | | | |
| 1 | 106.5 | 4.86, 1H, d, 7.8 Hz | C-3, Glc' C-5 |
| 2 | 74.9 | 3.99 | — |
| 3 | 78.2$^b$ | 4.20 | — |
| 4 | 70.8 | 4.36 | — |
| 5 | 76.5 | 3.95 | — |
| 6 | 70.5 | 4.40, 4.88 (d, 1H, 9.6 Hz) | Glc'' C-1 |
| Glc'' | | | |
| 1 | 105.5 | 5.12, 1H, d, 7.8 Hz | Glc' C-6, Glc'' C-5 |
| 2 | 75.0$^c$ | 4.03 | Glc'' C-1 |
| 3 | 78.2$^b$ | 4.20 | — |
| 4 | 71.5$^d$ | 4.20 | — |
| 5 | 78.3$^e$ | 3.91 | — |
| 6 | 62.4$^f$ | 4.40, 4.48 | Glc'' C-4, C-5 |
| 28-Glc''' | | | |
| 1 | 103.6 | 4.72, 1H, d, 7.2 Hz | C-28 |
| 2 | 75.3 | 4.22 | Glc''' C-1, C-3, Rha C-1 |
| 3 | 79.8 | 4.21 | — |
| 4 | 71.6 | 4.19 | — |
| 5 | 76.8 | 4.14 | Glc''' C-3 |
| 6 | 70.3 | 4.67, 2H, d, 10.2 Hz | Glc'''' C-1, Glc''' C-4, C-5 |
| Rha | | | |
| 1 | 100.6 | 6.51, 1H, br s | Glc''' C-2, Rha C-3, C-5 |
| 2 | 72.3$^g$ | 4.72, d, 3.0 Hz | Rha C-4 |
| 3 | 72.3$^g$ | 4.61, dd, 10.8/3.6 Hz, | Rha C-2 |
| 4 | 74.1 | 4.36 | Rha C-2, C-5 |
| 5 | 69.2 | 4.77 | — |
| 6 | 18.6 | 1.80, 3H, d, 6.0 Hz | Rha C-4, C-5 |
| Glc'''' | | | |
| 1 | 105.6 | 5.00, 1H, d, 7.8 Hz | Glc''' C-6, Glc'''' C-5 |
| 2 | 75.0$^c$ | 4.03 | Glc'''' C-1 |
| 3 | 78.2$^b$ | 4.20 | — |
| 4 | 71.5$^d$ | 4.20 | — |
| 5 | 78.3$^e$ | 3.91 | — |
| 6 | 62.5$^f$ | 4.40, 4.48 | Glc'''' C-4, C-5 |

$^a$The data were assigned based on COSY, HMQC and HMBC correlations.
$^{b,c,d,e,g}$The data with the same labels in each column were overlapped.
$^f$The data with the same labels in each column may be interchanged.

Conclusion

Based on the chemical shift analysis, the compound O54 isolated from extract of *Xanthoceras Sorbifolia* is a triterpenoid saponins with five sugars. The chemical structure of Compound O54 is:

The structure of compound O54 is presented in the following figure.

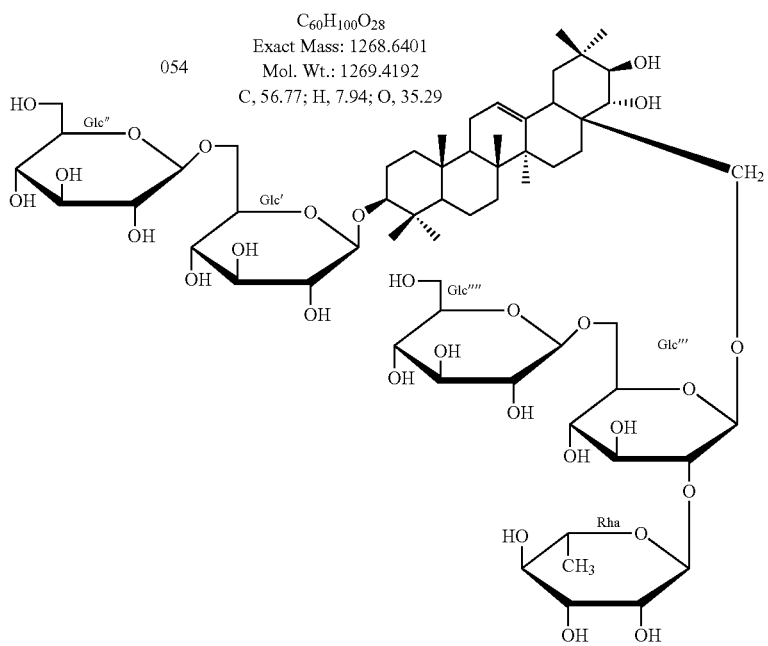

The formula of compound O54 is $C_{60}H_{100}O_{28}$, and the chemical name of O54 is: The chemical name of compound-O54 is: 3-O-β-D-glucopyranosyl-(1→6)]-β-D-glucopyranosyl-28-O-[α-L-rhamnopyranosyl-(1→2)-β-D-glucopyranosyl-(1→6)-β-D-glucopyranosyl-3β, 21β, 22α, 28-tetrahydroxyolean-12-ene.

Results of O28 Analysis

The profile of the proton NMR of O28 is presented in FIG. 55.

The profiles of 2D NMR (HMQC) of O28 is presented in FIG. 56.

Results of O34 Analysis

The profile of the proton NMR of O34 is presented in FIG. 57.

The profiles of 2D NMR (HMQC) of O34 is presented in FIG. 58.

Experiment 11: Extracts X and Y from the Wenguanguo Plant (*Xanthoceras Sorbifolia*) Improve Learning in Normal Aging Mice Extracts X and Y are Different Wenguanguo Extracts Aging male mice at 16 months of age weighing 35-55 gm were trained in a SMG-2 filled with water 11 cm deep (25-26° C.). The SMG-2 had a start point, 4 blind terminals, the escape platform and their routes. The mice were trained to find the escape platform, and the escape latencies from the water and error frequencies were recorded. After training 3 times, the mice which escaped from the water in 2 minutes were selected for the test. The selected aging mice were divided into 9 groups of 11: 1) control: receiving normal saline (NS); 2) Positive control: receiving Xi-en-kai 0.9 g/kg; 3) X-I group: receiving 100 mg/kg4; 4) X-11 group: receiving 200 mg/kg; 5) X-III group: receiving 400 mg/kg; 6) Y-1 group: receiving 125 mg/kg; 7) Y-11 group: receiving 250 mg/kg; 8) Y-III group: receiving 500 mg/kg and 9) model group.

All the drugs were received through oral administration, 20 ml/kg, 3, 6 and 9 days before the water maze test. The escape latencies (EL) from the water and error frequencies were recorded. All data were analyzed with t-test.

11.1. After 3 days of administration of extracts X and Y from Wenguanguo Plant, hereinafter as "X" and "Y", respectively, the escape latency in the water maze by the group 9 mice receiving 500 mg/kg of Y decreased significantly compared with the control (P<0.05). The other dosage treatments showed improvement too but not significant ones. See Table 11.1.

TABLE 11.1

The Learning Effects of Plant Extracts after Administration in Aging Mice for 3 days

| Group | Blind Terminal 1 | Blind Terminal 2 | Blind Terminal 3 | Blind Terminal 4 | Error Frequency | EL(sec) |
|---|---|---|---|---|---|---|
| control | 2.12 ± 2.27 | 3.62 ± 1.63 | 1.37 ± 2.41 | 2.68 ± 2.52 | 9.81 ± 3.42 | 64.12 ± 24.8 |
| positive | 1.09 ± 1.57 | 2.0 ± 0.89 | 2.0 ± 1.26 | 2.0 ± 2.64 | 7.09 ± 2.30 | 39.45 ± 16.32 |
| X I | 1.18 ± 1.4 | 3.36 ± 2.65 | 2.27 ± 2.14 | 0.81 ± 1.07 | 7.63 ± 4.47 | 51.72 ± 17.23 |
| X II | 2.2 ± 1.61 | 2.5 ± 1.51 | 2.0 ± 1.69 | 2.8 ± 1.03 | 9.5 ± 4.03 | 50.3 ± 20.84 |
| X III | 1.45 ± 2.33 | 2.72 ± 2.64 | 2.09 ± 2.11 | 1.81 ± 1.94 | 8.09 ± 4.67 | 46.91 ± 19.18 |
| Y I | 1.36 ± 1.91 | 3.0 ± 1.94 | 3.45 ± 3.2 | 1.09 ± 1.44 | 8.18 ± 3.78 | 46.36 ± 22.33 |
| Y II | 1.63 ± 1.80 | 3.81 ± 1.94 | 2.36 ± 1.12 | .36 ± 1.50 | 10.18 ± 3.02 | 48.36 ± 20.61 |
| Y III | 2.18 ± 3.34 | 1.63 ± 1.21 | 1.54 ± 1.29 | 1.81 ± 1.40 | 7.18 ± 4.30 | 41.45 ± 16.48* |

P < 0.05*

11.2. After 6 days of administration of X and Y, the error frequency in the water maze in the mice with all dosage treatments decreased significantly (P<0.05, P<0.01). The escape latency in the water maze by the group 9 mice receiving 500 mg/kg of Y decreased significantly (P<0.05). See Table 11.2.

TABLE 11.2

The Learning Effects of Plant Extract after Administration in aging mice for 6 days

| Group | Blind Terminal | Blind Terminal | Blind Terminal | Blind Terminal | Error Frequency | EL(sec) |
|---|---|---|---|---|---|---|
| Control | 2.74 ± 2.98 | 4.0 ± 2.67 | 3.26 ± 3.02 | 3.0 ± 2.67 | 12.9 ± 4.20 | 60.58 ± 24.6 |
| positive | 1.64 ± 2.06 | 3.73 ± 2.05 | 1.18 ± 1.47 | 2.0 ± 1.90 | 8.55 ± 4.61* | 38.64 ± 13.68 |
| X I | 1.7 ± 1.49 | 3.1 ± 2.02 | 1.8 ± 2.10 | 1.9 ± 1.66 | 8.5 ± 1.65* | 47.7 ± 11.13 |
| X II | 1.18 ± 1.66 | 3.5 ± 2.02 | 2.0 ± 1.73 | 1.73 ± 2.05 | 8.45 ± 3.14* | 49.0 ± 13.29 |
| X III | 1.09 ± 1.30 | 3.55 ± 2.07 | 1.91 ± 1.58 | 1.55 ± 1.44 | 8.0 ± 2.32* | 46.36 ± 13.31 |
| Y I | 1.0 ± 1.67 | 3.09 ± 1.58 | 2.64 ± 1.8 | 1.54 ± 2.02 | 8.36 ± 3.07* | 57.27 ± 19.88 |
| Y II | 1.36 ± 1.50 | 3.36 ± 2.06 | 2.0 ± 1.67 | 1.18 ± 1.17 | 7.91 ± 3.05** | 47.55 ± 22.93 |
| Y III | 1.2 ± 1.14 | 4.1 ± 1.79 | 2.5 ± 2.84 | 1.4 ± 1.90 | 9.0 ± 3.23* | 39.9 ± 8.56* |

P < 0.05*
P < 0.01**

Figure 60A:
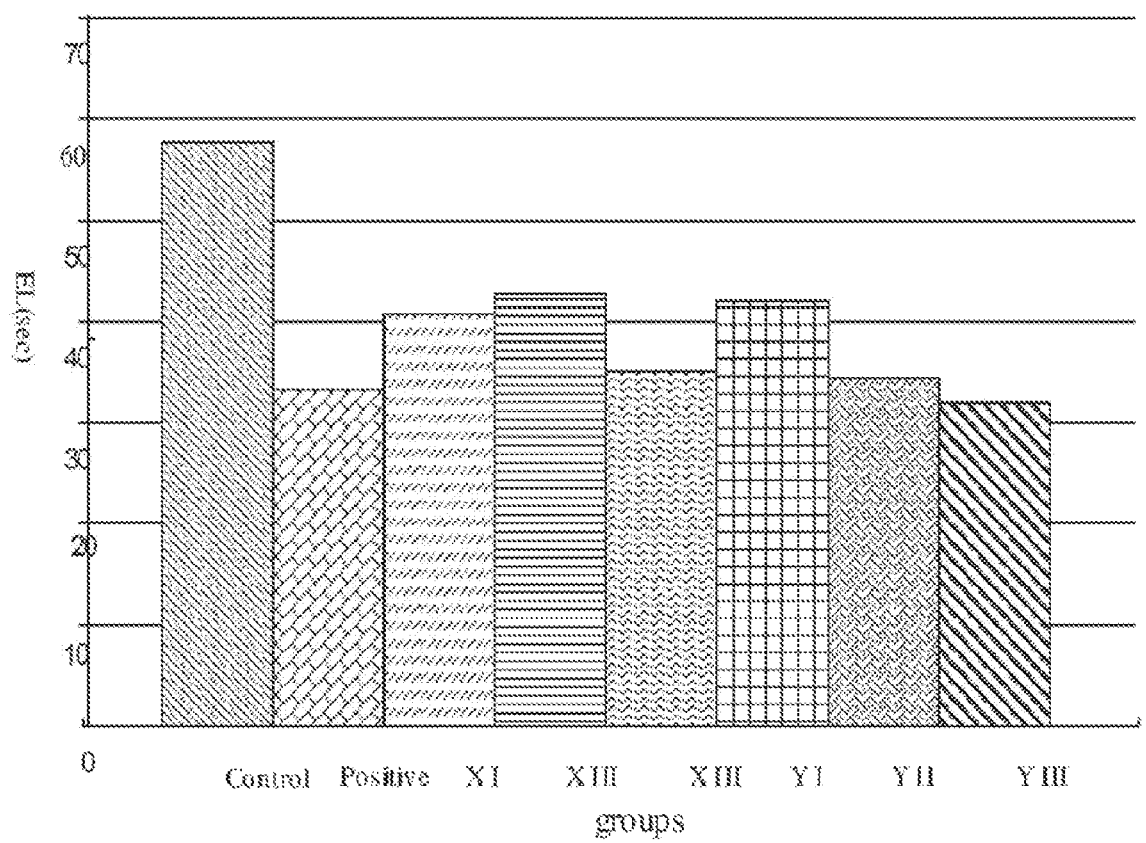
Figure 60B:
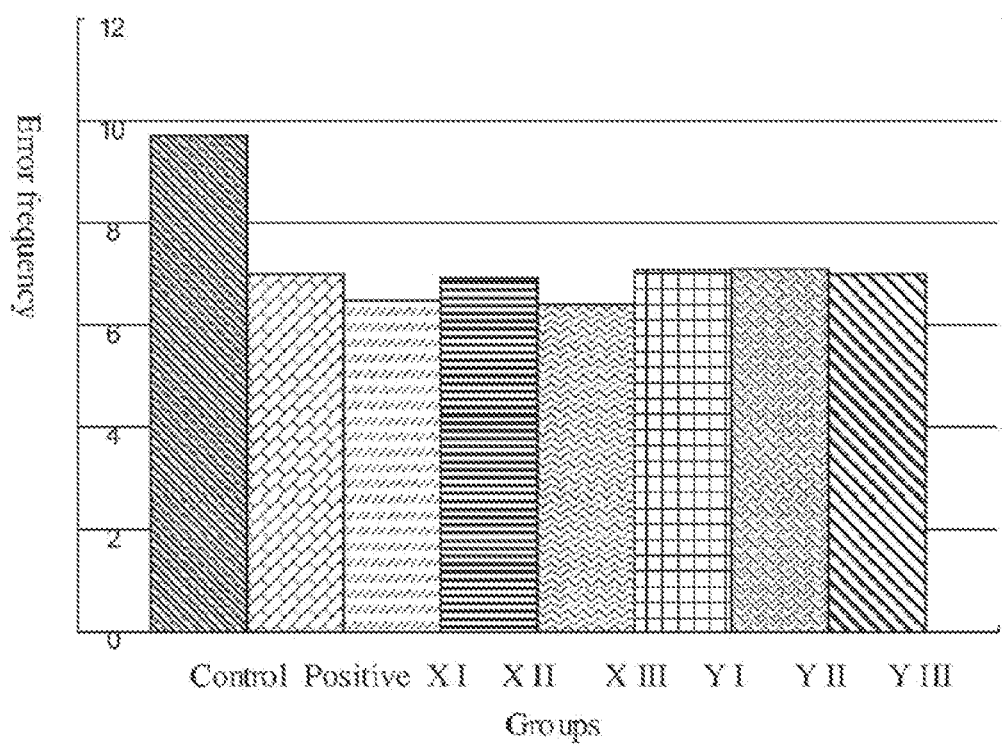

11.3. After 9 days of administration of X and Y, the error frequency in the water maze in the mice with all dosage treatments decreased significantly (P<0.05, P<0.01). The escape latency in the water maze by the group 9 mice receiving 500 mg/kg of Y decreased significantly (P<0.05). See Table 11.3. FIG. 60*a*, 60*b*.

TABLE 11.3

The Learning Effects of Plant Extracts after Administration in aging mice for 9 days

| Group | Blind Terminal 1 | Blind Terminal 2 | Blind Terminal 3 | Blind Terminal 4 | Error Frequency | EL(sec) |
|---|---|---|---|---|---|---|
| Control | 2.36 ± 1.65 | 2.64 ± 1.69 | 2.86 ± 2.54 | 1.5 ± 2.18 | 9.71 ± 3.52 | 59.71 ± 29.42 |
| positive | 1.64 ± 1.80 | 2.18 ± 1.54 | 1.55 ± 1.37 | 1.64 ± 2.20 | 7.0 ± 2.19* | 33.36 ± 10.87 |
| X I | 1.1 ± 1.29 | 2.5 ± 2.37 | 1.9 ± 0.74 | 1.0 ± 1.15 | 6.5 ± 3.27* | 40.8 ± 20.4 |
| X II | 1.18 ± 1.17 | 2.18 ± 1.60 | 1.36 ± 1.36 | 2.18 ± 1.25 | 6.91 ± 3.27* | 42.73 ± 15.82 |
| X III | 1.0 ± 1.25 | 1.9 ± 1.79 | 1.3 ± 1.25 | 2.2 ± 1.16 | 6.4 ± 2.84* | 35.1 ± 11.76* |
| Y I | 1.82 ± 1.33 | 1.64 ± 1.69 | 1.82 ± 1.33 | 1.82 ± 1.47 | 7.09 ± 2.47* | 42.09 ± 20.93 |
| Y II | 1.2 ± 1.32 | 1.9 ± 1.37 | 2.6 ± 1.58 | 1.2 ± 1.32 | 7.1 ± 1.52* | 34.4 ± 13.47* |
| Y III | 0.8 ± 1.03 | 2.5 ± 1.43 | 1.8 ± 1.40 | 2.0 ± 1.70 | 7.0 ± 1.41* | 31.9 ± 9.87** |

P < 0.05*
P < 0.01**

The results indicated that the extracts X and Y had positive effects on improving acquisition and retention of the tested aging mice. In addition, the effects increased with the period of receiving the extracts of X and Y prolonged Experiment 12: Effects of Extracts X and Y on Improving Impairment Induced by Pentobarbital Sodium in Water Maze Learning 12.1 After 10 days of administration of the extracts X and Y, the administrated mice were injected with pentobarbital sodium to induce amnesia.

After 1 day administration of pentobarbital sodium, the results of water maze learning showed that the time spent searching the terminal platform in the water maze by the mice receiving 100 mg/kg of X, and 125 mg, 250 mg/kg and 500 mg/kg of Y decreased significantly (P<0.05).

Error frequency made in the water maze by the mice receiving 500 mg/kg of Y decreased significantly (P<0.05). See Table 12.1.

TABLE 12.1

Results of Water Maze Learning (First Day after Injection with Pentobarbital)

| Group | Blind Terminal 1 | Blind Terminal 2 | Blind Terminal 3 | Blind Terminal 4 | Error Frequency | EL(sec) |
|---|---|---|---|---|---|---|
| control | 0.92 ± 0.76 | 1.46 ± 0.97 | 1.85 ± 1.07 | 1.23 ± 0.73 | 5.38 ± 2.33 | 63.0 ± 25.31 |
| positive | 0.69 ± 0.70 | 1.3 ± 0.95 | 1.1 ± 0.74 | 1.1 ± 0.74 | 4.1 ± 1.85 | 36.5 ± 15.76** |
| X I | 0.5 ± 0.53 | 1.7 ± 0.82 | 1.2 ± 0.92 | 0.9 ± 0.32 | 4.2 ± 1.62 | 42.2 ± 18.83* |
| X II | 0.9 ± 0.88 | 1.4 ± 0.70 | 1.6 ± 1.35 | 1.1 ± 0.88 | 5.0 ± 2.49 | 53.8 ± 16.10 |
| X III | 0.9 ± 0.74 | 1.7 ± 0.82 | 1.8 ± 0.42 | 0.9 ± 0.57 | 5.4 ± 1.58 | 58.1 ± 16.11 |
| Y I | 1.0 ± 0.89 | 1.36 ± 0.81 | 1.27 ± 1.01 | 0.73 ± 0.65 | 4.09 ± 2.02 | 42.73 ± 16.17* |
| Y II | 0.9 ± 0.74 | 1.7 ± 0.82* | 1.0 ± 0.82* | 0.6 ± 0.70* | 4.2 ± 1.87 | 38.4 ± 15.19** |
| Y III | 0.6 ± 0.70 | 0.8 ± 0.63 | 1.4 ± 1.35 | 0.8 ± 0.63 | 3.6 ± 1.26* | 38.5 ± 13.81** |

P < 0.05*
P < 0.01**

12.2. After two days of injected of pentobarbital sodium, the time spent searching the terminal platform and the error frequency made in the water maze by all groups of mice receiving X and Y decreased significantly (P<0.05). See Table 12.2.

TABLE 12.2

Results of Water Maze Learning (Second Day after Injection with Pentobarbital)

| Group | Blind Terminal 1 | Blind Terminal 2 | Blind Terminal 3 | Blind Terminal 4 | Error Frequency | EL(sec) |
|---|---|---|---|---|---|---|
| control | 1.36 ± 0.50 | 1.86 ± 0.53 | 1.29 ± 1.07 | 1.14 ± 0.66 | 5.64 ± 1.91 | 59.5 ± 34.95 |
| positive | 0.8 ± 0.63 | 1.8 ± 0.42 | 1.1 ± 0.74 | 0.6 ± 0.70 | 4.3 ± 0.95* | 34.7 ± 11.45* |
| X I | 0.9 ± 0.57* | 1.0 ± 0.67** | 1.2 ± 0.79 | 0.8 ± 0.63 | 3.9 ± 1.73* | 34.5 ± 12.67* |
| X II | 0.8 ± 0.79* | 1.5 ± 0.71 | 1.1 ± 0.88 | 0.5 ± 0.53* | 3.8 ± 1.40* | 35.9 ± 12.70* |
| X III | 1.0 ± 1.05 | 1.3 ± 0.48* | 1.3 ± 0.82 | 0.5 ± 0.53* | 4.1 ± 1.79* | 36.1 ± 11.10* |
| Y I | 1.09 ± 0.94 | 1.45 ± 0.52 | 0.91 ± 0.83 | 0.73 ± 0.65 | 4.18 ± 1.08* | 36.64 ± 14.38* |
| Y II | 0.9 ± 0.57* | 1.3 ± 0.82 | 1.1 ± 0.88 | 0.8 ± 0.63 | 4.1 ± 1.45* | 35.5 ± 14.27* |
| Y III | 0.8 ± 0.63* | 0.9 ± 0.74** | 0.9 ± 0.57 | 0.9 ± 0.57 | 3.4 ± 1.43** | 32.1 ± 13.12* |

$P < 0.05$*
$P < 0.01$**

12.3. After three days of administration of pentobarbital sodium, the time spent searching the terminal platform in the water maze by all groups of mice receiving X and Y decreased significantly (P<0.05). The error frequency made in the water maze by the mice receiving 250 mg/kg and 500 mg/kg of Y decreased significantly (P<0.05). See Table 12.3, FIG. 61a and FIG. 61b

TABLE 12.3

Results of Water Maze Learning (Third day after Injection with Pentobarbital)

| Group | Blind Terminal 1 | Blind Terminal 2 | Blind Terminal 3 | Blind Terminal 4 | Error Frequency | EL(sec) |
|---|---|---|---|---|---|---|
| control | 0.85 ± 0.99 | 1.0 ± 0.58 | 1.46 ± 1.05 | 0.62 ± 0.65 | 3.92 ± 1.75 | 48.92 ± 23.49 |
| positive | 0.4 ± 0.52 | 0.7 ± 0.48 | 0.9 ± 0.74 | 0.6 ± 0.70 | 2.6 ± 0.97* | 28.4 ± 13.78 |
| X I | 0.6 ± 0.70 | 0.8 ± 0.63 | 0.6 ± 0.70* | 0.8 ± 0.92 | 2.8 ± 1.69 | 28.0 ± 17.10* |
| X II | 0.4 ± 0.52 | 1.0 ± 0.47 | 1.0 ± 0.82 | 0.6 ± 0.84 | 3.0 ± 1.25 | 32.0 ± 12.36* |
| X III | 0.5 ± 0.71 | 0.8 ± 0.63 | 1.0 ± 0.82 | 0.9 ± 0.74 | 3.2 ± 1.23 | 31.8 ± 12.48* |
| Y I | 0.5 ± 0.53 | 0.7 ± 0.48 | 1.0 ± 0.67 | 0.6 ± 0.52 | 2.8 ± 0.63 | 31.0 ± 9.66* |
| Y II | 0.5 ± 0.53 | 0.6 ± 0.52 | 0.8 ± 0.42 | 0.6 ± 0.52 | 2.5 ± 0.53* | 29.0 ± 7.80* |
| Y III | 0.3 ± 0.48 | 1.0 ± 0.47 | 0.9 ± 0.57 | 0.4 ± 0.52 | 2.6 ± 0.84* | 30.2 ± 7.54* |

$P < 0.05$*

The results indicated that the extracts X and Y had distinct positive effects on improving spatial learning and retention impairment induced by pentobarbital sodium.

Experiment 13: Effects of Extracts X and Y on Improving Impairment Induced by Scopolamine Hydrobromide in Passive Avoidance ICR mice weighing 16-20 gm were trained in a STT-2. A mouse was placed on the platform and the SDL were recorded. When the mouse stepped down and all four feet were on the grid, it received electric shock (36 V) immediately, and the EL was recorded. The mice with SDL and EL within 2-60 seconds were selected for the test. The selected aging mice were divided into 9 groups. Each group had 5 male and 5 female mice. All the drugs were received with oral administration, 20 ml/kg, 3, 6 and 9 days before the platform training. The SDL, El and error frequency (the times of receiving electric shocks) made in 5 minutes were recorded. After 10 days of administration all the groups of mice received Scopolamine hydrobromide by injection, 3 mg/kg. After 30 minutes of administration of Scopolamine hydrobromide the mice were trained on the platform and the training was repeated the next day. The performances of the mice in the training were recorded. The SDL, EL and error frequency were recorded. All data were analyzed with t-test.

13.1. After 9 days of administration of X and Y, the results of passive avoidance in aging mice showed that the EL and the error frequency made by the mice received the X and Y in all doses reduced. See Table 13.1.

TABLE 13.1

Passive Avoidance in Aging Mice after 9 days of Administration

| Group | EL (sec) | SDL (min) | Error Frequency (in 5 min) |
|---|---|---|---|
| control | 6.8 ± 5.93 | 131.5 ± 106.50 | 2.5 ± 1.47 |
| positive | 5.3 ± 3.74 | 148.6 ± 81.26 | 1.7 ± 1.25 |
| X I | 7.0 ± 5.46 | 143.3 ± 19.77 | 1.8 ± 0.92 |
| X II | 6.2 ± 5.71 | 141.1 ± 109.89 | 2.0 ± 1.25 |
| X III | 4.9 ± 3.70 | 145.7 ± 107.0 | 1.9 ± 1.52 |
| Y I | 5.1 ± 3.95 | 153.0 ± 123.52 | 1.6 ± 1.33 |
| Y II | 3.9 ± 2.77 | 162.7 ± 108.92 | 1.8 ± 1.48 |
| Y III | 5.7 ± 3.12 | 159.4 ± 83.20 | 1.9 ± 0.93 |

13.2. After 10 days of administration of the X and Y, the tested mice were administrated with scopolamine. The results of passive avoidance in aging mice showed that the error frequency made in the passive avoidance by the mice receiving 400 mg/kg of X, 250 mg/kg and 500 mg/kg of Y reduced significantly (P<0.05, P<0.01). See Table 13.2.

TABLE 13.2

Effects of plant extract X and Y on improving impairment induced by Scopolamine

| Group | EL (sec) | Error Frequency (5 min) |
|---|---|---|
| control | 3.4 ± 3.03 | 0.9 ± 1.29 |
| model | 4.4 ± 4.09 | 1.6 ± 1.35 |
| positive | 3.1 ± 1.20 | 0.4 ± 0.52* |
| X I | 3.1 ± 2.08 | 0.8 ± 1.03 |
| X II | 3.7 ± 3.06 | 0.9 ± 1.52 |
| X III | 2.8 ± 1.48 | 0.3 ± 0.48** |
| Y I | 3.2 ± 2.49 | 0.7 ± 1.06 |
| Y II | 2.5 ± 0.97 | 0.5 ± 0.71* |
| Y III | 2.5 ± 0.71 | 0.5 ± 0.71* |

*p < 0.05
**p < 0.01

The results of passive avoidance test impaired mice by scopolamine showed that the error frequency made by the mice receiving X and Y in all doses reduced significantly ($P<0.05$). The SDL prolonged significantly in mice receiving 250 mg/kg of Y.

The results indicated that the extracts X and Y had distinct positive effects on improving learning and retention impairment induced by scopolamine. See Table 3.3.

TABLE 13.3

Effects of plant extract X and Y on improving impairment induced by Scopolamine.

| Group | SDL (sec) | Error Frequency (5 min) |
|---|---|---|
| control | 230.4 ± 96.61 | 0.7 ± 1.06 |
| model | 216.2 ± 100.77 | 1.5 ± 1.35 |
| positive | 286.0 ± 34.38* | 0.4 ± 0.70* |
| X I | 245.7 ± 114.48 | 0.4 ± 0.84* |
| X II | 260.4 ± 87.14 | 0.4 ± 0.84* |
| X III | 266.8 ± 65.64 | 0.5 ± 0.71* |
| Y I | 252.7 ± 101.11 | 0.4 ± 0.84* |
| Y II | 285.8 ± 29.21* | 0.4 ± 0.70* |
| Y III | 277.4 ± 47.62 | 0.4 ± 0.70* |

*p < 0.05

The results indicated that the extracts X and Y had distinct positive effects on improving learning and retention impairment induced by scopolamine hydrobromide.

Experiment 14: Effects of Extracts X and Y on Improving Impairment Induced by $NaNO_2$ in Water Maze Learning ICR male mice weighing 16-19 gm were trained in a SMG-2 filled with water 11 cm deep (25-26° C.). The SMG-2 has a start point, 4 blind terminals, the escape platform and their routes. The mice were trained to find the escape platform, and the escape latencies from the water and error frequencies were recorded. After training, the mice which escaped from the water within 1 minute were selected for the test. The selected aging mice were divided into 9 groups of 11 mice. All the drugs were received with oral administration, 20 ml/kg, 3, 6 and 9 days before the water maze test. After 10 days of administration all the groups of mice were received with $NaNO_2$ by injection, 120 mg/kg. After 24 hours of administration of $NaNO_2$ the mice were trained to find the escape platform, and the escape latencies from the water and error frequencies made in 2 minutes were recorded. The administration of pentobarbital sodium continued for 3 days and the performances of the mice in water maze test were recorded. The escape latencies (EL) from the water and errors frequencies were recorded. All data were analyzed with t-test.

14.1. After 3 days of administration of X and Y the escape latency from the water maze and error frequency by the mice receiving X and Y reduced, although not significantly. See Table 14.1.

TABLE 14.1

Effects of Extracts X and Y on Water Maze Learning in Mice after 3 Days of Administration

| Group | Blind Terminal 1 | Blind Terminal 2 | Blind Terminal 3 | Blind Terminal 4 | Error Frequency | EL(sec) |
|---|---|---|---|---|---|---|
| control | 1.05 ± 0.49 | 1.82 ± 0.66 | 1.09 ± 0.75 | 0.86 ± 0.47 | 4.82 ± 0.96 | 48.27 ± 21.47 |
| positive | 0.91 ± 0.30 | 1.27 ± 0.65 | 0.82 ± 0.60 | 0.64 ± 0.50 | 3.64 ± 0.92** | 36.27 ± 11.83 |
| X I | 1.36 ± 0.81 | 1.73 ± 0.79 | 1.09 ± 0.83 | 0.55 ± 0.52 | 4.73 ± 2.05 | 37.82 ± 14.24 |
| X II | 0.91 ± 0.30 | 1.82 ± 0.40 | 1.09 ± 0.94 | 1.00 ± 0.89 | 4.91 ± 1.51 | 36.46 ± 11.97 |
| X III | 1.09 ± 0.54 | 1.45 ± 0.52 | 0.91 ± 0.70 | 0.45 ± 0.52 | 3.91 ± 0.70 | 36.46 ± 11.78 |
| Y I | 1.55 ± 0.52 | 1.82 ± 0.40 | 1.0 ± 0.89 | 0.45 ± 0.69 | 4.82 ± 1.33 | 41.46 ± 16.37 |
| Y II | 0.91 ± 0.30 | 1.18 ± 0.60 | 1.27 ± 1.10 | 0.73 ± 0.79 | 4.09 ± 2.21 | 36.82 ± 20.61 |
| Y III | 0.91 ± 0.30 | 1.55 ± 0.82 | 0.45 ± 0.52 | 0.82 ± 0.40 | 3.73 ± 1.27 | 37.55 ± 13.85 |

*P < 0.05
**P < 0.01

14.2. After 6 days of administration of X and Y the escape latency from the water maze by the mice receiving 400 mg/kg of X and 500 mg/kg of Y reduced significantly compared with the control ($P<0.01$). See Table 14.2.

TABLE 14.2

Effects of Extracts X and Y on Water Maze Learning in Mice after 6 Days of Administration

| Group | Blind Terminal 1 | Blind Terminal 2 | Blind Terminal 3 | Blind Terminal 4 | Error Frequency | EL(sec) |
|---|---|---|---|---|---|---|
| control | 0.95 ± 0.38 | 1.09 ± 0.43 | 0.77 ± 0.61 | 0.91 ± 0.53 | 3.82 ± 0.80 | 42.96 ± 13.48 |
| positive | 0.73 ± 0.65 | 1.09 ± 0.30 | 0.55 ± 0.52 | 0.82 ± 0.40 | 3.18 ± 0.75* | 32.91 ± 7.15* |
| X I | 0.73 ± 0.65 | 1.27 ± 0.47 | 0.73 ± 0.65 | 0.73 ± 0.65 | 3.45 ± 1.21 | 37.18 ± 7.65 |
| X II | 0.91 ± 0.30 | 1.00 ± 0.45 | 0.64 ± 0.92 | 0.91 ± 0.54 | 3.45 ± 1.21 | 37.73 ± 13.26 |
| X III | 0.91 ± 0.30 | 1.09 ± 0.54 | 0.91 ± 0.83 | 0.82 ± 0.75 | 3.73 ± 1.19 | 31.09 ± 8.15** |
| Y I | 0.91 ± 0.30 | 1.0 ± 0.45 | 0.82 ± 0.40 | 0.55 ± 0.52 | 3.36 ± 0.67 | 35.82 ± 9.93 |
| Y II | 0.91 ± 0.54 | 1.09 ± 0.54 | 1.00 ± 0.77 | 0.64 ± 0.67 | 3.64 ± 1.12 | 35.09 ± 12.13 |
| Y III | 0.82 ± 0.40 | 1.09 ± 0.54 | 0.82 ± 0.60 | 0.55 ± 0.52 | 3.27 ± 1.10 | 31.73 ± 8.36** |

*P < 0.05
**P < 0.01

14.3. After 9 days of administration of X and Y, the escape latency from the water maze by the mice receiving 250 mg/kg of X, 250 mg and 500 mg/kg of Y reduced significantly compared with the control (P<0.05). See Table 14.3.

Tablet 14.3. Effects of Extracts X and Y on Water Maze Learning in Mice after 9 Days of Administration.

| Group | Blind Terminal 1 | Blind Terminal 2 | Blind Terminal 3 | Blind Terminal 4 | Error Frequency | EL(sec) |
|---|---|---|---|---|---|---|
| control | 0.59 ± 0.73 | 1.14 ± 0.64 | 0.55 ± 0.67 | 1.0 ± 0.76 | 3.27 ± 1.32 | 39.27 ± 15.52 |
| positive | 0.55 ± 0.52 | 1.00 ± 0.00 | 0.27 ± 0.65 | 0.91 ± 0.54 | 2.73 ± 0.65 | 27.64 ± 6.96* |
| X I | 0.45 ± 0.52 | 1.27 ± 0.47 | 0.73 ± 0.65 | 0.55 ± 0.52 | 3.00 ± 0.77 | 33.55 ± 9.59 |
| X II | 0.45 ± 0.52 | 0.91 ± 0.70 | 0.55 ± 0.69 | 0.82 ± 0.89 | 2.73 ± 0.90 | 28.00 ± 9.53* |
| X III | 0.45 ± 0.52 | 1.09 ± 0.70 | 0.82 ± 0.75 | 0.45 ± 0.52 | 2.82 ± 1.25 | 29.45 ± 8.49 |
| Y I | 0.91 ± 0.70 | 0.91 ± 0.54 | 0.45 ± 0.52 | 0.55 ± 0.52 | 2.82 ± 0.98 | 32.00 ± 9.49 |
| Y II | 0.64 ± 0.50 | 0.82 ± 0.75 | 0.64 ± 0.67 | 0.82 ± 0.60 | 2.91 ± 1.30 | 26.36 ± 9.82* |
| Y III | 0.73 ± 1.01 | 0.91 ± 0.30 | 0.45 ± 0.69 | 0.55 ± 0.69 | 2.64 ± 1.12 | 28.09 ± 9.26* |

*P < 0.05

14.4. After 10 days of administration of X and Y, the error frequency made in the water maze by the mice receiving 250 mg and 500 mg/kg of Y, the escape latency from the water maze by the mice receiving 500 mg/kg of Y reduced significantly compared with the control (P<0.05, P<0.01). See Table 14.4.

TABLE 14.4

Effects of Extracts X and Y on Water Maze Learning in Mice after 10 Days of Administration

| Group | Blind Terminal 1 | Blind Terminal 2 | Blind Terminal 3 | Blind Terminal 4 | Error Frequency | EL(sec) |
|---|---|---|---|---|---|---|
| control | 0.64 ± 0.73 | 1.14 ± 0.56 | 0.64 ± 0.66 | 0.91 ± 0.68 | 3.32 ± 0.95 | 36.73 ± 13.02 |
| positive | 0.45 ± 0.69 | 0.82 ± 0.40 | 0.55 ± 0.52 | 0.82 ± 0.40 | 2.64 ± 0.81* | 29.0 ± 10.10 |
| X I | 0.36 ± 0.67 | 0.91 ± 0.70 | 0.91 ± 0.83 | 0.64 ± 0.81 | 2.82 ± 1.08 | 33.09 ± 13.96 |
| X II | 0.73 ± 0.79 | 0.82 ± 0.40 | 0.55 ± 0.69 | 0.73 ± 0.47 | 2.82 ± 0.75 | 28.91 ± 13.34 |
| X III | 0.91 ± 0.70 | 0.91 ± 0.54 | 0.73 ± 0.65 | 0.36 ± 0.67 | 2.91 ± 0.94 | 32.45 ± 13.57 |
| Y I | 0.73 ± 0.79 | 0.91 ± 0.30 | 0.36 ± 0.50 | 0.73 ± 0.65 | 2.73 ± 0.90 | 29.55 ± 13.87 |
| Y II | 0.55 ± 0.52 | 0.64 ± 0.50 | 0.45 ± 0.52 | 0.64 ± 0.67 | 2.27 ± 0.79** | 30.36 ± 12.30 |
| Y III | 0.45 ± 0.69 | 1.09 ± 0.54 | 0.27 ± 0.65 | 0.55 ± 0.52 | 2.36 ± 1.21* | 25.64 ± 11.02* |

*P < 0.05
**P < 0.01

The results indicated that the extracts X and Y had distinct positive effects on improving the learning and retention in mice in a water maze. In addition, the effects increased with the period of receiving the extracts of X and Y prolonged.

14.5. After 10 days of receiving X and Y, the mice were administrated with Na NO2 after the test. The results of treatment with X and Y to prevent impairments induced by Na NO2 in water maze learning in aging mice showed that error frequency made by the mice receiving 100 mg/ka and 200 mg/kg of X, and Y of all doses reduced significantly (P<0.05). See Table 14.5. It indicated the extracts X and Y had distinct positive effects on preventing the impairments induced by Na $NO_2$. See Table 14.5.

TABLE 14.5

Effects of Extract X and Y on preventing Impairments Induced by NaNO₂

| Group | Blind Terminal 1 | Blind Terminal 2 | Blind Terminal 3 | Blind Terminal 4 | Error Frequency | EL(sec) |
|---|---|---|---|---|---|---|
| Control | 0.27 ± 0.47 | 0.91 ± 0.54 | 0.55 ± 0.52 | 1.09 ± 0.54 | 2.82 ± 0.75 | 30.91 ± 12.36 |
| Model | 1.18 ± 0.75 | 0.91 ± 0.30 | 0.45 ± 0.52 | 0.73 ± 0.65 | 3.27 ± 1.01 | 36.45 ± 16.89 |
| Positive | 0.45 ± 0.52 | 0.91 ± 0.30 | 0.55 ± 0.52 | 0.45 ± 0.52 | 2.36 ± 0.81* | 32.00 ± 15.83 |
| X I | 0.55 ± 0.52 | 0.82 ± 0.60 | 0.18 ± 0.40 | 0.82 ± 0.60 | 2.36 ± 0.81* | 29.09 ± 13.80 |
| X II | 0.18 ± 0.40 | 0.82 ± 0.60 | 0.55 ± 0.52 | 0.82 ± 0.75 | 2.36 ± 0.92* | 25.82 ± 10.82 |
| X III | 0.45 ± 0.52 | 0.64 ± 0.50 | 0.82 ± 0.40 | 0.91 ± 0.70 | 2.82 ± 1.33 | 31.09 ± 11.76 |
| Y I | 0.27 ± 0.47 | 0.91 ± 0.30 | 0.36 ± 0.50 | 0.73 ± 0.47 | 2.27 ± 0.79* | 27.00 ± 10.73 |
| Y II | 0.45 ± 0.52 | 0.64 ± 0.50 | 0.36 ± 0.50 | 0.91 ± 0.30 | 2.36 ± 0.81* | 25.82 ± 11.43 |
| Y III | 0.64 ± 0.50 | 0.82 ± 0.40 | 0.36 ± 0.50 | 0.64 ± 0.50 | 2.45 ± 0.82* | 25.09 ± 9.67 |

*P < 0.05
**P < 0.01

Experiment 15: Effects of Wenguanguo (*Xanthoceras sorbifolia*) Extracts on Urination in Mice As used herein, Extracts (or Fractions) X and Y are different extracts of Wenguanguo plant or *Xanthoceras sorbifolia*.

Methods of Experiment

One hundred twelve male ICR mice weighing 18-22 gm were divided into 8 groups of 14: 1, control: receiving normal saline (NS); 2, DCT group: receiving DCT 33.4 mg/kg; 3, X-I group: receiving 100 mg/kg4; 4, X-II group: receiving 200 mg/kg; 5, X-III receiving 400 mg/kg; 6, Y-I group: receiving 125 mg/kg; 7, Y-II group: receiving 250 mg/kg and 8, Y-III group: receiving 500 mg/kg.

All the drugs were received with oral administration, 20 ml/kg, once a day for 3 days. After the last administration, the mouse was placed on a filter paper. The filter paper was on the bottom of a 500 ml beak. The quantity of urine was measured at 30, 60, 120, 180, 240, 300, and 360 minutes by weighing the filter paper with the electronic analytical scale. All data were analyzed with t-test.

Results.

After 3 days of administration of X and Y the quantity of urine discharged at 30 minute by the mice receiving 400 mg/kg of X decreased significantly (P<0.01) compared with the mice receiving normal saline. The quantity of urine discharged at 60 minute by the mice receiving 600 mg/kg of Y decreased significantly compared with the mice receiving normal saline (P<0.01).

The quantity of urine discharged at 180 minutes by the mice receiving 200 mg/kg of X, 125 mg and 500 mg/kg of Y decreased significantly compared with the mice receiving normal saline (P<0.01). See Table 15.1.

TABLE 15.1

Effects of Extracts X and Y on the Quantity of Urine in Mice after 3 Days of Administration

| Group | 30 min | 60 min | 120 min |
|---|---|---|---|
| Control | 0.267 ± 0.105 | 0.367 ± 0.162 | 0.382 ± 0.109 |
| Positive | 0.348 ± 0.06* | 0.471 ± 0.169** | 0.574 ± 0.249 |
| X I | 0.304 ± 0.072 | 0.274 ± 0.076 | 0.323 ± 0.173 |
| X II | 0.341 ± 0.107 | 0.323 ± 0.102 | 0.404 ± 0.138 |
| X III | 0.155 ± 0.056** | 0.200 ± 0.140** | 0.455 ± 0.211 |
| Y I | 0.216 ± 0.130 | 0.309 ± 0.093 | 0.341 ± 0.061 |
| Y II | 0.278 ± 0.063 | 0.278 ± 0.119 | 0.437 ± 0.112 |
| Y III | 0.227 ± 0.058 | 0.235 ± 0.035** | 0.425 ± 0.133 |

Compared with the control group: P < 0.05* P < 0.01**

TABLE 15.1

Effects of Extracts X and Y on the Quantity of Urine in Mice After 3 Days of Administration (continued)

| Group | 180 min | 240 min | 300 min | 360 min |
|---|---|---|---|---|
| Control | 0.191 ± 0.080 | 0.161 ± 0.083 | 0.116 ± 0.06 | 0.103 ± 0.057 |
| Positive | 0.272 ± 0.131 | 0.182 ± 0.096 | 0.110 ± 0.051 | 0.085 ± 0.031 |
| X I | 0.184 ± 0.105 | 0.154 ± 0.093 | 0.124 ± 0.091 | 0.102 ± 0.064 |
| X II | 0.336 ± 0.103** | 0.163 ± 0.10 | 0.107 ± 0.076 | 0.106 ± 0.075 |
| X III | 0.207 ± 0.112 | 0.204 ± 0.088 | 0.150 ± 0.066 | 0.116 ± 0.077 |
| Y I | 0.367 ± 0.104** | 0.171 ± 0.085 | 0.173 ± 0.068* | 0.093 ± 0.053 |
| Y II | 0.275 ± 0.206 | 0.145 ± 0.029 | 0.109 ± 0.036 | 0.106 ± 0.045 |
| Y III | 0.319 ± 0.086** | 0.264 ± 0.114** | 0.152 ± 0.084 | 0.135 ± 0.051 |

Compared with the control P < 0.05* and P < 0.01**

The results indicated that the extract X and Y can regulate the quantity of urine after 3 days of administration of X and Y.

After 5 days of administration of X and Y, the quantity of urine discharged at 30 minute by the mice receiving 400 mg/kg of X and 500 mg/kg of Y decreased, but not significantly compared with the mice receiving normal saline. The quantity of urine discharged at 4 hour by the mice receiving 400 mg/kg of X and Y in all doses increased significantly compared with the mice receiving normal saline (P<0.05, P<0.01). See Table 15.2.

TABLE 15.2

Effects of Extracts X and Y on the Quantity of Urine in Mice after 5 Days of Administration

| Group | 30 min | 60 min | 120 min |
|---|---|---|---|
| Control | 0.327 ± 0.148 | 0.330 ± 0.194 | 0.291 ± 0.146 |
| Positive | 0.524 ± 0.206** | 0.478 ± 0.185* | 0.472 ± 0.292* |
| X I | 0.382 ± 0.138 | 0.251 ± 0.071 | 0.265 ± 0.172 |
| X II | 0.348 ± 0.144 | 0.324 ± 0.113 | 0.277 ± 0.131 |
| X III | 0.245 ± 0.167 | 0.236 ± 0.129 | 0.251 ± 0.142 |
| Y I | 0.331 ± 0.098 | 0.340 ± 0.133 | 0.291 ± 0.081 |
| Y II | 0.357 ± 0.130 | 0.290 ± 0.145 | 0.327 ± 0.157 |
| Y III | 0.230 ± 0.121 | 0.307 ± 0.082 | 0.363 ± 0.100 |

Compared with the control P < 0.05* and P < 0.01**

TABLE 15.2

Effects of Extracts X and Y on the Quantity of Urine in Mice After 5 Days of Administration (continued)

| Group | 180 min | 240 min | 300 min | 360 min |
|---|---|---|---|---|
| Control | 0.186 ± 0.086 | 0.117 ± 0.069 | 0.105 ± 0.06 | 0.104 ± 0.08 |
| Positive | 0.214 ± 0.151 | 0.110 ± 0.045 | 0.126 ± 0.056 | 0.112 ± 0.065 |
| X I | 0.188 ± 0.097 | 0.175 ± 0.088 | 0.177 ± 0.102* | 0.133 ± 0.092 |
| X II | 0.258 ± 0.143 | 0.150 ± 0.077 | 0.167 ± 0.097* | 0.130 ± 0.094 |
| X III | 0.226 ± 0.107 | 0.233 ± 0.132** | 0.120 ± 0.059 | 0.125 ± 0.048 |
| Y I | 0.273 ± 0.156 | 0.215 ± 0.095** | 0.166 ± 0.151 | 0.116 ± 0.068 |
| Y II | 0.181 ± 0.088 | 0.181 ± 0.089* | 0.151 ± 0.104 | 0.101 ± 0.042 |
| Y III | 0.193 ± 0.09 | 0.217 ± 0.092** | 0.112 ± 0.056 | 0.117 ± 0.043 |

Compared with the control P < 0.05* and P < 0.01**

The results indicated that the extract X and Y can regulate the quantity of urine after 5 days of administration of X and Y.

After 7 days of administration of X and Y, the quantity of urine was measured at 30, 60, 120, 180, 240, 300, and 360 minutes. The quantity of urine discharged at 30 minute by the mice receiving 200, 400 mg/kg of X and 250, 500 mg/kg of Y decreased significantly (P<0.05) but increased at 240 minutes compared with the mice receiving normal saline. See Table 15.3.

TABLE 15.3

Effects of Extracts X and Y on the Quantity of Urine in Mice after 7 Days of Administration

| Group | 30 min | 60 min | 120 min |
|---|---|---|---|
| Control | 0.252 ± 0.142 | 0.347 ± 0.159 | 0.430 ± 0.192 |
| Positive | 0.434 ± 0.230* | 0.606 ± 0.214** | 0.590 ± 0.333 |
| X I | 0.301 ± 0.152 | 0.314 ± 0.149 | 0.342 ± 0.186 |
| X II | 0.291 ± 0.161 | 0.332 ± 0.135 | 0.285 ± 0.173* |
| X III | 0.212 ± 0.113 | 0.260 ± 0.103 | 0.309 ± 0.117* |
| Y I | 0.254 ± 0.175 | 0.283 ± 0.137 | 0.313 ± 0.178 |
| Y II | 0.261 ± 0.189 | 0.292 ± 0.129 | 0.300 ± 0.128* |
| Y III | 0.246 ± 0.170 | 0.268 ± 0.240 | 0.281 ± 0.146* |

Compared with the control P < 0.05* and P < 0.01**

TABLE 15.3

Effects of Extracts X and Y on the Quantity of Urine in Mice after 7 Days of Administration (continued)

| Group | 180 min | 240 min | 300 min | 360 min |
|---|---|---|---|---|
| Control | 0.285 ± 0.136 | 0.155 ± 0.119 | 0.122 ± 0.071 | 0.111 ± 0.061 |
| Positive | 0.314 ± 0.119 | 0.279 ± 0.192* | 0.163 ± 0.087 | 0.148 ± 0.071 |
| X I | 0.267 ± 0.179 | 0.200 ± 0.114 | 0.176 ± 0.147 | 0.157 ± 0.077 |
| X II | 0.250 ± 0.116 | 0.203 ± 0.134 | 0.180 ± 0.079* | 0.129 ± 0.085 |
| X III | 0.293 ± 0.142 | 0.250 ± 0.116* | 0.194 ± 0.104* | 0.151 ± 0.076 |
| Y I | 0.310 ± 0.168 | 0.248 ± 0.178 | 0.155 ± 0.108 | 0.113 ± 0.05 |
| Y II | 0.334 ± 0.208 | 0.259 ± 0.205 | 0.205 ± 0.109* | 0.188 ± 0.113* |
| Y III | 0.267 ± 0.133 | 0.212 ± 0.125 | 0.205 ± 0.119* | 0.169 ± 0.073* |

Compared with the control P < 0.05* and P < 0.01**

The results indicated that the extract X and Y can regulate the quantity of urine after 7 days of administration of X and Y.

After 10 days of administration of X and Y, the quantity of urine discharged at 120 minutes by the mice receiving 200, 400 mg/kg of X and 250, 500 mg/kg of Y decreased significantly (P<0.05) compared with the mice receiving normal saline. See FIG. 59.

TABLE 15.4

Effects of Extracts X and Y on the Quantity of Urine in Mice after 10 Days of Administration

| Group | 30 min | 60 min | 120 min |
|---|---|---|---|
| Control | 0.292 ± 0.184 | 0.323 ± 0.158 | 0.418 ± 0.221 |
| Positive | 0.374 ± 0.159 | 0.432 ± 0.163* | 0.643 ± 0.181** |
| X I | 0.306 ± 0.124 | 0.317 ± 0.088 | 0.339 ± 0.145 |
| X II | 0.292 ± 0.082 | 0.343 ± 0.120 | 0.279 ± 0.118* |
| X III | 0.266 ± 0.116 | 0.348 ± 0.161 | 0.274 ± 0.111* |
| Y I | 0.273 ± 0.117 | 0.331 ± 0.103 | 0.406 ± 0.175 |
| Y II | 0.289 ± 0.126 | 0.344 ± 0.147 | 0.254 ± 0.102* |
| Y III | 0.227 ± 0.129 | 0.322 ± 0.162 | 0.255 ± 0.124* |

Compared with the control P < 0.05* and P < 0.01**

TABLE 15.4

Effects of Extracts X and Y on the Quantity of Urine in Mice after 10 Days of Administration (continued)

| Group | 180 min | 240 min | 300 min | 360 min |
|---|---|---|---|---|
| Control | 0.203 ± 0.087 | 0.144 ± 0.098 | 0.108 ± 0.074 | 0.091 ± 0.060 |
| Positive | 0.253 ± 0.116 | 0.147 ± 0.067 | 0.095 ± 0.094 | 0.068 ± 0.049 |
| X I | 0.249 ± 0.094 | 0.172 ± 0.093 | 0.120 ± 0.058 | 0.093 ± 0.050 |
| X II | 0.225 ± 0.074 | 0.163 ± 0.051 | 0.116 ± 0.052 | 0.093 ± 0.051 |
| X III | 0.247 ± 0.104 | 0.186 ± 0.102 | 0.121 ± 0.053 | 0.098 ± 0.065 |
| Y I | 0.243 ± 0.101 | 0.171 ± 0.098 | 0.126 ± 0.086 | 0.098 ± 0.058 |
| Y II | 0.229 ± 0.097 | 0.164 ± 0.091 | 0.124 ± 0.094 | 0.111 ± 0.067 |
| Y III | 0.213 ± 0.102 | 0.170 ± 0.081 | 0.121 ± 0.059 | 0.095 ± 0.045 |

Compared with the control P < 0.05* and P < 0.01**

The results indicated that the extract X and Y can regulate the quantity of urine after 10 days of administration of X and Y.

Conclusion.

The results indicated that the extract X and Y can regulate the quantity of urine after 3-10 days of administration of X and Y.

Experiment 15A: Antidiuresis Test of Rat in Metabolism Cage

The antidiuresis tests using *Xanthoceras Sorbifolia* Extract FS(X) and *Xanthoceras Sorbifolia* saponin extract FS(Y) were carried out in rats. Note: Extracts FS(X) and FS(Y) similar to Extracts X and Y respectively. FS(Y) and FS(X) are crude saponin extracts and the "FS(Y)" and "FS(X)" are the extract names that were used in the experiments.

SD rats were treated with FS(X) by oral administration, daily at the doses of 100, 200, 400 mg/kg for 25 days. The experiment included a negative control group and positive control. Collecting urine in Standard metabolism cage and observation indicators, including urine volume, urine Na+, K+, Cl– content, pH and osmotic pressure. The results obtained were as follows: (1) Extract FS(X) has dose-dependant antidiuresis effect. There is significant antidiuresis at all the time phases for 200 and 400 mg/kg. However, by urination rate, the 400 mg/kg dosage group has a more significant effect in that it can delay urination output by two hours. In addition, there is no change in the impact on total urine volume output. (2) The extract FS(X) increased the concentration of ions in urine after drug treatment. However, there is no apparent dose dependency. (3) FS (X) and FS (Y) have no significant impact on the pH value and osmotic pressure, but have slight impact on the specific gravity.

Objective.

Standard metabolism cage method was carried out in rats to research the antidiuresis of FS(X) and FS(Y).

Test Drug.

FS(X) is compositions of *Xanthoceras Sorbifolia* extract. FS(Y) is compositions of *Xanthoceras Sorbifolia* extract. The test drug is a suspension formulated with 0.5% sodium carboxymethyl cellulose (0.5% CMC-Na).

Test Animals.

Male SD rats, initial weight 150-200 g, 100 individuals. The test animals are raised in cages (volume: 20×30×45 cm), and each cage has 5 animals. The basal feed is the full-rate pellet feed for experimental rat, self-made by the Experimental Animal Center. The cage bottom padding is wood shaving and chaff, dried before use. After the padding replacement that is made every other day on average, the cages are disinfected before reuse. Laboratory temperature 23±2° C., humidity 40~70%, with air-conditioning, exhaust and ventilation equipment, natural lighting and a light-shade cycle of about 12 hours.

Animal Screening.

The animals are placed individually in the cage for adaptation once a day for 6-10 hours per day for 2 days. Before placing them into the case, press the lower abdomen gently to discharge the remaining urine, inject 38° C. distilled water into the stomach at the volume of 25 ml/kg as the water load. Collect the urine in the metabolism cage within 2 hours after stomach injection; collect the remaining urine by pressing the lower abdomen gently immediately before taking them out of the cage. Animals whose urine volume attains above 40% of the injection volume will be qualified ones.

Test Instruments.

Standard metabolism cage, Automatic urine analyzer (Miditron Junior II), Urine osmotic pressure tester, and Urine ion tester (EL-ISE, Beckman).

Methods

Test groups.

There are 3 groups for the FS (X), i.e., for 100, 200, 400 mg/kg/day, respectively. There is a dosage group for FS (Y): 400 mg/kg/day; once a day, fed at 30 min after administration, for 25 days. Control group were fed with 0.5% CMC-Na into the stomach every day. The positive control drug is pituitrin, injected into the abdominal cavity at the rate of 0.25 u/kg before the animals are placed in the cage. Each group includes 10 animals.

Urine Collection and Observation Indicators.

For the test groups, the animals that have experienced the administration period are on diet for 18 hours before urine collection without prohibiting drinking. After pressing their lower abdomen gently to discharge the remaining urine, apply the water load of 38° C. distilled water at the volume of 50 ml/kg, and place them in the cage for urine collection. Collect the urine volume and times at 0.25 hr, 0.5 hr, 1 hr, 2 hr, 3 hr, 4 hr, 5 hr and 6 hr after water feeding, when the animals are taken out of the cage at 6 hr, press their lower abdomen gently to collect the remaining urine in the bladder. Conduct the routine urine examination (pH, erythrocyte, leucocyte, protein, etc); measure urine Na+, K+, Cl− concentrations and urine osmotic pressure for the urine samples.

Data Processing.

Urination speed, Relative urine volume, Urine Na+, K+, Cl− content data are shown in X±Sd, and are compared with the control group and subject to a student t-test.

Results

Impact on Urine Volume.

FS (X) has dose-dependant antidiuresis effects. There is a significant antidiuresis effect at all the time phases using dosages of 200 and 400 mg/kg. See Table 15A-1, FIGS. 63 and 63A. However, by urination discharge rate, the 400 mg/kg group has a more significant effect in reducing the urine output during the first 2 hrs as compared with the control. See Table 15A-2, FIGS. 64 and 64A. The FS (Y) 400 mg/kg group has an equivalent drug efficacy to FX (X) 400 mg/kg during the first 2 hours of experiment. In addition, there is no apparent dose dependency in the impact on total urine volume during the whole experiment. The 400 mg/kg groups of FS(X) can significantly reduce the urine volume during the first 6 hours after the drug-treatment which is more effective than the positive control drug (pituitrin).

Impact on Na+, K+, Cl− Ions in Urine.

By reducing the urine volume, the test drug has increased the concentration of ions in urine to different extent. However, there is no apparent dose dependency. By ionic, there is almost no impact on Na+ and Cl− ions, there is a certain discharge promotion action on K+ ions. The concentration and discharge amount of all ions in urine from the positive drug have risen apparently.

Impact on Urine pH and Osmotic Pressure.

FS (X) and FS (Y) have no significant impact on the pH value and osmotic pressure, but have slight impact on the specific gravity.

FIGS. 63 and 63A, Table 15A-1, shows results of the urine volume with water load after FS(X) *Xanthoceras Sorbifolia* Extract administration for 25 days. FIGS. 64 and 64A, Table 15A-2, shows results of discharging urine speed with water load after FS(X) *Xanthoceras Sorbifolia* Extract administration for 25 days. FIG. 65, Table 15A-3, shows results of urine specific gravity and pH with water load after FS(X) *Xanthoceras Sorbifolia* Extract administration for 25 days. FIG. 66, Table 15A-4, Concentration of Na+, K+ and Cl− in urine with water load after FS(X) *Xanthoceras Sorbifolia* Extract administration for 25 days.

Although the present invention has been described in detail with particular reference to preferred embodiments thereof, it should be understood that the invention is capable of other different embodiments, and its details are capable of modifications in various obvious aspects. As is readily apparent to those skilled in the art, variations and modifications can be affected while remaining within the spirit and scope of the invention. Accordingly, the foregoing disclosure, description, and figures are for illustrative purpose only, and do not in any way limit the invention which is defined only by the claims.

TABLE 5.2

Chemical Shift Data of 2D NMR chemical shift of HMQC analysis of compound Y

DU = C:/Bruker/XWIN-NMR, USER = guest, NAME = chan,
EXPNO = 5, PROCNO = 1
F1PLO = 144.360 ppm, F1PHI = 10.797 ppm,
F2PLO = 7.966 ppm, F2PHI = 0.417 ppm
MI = 1.00 cm, MAXI = 10000.00 cm, PC = 1.400

| # | ADDRESS row col | FREQUENCY [Hz]F1 [Hz]F2 | [PPM]F1 [PPM]F2 | INTENSITY |
|---|---|---|---|---|
| 1 | 148 | 20698.986 | 137.1608 | |
|   | 384 | 3574.377 | 5.9557 | 2.00 |
| 2 | 152 | 20564.195 | 136.2676 | |
|   | 401 | 3471.337 | 5.7840 | 2.67 |
| 3 | 157 | 20465.209 | 135.6117 | |
|   | 220 | 4533.779 | 7.5543 | 45.24 |
| 4 | 223 | 18893.424 | 125.1963 | |
|   | 431 | 3295.261 | 5.4906 | 6.22 |
| 5 | 234 | 18649.311 | 123.5787 | |
|   | 258 | 4311.820 | 7.1845 | 100.00 |
| 6 | 315 | 16736.119 | 110.9011 | |
|   | 376 | 3620.289 | 6.0322 | 7.49 |
| 7 | 353 | 15834.069 | 104.9237 | |
|   | 493 | 2934.550 | 4.8896 | 3.98 |
| 8 | 355 | 15778.398 | 104.5548 | |
|   | 449 | 3192.387 | 5.3192 | 2.99 |
| 9 | 355 | 15778.398 | 104.5548 | |
|   | 492 | 2936.414 | 4.8927 | 1.18 |
| 10 | 451 | 13524.788 | 89.6213 | |
|   | 660 | 1951.827 | 3.2522 | 2.41 |
| 11 | 451 | 13524.788 | 89.6213 | |
|   | 663 | 1934.401 | 3.2231 | 2.60 |
| 12 | 473 | 12994.274 | 86.1059 | |
|   | 563 | 2520.987 | 4.2005 | 1.93 |
| 13 | 479 | 12861.933 | 85.2290 | |
|   | 500 | 2891.933 | 4.8186 | 3.96 |
| 14 | 491 | 12583.008 | 83.3807 | |
|   | 487 | 2967.012 | 4.9437 | 6.95 |
| 15 | 523 | 11826.204 | 78.3658 | |
|   | 307 | 4025.464 | 6.7073 | 3.92 |
| 16 | 523 | 11826.204 | 78.3658 | |
|   | 309 | 4011.801 | 6.6846 | 4.78 |
| 17 | 523 | 11826.204 | 78.3658 | |
|   | 545 | 2627.492 | 4.3780 | 1.99 |
| 18 | 529 | 11690.020 | 77.4633 | |
|   | 504 | 2866.164 | 4.7757 | 4.60 |
| 19 | 532 | 11624.016 | 77.0260 | |
|   | 530 | 2713.960 | 4.5221 | 2.32 |
| 20 | 532 | 11624.016 | 77.0260 | |
|   | 532 | 2703.563 | 4.5047 | 2.51 |
| 21 | 535 | 11536.339 | 76.4450 | |
|   | 590 | 2363.678 | 3.9384 | 3.34 |
| 22 | 545 | 11299.475 | 74.8754 | |
|   | 573 | 2461.387 | 4.1012 | 2.35 |
| 23 | 545 | 11299.475 | 74.8754 | |
|   | 576 | 2447.179 | 4.0775 | 2.10 |
| 24 | 555 | 11063.554 | 73.3121 | |
|   | 541 | 2653.693 | 4.4216 | 6.62 |
| 25 | 567 | 10795.113 | 71.5333 | |
|   | 537 | 2673.042 | 4.4539 | 1.84 |
| 26 | 567 | 10795.113 | 71.5333 | |
|   | 539 | 2662.683 | 4.4366 | 2.82 |
| 27 | 567 | 10795.113 | 71.5333 | |
|   | 541 | 2650.933 | 4.4170 | 1.72 |
| 28 | 579 | 10495.725 | 69.5494 | |
|   | 527 | 2734.037 | 4.5555 | 5.06 |
| 29 | 594 | 10156.363 | 67.3006 | |
|   | 563 | 2523.651 | 4.2050 | 7.18 |
| 30 | 622 | 9486.037 | 62.8588 | |
|   | 608 | 2256.690 | 3.7601 | 2.91 |
| 31 | 622 | 9486.037 | 62.8588 | |
|   | 611 | 2241.336 | 3.7346 | 2.67 |

TABLE 5.2-continued

| | | | | |
|---|---|---|---|---|
| 32 | 622 | 9486.037 | 62.8588 | |
| | 635 | 2100.199 | 3.4994 | 2.96 |
| 33 | 622 | 9486.037 | 62.8588 | |
| | 637 | 2086.756 | 3.4770 | 3.42 |
| 34 | 627 | 9381.439 | 62.1656 | |
| | 552 | 2586.967 | 4.3105 | 3.58 |
| 35 | 627 | 9381.439 | 62.1656 | |
| | 555 | 2568.334 | 4.2794 | 3.42 |
| 36 | 627 | 9381.439 | 62.1656 | |
| | 568 | 2494.546 | 4.1565 | 2.54 |
| 37 | 627 | 9381.439 | 62.1656 | |
| | 571 | 2474.559 | 4.1232 | 2.51 |
| 38 | 630 | 9297.809 | 61.6115 | |
| | 531 | 2709.734 | 4.5150 | 2.61 |
| 39 | 630 | 9297.809 | 61.6115 | |
| | 539 | 2660.734 | 4.4334 | 2.66 |
| 40 | 670 | 8349.676 | 55.3287 | |
| | 911 | 480.283 | 0.8003 | 2.14 |
| 41 | 670 | 8349.676 | 55.3287 | |
| | 913 | 465.738 | 0.7760 | 2.18 |
| 42 | 726 | 7038.860 | 46.6427 | |
| | 679 | 1839.659 | 3.0653 | 2.51 |
| 43 | 726 | 7038.860 | 46.6427 | |
| | 819 | 1016.627 | 1.6939 | 1.42 |
| 44 | 726 | 7038.860 | 46.6427 | |
| | 848 | 848.511 | 1.4138 | 2.49 |
| 45 | 764 | 6151.769 | 40.7644 | |
| | 679 | 1841.145 | 3.0678 | 6.40 |
| 46 | 764 | 6151.769 | 40.7644 | |
| | 682 | 1821.592 | 3.0352 | 1.04 |
| 47 | 777 | 5836.727 | 38.6768 | |
| | 850 | 837.869 | 1.3961 | 2.15 |
| 48 | 777 | 5836.727 | 38.6768 | |
| | 853 | 818.861 | 1.3644 | 2.05 |
| 49 | 777 | 5836.727 | 38.6768 | |
| | 907 | 500.256 | 0.8335 | 1.64 |
| 50 | 791 | 5512.022 | 36.5251 | |
| | 775 | 1277.340 | 2.1283 | 2.38 |
| 51 | 791 | 5512.022 | 36.5251 | |
| | 778 | 1258.929 | 2.0977 | 1.38 |
| 52 | 791 | 5512.022 | 36.5251 | |
| | 785 | 1218.892 | 2.0309 | 1.38 |
| 53 | 791 | 5512.022 | 36.5251 | |
| | 788 | 1201.847 | 2.0025 | 1.09 |
| 54 | 837 | 4417.038 | 29.2693 | |
| | 881 | 655.973 | 1.0930 | 23.74 |
| 55 | 848 | 4174.679 | 27.6633 | |
| | 864 | 757.206 | 1.2617 | 20.53 |
| 56 | 848 | 4174.679 | 27.6633 | |
| | 872 | 709.060 | 1.1815 | 3.17 |
| 57 | 856 | 3984.149 | 26.4008 | |
| | 774 | 1281.339 | 2.1350 | 1.66 |
| 58 | 856 | 3984.149 | 26.4008 | |
| | 778 | 1259.751 | 2.0990 | 1.59 |
| 59 | 856 | 3984.149 | 26.4008 | |
| | 804 | 1107.062 | 1.8446 | 1.02 |
| 60 | 856 | 3984.149 | 26.4008 | |
| | 807 | 1089.219 | 1.8149 | 1.21 |
| 61 | 873 | 3578.068 | 23.7099 | |
| | 799 | 1138.137 | 1.8964 | 1.68 |
| 62 | 873 | 3578.068 | 23.7099 | |
| | 814 | 1046.185 | 1.7432 | 1.26 |
| 63 | 891 | 3142.837 | 20.8259 | |
| | 788 | 1200.655 | 2.0006 | 13.95 |
| 64 | 891 | 3142.837 | 20.8259 | |
| | 804 | 1107.046 | 1.8446 | 28.24 |
| 65 | 894 | 3086.147 | 20.4502 | |
| | 788 | 1200.275 | 1.9999 | 3.08 |
| 66 | 894 | 3086.147 | 20.4502 | |
| | 804 | 1106.803 | 1.8442 | 1.17 |
| 67 | 894 | 3086.147 | 20.4502 | |
| | 815 | 1041.758 | 1.7358 | 27.19 |
| 68 | 894 | 3086.147 | 20.4502 | |
| | 858 | 789.804 | 1.3160 | 1.16 |
| 69 | 897 | 3015.337 | 19.9810 | |
| | 858 | 790.292 | 1.3168 | 33.47 |
| 70 | 906 | 2802.854 | 18.5730 | |
| | 830 | 953.652 | 1.5890 | 1.35 |
| 71 | 906 | 2802.854 | 18.5730 | |
| | 834 | 931.208 | 1.5516 | 1.89 |
| 72 | 914 | 2613.995 | 17.3215 | |
| | 892 | 592.663 | 0.9875 | 12.71 |
| 73 | 919 | 2490.082 | 16.5004 | |
| | 875 | 693.445 | 1.1554 | 8.90 |
| 74 | 919 | 2490.082 | 16.5004 | |
| | 880 | 660.343 | 1.1003 | 1.76 |
| 75 | 925 | 2342.840 | 15.5247 | |
| | 778 | 1258.345 | 2.0967 | 5.45 |
| 76 | 925 | 2342.840 | 15.5247 | |
| | 782 | 1237.122 | 2.0613 | 5.31 |
| 77 | 925 | 2342.840 | 15.5247 | |
| | 791 | 1183.410 | 1.9718 | 2.33 |
| 78 | 925 | 2342.840 | 15.5247 | |
| | 795 | 1159.732 | 1.9324 | 2.38 |
| 79 | 925 | 2342.840 | 15.5247 | |
| | 907 | 503.260 | 0.8385 | 6.27 |
| 80 | 925 | 2342.840 | 15.5247 | |
| | 912 | 474.699 | 0.7910 | 7.15 |

TABLE 5.3

Chemical Shift Data of 2D NMR chemical shift of HMBC analysis of Y

DU = C:/Bruker/XWIN-NMR,   USER = guest,   NAME = chan,
EXPNO = 6, PROCNO = 1
F1PLO = 178.339 ppm,   F1PHI = 10.721 ppm,   F2PLO = 6.881 ppm,
F2PHI = 0.573 ppm
MI = 1.00 cm, MAXI = 10000.00 cm, PC = 1.400

| # | ADDRESS row col | FREQUENCY [Hz]F1 [Hz]F2 | [PPM]F1 [PPM]F2 | INTENSITY |
|---|---|---|---|---|
| 1 | 123 | 26590.750 | 176.2058 | |
| | 895 | 573.276 | 0.9552 | 3.11 |
| 2 | 145 | 25939.373 | 171.8894 | |
| | 531 | 2710.686 | 4.5166 | 2.92 |
| 3 | 145 | 25939.373 | 171.8894 | |
| | 539 | 2662.033 | 4.4355 | 2.54 |
| 4 | 166 | 25312.006 | 167.7321 | |
| | 308 | 4016.437 | 6.6923 | 3.45 |
| 5 | 166 | 25312.006 | 167.7321 | |
| | 346 | 3793.847 | 6.3214 | 14.90 |
| 6 | 166 | 25312.006 | 167.7321 | |
| | 348 | 3785.322 | 6.3072 | 12.47 |
| 7 | 166 | 25312.006 | 167.7321 | |
| | 385 | 3564.443 | 5.9392 | 1.47 |
| 8 | 166 | 25312.006 | 167.7321 | |
| | 400 | 3477.948 | 5.7950 | 4.16 |
| 9 | 166 | 25312.006 | 167.7321 | |
| | 403 | 3458.552 | 5.7627 | 3.96 |
| 10 | 166 | 25312.006 | 167.7321 | |
| | 781 | 1243.983 | 2.0728 | 1.17 |
| 11 | 166 | 25312.006 | 167.7321 | |
| | 788 | 1200.447 | 2.0002 | 10.44 |
| 12 | 166 | 25312.006 | 167.7321 | |
| | 793 | 1171.992 | 1.9528 | 3.35 |
| 13 | 166 | 25312.006 | 167.7321 | |
| | 815 | 1041.336 | 1.7351 | 33.24 |
| 14 | 290 | 21640.068 | 143.3997 | |
| | 679 | 1839.970 | 3.0658 | 5.67 |
| 15 | 290 | 21640.068 | 143.3997 | |
| | 788 | 1199.609 | 1.9988 | 1.03 |
| 16 | 290 | 21640.068 | 143.3997 | |
| | 804 | 1107.222 | 1.8449 | 33.90 |
| 17 | 290 | 21640.068 | 143.3997 | |
| | 813 | 1053.918 | 1.7561 | 2.30 |
| 18 | 290 | 21640.068 | 143.3997 | |
| | 848 | 848.155 | 1.4132 | 1.25 |
| 19 | 322 | 20697.354 | 137.1527 | |
| | 780 | 1246.505 | 2.0770 | 31.46 |
| 20 | 322 | 20697.354 | 137.1527 | |
| | 788 | 1200.075 | 1.9996 | 44.60 |
| 21 | 322 | 20697.354 | 137.1527 | |
| | 793 | 1170.377 | 1.9501 | 3.79 |
| 22 | 322 | 20697.354 | 137.1527 | |
| | 815 | 1040.860 | 1.7343 | 4.31 |

TABLE 5.3-continued

| | | | | |
|---|---|---|---|---|
| 23 | 327 | 20566.367 | 136.2847 | |
| | 780 | 1246.629 | 2.0772 | 3.06 |
| 24 | 327 | 20566.367 | 136.2847 | |
| | 788 | 1201.192 | 2.0015 | 5.78 |
| 25 | 327 | 20566.367 | 136.2847 | |
| | 793 | 1170.748 | 1.9507 | 47.25 |
| 26 | 327 | 20566.367 | 136.2847 | |
| | 815 | 1041.067 | 1.7346 | 58.19 |
| 27 | 365 | 19434.006 | 128.7811 | |
| | 780 | 1245.861 | 2.0759 | 16.02 |
| 28 | 365 | 19434.006 | 128.7811 | |
| | 788 | 1200.442 | 2.0002 | 33.73 |
| 29 | 365 | 19434.006 | 128.7811 | |
| | 793 | 1171.204 | 1.9515 | 46.70 |
| 30 | 365 | 19434.006 | 128.7811 | |
| | 815 | 1040.940 | 1.7344 | 80.60 |
| 31 | 384 | 18893.113 | 125.1968 | |
| | 679 | 1839.547 | 3.0651 | 9.80 |
| 32 | 384 | 18893.113 | 125.1968 | |
| | 788 | 1200.729 | 2.0007 | 2.34 |
| 33 | 384 | 18893.113 | 125.1968 | |
| | 801 | 1124.942 | 1.8744 | 1.93 |
| 34 | 384 | 18893.113 | 125.1968 | |
| | 803 | 1113.960 | 1.8561 | 1.36 |
| 35 | 384 | 18893.113 | 125.1968 | |
| | 809 | 1077.556 | 1.7954 | 3.32 |
| 36 | 384 | 18893.113 | 125.1968 | |
| | 813 | 1051.694 | 1.7524 | 3.14 |
| 37 | 384 | 18893.113 | 125.1968 | |
| | 848 | 847.499 | 1.4121 | 1.45 |
| 38 | 457 | 16738.236 | 110.9173 | |
| | 361 | 3707.331 | 6.1772 | 6.44 |
| 39 | 457 | 16738.236 | 110.9173 | |
| | 390 | 3534.169 | 5.8887 | 6.75 |
| 40 | 457 | 16738.236 | 110.9173 | |
| | 486 | 2972.803 | 4.9534 | 1.24 |
| 41 | 457 | 16738.236 | 110.9173 | |
| | 488 | 2962.223 | 4.9357 | 1.40 |
| 42 | 457 | 16738.236 | 110.9173 | |
| | 563 | 2520.559 | 4.1998 | 12.21 |
| 43 | 488 | 15822.760 | 104.8508 | |
| | 531 | 2712.055 | 4.5189 | 1.39 |
| 44 | 488 | 15822.760 | 104.8508 | |
| | 538 | 2668.887 | 4.4470 | 4.68 |
| 45 | 488 | 15822.760 | 104.8508 | |
| | 545 | 2627.709 | 4.3783 | 14.61 |
| 46 | 488 | 15822.760 | 104.8508 | |
| | 660 | 1952.474 | 3.2533 | 2.34 |
| 47 | 488 | 15822.760 | 104.8508 | |
| | 662 | 1941.101 | 3.2343 | 3.52 |
| 48 | 488 | 15822.760 | 104.8508 | |
| | 664 | 1928.930 | 3.2140 | 2.41 |
| 49 | 489 | 15777.470 | 104.5507 | |
| | 538 | 2669.101 | 4.4473 | 12.69 |
| 50 | 489 | 15777.470 | 104.5507 | |
| | 546 | 2622.941 | 4.3704 | 6.06 |
| 51 | 489 | 15777.470 | 104.5507 | |
| | 590 | 2363.695 | 3.9384 | 3.08 |
| 52 | 489 | 15777.470 | 104.5507 | |
| | 660 | 1953.443 | 3.2549 | 2.02 |
| 53 | 489 | 15777.470 | 104.5507 | |
| | 662 | 1940.913 | 3.2340 | 1.47 |
| 54 | 566 | 13527.920 | 89.6439 | |
| | 492 | 2938.198 | 4.8957 | 11.15 |
| 55 | 566 | 13527.920 | 89.6439 | |
| | 805 | 1101.852 | 1.8359 | 1.93 |
| 56 | 566 | 13527.920 | 89.6439 | |
| | 851 | 830.552 | 1.3839 | 5.09 |
| 57 | 566 | 13527.920 | 89.6439 | |
| | 864 | 757.374 | 1.2620 | 53.64 |
| 58 | 566 | 13527.920 | 89.6439 | |
| | 874 | 696.110 | 1.1599 | 39.08 |
| 59 | 566 | 13527.920 | 89.6439 | |
| | 880 | 658.836 | 1.0978 | 4.62 |
| 60 | 566 | 13527.920 | 89.6439 | |
| | 911 | 480.432 | 0.8005 | 1.38 |
| 61 | 566 | 13527.920 | 89.6439 | |
| | 913 | 466.506 | 0.7773 | 1.40 |
| 62 | 584 | 12992.842 | 86.0981 | |
| | 376 | 3621.487 | 6.0342 | 5.29 |
| 63 | 584 | 12992.842 | 86.0981 | |
| | 531 | 2708.564 | 4.5131 | 1.17 |
| 64 | 584 | 12992.842 | 86.0981 | |
| | 539 | 2662.648 | 4.4366 | 4.18 |
| 65 | 584 | 12992.842 | 86.0981 | |
| | 545 | 2625.947 | 4.3754 | 6.92 |
| 66 | 584 | 12992.842 | 86.0981 | |
| | 864 | 757.040 | 1.2614 | 1.36 |
| 67 | 588 | 12860.941 | 85.2241 | |
| | 370 | 3655.044 | 6.0901 | 2.76 |
| 68 | 588 | 12860.941 | 85.2241 | |
| | 376 | 3621.609 | 6.0344 | 10.88 |
| 69 | 588 | 12860.941 | 85.2241 | |
| | 554 | 2574.294 | 4.2893 | 1.21 |
| 70 | 588 | 12860.941 | 85.2241 | |
| | 864 | 756.227 | 1.2600 | 1.05 |
| 71 | 598 | 12585.614 | 83.3996 | |
| | 376 | 3621.268 | 6.0338 | 1.92 |
| 72 | 598 | 12585.614 | 83.3996 | |
| | 475 | 3038.901 | 5.0635 | 1.23 |
| 73 | 598 | 12585.614 | 83.3996 | |
| | 500 | 2890.984 | 4.8170 | 1.60 |
| 74 | 598 | 12585.614 | 83.3996 | |
| | 505 | 2863.233 | 4.7708 | 3.39 |
| 75 | 598 | 12585.614 | 83.3996 | |
| | 881 | 655.156 | 1.0916 | 1.11 |
| 76 | 623 | 11822.784 | 78.3447 | |
| | 295 | 4093.818 | 6.8212 | 2.30 |
| 77 | 623 | 11822.784 | 78.3447 | |
| | 321 | 3940.803 | 6.5663 | 2.25 |
| 78 | 623 | 11822.784 | 78.3447 | |
| | 348 | 3785.120 | 6.3069 | 18.28 |
| 79 | 623 | 11822.784 | 78.3447 | |
| | 434 | 3277.040 | 5.4603 | 1.13 |
| 80 | 623 | 11822.784 | 78.3447 | |
| | 448 | 3194.918 | 5.3234 | 7.26 |
| 81 | 623 | 11822.784 | 78.3447 | |
| | 563 | 2521.171 | 4.2008 | 7.36 |
| 82 | 623 | 11822.784 | 78.3447 | |
| | 845 | 867.271 | 1.4451 | 1.26 |
| 83 | 623 | 11822.784 | 78.3447 | |
| | 849 | 844.669 | 1.4074 | 10.09 |
| 84 | 623 | 11822.784 | 78.3447 | |
| | 858 | 790.448 | 1.3171 | 26.63 |
| 85 | 623 | 11822.784 | 78.3447 | |
| | 881 | 656.434 | 1.0938 | 51.16 |
| 86 | 630 | 11619.674 | 76.9987 | |
| | 348 | 3785.085 | 6.3068 | 1.21 |
| 87 | 630 | 11619.674 | 76.9987 | |
| | 539 | 2661.936 | 4.4354 | 6.49 |
| 88 | 630 | 11619.674 | 76.9987 | |
| | 552 | 2584.607 | 4.3065 | 1.49 |
| 89 | 630 | 11619.674 | 76.9987 | |
| | 858 | 790.978 | 1.3179 | 2.74 |
| 90 | 630 | 11619.674 | 76.9987 | |
| | 881 | 655.977 | 1.0930 | 5.21 |
| 91 | 641 | 11304.499 | 74.9102 | |
| | 307 | 4021.328 | 6.7004 | 1.03 |
| 92 | 641 | 11304.499 | 74.9102 | |
| | 526 | 2736.013 | 4.5588 | 4.14 |
| 93 | 641 | 11304.499 | 74.9102 | |
| | 538 | 2670.608 | 4.4498 | 9.80 |
| 94 | 641 | 11304.499 | 74.9102 | |
| | 881 | 656.537 | 1.0939 | 1.61 |
| 95 | 650 | 11028.925 | 73.0841 | |
| | 308 | 4015.948 | 6.6915 | 16.79 |
| 96 | 650 | 11028.925 | 73.0841 | |
| | 346 | 3793.459 | 6.3207 | 13.94 |
| 97 | 650 | 11028.925 | 73.0841 | |
| | 526 | 2736.761 | 4.5601 | 7.46 |
| 98 | 650 | 11028.925 | 73.0841 | |
| | 574 | 2454.410 | 4.0896 | 4.70 |
| 99 | 650 | 11028.925 | 73.0841 | |
| | 610 | 2245.856 | 3.7421 | 11.08 |
| 100 | 650 | 11028.925 | 73.0841 | |
| | 637 | 2088.895 | 3.4806 | 5.03 |
| 101 | 650 | 11028.925 | 73.0841 | |
| | 679 | 1839.510 | 3.0650 | 8.83 |
| 102 | 650 | 11028.925 | 73.0841 | |
| | 848 | 850.226 | 1.4167 | 1.52 |

TABLE 5.3-continued

| | | | | | | | | | |
|---|---|---|---|---|---|---|---|---|---|
| 103 | 650 | 11028.925 | 73.0841 | | | 143 | 781 | 7163.191 | 47.4675 |
| | 881 | 656.986 | 1.0947 | 1.80 | | | 874 | 695.441 | 1.1588 | 1.07 |
| 104 | 658 | 10790.329 | 71.5030 | | | 144 | 781 | 7163.191 | 47.4675 |
| | 308 | 4016.477 | 6.6923 | 1.26 | | | 881 | 656.256 | 1.0935 | 6.01 |
| 105 | 658 | 10790.329 | 71.5030 | | | 145 | 781 | 7163.191 | 47.4675 |
| | 531 | 2708.840 | 4.5135 | 2.58 | | | 891 | 594.695 | 0.9909 | 39.60 |
| 106 | 658 | 10790.329 | 71.5030 | | | 146 | 781 | 7163.191 | 47.4675 |
| | 564 | 2518.203 | 4.1959 | 5.49 | | | 909 | 489.613 | 0.8158 | 3.90 |
| 107 | 658 | 10790.329 | 71.5030 | | | 147 | 786 | 7041.051 | 46.6581 |
| | 609 | 2253.841 | 3.7554 | 1.07 | | | 432 | 3290.762 | 5.4831 | 2.39 |
| 108 | 658 | 10790.329 | 71.5030 | | | 148 | 786 | 7041.051 | 46.6581 |
| | 881 | 655.677 | 1.0925 | 1.26 | | | 669 | 1898.191 | 3.1628 | 1.21 |
| 109 | 668 | 10496.015 | 69.5527 | | | 149 | 786 | 7041.051 | 46.6581 |
| | 530 | 2715.370 | 4.5244 | 1.73 | | | 677 | 1850.653 | 3.0836 | 2.37 |
| 110 | 668 | 10496.015 | 69.5527 | | | 150 | 786 | 7041.051 | 46.6581 |
| | 533 | 2699.760 | 4.4984 | 1.85 | | | 680 | 1835.948 | 3.0591 | 2.84 |
| 111 | 668 | 10496.015 | 69.5527 | | | 151 | 786 | 7041.051 | 46.6581 |
| | 540 | 2658.708 | 4.4300 | 3.19 | | | 682 | 1821.518 | 3.0351 | 2.66 |
| 112 | 668 | 10496.015 | 69.5527 | | | 152 | 786 | 7041.051 | 46.6581 |
| | 590 | 2363.392 | 3.9379 | 4.52 | | | 689 | 1782.432 | 2.9699 | 2.02 |
| 113 | 668 | 10496.015 | 69.5527 | | | 153 | 786 | 7041.051 | 46.6581 |
| | 804 | 1107.602 | 1.8455 | 1.00 | | | 776 | 1274.214 | 2.1231 | 2.05 |
| 114 | 668 | 10496.015 | 69.5527 | | | 154 | 786 | 7041.051 | 46.6581 |
| | 881 | 656.508 | 1.0939 | 1.01 | | | 800 | 1129.576 | 1.8821 | 1.51 |
| 115 | 680 | 10155.364 | 67.2954 | | | 155 | 786 | 7041.051 | 46.6581 |
| | 541 | 2651.054 | 4.4172 | 2.15 | | | 804 | 1106.939 | 1.8444 | 6.33 |
| 116 | 680 | 10155.364 | 67.2954 | | | 156 | 786 | 7041.051 | 46.6581 |
| | 804 | 1107.228 | 1.8449 | 32.23 | | | 808 | 1082.787 | 1.8042 | 3.27 |
| 117 | 680 | 10155.364 | 67.2954 | | | 157 | 786 | 7041.051 | 46.6581 |
| | 881 | 656.545 | 1.0939 | 1.00 | | | 811 | 1065.178 | 1.7748 | 3.51 |
| 118 | 703 | 9486.470 | 62.8629 | | | 158 | 786 | 7041.051 | 46.6581 |
| | 346 | 3793.169 | 6.3203 | 9.40 | | | 829 | 959.508 | 1.5988 | 3.10 |
| 119 | 703 | 9486.470 | 62.8629 | | | 159 | 786 | 7041.051 | 46.6581 |
| | 348 | 3784.896 | 6.3065 | 9.63 | | | 838 | 906.837 | 1.5110 | 1.42 |
| 120 | 703 | 9486.470 | 62.8629 | | | 160 | 786 | 7041.051 | 46.6581 |
| | 679 | 1839.346 | 3.0648 | 3.08 | | | 848 | 847.280 | 1.4118 | 1.15 |
| 121 | 703 | 9486.470 | 62.8629 | | | 161 | 786 | 7041.051 | 46.6581 |
| | 863 | 758.265 | 1.2634 | 1.07 | | | 858 | 790.530 | 1.3172 | 49.82 |
| 122 | 706 | 9376.976 | 62.1373 | | | 162 | 786 | 7041.051 | 46.6581 |
| | 347 | 3790.748 | 6.3162 | 1.61 | | | 874 | 696.770 | 1.1610 | 1.14 |
| 123 | 706 | 9376.976 | 62.1373 | | | 163 | 786 | 7041.051 | 46.6581 |
| | 505 | 2862.456 | 4.7695 | 2.79 | | | 881 | 656.443 | 1.0938 | 70.13 |
| 124 | 706 | 9376.976 | 62.1373 | | | 164 | 786 | 7041.051 | 46.6581 |
| | 881 | 655.399 | 1.0920 | 1.01 | | | 891 | 594.532 | 0.9906 | 18.99 |
| 125 | 709 | 9296.042 | 61.6010 | | | 165 | 786 | 7041.051 | 46.6581 |
| | 590 | 2363.684 | 3.9384 | 7.53 | | | 909 | 489.363 | 0.8154 | 21.10 |
| 126 | 741 | 8346.307 | 55.3075 | | | 166 | 814 | 6218.377 | 41.2066 |
| | 777 | 1264.802 | 2.1074 | 3.77 | | | 431 | 3293.885 | 5.4883 | 1.45 |
| 127 | 741 | 8346.307 | 55.3075 | | | 167 | 814 | 6218.377 | 41.2066 |
| | 852 | 825.908 | 1.3761 | 3.30 | | | 561 | 2531.574 | 4.2182 | 3.03 |
| 128 | 741 | 8346.307 | 55.3075 | | | 168 | 814 | 6218.377 | 41.2066 |
| | 864 | 757.401 | 1.2620 | 35.15 | | | 564 | 2517.867 | 4.1953 | 3.26 |
| 129 | 741 | 8346.307 | 55.3075 | | | 169 | 814 | 6218.377 | 41.2066 |
| | 874 | 696.341 | 1.1603 | 25.71 | | | 635 | 2096.944 | 3.4940 | 2.64 |
| 130 | 741 | 8346.307 | 55.3075 | | | 170 | 814 | 6218.377 | 41.2066 |
| | 881 | 658.199 | 1.0967 | 3.92 | | | 678 | 1846.079 | 3.0760 | 2.51 |
| 131 | 741 | 8346.307 | 55.3075 | | | 171 | 814 | 6218.377 | 41.2066 |
| | 891 | 595.647 | 0.9925 | 1.15 | | | 776 | 1274.484 | 2.1236 | 1.75 |
| 132 | 741 | 8346.307 | 55.3075 | | | 172 | 814 | 6218.377 | 41.2066 |
| | 909 | 489.518 | 0.8156 | 23.33 | | | 783 | 1228.144 | 2.0464 | 1.41 |
| 133 | 781 | 7163.191 | 47.4675 | | | 173 | 814 | 6218.377 | 41.2066 |
| | 346 | 3793.181 | 6.3203 | 1.69 | | | 786 | 1211.726 | 2.0190 | 1.51 |
| 134 | 781 | 7163.191 | 47.4675 | | | 174 | 814 | 6218.377 | 41.2066 |
| | 431 | 3294.477 | 5.4893 | 5.30 | | | 799 | 1136.142 | 1.8931 | 1.43 |
| 135 | 781 | 7163.191 | 47.4675 | | | 175 | 814 | 6218.377 | 41.2066 |
| | 539 | 2661.476 | 4.4346 | 3.10 | | | 804 | 1107.204 | 1.8448 | 67.13 |
| 136 | 781 | 7163.191 | 47.4675 | | | 176 | 814 | 6218.377 | 41.2066 |
| | 541 | 2647.966 | 4.4121 | 3.42 | | | 819 | 1018.301 | 1.6967 | 4.37 |
| 137 | 781 | 7163.191 | 47.4675 | | | 177 | 814 | 6218.377 | 41.2066 |
| | 564 | 2517.984 | 4.1955 | 1.14 | | | 822 | 1001.489 | 1.6687 | 4.96 |
| 138 | 781 | 7163.191 | 47.4675 | | | 178 | 814 | 6218.377 | 41.2066 |
| | 679 | 1839.442 | 3.0649 | 3.64 | | | 833 | 939.695 | 1.5657 | 3.66 |
| 139 | 781 | 7163.191 | 47.4675 | | | 179 | 814 | 6218.377 | 41.2066 |
| | 804 | 1107.164 | 1.8448 | 37.94 | | | 864 | 756.271 | 1.2601 | 2.02 |
| 140 | 781 | 7163.191 | 47.4675 | | | 180 | 814 | 6218.377 | 41.2066 |
| | 822 | 1002.093 | 1.6697 | 1.62 | | | 874 | 695.963 | 1.1596 | 2.98 |
| 141 | 781 | 7163.191 | 47.4675 | | | 181 | 814 | 6218.377 | 41.2066 |
| | 849 | 845.058 | 1.4081 | 2.98 | | | 880 | 659.072 | 1.0982 | 1.66 |
| 142 | 781 | 7163.191 | 47.4675 | | | 182 | 814 | 6218.377 | 41.2066 |
| | 858 | 790.203 | 1.3167 | 4.12 | | | 891 | 594.287 | 0.9902 | 49.75 |

TABLE 5.3-continued

| | | | | |
|---|---|---|---|---|
| 183 | 814 | 6218.377 | 41.2066 | |
| | 895 | 572.724 | 0.9543 | 2.16 |
| 184 | 814 | 6218.377 | 41.2066 | |
| | 909 | 489.811 | 0.8161 | 1.62 |
| 185 | 823 | 5950.421 | 39.4310 | |
| | 662 | 1940.805 | 3.2338 | 1.07 |
| 186 | 823 | 5950.421 | 39.4310 | |
| | 776 | 1271.011 | 2.1178 | 1.62 |
| 187 | 823 | 5950.421 | 39.4310 | |
| | 804 | 1107.587 | 1.8455 | 2.29 |
| 188 | 823 | 5950.421 | 39.4310 | |
| | 831 | 947.726 | 1.5791 | 1.04 |
| 189 | 823 | 5950.421 | 39.4310 | |
| | 858 | 790.520 | 1.3172 | 1.45 |
| 190 | 823 | 5950.421 | 39.4310 | |
| | 864 | 757.090 | 1.2615 | 54.14 |
| 191 | 823 | 5950.421 | 39.4310 | |
| | 874 | 696.048 | 1.1598 | 72.55 |
| 192 | 823 | 5950.421 | 39.4310 | |
| | 880 | 658.503 | 1.0972 | 9.62 |
| 193 | 823 | 5950.421 | 39.4310 | |
| | 891 | 594.530 | 0.9906 | 2.75 |
| 194 | 823 | 5950.421 | 39.4310 | |
| | 911 | 479.432 | 0.7988 | 7.32 |
| 195 | 823 | 5950.421 | 39.4310 | |
| | 913 | 465.776 | 0.7761 | 7.03 |
| 196 | 827 | 5834.797 | 38.6648 | |
| | 804 | 1106.687 | 1.8440 | 2.69 |
| 197 | 827 | 5834.797 | 38.6648 | |
| | 819 | 1017.803 | 1.6959 | 1.66 |
| 198 | 827 | 5834.797 | 38.6648 | |
| | 822 | 1001.708 | 1.6691 | 1.68 |
| 199 | 827 | 5834.797 | 38.6648 | |
| | 841 | 889.985 | 1.4829 | 1.01 |
| 200 | 827 | 5834.797 | 38.6648 | |
| | 858 | 789.621 | 1.3157 | 1.33 |
| 201 | 827 | 5834.797 | 38.6648 | |
| | 864 | 758.164 | 1.2633 | 3.94 |
| 202 | 827 | 5834.797 | 38.6648 | |
| | 874 | 696.137 | 1.1599 | 6.09 |
| 203 | 827 | 5834.797 | 38.6648 | |
| | 881 | 656.905 | 1.0945 | 2.43 |
| 204 | 827 | 5834.797 | 38.6648 | |
| | 892 | 593.606 | 0.9891 | 1.90 |
| 205 | 827 | 5834.797 | 38.6648 | |
| | 909 | 489.245 | 0.8152 | 51.13 |
| 206 | 830 | 5743.329 | 38.0586 | |
| | 804 | 1108.031 | 1.8462 | 1.40 |
| 207 | 830 | 5743.329 | 38.0586 | |
| | 858 | 790.551 | 1.3172 | 1.95 |
| 208 | 830 | 5743.329 | 38.0586 | |
| | 864 | 757.091 | 1.2615 | 2.85 |
| 209 | 830 | 5743.329 | 38.0586 | |
| | 874 | 696.052 | 1.1598 | 3.54 |
| 210 | 830 | 5743.329 | 38.0586 | |
| | 881 | 655.620 | 1.0924 | 2.41 |
| 211 | 830 | 5743.329 | 38.0586 | |
| | 891 | 594.762 | 0.9910 | 3.06 |
| 212 | 830 | 5743.329 | 38.0586 | |
| | 909 | 489.474 | 0.8156 | 10.76 |
| 213 | 834 | 5623.896 | 37.2672 | |
| | 804 | 1107.433 | 1.8452 | 1.25 |
| 214 | 834 | 5623.896 | 37.2672 | |
| | 822 | 1002.039 | 1.6696 | 1.43 |
| 215 | 834 | 5623.896 | 37.2672 | |
| | 833 | 939.620 | 1.5656 | 1.01 |
| 216 | 834 | 5623.896 | 37.2672 | |
| | 858 | 790.603 | 1.3173 | 4.03 |
| 217 | 834 | 5623.896 | 37.2672 | |
| | 864 | 756.768 | 1.2609 | 1.89 |
| 218 | 834 | 5623.896 | 37.2672 | |
| | 874 | 696.444 | 1.1604 | 2.15 |
| 219 | 834 | 5623.896 | 37.2672 | |
| | 881 | 656.011 | 1.0931 | 4.39 |
| 220 | 834 | 5623.896 | 37.2672 | |
| | 891 | 594.776 | 0.9910 | 4.19 |
| 221 | 834 | 5623.896 | 37.2672 | |
| | 909 | 489.272 | 0.8152 | 10.53 |
| 222 | 837 | 5533.835 | 36.6704 | |
| | 777 | 1268.681 | 2.1139 | 1.72 |
| 223 | 837 | 5533.835 | 36.6704 | |
| | 804 | 1108.282 | 1.8466 | 1.01 |
| 224 | 837 | 5533.835 | 36.6704 | |
| | 811 | 1067.120 | 1.7781 | 1.70 |
| 225 | 837 | 5533.835 | 36.6704 | |
| | 819 | 1017.407 | 1.6952 | 4.37 |
| 226 | 837 | 5533.835 | 36.6704 | |
| | 822 | 1001.730 | 1.6691 | 4.67 |
| 227 | 837 | 5533.835 | 36.6704 | |
| | 832 | 943.762 | 1.5725 | 2.78 |
| 228 | 837 | 5533.835 | 36.6704 | |
| | 849 | 841.934 | 1.4028 | 2.09 |
| 229 | 837 | 5533.835 | 36.6704 | |
| | 858 | 790.630 | 1.3174 | 8.57 |
| 230 | 837 | 5533.835 | 36.6704 | |
| | 864 | 757.963 | 1.2629 | 2.10 |
| 231 | 837 | 5533.835 | 36.6704 | |
| | 874 | 695.245 | 1.1584 | 1.83 |
| 232 | 837 | 5533.835 | 36.6704 | |
| | 881 | 656.351 | 1.0936 | 11.03 |
| 233 | 837 | 5533.835 | 36.6704 | |
| | 891 | 594.692 | 0.9909 | 25.74 |
| 234 | 837 | 5533.835 | 36.6704 | |
| | 909 | 489.139 | 0.8150 | 53.53 |
| 235 | 837 | 5533.835 | 36.6704 | |
| | 913 | 467.893 | 0.7796 | 6.55 |
| 236 | 840 | 5450.419 | 36.1177 | |
| | 307 | 4023.448 | 6.7040 | 5.35 |
| 237 | 840 | 5450.419 | 36.1177 | |
| | 309 | 4013.866 | 6.6880 | 5.05 |
| 238 | 840 | 5450.419 | 36.1177 | |
| | 346 | 3794.546 | 6.3226 | 1.25 |
| 239 | 840 | 5450.419 | 36.1177 | |
| | 679 | 1839.242 | 3.0646 | 3.88 |
| 240 | 840 | 5450.419 | 36.1177 | |
| | 849 | 842.830 | 1.4043 | 6.34 |
| 241 | 840 | 5450.419 | 36.1177 | |
| | 858 | 790.237 | 1.3167 | 88.69 |
| 242 | 840 | 5450.419 | 36.1177 | |
| | 862 | 767.125 | 1.2782 | 1.79 |
| 243 | 840 | 5450.419 | 36.1177 | |
| | 864 | 755.041 | 1.2581 | 1.99 |
| 244 | 840 | 5450.419 | 36.1177 | |
| | 874 | 695.441 | 1.1588 | 2.24 |
| 245 | 840 | 5450.419 | 36.1177 | |
| | 881 | 656.060 | 1.0931 | 84.89 |
| 246 | 840 | 5450.419 | 36.1177 | |
| | 891 | 594.675 | 0.9909 | 7.64 |
| 247 | 840 | 5450.419 | 36.1177 | |
| | 909 | 489.300 | 0.8153 | 8.88 |
| 248 | 875 | 4418.238 | 29.2778 | |
| | 307 | 4022.778 | 6.7028 | 8.21 |
| 249 | 875 | 4418.238 | 29.2778 | |
| | 309 | 4014.385 | 6.6889 | 7.83 |
| 250 | 875 | 4418.238 | 29.2778 | |
| | 679 | 1841.576 | 3.0685 | 1.85 |
| 251 | 875 | 4418.238 | 29.2778 | |
| | 849 | 844.669 | 1.4074 | 1.65 |
| 252 | 875 | 4418.238 | 29.2778 | |
| | 858 | 790.492 | 1.3171 | 100.00 |
| 253 | 875 | 4418.238 | 29.2778 | |
| | 863 | 763.811 | 1.2727 | 3.72 |
| 254 | 875 | 4418.238 | 29.2778 | |
| | 870 | 718.885 | 1.1978 | 22.51 |
| 255 | 875 | 4418.238 | 29.2778 | |
| | 875 | 691.903 | 1.1529 | 4.90 |
| 256 | 875 | 4418.238 | 29.2778 | |
| | 878 | 670.147 | 1.1166 | 1.92 |
| 257 | 875 | 4418.238 | 29.2778 | |
| | 882 | 648.470 | 1.0805 | 1.77 |
| 258 | 875 | 4418.238 | 29.2778 | |
| | 892 | 593.301 | 0.9886 | 19.66 |
| 259 | 883 | 4176.082 | 27.6732 | |
| | 662 | 1941.300 | 3.2346 | 1.71 |
| 260 | 883 | 4176.082 | 27.6732 | |
| | 853 | 819.336 | 1.3652 | 15.64 |
| 261 | 883 | 4176.082 | 27.6732 | |
| | 857 | 794.801 | 1.3243 | 4.59 |
| 262 | 883 | 4176.082 | 27.6732 | |
| | 863 | 763.374 | 1.2720 | 1.70 |

TABLE 5.3-continued

| | | | | |
|---|---|---|---|---|
| 263 | 883 | 4176.082 | 27.6732 | |
| | 874 | 696.058 | 1.1598 | 89.76 |
| 264 | 883 | 4176.082 | 27.6732 | |
| | 878 | 671.861 | 1.1195 | 2.96 |
| 265 | 883 | 4176.082 | 27.6732 | |
| | 881 | 657.198 | 1.0950 | 7.96 |
| 266 | 883 | 4176.082 | 27.6732 | |
| | 911 | 479.487 | 0.7989 | 2.54 |
| 267 | 883 | 4176.082 | 27.6732 | |
| | 913 | 466.645 | 0.7775 | 2.27 |
| 268 | 903 | 3588.775 | 23.7813 | |
| | 431 | 3296.117 | 5.4921 | 2.85 |
| 269 | 903 | 3588.775 | 23.7813 | |
| | 791 | 1182.756 | 1.9707 | 1.05 |
| 270 | 903 | 3588.775 | 23.7813 | |
| | 801 | 1127.886 | 1.8793 | 1.45 |
| 271 | 903 | 3588.775 | 23.7813 | |
| | 804 | 1108.540 | 1.8471 | 1.43 |
| 272 | 903 | 3588.775 | 23.7813 | |
| | 811 | 1064.128 | 1.7731 | 1.37 |
| 273 | 903 | 3588.775 | 23.7813 | |
| | 821 | 1006.100 | 1.6764 | 3.82 |
| 274 | 903 | 3588.775 | 23.7813 | |
| | 874 | 696.649 | 1.1608 | 2.42 |
| 275 | 903 | 3588.775 | 23.7813 | |
| | 881 | 655.757 | 1.0926 | 2.43 |
| 276 | 917 | 3174.632 | 21.0370 | |
| | 307 | 4021.419 | 6.7006 | 1.44 |
| 277 | 917 | 3174.632 | 21.0370 | |
| | 384 | 3571.435 | 5.9508 | 2.36 |
| 278 | 917 | 3174.632 | 21.0370 | |
| | 403 | 3463.331 | 5.7707 | 1.11 |
| 279 | 917 | 3174.632 | 21.0370 | |
| | 561 | 2531.850 | 4.2186 | 5.21 |
| 280 | 917 | 3174.632 | 21.0370 | |
| | 564 | 2517.700 | 4.1950 | 5.22 |
| 281 | 917 | 3174.632 | 21.0370 | |
| | 778 | 1262.748 | 2.1040 | 3.52 |
| 282 | 917 | 3174.632 | 21.0370 | |
| | 793 | 1170.055 | 1.9496 | 22.51 |
| 283 | 917 | 3174.632 | 21.0370 | |
| | 800 | 1133.275 | 1.8883 | 2.77 |
| 284 | 917 | 3174.632 | 21.0370 | |
| | 805 | 1100.419 | 1.8335 | 3.08 |
| 285 | 917 | 3174.632 | 21.0370 | |
| | 809 | 1079.427 | 1.7986 | 2.91 |
| 286 | 917 | 3174.632 | 21.0370 | |
| | 815 | 1043.118 | 1.7381 | 24.13 |
| 287 | 917 | 3174.632 | 21.0370 | |
| | 827 | 975.020 | 1.6246 | 2.05 |
| 288 | 917 | 3174.632 | 21.0370 | |
| | 848 | 851.242 | 1.4184 | 1.60 |
| 289 | 917 | 3174.632 | 21.0370 | |
| | 864 | 757.267 | 1.2618 | 1.67 |
| 290 | 917 | 3174.632 | 21.0370 | |
| | 869 | 727.306 | 1.2119 | 1.80 |
| 291 | 917 | 3174.632 | 21.0370 | |
| | 881 | 656.407 | 1.0937 | 6.11 |
| 292 | 922 | 3013.427 | 19.9687 | |
| | 309 | 4014.743 | 6.6895 | 13.55 |
| 293 | 922 | 3013.427 | 19.9687 | |
| | 401 | 3472.374 | 5.7857 | 2.11 |
| 294 | 922 | 3013.427 | 19.9687 | |
| | 679 | 1841.875 | 3.0690 | 7.26 |
| 295 | 922 | 3013.427 | 19.9687 | |
| | 777 | 1263.952 | 2.1060 | 1.96 |
| 296 | 922 | 3013.427 | 19.9687 | |
| | 794 | 1165.725 | 1.9424 | 1.57 |
| 297 | 922 | 3013.427 | 19.9687 | |
| | 799 | 1137.940 | 1.8961 | 2.13 |
| 298 | 922 | 3013.427 | 19.9687 | |
| | 804 | 1104.456 | 1.8403 | 3.32 |
| 299 | 922 | 3013.427 | 19.9687 | |
| | 815 | 1043.070 | 1.7380 | 1.92 |
| 300 | 922 | 3013.427 | 19.9687 | |
| | 826 | 975.688 | 1.6257 | 3.29 |
| 301 | 922 | 3013.427 | 19.9687 | |
| | 847 | 852.676 | 1.4207 | 19.79 |
| 302 | 922 | 3013.427 | 19.9687 | |
| | 863 | 759.553 | 1.2656 | 3.39 |
| 303 | 922 | 3013.427 | 19.9687 | |
| | 869 | 726.647 | 1.2108 | 19.23 |
| 304 | 922 | 3013.427 | 19.9687 | |
| | 881 | 656.158 | 1.0933 | 72.09 |
| 305 | 929 | 2803.190 | 18.5756 | |
| | 308 | 4021.188 | 6.7002 | 1.12 |
| 306 | 929 | 2803.190 | 18.5756 | |
| | 823 | 997.155 | 1.6615 | 1.03 |
| 307 | 929 | 2803.190 | 18.5756 | |
| | 847 | 852.409 | 1.4203 | 2.46 |
| 308 | 929 | 2803.190 | 18.5756 | |
| | 864 | 756.417 | 1.2604 | 2.78 |
| 309 | 929 | 2803.190 | 18.5756 | |
| | 869 | 728.727 | 1.2142 | 2.15 |
| 310 | 929 | 2803.190 | 18.5756 | |
| | 881 | 657.345 | 1.0953 | 5.08 |
| 311 | 929 | 2803.190 | 18.5756 | |
| | 902 | 531.583 | 0.8857 | 1.25 |
| 312 | 929 | 2803.190 | 18.5756 | |
| | 911 | 478.022 | 0.7965 | 4.88 |
| 313 | 929 | 2803.190 | 18.5756 | |
| | 913 | 466.494 | 0.7773 | 5.42 |
| 314 | 936 | 2611.793 | 17.3073 | |
| | 777 | 1266.005 | 2.1094 | 1.92 |
| 315 | 936 | 2611.793 | 17.3073 | |
| | 783 | 1228.491 | 2.0469 | 2.67 |
| 316 | 936 | 2611.793 | 17.3073 | |
| | 786 | 1211.785 | 2.0191 | 2.98 |
| 317 | 936 | 2611.793 | 17.3073 | |
| | 819 | 1018.301 | 1.6967 | 5.90 |
| 318 | 936 | 2611.793 | 17.3073 | |
| | 822 | 1001.860 | 1.6693 | 7.01 |
| 319 | 936 | 2611.793 | 17.3073 | |
| | 864 | 757.418 | 1.2620 | 6.44 |
| 320 | 936 | 2611.793 | 17.3073 | |
| | 869 | 725.753 | 1.2093 | 1.48 |
| 321 | 936 | 2611.793 | 17.3073 | |
| | 872 | 707.264 | 1.1785 | 1.56 |
| 322 | 936 | 2611.793 | 17.3073 | |
| | 881 | 654.782 | 1.0910 | 17.83 |
| 323 | 936 | 2611.793 | 17.3073 | |
| | 902 | 531.793 | 0.8861 | 19.86 |
| 324 | 936 | 2611.793 | 17.3073 | |
| | 909 | 490.194 | 0.8168 | 2.94 |
| 325 | 936 | 2611.793 | 17.3073 | |
| | 920 | 427.649 | 0.7126 | 1.52 |
| 326 | 940 | 2489.586 | 16.4974 | |
| | 662 | 1941.819 | 3.2355 | 2.46 |
| 327 | 940 | 2489.586 | 16.4974 | |
| | 664 | 1929.172 | 3.2144 | 1.76 |
| 328 | 940 | 2489.586 | 16.4974 | |
| | 822 | 1001.010 | 1.6679 | 1.20 |
| 329 | 940 | 2489.586 | 16.4974 | |
| | 864 | 757.021 | 1.2614 | 66.00 |
| 330 | 940 | 2489.586 | 16.4974 | |
| | 871 | 712.622 | 1.1874 | 10.06 |
| 331 | 940 | 2489.586 | 16.4974 | |
| | 880 | 660.618 | 1.1007 | 2.75 |
| 332 | 940 | 2489.586 | 16.4974 | |
| | 885 | 632.387 | 1.0537 | 18.76 |
| 333 | 940 | 2489.586 | 16.4974 | |
| | 891 | 594.244 | 0.9901 | 3.19 |
| 334 | 940 | 2489.586 | 16.4974 | |
| | 899 | 548.142 | 0.9133 | 1.83 |
| 335 | 940 | 2489.586 | 16.4974 | |
| | 911 | 478.615 | 0.7975 | 8.03 |
| 336 | 940 | 2489.586 | 16.4974 | |
| | 913 | 466.429 | 0.7772 | 10.10 |
| 337 | 940 | 2489.586 | 16.4974 | |
| | 920 | 426.462 | 0.7106 | 1.57 |
| 338 | 945 | 2348.374 | 15.5617 | |
| | 383 | 3576.612 | 5.9594 | 2.25 |
| 339 | 945 | 2348.374 | 15.5617 | |
| | 402 | 3464.839 | 5.7732 | 1.77 |
| 340 | 945 | 2348.374 | 15.5617 | |
| | 769 | 1311.156 | 2.1847 | 9.92 |
| 341 | 945 | 2348.374 | 15.5617 | |
| | 783 | 1233.208 | 2.0548 | 4.90 |
| 342 | 945 | 2348.374 | 15.5617 | |
| | 791 | 1184.039 | 1.9729 | 8.41 |

TABLE 5.3-continued

| # | ADDRESS | [Hz] | [PPM] | INTENSITY |
|---|---|---|---|---|
| 343 | 945 | 2348.374 | 15.5617 | |
|  | 804 | 1106.429 | 1.8436 | 5.06 |
| 344 | 945 | 2348.374 | 15.5617 | |
|  | 819 | 1018.365 | 1.6968 | 3.91 |
| 345 | 945 | 2348.374 | 15.5617 | |
|  | 822 | 1001.834 | 1.6693 | 5.15 |
| 346 | 945 | 2348.374 | 15.5617 | |
|  | 864 | 756.741 | 1.2609 | 6.60 |
| 347 | 945 | 2348.374 | 15.5617 | |
|  | 872 | 710.417 | 1.1837 | 1.20 |
| 348 | 945 | 2348.374 | 15.5617 | |
|  | 881 | 655.039 | 1.0914 | 2.79 |
| 349 | 945 | 2348.374 | 15.5617 | |
|  | 885 | 632.486 | 1.0539 | 2.24 |
| 350 | 945 | 2348.374 | 15.5617 | |
|  | 899 | 550.147 | 0.9167 | 19.61 |
| 351 | 945 | 2348.374 | 15.5617 | |
|  | 906 | 510.518 | 0.8506 | 3.78 |
| 352 | 945 | 2348.374 | 15.5617 | |
|  | 911 | 480.301 | 0.8003 | 8.74 |
| 353 | 945 | 2348.374 | 15.5617 | |
|  | 914 | 464.362 | 0.7737 | 8.49 |
| 354 | 945 | 2348.374 | 15.5617 | |
|  | 920 | 426.538 | 0.7107 | 18.76 |

TABLE 5.5

Chemical Shift of the Proton NMR of compound Y of *Xanthoceras Sorbifolia* Extract

| # | ADDRESS | FREQUENCY [Hz] | [PPM] | INTENSITY |
|---|---|---|---|---|
| 1 | 5031.9 | 5309.524 | 8.8468 | 0.46 |
| 2 | 5430.0 | 5222.264 | 8.7015 | 134.66 |
| 3 | 5840.9 | 5132.173 | 8.5513 | 0.48 |
| 4 | 8204.9 | 4613.901 | 7.6878 | 0.26 |
| 5 | 8568.1 | 4534.263 | 7.5551 | 88.28 |
| 6 | 8943.7 | 4451.919 | 7.4179 | 0.33 |
| 7 | 9209.7 | 4393.602 | 7.3207 | 0.80 |
| 8 | 9575.2 | 4313.488 | 7.1872 | 180.00 |
| 9 | 9952.1 | 4230.846 | 7.0495 | 0.87 |
| 10 | 10277.2 | 4159.585 | 6.9308 | 1.02 |
| 11 | 10886.8 | 4025.922 | 6.7081 | 5.68 |
| 12 | 10933.6 | 4015.677 | 6.6910 | 6.19 |
| 13 | 11939.8 | 3795.084 | 6.3235 | 6.26 |
| 14 | 11986.7 | 3784.803 | 6.3063 | 5.85 |
| 15 | 12576.0 | 3655.587 | 6.0910 | 1.47 |
| 16 | 12728.0 | 3622.280 | 6.0355 | 6.92 |
| 17 | 12880.5 | 3588.844 | 5.9798 | 1.87 |
| 18 | 12914.2 | 3581.450 | 5.9675 | 4.48 |
| 19 | 12946.5 | 3574.366 | 5.9557 | 4.59 |
| 20 | 12979.5 | 3567.130 | 5.9436 | 2.00 |
| 21 | 13382.6 | 3478.754 | 5.7964 | 2.41 |
| 22 | 13415.6 | 3471.539 | 5.7844 | 5.03 |
| 23 | 13447.3 | 3464.568 | 5.7727 | 5.15 |
| 24 | 13479.1 | 3457.598 | 5.7611 | 2.66 |
| 25 | 14218.8 | 3295.432 | 5.4909 | 14.00 |
| 26 | 14655.9 | 3199.603 | 5.3312 | 28.97 |
| 27 | 14691.2 | 3191.875 | 5.3184 | 27.63 |
| 28 | 15715.3 | 2967.359 | 4.9443 | 5.64 |
| 29 | 15826.3 | 2943.028 | 4.9037 | 4.82 |
| 30 | 15860.6 | 2935.504 | 4.8912 | 5.15 |
| 31 | 16047.0 | 2894.632 | 4.8231 | 4.20 |
| 32 | 16149.6 | 2872.131 | 4.7856 | 3.79 |
| 33 | 16171.9 | 2867.242 | 4.7775 | 4.42 |
| 34 | 16774.1 | 2735.249 | 4.5575 | 5.92 |
| 35 | 16856.4 | 2717.187 | 4.5274 | 4.26 |
| 36 | 16883.5 | 2711.235 | 4.5175 | 4.56 |
| 37 | 16903.5 | 2706.854 | 4.5102 | 5.89 |
| 38 | 16930.6 | 2700.914 | 4.5003 | 4.68 |
| 39 | 17021.2 | 2681.046 | 4.4672 | 2.99 |
| 40 | 17056.9 | 2673.228 | 4.4542 | 8.41 |
| 41 | 17099.1 | 2663.974 | 4.4388 | 8.87 |
| 42 | 17135.6 | 2655.976 | 4.4254 | 8.11 |
| 43 | 17200.4 | 2641.771 | 4.4018 | 1.88 |
| 44 | 17232.6 | 2634.706 | 4.3900 | 2.90 |
| 45 | 17271.0 | 2626.288 | 4.3760 | 4.33 |
| 46 | 17308.8 | 2618.001 | 4.3622 | 2.85 |
| 47 | 17401.8 | 2597.607 | 4.3282 | 0.83 |
| 48 | 17459.1 | 2585.043 | 4.3073 | 3.41 |
| 49 | 17512.6 | 2573.328 | 4.2877 | 4.04 |
| 50 | 17596.4 | 2554.947 | 4.2571 | 0.89 |
| 51 | 17628.2 | 2547.968 | 4.2455 | 0.80 |
| 52 | 17666.8 | 2539.518 | 4.2314 | 1.30 |
| 53 | 17723.0 | 2527.184 | 4.2109 | 6.71 |
| 54 | 17745.9 | 2522.172 | 4.2025 | 7.98 |
| 55 | 17791.2 | 2512.248 | 4.1860 | 2.28 |
| 56 | 17874.1 | 2494.071 | 4.1557 | 2.90 |
| 57 | 17895.0 | 2489.477 | 4.1480 | 3.09 |
| 58 | 17927.1 | 2482.454 | 4.1363 | 2.64 |
| 59 | 17948.8 | 2477.683 | 4.1284 | 2.51 |
| 60 | 18034.1 | 2458.993 | 4.0972 | 3.27 |
| 61 | 18064.6 | 2452.313 | 4.0861 | 2.96 |
| 62 | 18076.5 | 2449.702 | 4.0817 | 2.96 |
| 63 | 18118.3 | 2440.538 | 4.0665 | 0.72 |
| 64 | 18156.4 | 2432.180 | 4.0526 | 0.89 |
| 65 | 18196.3 | 2423.432 | 4.0380 | 0.44 |
| 66 | 18432.1 | 2371.735 | 3.9518 | 2.34 |
| 67 | 18459.7 | 2365.684 | 3.9418 | 4.30 |
| 68 | 18487.4 | 2359.600 | 3.9316 | 2.24 |
| 69 | 18962.4 | 2255.466 | 3.7581 | 3.86 |
| 70 | 19011.0 | 2244.816 | 3.7404 | 4.38 |
| 71 | 19669.3 | 2100.485 | 3.4999 | 4.39 |
| 72 | 19717.6 | 2089.898 | 3.4822 | 4.16 |
| 73 | 20365.2 | 1947.920 | 3.2457 | 2.42 |
| 74 | 20401.1 | 1940.054 | 3.2326 | 2.35 |
| 75 | 20418.9 | 1936.161 | 3.2261 | 2.38 |
| 76 | 20751.3 | 1863.290 | 3.1047 | 0.70 |
| 77 | 20815.8 | 1849.152 | 3.0811 | 3.20 |
| 78 | 20857.9 | 1839.919 | 3.0657 | 11.24 |
| 79 | 20924.8 | 1825.236 | 3.0412 | 1.13 |
| 80 | 23431.3 | 1275.730 | 2.1257 | 3.95 |
| 81 | 23491.3 | 1262.573 | 2.1037 | 5.36 |
| 82 | 23538.7 | 1252.187 | 2.0864 | 15.56 |
| 83 | 23570.5 | 1245.203 | 2.0748 | 15.89 |
| 84 | 23696.1 | 1217.673 | 2.0289 | 2.98 |
| 85 | 23770.1 | 1201.463 | 2.0019 | 27.17 |
| 86 | 23827.6 | 1188.849 | 1.9809 | 1.36 |
| 87 | 23887.4 | 1175.734 | 1.9590 | 15.22 |
| 88 | 23919.5 | 1168.700 | 1.9473 | 15.28 |
| 89 | 24010.2 | 1148.811 | 1.9142 | 0.49 |
| 90 | 24104.2 | 1128.207 | 1.8798 | 1.77 |
| 91 | 24197.7 | 1107.716 | 1.8457 | 28.22 |
| 92 | 24263.8 | 1093.228 | 1.8216 | 3.27 |
| 93 | 24321.8 | 1080.503 | 1.8004 | 2.93 |
| 94 | 24373.5 | 1069.166 | 1.7815 | 2.83 |
| 95 | 24497.0 | 1042.094 | 1.7364 | 26.10 |
| 96 | 24598.4 | 1019.871 | 1.6993 | 3.17 |
| 97 | 24626.1 | 1013.793 | 1.6892 | 3.14 |
| 98 | 24676.1 | 1002.826 | 1.6709 | 1.84 |
| 99 | 24931.2 | 946.900 | 1.5777 | 2.14 |
| 100 | 24983.0 | 935.533 | 1.5588 | 3.02 |
| 101 | 25226.8 | 882.103 | 1.4698 | 0.25 |
| 102 | 25370.4 | 850.608 | 1.4173 | 4.11 |
| 103 | 25412.0 | 841.492 | 1.4021 | 4.88 |
| 104 | 25499.7 | 822.270 | 1.3701 | 4.07 |
| 105 | 25556.8 | 809.746 | 1.3492 | 2.62 |
| 106 | 25639.9 | 791.527 | 1.3189 | 31.95 |
| 107 | 25717.9 | 774.418 | 1.2904 | 2.84 |
| 108 | 25790.4 | 758.539 | 1.2639 | 22.85 |
| 109 | 26011.7 | 710.018 | 1.1830 | 4.66 |
| 110 | 26070.7 | 697.082 | 1.1615 | 24.95 |
| 111 | 26249.2 | 657.953 | 1.0963 | 31.39 |
| 112 | 26536.4 | 594.981 | 0.9914 | 25.26 |
| 113 | 26610.9 | 578.657 | 0.9642 | 0.97 |
| 114 | 26914.0 | 512.196 | 0.8534 | 2.04 |
| 115 | 27012.2 | 490.676 | 0.8176 | 25.88 |
| 116 | 27118.1 | 467.463 | 0.7789 | 3.69 |

TABLE 5.5-continued

Chemical Shift of the Proton NMR of compound Y of *Xanthoceras Sorbifolia* Extract

| # | ADDRESS | FREQUENCY [Hz] | [PPM] | INTENSITY |
|---|---------|----------------|-------|-----------|
| 117 | 27226.4 | 443.715 | 0.7393 | 1.07 |
| 118 | 28513.4 | 161.554 | 0.2692 | 0.89 |
| 119 | 28539.8 | 155.777 | 0.2596 | 1.54 |

TABLE 6.2

HMQC of Y1 peaklist

| # | # | ADDRESS | FREQUENCY | | INTENSITY |
|---|---|---------|-----------|---|-----------|
| 1 | 1 | 315 | 16740.193 | 110.9281 | 30.72 |
|   |   | 375 | 3624.445 | 6.0391 |   |
|   | 2 | 352 | 15855.943 | 105.0686 | 20.34 |
|   |   | 490 | 2950.420 | 4.9161 |   |
|   | 3 | 450 | 13537.575 | 89.7061 | 20.34 |
|   |   | 490 | 2950.420 | 4.9161 |   |
|   | 4 | 479 | 12863.844 | 85.2416 | 12.42 |
|   |   | 476 | 3032.063 | 5.0521 |   |
|   | 5 | 479 | 12863.844 | 85.2416 | 17.76 |
|   |   | 500 | 2892.360 | 4.8193 |   |
|   | 6 | 491 | 12577.806 | 83.3462 | 25.72 |
|   |   | 487 | 2969.087 | 4.9472 |   |
|   | 7 | 522 | 11857.070 | 78.5703 | 13.55 |
|   |   | 545 | 2627.024 | 4.3772 |   |
|   | 8 | 529 | 11685.553 | 77.4337 | 16.93 |
|   |   | 504 | 2870.087 | 4.7822 |   |
|   | 9 | 535 | 11537.104 | 76.4500 | 15.06 |
|   |   | 589 | 2370.150 | 3.9492 |   |
|   | 10 | 550 | 11191.633 | 74.1608 | 12.94 |
|   |   | 421 | 3355.320 | 5.5907 |   |
|   | 11 | 550 | 11191.633 | 74.1608 | 15.14 |
|   |   | 423 | 3342.807 | 5.5699 |   |
|   | 12 | 569 | 10733.316 | 71.1238 | 24.93 |
|   |   | 410 | 3421.295 | 5.7006 |   |
|   | 13 | 579 | 10497.793 | 69.5631 | 26.50 |
|   |   | 526 | 2740.480 | 4.5662 |   |
|   | 14 | 586 | 10332.951 | 68.4708 | 14.53 |
|   |   | 537 | 2674.056 | 4.4556 |   |
|   | 15 | 586 | 10332.951 | 68.4708 | 11.00 |
|   |   | 596 | 2330.159 | 3.8826 |   |
|   | 16 | 617 | 9621.364 | 63.7555 | 12.23 |
|   |   | 643 | 2051.886 | 3.4189 |   |
|   | 17 | 630 | 9299.908 | 61.6254 | 13.25 |
|   |   | 529 | 2718.381 | 4.5294 |   |
|   | 18 | 630 | 9299.908 | 61.6254 | 14.42 |
|   |   | 539 | 2665.365 | 4.4411 |   |
|   | 19 | 669 | 8391.979 | 55.6090 | 13.25 |
|   |   | 529 | 2718.381 | 4.5294 |   |
|   | 20 | 669 | 8391.979 | 55.6090 | 14.42 |
|   |   | 539 | 2665.365 | 4.4411 |   |
|   | 21 | 720 | 7193.972 | 47.6705 | 10.83 |
|   |   | 682 | 1821.991 | 3.0358 |   |
|   | 22 | 725 | 7055.427 | 46.7524 | 8.84 |
|   |   | 820 | 1015.280 | 1.6917 |   |
|   | 23 | 770 | 5994.782 | 39.7241 | 21.78 |
|   |   | 682 | 1822.241 | 3.0363 |   |
|   | 24 | 778 | 5810.328 | 38.5019 | 21.78 |
|   |   | 682 | 1822.241 | 3.0363 |   |
|   | 25 | 803 | 5229.784 | 34.6549 | 9.20 |
|   |   | 836 | 918.974 | 1.5312 |   |
|   | 26 | 813 | 4978.483 | 32.9897 | 9.04 |
|   |   | 866 | 743.550 | 1.2389 |   |
|   | 27 | 833 | 4517.225 | 29.9332 | 64.24 |
|   |   | 847 | 852.860 | 1.4211 |   |
|   | 28 | 847 | 4185.850 | 27.7373 | 74.68 |
|   |   | 861 | 773.417 | 1.2887 |   |
|   | 29 | 850 | 4113.891 | 27.2605 | 80.21 |
|   |   | 806 | 1096.582 | 1.8271 |   |
|   | 30 | 850 | 4113.891 | 27.2605 | 31.46 |
|   |   | 861 | 773.392 | 1.2886 |   |
|   | 31 | 885 | 3291.884 | 21.8135 | 100.00 |
|   |   | 756 | 1389.088 | 2.3145 |   |
|   | 32 | 893 | 3110.641 | 20.6125 | 89.09 |
|   |   | 796 | 1153.093 | 1.9213 |   |
|   | 33 | 893 | 3110.641 | 20.6125 | 50.66 |
|   |   | 803 | 1110.425 | 1.8502 |   |
|   | 34 | 897 | 2998.505 | 19.8694 | 45.64 |
|   |   | 803 | 1111.101 | 1.8513 |   |
|   | 35 | 897 | 2998.505 | 19.8694 | 78.07 |
|   |   | 853 | 820.195 | 1.3666 |   |
|   | 36 | 919 | 2497.783 | 16.5514 | 72.04 |
|   |   | 874 | 699.217 | 1.1651 |   |
|   | 37 | 919 | 2497.783 | 16.5514 | 37.18 |
|   |   | 910 | 483.491 | 0.8056 |   |
|   | 38 | 926 | 2336.725 | 15.4842 | 17.70 |
|   |   | 794 | 1165.059 | 1.9412 |   |
|   | 39 | 926 | 2336.725 | 15.4842 | 31.53 |
|   |   | 910 | 484.392 | 0.8071 |   | row [Hz]F1 [PPM]F1
col [Hz]F2 [PPM]F2

TABLE 6.2A

2D NMR (HMQC) data of Y1

| Assignment | w1 | w2 | Data Height |
|------------|--------|-------|-------------|
| 1C-H | 110.904 | 6.038 | 24704052 |
| 2C-H | 105.023 | 4.914 | 15964054 |
| 3C-H | 104.615 | 5.339 | 11824459 |
| 4C-H | 89.823 | 3.243 | 7951700 |
| 5C-H | 89.712 | 3.222 | 7911944 |
| 6C-H | 85.528 | 5.038 | 10494958 |
| 7C-H | 85.417 | 5.054 | 8839478 |
| 8C-H | 85.338 | 4.831 | 10297378 |
| 9C-H | 85.248 | 4.817 | 12857784 |
| 10C-H | 83.397 | 4.948 | 19288902 |
| 11C-H | 78.655 | 4.381 | 7900396 |
| 12C-H | 78.602 | 4.366 | 8972991 |
| 13C-H | 77.420 | 4.784 | 13438428 |
| 14C-H | 77.007 | 4.497 | 7206874 |
| 15C-H | 76.570 | 3.951 | 12216028 |
| 16C-H | 74.994 | 4.092 | 11486882 |
| 17C-H | 74.790 | 4.106 | 12904558 |
| 18C-H | 74.220 | 5.593 | 10130728 |
| 19C-H | 74.062 | 5.574 | 9532875 |
| 20C-H | 73.856 | 6.173 | 11098625 |
| 21C-H | 73.802 | 6.156 | 10393206 |
| 22C-H | 73.350 | 4.468 | 11007188 |
| 23C-H | 73.277 | 4.446 | 7281630 |
| 24C-H | 71.577 | 4.453 | 8645994 |
| 25C-H | 71.219 | 5.701 | 24595648 |
| 26C-H | 70.611 | 3.615 | 9076031 |
| 27C-H | 70.067 | 4.256 | 9261139 |
| 28C-H | 69.616 | 4.567 | 18994736 |
| 29C-H | 68.771 | 3.895 | 8451744 |
| 30C-H | 68.543 | 4.455 | 12573076 |
| 31C-H | 63.679 | 3.604 | 8239119 |
| 32C-H | 63.781 | 3.415 | 7458621 |
| 33C-H | 63.862 | 3.393 | 7841054 |
| 34C-H | 62.192 | 4.312 | 10795595 |
| 35C-H | 62.172 | 4.287 | 8408334 |
| 36C-H | 62.266 | 4.162 | 7944312 |
| 37C-H | 62.071 | 4.131 | 10031945 |
| 38C-H | 61.811 | 4.529 | 12476046 |
| 39C-H | 61.793 | 4.440 | 11880108 |
| 40C-H | 61.705 | 4.463 | 8055856 |
| 41C-H | 47.663 | 3.034 | 7772454 |
| 42C-H | 46.740 | 1.693 | 8583785 |
| 43C-H | 39.795 | 3.034 | 18038864 |
| 44C-H | 38.453 | 1.337 | 7912356 |
| 45C-H | 34.666 | 1.567 | 7317314 |
| 46C-H | 32.884 | 1.264 | 7887187 |

TABLE 6.2A-continued

2D NMR (HMQC) data of Y1

| Assignment | w1 | w2 | Data Height |
|---|---|---|---|
| 47C-H | 29.954 | 1.421 | 58253544 |
| 48C-H | 29.632 | 1.242 | 16326471 |
| 49C-H | 29.318 | 1.117 | 9248448 |
| 50C-H | 27.723 | 1.292 | 47380240 |
| 51C-H | 27.251 | 1.831 | 59260700 |
| 52C-H | 21.835 | 2.317 | 68135008 |
| 53C-H | 20.604 | 1.919 | 59543524 |
| 54C-H | 20.377 | 1.852 | 66987324 |
| 55C-H | 19.850 | 1.369 | 68067232 |
| 56C-H | 16.547 | 1.167 | 54857956 |
| 57C-H | 16.223 | 0.807 | 25159514 |
| 58C-H | 15.890 | 2.028 | 14256620 |
| 59C-H | 15.674 | 1.978 | 12750140 |
| 60C-H | 15.693 | 1.940 | 10562185 |
| 61C-H | 15.378 | 0.758 | 16911768 |
| 62C-H | 15.149 | 0.799 | 12756197 |
| 63C-H | 138.670 | 5.985 | 8925989 |
| 64C-H | 137.837 | 5.881 | 6871625 |
| 65C-H | 123.420 | 5.365 | 15877691 |

TABLE 6.3

2D NMR (HMBC) data of Y1 peaklist

| # | ADDRESS | FREQUENCY | INTENSITY |
|---|---|---|---|
| 1 | 148 | 25871.928 | 171.4391 | 11.03 |
|   | 362 | 3702.490 | 6.1692 |   |
| 2 | 148 | 25871.928 | 171.4391 | 93.44 |
|   | 756 | 1390.051 | 2.3161 |   |
| 3 | 169 | 25232.139 | 167.1995 | 28.04 |
|   | 796 | 1153.459 | 1.9219 |   |
| 4 | 169 | 25232.139 | 167.1995 | 29.81 |
|   | 803 | 1112.088 | 1.8530 |   |
| 5 | 293 | 21555.236 | 142.8347 | 25.74 |
|   | 806 | 1097.351 | 1.8284 |   |
| 6 | 314 | 20935.686 | 138.7293 | 33.12 |
|   | 786 | 1215.627 | 2.0255 |   |
| 7 | 314 | 20935.686 | 138.7293 | 46.88 |
|   | 796 | 1153.008 | 1.9212 |   |
| 8 | 318 | 20813.068 | 137.9168 | 9.66 |
|   | 786 | 1213.951 | 2.0227 |   |
| 9 | 318 | 20813.068 | 137.9168 | 29.47 |
|   | 792 | 1175.438 | 1.9585 |   |
| 10 | 318 | 20813.068 | 137.9168 | 46.19 |
|   | 803 | 1110.584 | 1.8505 |   |
| 11 | 369 | 19321.684 | 128.0342 | 13.34 |
|   | 785 | 1218.100 | 2.0296 |   |
| 12 | 369 | 19321.684 | 128.0342 | 28.29 |
|   | 792 | 1175.050 | 1.9579 |   |
| 13 | 369 | 19321.684 | 128.0342 | 26.99 |
|   | 796 | 1153.691 | 1.9223 |   |
| 14 | 369 | 19321.684 | 128.0342 | 65.83 |
|   | 803 | 1111.953 | 1.8528 |   |
| 15 | 486 | 15874.223 | 105.1898 | 16.48 |
|   | 477 | 3026.433 | 5.0427 |   |
| 16 | 486 | 15874.223 | 105.1898 | 9.96 |
|   | 545 | 2628.184 | 4.3791 |   |
| 17 | 486 | 15874.223 | 105.1898 | 10.46 |
|   | 557 | 2559.578 | 4.2648 |   |
| 18 | 565 | 13533.447 | 89.6787 | 10.78 |
|   | 491 | 2942.427 | 4.9027 |   |
| 19 | 565 | 13533.447 | 89.6787 | 41.26 |
|   | 861 | 774.469 | 1.2904 |   |
| 20 | 565 | 13533.447 | 89.6787 | 36.06 |
|   | 874 | 696.834 | 1.1611 |   |
| 21 | 587 | 12903.256 | 85.5028 | 20.78 |
|   | 362 | 3702.844 | 6.1698 |   |
| 22 | 587 | 12903.256 | 85.5028 | 12.97 |
|   | 375 | 3625.743 | 6.0413 |   |
| 23 | 587 | 12903.256 | 85.5028 | 35.15 |
|   | 847 | 852.970 | 1.4212 |   |

TABLE 6.3-continued

2D NMR (HMBC) data of Y1 peaklist

| # | ADDRESS | FREQUENCY | INTENSITY |
|---|---|---|---|
| 24 | 587 | 12903.256 | 85.5028 | 30.07 |
|   | 853 | 821.094 | 1.3681 |   |
| 25 | 622 | 11874.164 | 78.6836 | 9.13 |
|   | 447 | 3202.899 | 5.3367 |   |
| 26 | 622 | 11874.164 | 78.6836 | 9.75 |
|   | 563 | 2519.490 | 4.1980 |   |
| 27 | 647 | 11136.594 | 73.7961 | 19.44 |
|   | 476 | 3029.853 | 5.0484 |   |
| 28 | 647 | 11136.594 | 73.7961 | 9.88 |
|   | 625 | 2159.425 | 3.5981 |   |
| 29 | 660 | 10736.229 | 71.1431 | 30.15 |
|   | 873 | 702.447 | 1.1704 |   |
| 30 | 668 | 10508.083 | 69.6313 | 11.82 |
|   | 873 | 702.134 | 1.1699 |   |
| 31 | 673 | 10374.060 | 68.7432 | 41.29 |
|   | 873 | 702.539 | 1.1706 |   |
| 32 | 709 | 9310.579 | 61.6961 | 9.48 |
|   | 588 | 2374.061 | 3.9557 |   |
| 33 | 740 | 8380.918 | 55.5357 | 42.71 |
|   | 861 | 775.074 | 1.2914 |   |
| 34 | 740 | 8380.918 | 55.5357 | 30.33 |
|   | 874 | 696.643 | 1.1608 |   |
| 35 | 740 | 8380.918 | 55.5357 | 21.32 |
|   | 913 | 469.072 | 0.7816 |   |
| 36 | 781 | 7183.864 | 47.6035 | 43.72 |
|   | 847 | 853.277 | 1.4217 |   |
| 37 | 781 | 7183.864 | 47.6035 | 35.29 |
|   | 853 | 821.688 | 1.3691 |   |
| 38 | 786 | 7044.034 | 46.6769 | 9.09 |
|   | 848 | 851.746 | 1.4192 |   |
| 39 | 786 | 7044.034 | 46.6769 | 8.36 |
|   | 880 | 661.983 | 1.1030 |   |
| 40 | 786 | 7044.034 | 46.6769 | 27.00 |
|   | 913 | 469.396 | 0.7821 |   |
| 41 | 813 | 6236.901 | 41.3285 | 38.52 |
|   | 806 | 1097.285 | 1.8283 |   |
| 42 | 813 | 6236.901 | 41.3285 | 43.99 |
|   | 910 | 485.026 | 0.8082 |   |
| 43 | 822 | 5962.607 | 39.5109 | 32.36 |
|   | 806 | 1097.624 | 1.8289 |   |
| 44 | 822 | 5962.607 | 39.5109 | 41.54 |
|   | 861 | 774.567 | 1.2906 |   |
| 45 | 822 | 5962.607 | 39.5109 | 63.83 |
|   | 874 | 696.338 | 1.1603 |   |
| 46 | 822 | 5962.607 | 39.5109 | 32.10 |
|   | 910 | 484.561 | 0.8074 |   |
| 47 | 828 | 5792.666 | 38.3848 | 9.58 |
|   | 853 | 821.024 | 1.3680 |   |
| 48 | 828 | 5792.666 | 38.3848 | 39.07 |
|   | 913 | 469.203 | 0.7818 |   |
| 49 | 832 | 5676.145 | 37.6127 | 42.80 |
|   | 847 | 852.643 | 1.4207 |   |
| 50 | 832 | 5676.145 | 37.6127 | 53.76 |
|   | 853 | 821.900 | 1.3695 |   |
| 51 | 832 | 5676.145 | 37.6127 | 10.57 |
|   | 912 | 471.157 | 0.7851 |   |
| 52 | 837 | 5531.661 | 36.6553 | 8.78 |
|   | 853 | 822.175 | 1.3699 |   |
| 53 | 837 | 5531.661 | 36.6553 | 45.56 |
|   | 913 | 468.520 | 0.7807 |   |
| 54 | 847 | 5226.124 | 34.6307 | 27.35 |
|   | 805 | 1099.040 | 1.8312 |   |
| 55 | 856 | 4961.126 | 32.8747 | 32.47 |
|   | 910 | 484.632 | 0.8075 |   |
| 56 | 871 | 4515.250 | 29.9201 | 7.66 |
|   | 477 | 3025.946 | 5.0419 |   |
| 57 | 871 | 4515.250 | 29.9201 | 8.91 |
|   | 837 | 913.407 | 1.5219 |   |
| 58 | 871 | 4515.250 | 29.9201 | 52.28 |
|   | 853 | 821.483 | 1.3688 |   |
| 59 | 883 | 4184.067 | 27.7255 | 8.46 |
|   | 795 | 1160.819 | 1.9342 |   |
| 60 | 883 | 4184.067 | 27.7255 | 11.68 |
|   | 850 | 836.992 | 1.3946 |   |
| 61 | 883 | 4184.067 | 27.7255 | 77.80 |
|   | 874 | 696.591 | 1.1607 |   |

TABLE 6.3-continued

2D NMR (HMBC) data of Y1 peaklist

| # | ADDRESS | FREQUENCY | | INTENSITY |
|---|---|---|---|---|
| 62 | 913 | 3294.604 | 21.8315 | 16.90 |
|  | 745 | 1453.362 | 2.4216 |  |
| 63 | 913 | 3294.604 | 21.8315 | 15.41 |
|  | 767 | 1324.146 | 2.2063 |  |
| 64 | 923 | 2998.099 | 19.8668 | 12.57 |
|  | 477 | 3025.408 | 5.0410 |  |
| 65 | 923 | 2998.099 | 19.8668 | 9.99 |
|  | 683 | 1819.240 | 3.0313 |  |
| 66 | 923 | 2998.099 | 19.8668 | 18.02 |
|  | 842 | 883.190 | 1.4716 |  |
| 67 | 923 | 2998.099 | 19.8668 | 51.49 |
|  | 847 | 853.156 | 1.4215 |  |
| 68 | 923 | 2998.099 | 19.8668 | 16.19 |
|  | 864 | 757.915 | 1.2629 |  |
| 69 | 923 | 2998.099 | 19.8668 | 10.30 |
|  | 879 | 666.328 | 1.1103 |  |
| 70 | 940 | 2480.249 | 16.4352 | 42.66 |
|  | 861 | 775.278 | 1.2918 |  |
| 71 | 940 | 2480.249 | 16.4352 | 14.60 |
|  | 884 | 636.584 | 1.0607 |  |
| 72 | 940 | 2480.249 | 16.4352 | 12.91 |
|  | 900 | 544.736 | 0.9077 |  |
| 73 | 940 | 2480.249 | 16.4352 | 12.28 |
|  | 921 | 420.806 | 0.7012 |  |
| 74 | 946 | 2313.568 | 15.3307 | 14.80 |
|  | 902 | 531.201 | 0.8851 |  |
| 75 | 946 | 2313.568 | 15.3307 | 12.79 |
|  | 923 | 407.732 | 0.6794 |  | row [Hz]F1 [PPM]F1
col [Hz]F2 [PPM]F2

TABLE 6.4.

2D NMR (COSY) data of Y1.

| Assignment | w1 | w2 | Data Height |
|---|---|---|---|
| 1H-H | 6.704 | 6.322 | 9224233 |
| 2H-H | 6.678 | 6.372 | 9898637 |
| 3H-H | 6.419 | 4.456 | 20015776 |
| 4H-H | 6.368 | 6.681 | 11333652 |
| 5H-H | 6.320 | 6.706 | 11307411 |
| 6H-H | 6.171 | 5.044 | 134583264 |
| 7H-H | 6.043 | 4.952 | 12934876 |
| 8H-H | 5.980 | 2.030 | 80531096 |
| 9H-H | 5.980 | 2.021 | 105609248 |
| 10H-H | 5.881 | 1.963 | 81350000 |
| 11H-H | 5.881 | 1.952 | 75881512 |
| 12H-H | 5.701 | 5.700 | 215204304 |
| 13H-H | 5.700 | 5.590 | 18340750 |
| 14H-H | 5.699 | 5.575 | 15251625 |
| 15H-H | 5.582 | 5.701 | 24882492 |
| 16H-H | 5.583 | 4.930 | 32200604 |
| 17H-H | 5.583 | 4.269 | 54166860 |
| 18H-H | 5.582 | 4.260 | 100437000 |
| 19H-H | 5.582 | 4.251 | 50904084 |
| 20H-H | 5.335 | 4.478 | 54908116 |
| 21H-H | 5.335 | 4.462 | 48000284 |
| 22H-H | 5.334 | 4.100 | 20768318 |
| 23H-H | 5.048 | 6.174 | 89161792 |
| 24H-H | 4.949 | 4.792 | 11766272 |
| 25H-H | 4.950 | 4.782 | 9033592 |
| 26H-H | 4.930 | 5.583 | 17147768 |
| 27H-H | 4.929 | 4.269 | 30517720 |
| 28H-H | 4.927 | 4.251 | 28975240 |
| 29H-H | 4.901 | 4.390 | 27806448 |
| 30H-H | 4.900 | 4.373 | 34077108 |
| 31H-H | 4.831 | 4.790 | 99849200 |
| 32H-H | 4.820 | 4.310 | 7275091 |
| 33H-H | 4.819 | 4.296 | 7797132 |
| 34H-H | 4.822 | 4.157 | 13857122 |
| 35H-H | 4.821 | 4.138 | 18211468 |
| 36H-H | 4.794 | 4.953 | 30630578 |

TABLE 6.4.-continued

2D NMR (COSY) data of Y1.

| Assignment | w1 | w2 | Data Height |
|---|---|---|---|
| 37H-H | 4.787 | 4.827 | 86722272 |
| 38H-H | 4.568 | 4.109 | 17535982 |
| 39H-H | 4.567 | 4.093 | 15653847 |
| 40H-H | 4.542 | 4.466 | 32239438 |
| 41H-H | 4.522 | 4.453 | 145233152 |
| 42H-H | 4.517 | 4.205 | 7769614 |
| 43H-H | 4.523 | 3.952 | 73572400 |
| 44H-H | 4.507 | 4.436 | 11835048 |
| 45H-H | 4.468 | 5.337 | 79724560 |
| 46H-H | 4.468 | 4.099 | 83781344 |
| 47H-H | 4.461 | 3.954 | 44029948 |
| 48H-H | 4.454 | 6.528 | 9453154 |
| 49H-H | 4.454 | 6.418 | 79266688 |
| 50H-H | 4.450 | 4.381 | 13566321 |
| 51H-H | 4.449 | 4.321 | 8581714 |
| 52H-H | 4.444 | 4.214 | 29697092 |
| 53H-H | 4.445 | 4.205 | 23505830 |
| 54H-H | 4.443 | 4.195 | 23169768 |
| 55H-H | 4.382 | 4.902 | 75968808 |
| 56H-H | 4.380 | 4.214 | 34194940 |
| 57H-H | 4.379 | 4.204 | 34462264 |
| 58H-H | 4.380 | 4.195 | 34413552 |
| 59H-H | 4.302 | 4.823 | 16076232 |
| 60H-H | 4.302 | 4.148 | 221634448 |
| 61H-H | 4.262 | 5.582 | 80620088 |
| 62H-H | 4.261 | 4.930 | 59383108 |
| 63H-H | 4.203 | 4.900 | 12911051 |
| 64H-H | 4.204 | 4.433 | 20195584 |
| 65H-H | 4.150 | 4.832 | 17371252 |
| 66H-H | 4.153 | 4.819 | 18323128 |
| 67H-H | 4.149 | 4.305 | 216562864 |
| 68H-H | 4.099 | 5.337 | 25030224 |
| 69H-H | 4.100 | 4.571 | 36121208 |
| 70H-H | 4.101 | 4.472 | 68659520 |
| 71H-H | 4.095 | 4.460 | 36864516 |
| 72H-H | 4.028 | 4.468 | 7964866 |
| 73H-H | 4.028 | 4.458 | 8388422 |
| 74H-H | 3.961 | 4.463 | 41897776 |
| 75H-H | 3.953 | 4.539 | 34935532 |
| 76H-H | 3.952 | 4.523 | 50083884 |
| 77H-H | 3.953 | 4.447 | 24637258 |
| 78H-H | 3.893 | 1.162 | 59572844 |
| 79H-H | 3.887 | 1.175 | 95668312 |
| 80H-H | 3.766 | 3.516 | 11119055 |
| 81H-H | 3.744 | 3.494 | 6884830 |
| 82H-H | 3.598 | 3.413 | 146852352 |
| 83H-H | 3.598 | 3.404 | 128194976 |
| 84H-H | 3.517 | 3.767 | 10865892 |
| 85H-H | 3.508 | 3.759 | 9535602 |
| 86H-H | 3.480 | 3.741 | 8054603 |
| 87H-H | 3.475 | 3.734 | 6268863 |
| 88H-H | 3.409 | 3.599 | 107289744 |
| 89H-H | 3.406 | 3.592 | 110786000 |
| 90H-H | 3.229 | 2.109 | 12003553 |
| 91H-H | 2.110 | 1.838 | 8593652 |
| 92H-H | 2.107 | 1.822 | 11474128 |
| 93H-H | 2.107 | 1.811 | 10279236 |
| 94H-H | 2.105 | 1.794 | 8116300 |
| 95H-H | 2.029 | 5.992 | 47626580 |
| 96H-H | 2.027 | 5.984 | 47768532 |
| 97H-H | 2.026 | 5.972 | 51874608 |
| 98H-H | 2.030 | 2.118 | 7536440 |
| 99H-H | 2.027 | 1.919 | 89540200 |
| 100H-H | 2.024 | 5.964 | 41580316 |
| 101H-H | 1.959 | 5.891 | 49355596 |
| 102H-H | 1.955 | 5.882 | 46234528 |
| 103H-H | 1.956 | 5.870 | 51174608 |
| 104H-H | 1.954 | 1.848 | 77092128 |
| 105H-H | 1.923 | 2.030 | 54674196 |
| 106H-H | 1.917 | 2.020 | 54160620 |
| 107H-H | 1.848 | 1.958 | 62600468 |
| 108H-H | 1.834 | 1.756 | 16637570 |
| 109H-H | 1.829 | 1.732 | 26336268 |
| 110H-H | 1.828 | 1.711 | 15651960 |
| 111H-H | 1.835 | 1.677 | 25025304 |
| 112H-H | 1.830 | 1.553 | 106561752 |

TABLE 6.4.-continued

2D NMR (COSY) data of Y1.

| Assignment | w1 | w2 | Data Height |
|---|---|---|---|
| 113H-H | 1.828 | 1.536 | 92597192 |
| 114H-H | 1.820 | 3.231 | 15325426 |
| 115H-H | 1.819 | 3.220 | 13169861 |
| 116H-H | 1.818 | 2.114 | 14925469 |
| 117H-H | 1.818 | 2.106 | 16020545 |
| 118H-H | 1.742 | 1.848 | 24286072 |
| 119H-H | 1.745 | 1.827 | 35995120 |
| 120H-H | 1.669 | 1.827 | 14851102 |
| 121H-H | 1.546 | 1.834 | 96039856 |
| 122H-H | 1.543 | 1.819 | 72780528 |
| 123H-H | 1.545 | 1.270 | 7218780 |
| 124H-H | 1.546 | 1.255 | 36723868 |
| 125H-H | 1.544 | 1.241 | 22604678 |
| 126H-H | 1.476 | 1.271 | 6846019 |
| 127H-H | 1.477 | 1.255 | 10952480 |
| 128H-H | 1.471 | 1.242 | 8182750 |
| 129H-H | 1.474 | 0.727 | 7531610 |
| 130H-H | 1.348 | 0.812 | 23199942 |
| 131H-H | 1.348 | 0.796 | 27081584 |
| 132H-H | 1.344 | 0.784 | 22663138 |
| 133H-H | 1.260 | 1.540 | 12084268 |
| 134H-H | 1.263 | 1.489 | 14416738 |
| 135H-H | 1.263 | 1.474 | 17048864 |
| 136H-H | 1.267 | 0.736 | 16594936 |
| 137H-H | 1.266 | 0.719 | 16949332 |
| 138H-H | 1.252 | 1.558 | 13171360 |
| 139H-H | 1.250 | 1.525 | 19080828 |
| 140H-H | 1.237 | 0.837 | 11506187 |
| 141H-H | 1.167 | 3.901 | 86146744 |
| 142H-H | 1.167 | 3.877 | 80709560 |
| 143H-H | 0.840 | 1.234 | 8462904 |
| 144H-H | 0.798 | 1.351 | 39178912 |
| 145H-H | 0.798 | 1.342 | 32789168 |
| 146H-H | 0.730 | 1.482 | 11378742 |
| 147H-H | 0.731 | 1.270 | 11791943 |
| 148H-H | 0.729 | 1.255 | 15935769 |
| 149H-H | 4.460 | 4.531 | 92968608 |
| 150H-H | 4.203 | 4.382 | 45014720 |
| 151H-H | 4.203 | 4.373 | 32816148 |
| 152H-H | 1.795 | 1.675 | 4628933 |

TABLE 6.5.

Proton NMR chemical shift data of Y1

| # | ADDRESS | FREQUENCY [Hz] | [PPM] | INTENSITY |
|---|---|---|---|---|
| 1 | 5803.6 | 5312.007 | 8.8510 | 1.05 |
| 2 | 6201.8 | 5224.701 | 8.7055 | 180.00 |
| 3 | 6517.2 | 5155.558 | 8.5903 | 0.09 |
| 4 | 6612.7 | 5134.626 | 8.5554 | 1.05 |
| 5 | 8992.9 | 4612.799 | 7.6859 | 0.41 |
| 6 | 9356.8 | 4533.029 | 7.5530 | 62.60 |
| 7 | 9733.1 | 4450.514 | 7.4155 | 0.40 |
| 8 | 9952.7 | 4402.383 | 7.3353 | 0.13 |
| 9 | 9996.2 | 4392.832 | 7.3194 | 0.90 |
| 10 | 10361.5 | 4312.746 | 7.1860 | 134.51 |
| 11 | 10641.7 | 4251.327 | 7.0837 | 0.05 |
| 12 | 10739.1 | 4229.980 | 7.0481 | 0.87 |
| 13 | 12483.6 | 3847.521 | 6.4108 | 0.10 |
| 14 | 12504.0 | 3843.034 | 6.4033 | 0.10 |
| 15 | 13117.1 | 3708.630 | 6.1794 | 0.31 |
| 16 | 13161.7 | 3698.843 | 6.1631 | 0.31 |
| 17 | 13503.5 | 3623.905 | 6.0382 | 0.38 |
| 18 | 13617.2 | 3598.988 | 5.9967 | 0.08 |
| 19 | 13649.9 | 3591.811 | 5.9848 | 0.19 |
| 20 | 13679.2 | 3585.404 | 5.9741 | 0.18 |
| 21 | 13712.9 | 3577.998 | 5.9617 | 0.08 |
| 22 | 13886.8 | 3539.884 | 5.8982 | 0.09 |
| 23 | 13920.0 | 3532.594 | 5.8861 | 0.19 |
| 24 | 13952.5 | 3525.479 | 5.8742 | 0.17 |
| 25 | 13983.6 | 3518.658 | 5.8629 | 0.06 |
| 26 | 14413.7 | 3424.364 | 5.7058 | 0.36 |
| 27 | 14428.7 | 3421.080 | 5.7003 | 0.36 |
| 28 | 14720.0 | 3357.206 | 5.5939 | 0.19 |
| 29 | 14735.6 | 3353.801 | 5.5882 | 0.18 |
| 30 | 14766.4 | 3347.042 | 5.5769 | 0.20 |
| 31 | 14781.9 | 3343.652 | 5.5713 | 0.17 |
| 32 | 15028.7 | 3289.533 | 5.4811 | 0.05 |
| 33 | 15343.4 | 3220.543 | 5.3661 | 0.33 |
| 34 | 15404.6 | 3207.131 | 5.3438 | 0.25 |
| 35 | 15439.6 | 3199.461 | 5.3310 | 0.25 |
| 36 | 16193.8 | 3034.111 | 5.0555 | 0.14 |
| 37 | 16238.8 | 3024.240 | 5.0391 | 0.15 |
| 38 | 16381.2 | 2993.014 | 4.9870 | 0.17 |
| 39 | 16518.3 | 2962.967 | 4.9370 | 0.12 |
| 40 | 16553.7 | 2955.209 | 4.9240 | 0.12 |
| 41 | 16599.3 | 2945.198 | 4.9074 | 0.08 |
| 42 | 16633.5 | 2937.700 | 4.8949 | 0.08 |
| 43 | 16843.2 | 2891.736 | 4.8183 | 0.18 |
| 44 | 16905.3 | 2878.117 | 4.7956 | 0.17 |
| 45 | 16927.0 | 2873.370 | 4.7877 | 0.19 |
| 46 | 17523.6 | 2742.566 | 4.5697 | 0.33 |
| 47 | 17586.3 | 2728.818 | 4.5468 | 0.18 |
| 48 | 17617.6 | 2721.965 | 4.5354 | 0.23 |
| 49 | 17635.4 | 2718.066 | 4.5289 | 0.31 |
| 50 | 17665.9 | 2711.371 | 4.5177 | 0.32 |
| 51 | 17716.2 | 2700.349 | 4.4994 | 0.21 |
| 52 | 17760.5 | 2690.632 | 4.4832 | 0.20 |
| 53 | 17810.9 | 2679.588 | 4.4648 | 0.55 |
| 54 | 17835.7 | 2674.141 | 4.4557 | 0.72 |
| 55 | 17857.9 | 2669.267 | 4.4476 | 0.54 |
| 56 | 18007.8 | 2636.409 | 4.3928 | 0.17 |
| 57 | 18046.2 | 2627.986 | 4.3788 | 0.26 |
| 58 | 18083.2 | 2619.886 | 4.3653 | 0.19 |
| 59 | 18189.9 | 2596.493 | 4.3263 | 0.11 |
| 60 | 18233.6 | 2586.912 | 4.3104 | 0.27 |
| 61 | 18277.8 | 2577.209 | 4.2942 | 0.31 |
| 62 | 18331.5 | 2565.443 | 4.2746 | 0.21 |
| 63 | 18367.6 | 2557.542 | 4.2614 | 0.23 |
| 64 | 18412.4 | 2547.721 | 4.2451 | 0.19 |
| 65 | 18458.8 | 2537.540 | 4.2281 | 0.10 |
| 66 | 18491.9 | 2530.283 | 4.2160 | 0.21 |
| 67 | 18532.6 | 2521.359 | 4.2011 | 0.28 |
| 68 | 18567.2 | 2513.770 | 4.1885 | 0.14 |
| 69 | 18645.4 | 2496.625 | 4.1599 | 0.25 |
| 70 | 18666.5 | 2491.997 | 4.1522 | 0.25 |
| 71 | 18699.9 | 2484.686 | 4.1400 | 0.24 |
| 72 | 18721.5 | 2479.943 | 4.1321 | 0.19 |
| 73 | 18778.7 | 2467.413 | 4.1113 | 0.20 |
| 74 | 18792.8 | 2464.305 | 4.1061 | 0.20 |
| 75 | 18821.9 | 2457.939 | 4.0955 | 0.19 |
| 76 | 18835.7 | 2454.909 | 4.0904 | 0.18 |
| 77 | 19186.2 | 2378.063 | 3.9624 | 0.17 |
| 78 | 19213.7 | 2372.029 | 3.9523 | 0.29 |
| 79 | 19239.6 | 2366.350 | 3.9429 | 0.16 |
| 80 | 19338.7 | 2344.635 | 3.9067 | 0.08 |
| 81 | 19366.7 | 2338.490 | 3.8964 | 0.22 |
| 82 | 19396.9 | 2331.872 | 3.8854 | 0.21 |
| 83 | 19428.2 | 2325.007 | 3.8740 | 0.06 |
| 84 | 20015.2 | 2196.324 | 3.6596 | 0.05 |
| 85 | 20048.6 | 2188.994 | 3.6474 | 0.08 |
| 86 | 20131.1 | 2170.900 | 3.6172 | 0.13 |
| 87 | 20161.7 | 2164.211 | 3.6061 | 0.28 |
| 88 | 20208.1 | 2154.040 | 3.5891 | 0.31 |
| 89 | 20679.1 | 2050.765 | 3.4170 | 0.24 |
| 90 | 20727.6 | 2040.135 | 3.3993 | 0.23 |
| 91 | 20782.4 | 2028.119 | 3.3793 | 0.08 |
| 92 | 21179.2 | 1941.123 | 3.2343 | 0.14 |
| 93 | 21213.6 | 1933.579 | 3.2218 | 0.13 |
| 94 | 21586.4 | 1851.862 | 3.0856 | 0.07 |
| 95 | 21649.4 | 1838.049 | 3.0626 | 0.09 |
| 96 | 21715.8 | 1823.490 | 3.0383 | 0.67 |
| 97 | 21747.5 | 1816.527 | 3.0267 | 0.23 |
| 98 | 23153.9 | 1508.199 | 2.5130 | 0.06 |

TABLE 6.5.-continued

Proton NMR chemical shift data of Y1

| # | ADDRESS | FREQUENCY [Hz] | [PPM] | INTENSITY |
|---|---------|----------------|-------|-----------|
| 99 | 23693.5 | 1389.916 | 2.3159 | 2.02 |
| 100 | 24231.4 | 1271.971 | 2.1194 | 0.22 |
| 101 | 24282.2 | 1260.831 | 2.1008 | 0.22 |
| 102 | 24341.3 | 1247.878 | 2.0792 | 0.16 |
| 103 | 24413.6 | 1232.024 | 2.0528 | 0.15 |
| 104 | 24464.0 | 1220.989 | 2.0344 | 0.83 |
| 105 | 24468.7 | 1219.963 | 2.0327 | 0.83 |
| 106 | 24496.7 | 1213.827 | 2.0225 | 0.82 |
| 107 | 24540.5 | 1204.212 | 2.0065 | 0.24 |
| 108 | 24614.2 | 1188.066 | 1.9796 | 0.24 |
| 109 | 24658.3 | 1178.391 | 1.9635 | 0.88 |
| 110 | 24686.0 | 1172.311 | 1.9533 | 0.86 |
| 111 | 24690.9 | 1171.249 | 1.9516 | 0.85 |
| 112 | 24774.5 | 1152.908 | 1.9210 | 1.65 |
| 113 | 24824.7 | 1141.905 | 1.9027 | 0.22 |
| 114 | 24966.5 | 1110.815 | 1.8509 | 2.07 |
| 115 | 25021.9 | 1098.679 | 1.8306 | 2.09 |
| 116 | 25154.1 | 1069.689 | 1.7823 | 0.22 |
| 117 | 25213.5 | 1056.676 | 1.7607 | 0.20 |
| 118 | 25280.4 | 1042.010 | 1.7362 | 0.33 |
| 119 | 25347.2 | 1027.363 | 1.7118 | 0.24 |
| 120 | 25396.2 | 1016.604 | 1.6939 | 0.38 |
| 121 | 25591.3 | 973.839 | 1.6226 | 0.16 |
| 122 | 25626.4 | 966.149 | 1.6098 | 0.22 |
| 123 | 25673.7 | 955.785 | 1.5926 | 0.16 |
| 124 | 25759.1 | 937.061 | 1.5614 | 0.45 |
| 125 | 25837.0 | 919.968 | 1.5329 | 0.32 |
| 126 | 25932.6 | 899.023 | 1.4980 | 0.22 |
| 127 | 25995.9 | 885.130 | 1.4748 | 0.28 |
| 128 | 26142.6 | 852.967 | 1.4212 | 1.52 |
| 129 | 26284.2 | 821.936 | 1.3695 | 1.99 |
| 130 | 26355.3 | 806.354 | 1.3436 | 0.49 |
| 131 | 26405.2 | 795.414 | 1.3253 | 0.53 |
| 132 | 26437.0 | 788.423 | 1.3137 | 0.61 |
| 133 | 26495.4 | 775.620 | 1.2924 | 1.83 |
| 134 | 26547.6 | 764.186 | 1.2733 | 0.62 |
| 135 | 26578.6 | 757.400 | 1.2620 | 0.75 |
| 136 | 26635.0 | 745.018 | 1.2414 | 0.66 |
| 137 | 26710.2 | 728.529 | 1.2139 | 0.35 |
| 138 | 26742.2 | 721.515 | 1.2022 | 0.34 |
| 139 | 26774.1 | 714.532 | 1.1906 | 0.38 |
| 140 | 26818.0 | 704.909 | 1.1745 | 1.47 |
| 141 | 26852.6 | 697.329 | 1.1619 | 2.39 |
| 142 | 26939.0 | 678.382 | 1.1303 | 0.28 |
| 143 | 26967.1 | 672.226 | 1.1201 | 0.28 |
| 144 | 26987.0 | 667.851 | 1.1128 | 0.31 |
| 145 | 27035.8 | 657.144 | 1.0949 | 0.25 |
| 146 | 27059.9 | 651.863 | 1.0861 | 0.21 |
| 147 | 27091.3 | 644.992 | 1.0747 | 0.18 |
| 148 | 27116.3 | 639.514 | 1.0656 | 0.13 |
| 149 | 27306.1 | 597.891 | 0.9962 | 0.21 |
| 150 | 27331.8 | 592.271 | 0.9869 | 0.20 |
| 151 | 27362.1 | 585.622 | 0.9758 | 0.18 |
| 152 | 27426.7 | 571.457 | 0.9522 | 0.07 |
| 153 | 27465.2 | 563.025 | 0.9381 | 0.12 |
| 154 | 27550.1 | 544.395 | 0.9071 | 0.06 |
| 155 | 27604.4 | 532.507 | 0.8873 | 0.09 |
| 156 | 27723.7 | 506.347 | 0.8437 | 0.23 |
| 157 | 27778.4 | 494.349 | 0.8237 | 0.48 |
| 158 | 27825.7 | 483.975 | 0.8064 | 1.88 |
| 159 | 27892.5 | 469.335 | 0.7820 | 1.79 |
| 160 | 27999.1 | 445.968 | 0.7431 | 0.28 |
| 161 | 28054.1 | 433.917 | 0.7230 | 0.23 |
| 162 | 28134.1 | 416.375 | 0.6938 | 0.08 |
| 163 | 28228.5 | 395.678 | 0.6593 | 0.07 |
| 164 | 28262.5 | 388.209 | 0.6468 | 0.09 |

TABLE 8.2.

2D NMR (HMQC) of R1 peaklist.

| # | ADDRESS row col | FREQUENCY [Hz]F1 [Hz]F2 | [PPM]F1 [PPM]F2 | INTENSITY |
|---|-----|-----|-----|-----|
| 1 | 151 | 20624.836 | 136.6695 | 4.88 |
|   | 397 | 3494.332 | 5.8223 | |
| 2 | 157 | 20461.906 | 135.5898 | 67.68 |
|   | 220 | 4534.469 | 7.5554 | |
| 3 | 234 | 18646.779 | 123.5620 | 100.00 |
|   | 258 | 4313.193 | 7.1867 | |
| 4 | 234 | 18646.779 | 123.5620 | 9.18 |
|   | 445 | 3213.863 | 5.3550 | |
| 5 | 343 | 16069.902 | 106.4864 | 7.58 |
|   | 496 | 2913.367 | 4.8543 | |
| 6 | 343 | 16069.902 | 106.4864 | 7.61 |
|   | 498 | 2904.202 | 4.8390 | |
| 7 | 350 | 15895.188 | 105.3287 | 7.99 |
|   | 471 | 3059.891 | 5.0985 | |
| 8 | 350 | 15895.188 | 105.3287 | 9.11 |
|   | 473 | 3050.642 | 5.0830 | |
| 9 | 350 | 15895.188 | 105.3287 | 8.79 |
|   | 481 | 3004.427 | 5.0060 | |
| 10 | 363 | 15605.384 | 103.4083 | 7.96 |
|   | 510 | 2835.541 | 4.7246 | |
| 11 | 380 | 15192.972 | 100.6755 | 16.30 |
|   | 326 | 3912.206 | 6.5186 | |
| 12 | 454 | 13447.552 | 89.1095 | 4.35 |
|   | 656 | 1974.610 | 3.2901 | |
| 13 | 454 | 13447.552 | 89.1095 | 4.45 |
|   | 659 | 1958.017 | 3.2625 | |
| 14 | 515 | 12025.116 | 79.6838 | 4.85 |
|   | 561 | 2533.049 | 4.2206 | |
| 15 | 518 | 11934.442 | 79.0830 | 4.52 |
|   | 389 | 3540.938 | 5.9000 | |
| 16 | 524 | 11802.268 | 78.2071 | 12.80 |
|   | 562 | 2525.183 | 4.2075 | |
| 17 | 524 | 11802.268 | 78.2071 | 11.92 |
|   | 594 | 2340.880 | 3.9004 | |
| 18 | 534 | 11563.501 | 76.6250 | 4.43 |
|   | 571 | 2474.88 | 34.1237 | |
| 19 | 534 | 11563.501 | 76.6250 | 3.52 |
|   | 588 | 2372.543 | 3.9532 | |
| 20 | 534 | 11563.501 | 76.6250 | 5.94 |
|   | 610 | 2246.165 | 3.7426 | |
| 21 | 534 | 11563.501 | 76.6250 | 6.60 |
|   | 612 | 2234.362 | 3.7229 | |
| 22 | 540 | 11437.312 | 75.7888 | 20.96 |
|   | 574 | 2457.347 | 4.0945 | |
| 23 | 545 | 11309.472 | 74.9417 | 5.29 |
|   | 553 | 2580.628 | 4.2999 | |
| 24 | 545 | 11309.472 | 74.9417 | 6.15 |
|   | 555 | 2569.264 | 4.2810 | |
| 25 | 545 | 11309.472 | 74.9417 | 3.23 |
|   | 561 | 2533.966 | 4.2222 | |
| 26 | 545 | 11309.472 | 74.9417 | 9.38 |
|   | 582 | 2411.457 | 4.0180 | |
| 27 | 551 | 11175.793 | 74.0558 | 3.74 |
|   | 550 | 2597.570 | 4.3281 | |
| 28 | 551 | 11175.793 | 74.0558 | 7.04 |
|   | 552 | 2585.925 | 4.3087 | |
| 29 | 551 | 11175.793 | 74.0558 | 3.84 |
|   | 554 | 2574.515 | 4.2897 | |
| 30 | 556 | 11047.378 | 73.2049 | 5.90 |
|   | 586 | 2386.166 | 3.9759 | |
| 31 | 562 | 10907.159 | 72.2758 | 15.78 |
|   | 511 | 2826.203 | 4.7091 | |
| 32 | 562 | 10907.159 | 72.2758 | 5.35 |
|   | 520 | 2777.020 | 4.6271 | |
| 33 | 567 | 10784.600 | 71.4636 | 12.61 |
|   | 562 | 2525.038 | 4.2073 | |
| 34 | 567 | 10784.600 | 71.4636 | 4.33 |
|   | 567 | 2497.664 | 4.1617 | |
| 35 | 577 | 10543.526 | 69.8662 | 4.00 |
|   | 497 | 2908.530 | 4.8463 | |
| 36 | 577 | 10543.526 | 69.8662 | 3.60 |
|   | 500 | 2892.560 | 4.8196 | |

TABLE 8.2.-continued

2D NMR (HMQC) of R1 peaklist.

| # | ADDRESS row col | FREQUENCY [Hz]F1 [Hz]F2 | [PPM]F1 [PPM]F2 | INTENSITY |
|---|---|---|---|---|
| 37 | 577 | 10543.526 | 69.8662 | 5.98 |
|    | 514 | 2810.206  | 4.6824  |      |
| 38 | 577 | 10543.526 | 69.8662 | 5.96 |
|    | 516 | 2796.413  | 4.6594  |      |
| 39 | 577 | 10543.526 | 69.8662 | 6.72 |
|    | 548 | 2609.404  | 4.3478  |      |
| 40 | 624 | 9434.661  | 62.5183 | 11.62 |
|    | 532 | 2705.029  | 4.5072  |      |
| 41 | 624 | 9434.661  | 62.5183 | 8.01 |
|    | 534 | 2689.727  | 4.4817  |      |
| 42 | 624 | 9434.661  | 62.5183 | 7.54 |
|    | 547 | 2616.577  | 4.3598  |      |
| 43 | 669 | 8381.180  | 55.5375 | 4.80 |
|    | 919 | 431.689   | 0.7193  |      |
| 44 | 669 | 8381.180  | 55.5375 | 5.21 |
|    | 922 | 414.881   | 0.6913  |      |
| 45 | 719 | 7203.831  | 47.7358 | 3.32 |
|    | 827 | 972.057   | 1.6197  |      |
| 46 | 728 | 6986.542  | 46.2960 | 3.85 |
|    | 777 | 1265.417  | 2.1085  |      |
| 47 | 728 | 6986.542  | 46.2960 | 3.19 |
|    | 859 | 784.626   | 1.3074  |      |
| 48 | 728 | 6986.542  | 46.2960 | 3.45 |
|    | 862 | 764.970   | 1.2746  |      |
| 49 | 759 | 6273.788  | 41.5729 | 3.64 |
|    | 724 | 1575.188  | 2.6246  |      |
| 50 | 759 | 6273.788  | 41.5729 | 3.54 |
| 728 | 1556.033 | 2.5927 |       |      |
| 51 | 817 | 4904.791  | 32.5014 | 9.21 |
|    | 849 | 844.868   | 1.4077  |      |
| 52 | 831 | 4556.851  | 30.1957 | 40.19 |
|    | 868 | 732.276   | 1.2201  |      |
| 53 | 846 | 4212.870  | 27.9164 | 45.73 |
|    | 870 | 719.170   | 1.1983  |      |
| 54 | 858 | 3932.408  | 26.0579 | 45.69 |
|    | 865 | 749.675   | 1.2491  |      |
| 55 | 893 | 3102.798  | 20.5605 | 37.60 |
|    | 808 | 1085.904  | 1.8094  |      |
| 56 | 900 | 2935.044  | 19.4489 | 42.87 |
|    | 864 | 755.857   | 1.2594  |      |
| 57 | 905 | 2821.322  | 18.6953 | 25.73 |
|    | 808 | 1086.381  | 1.8102  |      |
| 58 | 918 | 2523.121  | 16.7193 | 36.59 |
|    | 883 | 644.770   | 1.0743  |      |
| 59 | 918 | 2523.121  | 16.7193 | 43.39 |
|    | 895 | 571.319   | 0.9519  |      |
| 60 | 924 | 2368.333  | 15.6936 | 21.68 |
|    | 794 | 1163.335  | 1.9384  |      |
| 61 | 924 | 2368.333  | 15.6936 | 45.90 |
|    | 895 | 573.050   | 0.9548  |      |

TABLE 8.3.

HMBC R1 peaklist
DU = C: /Bruker/XWIN-NMR, USER = guest,
NAME = chan, EXPNO = F1PLO = 173.650 ppm,
F1PHI = 11.502 ppm, F2PLO = 6.832 ppm,
F2IMI = 5.00 cm, MAXI = 10000.00 cm, PC = 3.000

| # | ADDRESS row col | FREQUENCY [Hz]F1 [Hz]F2 | [PPM]F1 [PPM]F2 | INTENSITY |
|---|---|---|---|---|
| 1 | 166 | 25330.719 | 167.8561 | 11.00 |
|   | 389 | 3542.372  | 5.9024   |       |
| 2 | 166 | 25330.719 | 167.8561 | 37.94 |
|   | 808 | 1085.572  | 1.8088   |       |
| 3 | 293 | 21569.176 | 142.9299 | 39.69 |
|   | 865 | 750.004   | 1.2497   |       |

TABLE 8.3.-continued

HMBC R1 peaklist
DU = C: /Bruker/XWIN-NMR, USER = guest,
NAME = chan, EXPNO = F1PLO = 173.650 ppm,
F1PHI = 11.502 ppm, F2PLO = 6.832 ppm,
F2IMI = 5.00 cm, MAXI = 10000.00 cm, PC = 3.000

| # | ADDRESS row col | FREQUENCY [Hz]F1 [Hz]F2 | [PPM]F1 [PPM]F2 | INTENSITY |
|---|---|---|---|---|
| 4 | 325 | 20624.461 | 136.6697 | 54.15 |
|   | 795 | 1160.826  | 1.9342   |       |
| 5 | 325 | 20624.461 | 136.6697 | 67.95 |
|   | 808 | 1085.191  | 1.8082   |       |
| 6 | 366 | 19424.748 | 128.7197 | 54.29 |
|   | 795 | 1161.341  | 1.9351   |       |
| 7 | 366 | 19424.748 | 128.7197 | 100.00 |
|   | 808 | 1085.293  | 1.8083   |       |
| 8 | 479 | 16074.168 | 106.5168 | 17.03 |
|   | 587 | 2382.396  | 3.9696   |       |
| 9 | 485 | 15911.199 | 105.4369 | 13.64 |
|   | 582 | 2411.570  | 4.0182   |       |
| 10 | 495 | 15610.658 | 103.4453 | 7.40 |
|    | 559 | 2544.112  | 4.2391   |      |
| 11 | 495 | 15610.658 | 103.4453 | 7.72 |
|    | 574 | 2457.717  | 4.0951   |      |
| 12 | 509 | 15196.733 | 100.7024 | 10.46 |
|    | 311 | 3999.566  | 6.6642   |      |
| 13 | 509 | 15196.733 | 100.7024 | 10.97 |
|    | 341 | 3825.973  | 6.3749   |      |
| 14 | 568 | 13447.739 | 89.1126  | 13.78 |
|    | 497 | 2908.018  | 4.8454   |      |
| 15 | 568 | 13447.739 | 89.1126  | 52.71 |
|    | 870 | 718.459   | 1.1971   |      |
| 16 | 568 | 13447.739 | 89.1126  | 33.62 |
|    | 896 | 570.271   | 0.9502   |      |
| 17 | 616 | 12037.521 | 79.7676  | 10.39 |
|    | 560 | 2540.187  | 4.2325   |      |
| 18 | 616 | 12037.521 | 79.7676  | 12.77 |
|    | 567 | 2496.423  | 4.1596   |      |
| 19 | 620 | 11934.375 | 79.0841  | 16.69 |
|    | 557 | 2555.670  | 4.2583   |      |
| 20 | 620 | 11934.375 | 79.0841  | 18.17 |
|    | 586 | 2384.236  | 3.9727   |      |
| 21 | 624 | 11794.329 | 78.1561  | 29.22 |
|    | 561 | 2532.465  | 4.2196   |      |
| 22 | 624 | 11794.329 | 78.1561  | 13.90 |
|    | 581 | 2415.675  | 4.0251   |      |
| 23 | 632 | 11561.078 | 76.6104  | 11.27 |
|    | 554 | 2575.363  | 4.2911   |      |
| 24 | 632 | 11561.078 | 76.6104  | 8.95 |
|    | 861 | 774.214   | 1.2900   |      |
| 25 | 632 | 11561.078 | 76.6104  | 31.05 |
|    | 864 | 757.631   | 1.2624   |      |
| 26 | 632 | 11561.078 | 76.6104  | 52.22 |
|    | 868 | 733.017   | 1.2214   |      |
| 27 | 640 | 11319.147 | 75.0073  | 14.09 |
|    | 562 | 2529.498  | 4.2147   |      |
| 28 | 640 | 11319.147 | 75.0073  | 12.03 |
|    | 574 | 2457.979  | 4.0955   |      |
| 29 | 640 | 11319.147 | 75.0073  | 7.35 |
|    | 611 | 2238.440  | 3.7297   |      |
| 30 | 645 | 11173.489 | 74.0421  | 5.08 |
|    | 511 | 2826.331  | 4.7093   |      |
| 31 | 645 | 11173.489 | 74.0421  | 27.89 |
|    | 807 | 1087.742  | 1.8124   |      |
| 32 | 650 | 11046.945 | 73.2035  | 14.57 |
|    | 389 | 3541.020  | 5.9001   |      |
| 33 | 655 | 10904.058 | 72.2566  | 23.27 |
|    | 326 | 3913.536  | 6.5208   |      |
| 34 | 655 | 10904.058 | 72.2566  | 9.96 |
|    | 552 | 2586.768  | 4.3101   |      |
| 35 | 655 | 10904.058 | 72.2566  | 6.06 |
|    | 563 | 2521.903  | 4.2021   |      |
| 36 | 659 | 10780.204 | 71.4359  | 6.93 |
|    | 532 | 2702.900  | 4.5036   |      |
| 37 | 659 | 10780.204 | 71.4359  | 8.19 |
|    | 534 | 2692.127  | 4.4857   |      |

TABLE 8.3.-continued

HMBC R1 peaklist
DU = C: /Bruker/XWIN-NMR, USER = guest,
NAME = chan, EXPNO = F1PLO = 173.650 ppm,
F1PHI = 11.502 ppm, F2PLO = 6.832 ppm,
F2IMI = 5.00 cm, MAXI = 10000.00 cm, PC = 3.000

| # | ADDRESS row col | FREQUENCY [Hz]F1 [Hz]F2 | [PPM]F1 [PPM]F2 | INTENSITY |
|---|---|---|---|---|
| 38 | 659 | 10780.204 | 71.4359 | 48.21 |
|    | 563 | 2520.533 | 4.1998 |  |
| 39 | 667 | 10532.287 | 69.7931 | 11.46 |
|    | 472 | 3054.495 | 5.0895 |  |
| 40 | 667 | 10532.287 | 69.7931 | 18.84 |
|    | 480 | 3007.639 | 5.0114 |  |
| 41 | 671 | 10425.301 | 69.0841 | 32.61 |
|    | 326 | 3913.495 | 6.5208 |  |
| 42 | 671 | 10425.301 | 69.0841 | 7.93 |
|    | 552 | 2586.054 | 4.3089 |  |
| 43 | 671 | 10425.301 | 69.0841 | 58.15 |
|    | 807 | 1088.313 | 1.8134 |  |
| 44 | 705 | 9430.492 | 62.4919 | 5.37 |
|    | 560 | 2539.835 | 4.2319 |  |
| 45 | 740 | 8372.175 | 55.4789 | 8.08 |
|    | 870 | 718.660 | 1.19743 |  |
| 46 | 740 | 8372.175 | 55.4789 | 44.50 |
|    | 895 | 571.407 | 0.9521 |  |
| 47 | 780 | 7199.307 | 47.7068 | 27.47 |
|    | 883 | 644.628 | 1.0741 |  |
| 48 | 780 | 7199.307 | 47.7068 | 31.41 |
|    | 895 | 572.447 | 0.9538 |  |
| 49 | 788 | 6981.523 | 46.2636 | 51.63 |
|    | 864 | 757.767 | 1.2626 |  |
| 50 | 788 | 6981.523 | 46.2636 | 78.63 |
|    | 868 | 732.960 | 1.2213 |  |
| 51 | 804 | 6495.941 | 43.0459 | 8.82 |
|    | 574 | 2458.027 | 4.0956 |  |
| 52 | 804 | 6495.941 | 43.0459 | 8.89 |
|    | 861 | 774.879 | 1.2911 |  |
| 53 | 804 | 6495.941 | 43.0459 | 6.55 |
|    | 867 | 737.966 | 1.2296 |  |
| 54 | 810 | 6313.906 | 41.8396 | 8.33 |
|    | 445 | 3213.454 | 5.3543 |  |
| 55 | 810 | 6313.906 | 41.8396 | 5.40 |
|    | 755 | 1397.464 | 2.3285 |  |
| 56 | 810 | 6313.906 | 41.8396 | 42.24 |
|    | 865 | 749.894 | 1.2495 |  |
| 57 | 810 | 6313.906 | 41.8396 | 52.86 |
|    | 883 | 644.620 | 1.0741 |  |
| 58 | 814 | 6189.256 | 41.0136 | 6.31 |
|    | 865 | 749.287 | 1.2485 |  |
| 59 | 814 | 6189.256 | 41.0136 | 8.62 |
|    | 883 | 643.362 | 1.0720 |  |
| 60 | 817 | 6120.849 | 40.5603 | 15.69 |
|    | 865 | 749.159 | 1.2483 |  |
| 61 | 817 | 6120.849 | 40.5603 | 17.94 |
|    | 883 | 644.286 | 1.0735 |  |
| 62 | 817 | 6120.849 | 40.5603 | 6.27 |
|    | 896 | 570.189 | 0.9501 |  |
| 63 | 819 | 6053.888 | 40.1166 | 43.77 |
|    | 865 | 749.605 | 1.2490 |  |
| 64 | 819 | 6053.888 | 40.1166 | 47.98 |
|    | 883 | 644.397 | 1.0737 |  |
| 65 | 819 | 6053.888 | 40.1166 | 8.91 |
|    | 896 | 570.067 | 0.9499 |  |
| 66 | 824 | 5921.430 | 39.2388 | 5.80 |
|    | 864 | 754.133 | 1.2566 |  |
| 67 | 824 | 5921.430 | 39.2388 | 70.97 |
|    | 870 | 718.264 | 1.1968 |  |
| 68 | 824 | 5921.430 | 39.2388 | 65.30 |
|    | 896 | 569.449 | 0.9488 |  |
| 69 | 824 | 5921.430 | 39.2388 | 6.70 |
|    | 920 | 427.451 | 0.7122 |  |
| 70 | 824 | 5921.430 | 39.2388 | 7.41 |
|    | 922 | 414.558 | 0.6907 |  |
| 71 | 827 | 5818.316 | 38.5556 | 8.71 |
|    | 870 | 718.161 | 1.1966 |  |
| 72 | 827 | 5818.316 | 38.5556 | 35.78 |
|    | 895 | 572.960 | 0.9547 |  |
| 73 | 829 | 5749.308 | 38.0983 | 8.61 |
|    | 896 | 570.060 | 0.9498 |  |
| 74 | 837 | 5529.916 | 36.6444 | 5.22 |
|    | 829 | 959.437 | 1.5986 |  |
| 75 | 837 | 5529.916 | 36.6444 | 12.15 |
|    | 864 | 755.929 | 1.2595 |  |
| 76 | 837 | 5529.916 | 36.6444 | 8.77 |
|    | 868 | 732.618 | 1.2207 |  |
| 77 | 837 | 5529.916 | 36.6444 | 51.81 |
|    | 895 | 572.369 | 0.9537 |  |
| 78 | 837 | 5529.916 | 36.6444 | 5.36 |
|    | 920 | 427.331 | 0.7120 |  |
| 79 | 837 | 5529.916 | 36.6444 | 6.76 |
|    | 922 | 414.571 | 0.6908 |  |
| 80 | 840 | 5443.605 | 36.0725 | 5.25 |
|    | 777 | 1264.89 | 12.1076 |  |
| 81 | 840 | 5443.605 | 36.0725 | 68.88 |
|    | 864 | 757.333 | 1.2619 |  |
| 82 | 840 | 5443.605 | 36.0725 | 83.66 |
|    | 868 | 732.776 | 1.2210 |  |
| 83 | 840 | 5443.605 | 36.0725 | 11.13 |
|    | 895 | 571.988 | 0.9531 |  |
| 84 | 858 | 4903.620 | 32.4942 | 38.16 |
|    | 883 | 644.423 | 1.0738 |  |
| 85 | 870 | 4556.862 | 30.1964 | 8.07 |
|    | 611 | 2240.976 | 3.7340 |  |
| 86 | 870 | 4556.862 | 30.1964 | 18.78 |
|    | 857 | 794.987 | 1.3246 |  |
| 87 | 870 | 4556.862 | 30.1964 | 79.89 |
|    | 864 | 756.793 | 1.2610 |  |
| 88 | 870 | 4556.862 | 30.1964 | 18.43 |
|    | 878 | 670.310 | 1.1169 |  |
| 89 | 872 | 4487.079 | 29.7340 | 16.38 |
|    | 864 | 756.125 | 1.2599 |  |
| 90 | 874 | 4422.445 | 29.3057 | 8.16 |
|    | 863 | 758.384 | 1.2636 |  |
| 91 | 877 | 4356.193 | 28.8667 | 8.79 |
|    | 864 | 755.084 | 1.2581 |  |
| 92 | 877 | 4356.193 | 28.8667 | 6.22 |
|    | 896 | 569.898 | 0.9496 |  |
| 93 | 882 | 4211.267 | 27.9063 | 19.55 |
|    | 860 | 779.212 | 1.2983 |  |
| 94 | 882 | 4211.267 | 27.9063 | 5.59 |
|    | 864 | 754.574 | 1.2573 |  |
| 95 | 882 | 4211.267 | 27.9063 | 19.01 |
|    | 881 | 654.994 | 1.0914 |  |
| 96 | 882 | 4211.267 | 27.9063 | 87.84 |
|    | 896 | 570.162 | 0.9500 |  |
| 97 | 891 | 3938.165 | 26.0966 | 19.50 |
|    | 854 | 812.119 | 1.3532 |  |
| 98 | 891 | 3938.165 | 26.0966 | 10.44 |
|    | 865 | 751.828 | 1.2527 |  |
| 99 | 891 | 3938.165 | 26.0966 | 17.89 |
|    | 876 | 686.003 | 1.1430 |  |
| 100 | 891 | 3938.165 | 26.0966 | 5.20 |
|    | 896 | 569.852 | 0.9495 |  |
| 101 | 893 | 3876.630 | 25.6888 | 40.70 |
|    | 865 | 749.874 | 1.2495 |  |
| 102 | 893 | 3876.630 | 25.6888 | 5.01 |
|    | 876 | 686.400 | 1.1437 |  |
| 103 | 919 | 3095.315 | 20.5114 | 7.58 |
|    | 398 | 3488.142 | 5.8120 |  |
| 104 | 919 | 3095.315 | 20.5114 | 9.43 |
|    | 797 | 1150.511 | 1.9170 |  |
| 105 | 919 | 3095.315 | 20.5114 | 9.18 |
|    | 818 | 1022.904 | 1.7044 |  |

TABLE 8.3.-continued

HMBC R1 peaklist
DU = C: /Bruker/XWIN-NMR, USER = guest,
NAME = chan, EXPNO = F1PLO = 173.650 ppm,
F1PHI = 11.502 ppm, F2PLO = 6.832 ppm,
F2IMI = 5.00 cm, MAXI = 10000.00 cm, PC = 3.000

| # | ADDRESS row col | FREQUENCY [Hz]F1 [Hz]F2 | [PPM]F1 [PPM]F2 | INTENSITY |
|---|---|---|---|---|
| 106 | 919 | 3095.315 | 20.5114 | 5.53 |
|  | 868 | 732.855 | 1.2211 |  |
| 107 | 925 | 2937.158 | 19.4633 | 13.27 |
|  | 611 | 2240.910 | 3.7339 |  |
| 108 | 925 | 2937.158 | 19.4633 | 11.35 |
|  | 777 | 1265.381 | 2.1084 |  |
| 109 | 925 | 2937.158 | 19.4633 | 5.80 |
|  | 780 | 1248.250 | 2.0799 |  |
| 110 | 925 | 2937.158 | 19.4633 | 23.23 |
|  | 853 | 818.856 | 1.3644 |  |
| 111 | 925 | 2937.158 | 19.4633 | 89.32 |
|  | 868 | 733.355 | 1.2219 |  |
| 112 | 925 | 2937.158 | 19.4633 | 20.36 |
|  | 875 | 693.473 | 1.1555 |  |
| 113 | 932 | 2710.756 | 17.9630 | 6.54 |
|  | 554 | 2574.880 | 4.2903 |  |
| 114 | 932 | 2710.756 | 17.9630 | 5.24 |
|  | 849 | 843.916 | 1.4062 |  |
| 115 | 932 | 2710.756 | 17.9630 | 6.51 |
|  | 868 | 732.674 | 1.2208 |  |
| 116 | 939 | 2527.765 | 16.7504 | 6.70 |
|  | 829 | 960.874 | 1.6010 |  |
| 117 | 939 | 2527.765 | 16.7504 | 83.68 |
|  | 870 | 718.686 | 1.1975 |  |
| 118 | 939 | 2527.765 | 16.7504 | 21.97 |
|  | 885 | 631.287 | 1.0519 |  |
| 119 | 939 | 2527.765 | 16.7504 | 14.30 |
|  | 893 | 583.038 | 0.9715 |  |
| 120 | 939 | 2527.765 | 16.7504 | 22.28 |
|  | 906 | 506.673 | 0.8442 |  |
| 121 | 939 | 2527.765 | 16.7504 | 7.71 |
|  | 920 | 426.044 | 0.7099 |  |
| 122 | 939 | 2527.765 | 16.7504 | 10.74 |
|  | 922 | 414.883 | 0.6913 |  |
| 123 | 944 | 2376.340 | 15.7470 | 9.28 |
|  | 784 | 1224.570 | 2.0404 |  |
| 124 | 944 | 2376.340 | 15.7470 | 8.54 |
|  | 806 | 1096.659 | 1.8273 |  |
| 125 | 944 | 2376.340 | 15.7470 | 6.60 |
|  | 870 | 718.378 | 1.1970 |  |
| 126 | 944 | 2376.340 | 15.7470 | 19.99 |
|  | 885 | 633.381 | 1.0554 |  |
| 127 | 944 | 2376.340 | 15.7470 | 20.05 |
|  | 906 | 509.452 | 0.8489 |  |
| 128 | 944 | 2376.340 | 15.7470 | 8.96 |
|  | 920 | 426.988 | 0.7115 |  |
| 129 | 944 | 2376.340 | 15.7470 | 10.34 |
|  | 922 | 415.107 | 0.6917 |  |

TABLE 8.4.

2D NMR (cosy) of R1 peak list

| Assignment | w1 | w2 | Data Height |
|---|---|---|---|
| 1 | 6.521 | 6.522 | 257252096 |
| 2 | 6.522 | 4.711 | 7840252 |
| 3 | 6.129 | 0.959 | 3905950 |
| 4 | 5.898 | 5.901 | 32367934 |
| 5 | 5.902 | 4.847 | 10836326 |
| 6 | 5.902 | 4.258 | 10138593 |
| 7 | 5.899 | 4.127 | 9360363 |
| 8 | 5.906 | 3.975 | 16282743 |
| 9 | 5.821 | 1.810 | 7215536 |
| 10 | 5.817 | 5.822 | 31028110 |
| 11 | 5.817 | 1.944 | 43526536 |
| 12 | 5.816 | 1.929 | 44815556 |
| 13 | 5.355 | 5.355 | 178856592 |
| 14 | 5.094 | 5.102 | 109124320 |
| 15 | 5.094 | 5.085 | 116649128 |
| 16 | 5.092 | 4.205 | 15712139 |
| 17 | 5.093 | 4.048 | 38195456 |
| 18 | 5.011 | 5.021 | 112612352 |
| 19 | 5.010 | 5.004 | 121053544 |
| 20 | 5.008 | 4.210 | 14216868 |
| 21 | 5.011 | 4.021 | 38155584 |
| 22 | 4.847 | 5.913 | 5875469 |
| 23 | 4.845 | 5.900 | 4787344 |
| 24 | 4.845 | 5.889 | 7478266 |
| 25 | 4.841 | 4.855 | 118994368 |
| 26 | 4.836 | 4.823 | 47239140 |
| 27 | 4.836 | 4.369 | 92117104 |
| 28 | 4.831 | 4.134 | 9652155 |
| 29 | 4.834 | 4.116 | 7044446 |
| 30 | 4.844 | 3.987 | 44245188 |
| 31 | 4.845 | 3.962 | 44209660 |
| 32 | 4.798 | 4.795 | 12493983 |
| 33 | 4.795 | 4.621 | 15346245 |
| 34 | 4.796 | 1.821 | 57265952 |
| 35 | 4.796 | 1.809 | 75309312 |
| 36 | 4.792 | 4.312 | 21750568 |
| 37 | 4.753 | 4.360 | 24472454 |
| 38 | 4.725 | 4.733 | 72665064 |
| 39 | 4.721 | 4.719 | 99191696 |
| 40 | 4.727 | 4.226 | 50380324 |
| 41 | 4.709 | 6.523 | 22903380 |
| 42 | 4.702 | 4.629 | 20594276 |
| 43 | 4.707 | 4.612 | 19038358 |
| 44 | 4.706 | 4.326 | 11671381 |
| 45 | 4.670 | 4.688 | 34985344 |
| 46 | 4.669 | 4.660 | 40038520 |
| 47 | 4.669 | 4.355 | 94428136 |
| 48 | 4.670 | 3.958 | 8587019 |
| 49 | 4.672 | 3.941 | 7812038 |
| 50 | 4.620 | 4.800 | 8615562 |
| 51 | 4.619 | 4.711 | 21326744 |
| 52 | 4.618 | 4.633 | 29866052 |
| 53 | 4.619 | 4.607 | 44064012 |
| 54 | 4.621 | 4.312 | 23669784 |
| 55 | 4.584 | 4.355 | 27276566 |
| 56 | 4.566 | 4.365 | 23402122 |
| 57 | 4.492 | 4.513 | 55339136 |
| 58 | 4.491 | 4.482 | 71439344 |
| 59 | 4.496 | 4.370 | 164934224 |
| 60 | 4.495 | 4.360 | 174062528 |
| 61 | 4.499 | 3.912 | 17609992 |
| 62 | 4.498 | 3.896 | 17924064 |
| 63 | 4.377 | 4.349 | 24720128 |
| 64 | 4.365 | 4.843 | 97382152 |
| 65 | 4.364 | 4.829 | 127752656 |
| 66 | 4.356 | 4.680 | 67867680 |
| 67 | 4.355 | 4.667 | 81378376 |
| 68 | 4.361 | 4.491 | 211941920 |
| 69 | 4.374 | 4.393 | 38442384 |
| 70 | 4.364 | 4.372 | 27706436 |
| 71 | 4.358 | 4.335 | 31327086 |
| 72 | 4.364 | 4.137 | 14876345 |
| 73 | 4.363 | 4.113 | 13081764 |
| 74 | 4.355 | 3.960 | 10728486 |
| 75 | 4.357 | 3.940 | 9552408 |
| 76 | 4.371 | 3.913 | 20295026 |
| 77 | 4.372 | 3.895 | 17021364 |
| 78 | 4.309 | 4.799 | 25905518 |
| 79 | 4.309 | 4.619 | 43016120 |
| 80 | 4.306 | 4.310 | 56206892 |
| 81 | 4.294 | 3.742 | 80581928 |
| 82 | 4.295 | 3.731 | 101483432 |
| 83 | 4.280 | 4.354 | 9482896 |
| 84 | 4.251 | 5.915 | 17374606 |
| 85 | 4.250 | 5.901 | 10701927 |
| 86 | 4.251 | 5.887 | 17140758 |
| 87 | 4.253 | 4.259 | 32444480 |

TABLE 8.4.-continued

2D NMR (cosy) of R1 peak list

| Assignment | w1 | w2 | Data Height |
|---|---|---|---|
| 88 | 4.258 | 4.125 | 31047850 |
| 89 | 4.257 | 3.976 | 5638105 |
| 90 | 4.229 | 4.730 | 34642484 |
| 91 | 4.207 | 5.092 | 13039638 |
| 92 | 4.209 | 5.012 | 11226875 |
| 93 | 4.217 | 4.179 | 33544654 |
| 94 | 4.209 | 4.058 | 28007252 |
| 95 | 4.207 | 4.047 | 46281960 |
| 96 | 4.211 | 4.020 | 33876260 |
| 97 | 4.207 | 4.005 | 21146824 |
| 98 | 4.210 | 3.904 | 80923600 |
| 99 | 4.204 | 4.365 | 9066176 |
| 100 | 4.202 | 4.032 | 40055832 |
| 101 | 4.167 | 3.951 | 18178542 |
| 102 | 4.150 | 4.209 | 11484229 |
| 103 | 4.126 | 5.912 | 6719130 |
| 104 | 4.122 | 5.890 | 7671593 |
| 105 | 4.126 | 4.378 | 9045784 |
| 106 | 4.127 | 4.273 | 34269312 |
| 107 | 4.119 | 4.258 | 32734018 |
| 108 | 4.133 | 4.246 | 34046856 |
| 109 | 4.131 | 4.140 | 18941800 |
| 110 | 4.116 | 4.355 | 11770206 |
| 111 | 4.092 | 4.096 | 279326848 |
| 112 | 4.043 | 5.095 | 84940104 |
| 113 | 4.035 | 4.208 | 50268828 |
| 114 | 4.042 | 4.183 | 15655260 |
| 115 | 4.043 | 4.064 | 26875002 |
| 116 | 4.019 | 5.015 | 77663464 |
| 117 | 4.015 | 4.241 | 9036684 |
| 118 | 4.027 | 4.226 | 11811450 |
| 119 | 4.016 | 4.037 | 19835598 |
| 120 | 3.973 | 5.915 | 24059896 |
| 121 | 3.974 | 5.901 | 20609464 |
| 122 | 3.973 | 5.887 | 22835978 |
| 123 | 3.975 | 4.853 | 37923332 |
| 124 | 3.977 | 3.995 | 18827896 |
| 125 | 3.949 | 4.682 | 5809583 |
| 126 | 3.950 | 4.371 | 10668304 |
| 127 | 3.953 | 4.348 | 15916606 |
| 128 | 3.949 | 4.175 | 18189762 |
| 129 | 3.948 | 4.161 | 30027716 |
| 130 | 3.953 | 4.149 | 19945408 |
| 131 | 3.940 | 3.966 | 14571032 |
| 132 | 3.903 | 4.505 | 10048077 |
| 133 | 3.903 | 4.488 | 14760281 |
| 134 | 3.903 | 4.387 | 19898852 |
| 135 | 3.912 | 4.342 | 16459215 |
| 136 | 3.904 | 4.239 | 12064081 |
| 137 | 3.907 | 4.214 | 108106008 |
| 138 | 3.898 | 4.364 | 32756190 |
| 139 | 3.900 | 4.199 | 27604272 |
| 140 | 3.901 | 3.917 | 43085776 |
| 141 | 3.897 | 3.888 | 38415896 |
| 142 | 3.735 | 4.300 | 93317560 |
| 143 | 3.736 | 4.290 | 98467152 |
| 144 | 3.736 | 3.748 | 65327612 |
| 145 | 3.735 | 3.725 | 50388764 |
| 146 | 3.270 | 3.283 | 17369858 |
| 147 | 3.269 | 3.267 | 22139430 |
| 148 | 3.271 | 2.354 | 5853844 |
| 149 | 3.271 | 2.342 | 7970904 |
| 150 | 3.271 | 1.912 | 5107326 |
| 151 | 3.271 | 1.896 | 5093256 |
| 152 | 2.602 | 2.631 | 5486520 |
| 153 | 2.600 | 2.598 | 5094291 |
| 154 | 2.601 | 2.590 | 7143968 |
| 155 | 2.602 | 2.132 | 14357642 |
| 156 | 2.602 | 2.109 | 26185532 |
| 157 | 2.601 | 2.086 | 14739034 |
| 158 | 2.603 | 1.289 | 14662965 |
| 159 | 2.341 | 3.287 | 5980422 |
| 160 | 2.342 | 3.264 | 5054491 |
| 161 | 2.334 | 2.360 | 5303651 |
| 162 | 2.336 | 1.932 | 6500135 |
| 163 | 2.334 | 1.872 | 7760766 |
| 164 | 2.325 | 2.341 | 13008529 |
| 165 | 2.325 | 2.315 | 11101831 |
| 166 | 2.328 | 1.923 | 6345431 |
| 167 | 2.326 | 1.895 | 9356538 |
| 168 | 2.289 | 2.294 | 14262412 |
| 169 | 2.186 | 2.193 | 4223454 |
| 170 | 2.103 | 2.620 | 30164346 |
| 171 | 2.103 | 2.598 | 27444406 |
| 172 | 2.101 | 2.109 | 7249900 |
| 173 | 2.105 | 1.307 | 22762886 |
| 174 | 2.102 | 1.300 | 18897670 |
| 175 | 2.103 | 1.279 | 18250726 |
| 176 | 2.070 | 2.078 | 4104108 |
| 177 | 1.967 | 1.969 | 13308390 |
| 178 | 1.977 | 1.609 | 7894784 |
| 179 | 1.956 | 1.909 | 11551598 |
| 180 | 1.961 | 1.874 | 10608534 |
| 181 | 1.965 | 1.625 | 5946444 |
| 182 | 1.931 | 5.834 | 39974876 |
| 183 | 1.931 | 5.824 | 42157648 |
| 184 | 1.932 | 5.812 | 40474008 |
| 185 | 1.931 | 5.798 | 30554264 |
| 186 | 1.931 | 2.320 | 12384753 |
| 187 | 1.931 | 1.942 | 228192416 |
| 188 | 1.931 | 1.810 | 59524928 |
| 189 | 1.913 | 2.339 | 13306613 |
| 190 | 1.902 | 2.001 | 6772636 |
| 191 | 1.895 | 3.287 | 9744711 |
| 192 | 1.896 | 3.264 | 9357915 |
| 193 | 1.897 | 2.362 | 8772959 |
| 194 | 1.886 | 1.973 | 16266749 |
| 195 | 1.885 | 1.885 | 5269322 |
| 196 | 1.882 | 1.616 | 15011650 |
| 197 | 1.883 | 1.242 | 8077304 |
| 198 | 1.878 | 1.219 | 8767326 |
| 199 | 1.818 | 5.840 | 3029832 |
| 200 | 1.805 | 5.829 | 3553817 |
| 201 | 1.804 | 5.808 | 3418502 |
| 202 | 1.805 | 4.822 | 22320414 |
| 203 | 1.805 | 4.813 | 19315348 |
| 204 | 1.806 | 4.797 | 27156710 |
| 205 | 1.806 | 4.785 | 23402710 |
| 206 | 1.806 | 4.774 | 22620674 |
| 207 | 1.806 | 4.322 | 15274810 |
| 208 | 1.806 | 4.312 | 11189881 |
| 209 | 1.806 | 4.302 | 17586586 |
| 210 | 1.802 | 1.943 | 42426312 |
| 211 | 1.804 | 1.932 | 30620986 |
| 212 | 1.804 | 1.810 | 1349507072 |
| 213 | 1.776 | 1.778 | 8674281 |
| 214 | 1.703 | 1.710 | 5954890 |
| 215 | 1.696 | 1.702 | 9409535 |
| 216 | 1.613 | 1.911 | 8734371 |
| 217 | 1.611 | 1.635 | 17314310 |
| 218 | 1.609 | 1.610 | 29144662 |
| 219 | 1.609 | 1.599 | 16356248 |
| 220 | 1.613 | 1.032 | 9463035 |
| 221 | 1.614 | 1.017 | 7358422 |
| 222 | 1.613 | 0.991 | 9572058 |
| 223 | 1.406 | 1.303 | 9782705 |
| 224 | 1.395 | 1.406 | 70684776 |
| 225 | 1.393 | 1.385 | 22170084 |
| 226 | 1.390 | 1.293 | 11202919 |
| 227 | 1.307 | 1.318 | 7420988 |
| 228 | 1.285 | 2.609 | 28951250 |
| 229 | 1.284 | 2.133 | 16431712 |
| 230 | 1.285 | 2.110 | 23106420 |
| 231 | 1.283 | 2.083 | 14481833 |
| 232 | 1.279 | 1.407 | 11364364 |
| 233 | 1.288 | 1.384 | 6974150 |
| 234 | 1.286 | 1.299 | 18845462 |
| 235 | 1.288 | 0.712 | 21876642 |
| 236 | 1.288 | 0.696 | 27076318 |
| 237 | 1.251 | 1.260 | 768046912 |
| 238 | 1.221 | 1.927 | 5903658 |
| 239 | 1.217 | 1.223 | 1002405376 |

TABLE 8.4.-continued

2D NMR (cosy) of R1 peak list

| Assignment | w1 | w2 | Data Height |
|---|---|---|---|
| 240 | 1.188 | 1.197 | 664805376 |
| 241 | 1.168 | 1.171 | 16019256 |
| 242 | 1.137 | 1.145 | 30540644 |
| 243 | 1.113 | 1.120 | 37708240 |
| 244 | 1.070 | 1.077 | 775147520 |
| 245 | 1.058 | 1.058 | 17850510 |
| 246 | 1.004 | 2.349 | 5175155 |
| 247 | 1.003 | 1.916 | 6850918 |
| 248 | 1.003 | 1.892 | 5963474 |
| 249 | 1.005 | 1.630 | 21215516 |
| 250 | 1.005 | 1.610 | 23547650 |
| 251 | 1.000 | 1.008 | 25525576 |
| 252 | 1.016 | 0.959 | 33680632 |
| 253 | 0.985 | 0.999 | 11598959 |
| 254 | 0.963 | 0.985 | 13491636 |
| 255 | 0.944 | 0.953 | 1674528384 |
| 256 | 0.912 | 0.912 | 21859108 |
| 257 | 0.872 | 0.878 | 12589871 |
| 258 | 0.697 | 0.716 | 28731108 |
| 259 | 0.699 | 0.693 | 23421302 |
| 260 | 0.694 | 1.297 | 7870457 |
| 261 | 0.692 | 1.289 | 8126754 |

TABLE 8.5

R1-proton-NMR-peaklist

| # | ADDRESS | FREQUENCY [Hz] | [PPM] | INTENSITY |
|---|---|---|---|---|
| 1 | 13957.6 | 3913.934 | 6.5215 | 20.81 |
| 2 | 15614.0 | 3550.810 | 5.9164 | 7.03 |
| 3 | 15656.8 | 3541.408 | 5.9008 | 14.16 |
| 4 | 15699.7 | 3532.016 | 5.8851 | 7.43 |
| 5 | 15839.6 | 3501.350 | 5.8340 | 2.56 |
| 6 | 15872.2 | 3494.204 | 5.8221 | 6.47 |
| 7 | 15905.1 | 3486.992 | 5.8101 | 6.47 |
| 8 | 15932.8 | 3480.916 | 5.8000 | 2.49 |
| 9 | 17152.3 | 3213.554 | 5.3545 | 12.90 |
| 10 | 17853.4 | 3059.848 | 5.0984 | 17.52 |
| 11 | 17888.8 | 3052.093 | 5.0855 | 18.03 |
| 12 | 18074.5 | 3011.286 | 5.0175 | 16.80 |
| 13 | 18110.2 | 3003.544 | 5.0046 | 17.26 |
| 14 | 18524.3 | 2912.751 | 4.8533 | 15.71 |
| 15 | 18558.4 | 2905.282 | 4.8408 | 20.27 |
| 16 | 18597.3 | 2896.749 | 4.8266 | 12.17 |
| 17 | 18638.6 | 2887.709 | 4.8116 | 5.88 |
| 18 | 18667.2 | 2881.421 | 4.8011 | 6.29 |
| 19 | 18680.9 | 2878.427 | 4.7961 | 6.65 |
| 20 | 18709.4 | 2872.187 | 4.7857 | 5.58 |
| 21 | 18857.7 | 2839.672 | 4.7315 | 13.15 |
| 22 | 18891.0 | 2832.356 | 4.7193 | 15.61 |
| 23 | 18902.5 | 2829.844 | 4.7151 | 13.51 |
| 24 | 18918.1 | 2826.431 | 4.7095 | 13.25 |
| 25 | 18996.6 | 2809.208 | 4.6808 | 8.60 |
| 26 | 19038.5 | 2800.032 | 4.6655 | 9.32 |
| 27 | 19136.8 | 2778.471 | 4.6296 | 7.89 |
| 28 | 19151.7 | 2775.208 | 4.6241 | 6.99 |
| 29 | 19179.0 | 2769.220 | 4.6141 | 8.39 |
| 30 | 19194.1 | 2765.907 | 4.6086 | 7.85 |
| 31 | 19474.8 | 2704.369 | 4.5061 | 16.52 |
| 32 | 19515.8 | 2695.385 | 4.4911 | 14.33 |
| 33 | 19529.0 | 2692.503 | 4.4863 | 20.98 |
| 34 | 19797.2 | 2633.699 | 4.3883 | 10.45 |
| 35 | 19819.7 | 2628.754 | 4.3801 | 17.64 |
| 36 | 19850.7 | 2621.968 | 4.3688 | 26.32 |
| 37 | 19872.3 | 2617.228 | 4.3609 | 27.93 |
| 38 | 19897.2 | 2611.771 | 4.3518 | 17.82 |
| 39 | 19930.6 | 2604.438 | 4.3396 | 11.93 |
| 40 | 19963.7 | 2597.191 | 4.3275 | 8.30 |
| 41 | 20006.6 | 2587.791 | 4.3118 | 14.07 |
| 42 | 20031.7 | 2582.289 | 4.3027 | 11.75 |

TABLE 8.5-continued

R1-proton-NMR-peaklist

| # | ADDRESS | FREQUENCY [Hz] | [PPM] | INTENSITY |
|---|---|---|---|---|
| 43 | 20048.8 | 2578.545 | 4.2964 | 8.57 |
| 44 | 20076.5 | 2572.467 | 4.2863 | 11.71 |
| 45 | 20107.9 | 2565.584 | 4.2748 | 7.33 |
| 46 | 20151.6 | 2556.001 | 4.2589 | 14.11 |
| 47 | 20174.3 | 2551.024 | 4.2506 | 6.12 |
| 48 | 20196.3 | 2546.196 | 4.2425 | 13.56 |
| 49 | 20214.9 | 2542.128 | 4.2358 | 16.39 |
| 50 | 20247.5 | 2534.968 | 4.2238 | 26.96 |
| 51 | 20285.9 | 2526.555 | 4.2098 | 39.00 |
| 52 | 20305.4 | 2522.271 | 4.2027 | 24.70 |
| 53 | 20319.5 | 2519.190 | 4.1975 | 23.22 |
| 54 | 20346.4 | 2513.298 | 4.1877 | 7.91 |
| 55 | 20358.9 | 2510.546 | 4.1831 | 7.69 |
| 56 | 20379.8 | 2505.959 | 4.1755 | 8.17 |
| 57 | 20422.0 | 2496.719 | 4.1601 | 10.22 |
| 58 | 20461.6 | 2488.043 | 4.1456 | 5.87 |
| 59 | 20487.5 | 2482.352 | 4.1362 | 7.27 |
| 60 | 20514.7 | 2476.402 | 4.1262 | 7.42 |
| 61 | 20558.8 | 2466.727 | 4.1101 | 7.60 |
| 62 | 20596.2 | 2458.528 | 4.0965 | 31.95 |
| 63 | 20697.7 | 2436.266 | 4.0594 | 8.35 |
| 64 | 20735.2 | 2428.056 | 4.0457 | 13.12 |
| 65 | 20773.1 | 2419.740 | 4.0318 | 13.77 |
| 66 | 20811.2 | 2411.385 | 4.0179 | 12.76 |
| 67 | 20848.0 | 2403.322 | 4.0045 | 7.29 |
| 68 | 20890.7 | 2393.971 | 3.9889 | 7.87 |
| 69 | 20932.7 | 2384.749 | 3.9735 | 10.17 |
| 70 | 20970.3 | 2376.499 | 3.9598 | 12.68 |
| 71 | 21017.7 | 2366.108 | 3.9425 | 6.44 |
| 72 | 21123.5 | 2342.921 | 3.9038 | 16.37 |
| 73 | 21559.5 | 2247.327 | 3.7445 | 11.72 |
| 74 | 21604.4 | 2237.496 | 3.7282 | 11.07 |
| 75 | 22810.2 | 1973.141 | 3.2877 | 6.60 |
| 76 | 22829.6 | 1968.890 | 3.2806 | 6.56 |
| 77 | 22863.1 | 1961.542 | 3.2684 | 6.70 |
| 78 | 22883.5 | 1957.180 | 3.2611 | 6.59 |
| 79 | 24645.4 | 1570.792 | 2.6173 | 4.82 |
| 80 | 24691.2 | 1560.756 | 2.6006 | 5.30 |
| 81 | 25359.9 | 1414.147 | 2.3563 | 5.53 |
| 82 | 25407.3 | 1403.761 | 2.3390 | 10.56 |
| 83 | 25464.1 | 1391.301 | 2.3182 | 6.50 |
| 84 | 25529.5 | 1376.964 | 2.2943 | 2.87 |
| 85 | 25976.1 | 1279.056 | 2.1312 | 4.43 |
| 86 | 26038.8 | 1265.317 | 2.1083 | 9.07 |
| 87 | 26101.1 | 1251.649 | 2.0855 | 4.68 |
| 88 | 26348.4 | 1197.433 | 1.9952 | 2.18 |
| 89 | 26423.1 | 1181.067 | 1.9679 | 6.86 |
| 90 | 26495.7 | 1165.147 | 1.9414 | 40.57 |
| 91 | 26523.1 | 1159.138 | 1.9314 | 35.58 |
| 92 | 26528.4 | 1157.984 | 1.9295 | 36.42 |
| 93 | 26565.0 | 1149.953 | 1.9161 | 14.14 |
| 94 | 26612.0 | 1139.641 | 1.8989 | 12.71 |
| 95 | 26673.0 | 1126.283 | 1.8766 | 9.66 |
| 96 | 26829.5 | 1091.957 | 1.8194 | 48.60 |
| 97 | 26857.0 | 1085.929 | 1.8094 | 113.02 |
| 98 | 27349.4 | 977.978 | 1.6295 | 11.86 |
| 99 | 27403.6 | 966.099 | 1.6097 | 12.07 |
| 100 | 27963.7 | 843.313 | 1.4051 | 22.40 |
| 101 | 28018.6 | 831.275 | 1.3851 | 8.46 |
| 102 | 28254.5 | 779.546 | 1.2989 | 11.85 |
| 103 | 28298.3 | 769.948 | 1.2829 | 12.55 |
| 104 | 28317.6 | 765.717 | 1.2759 | 13.04 |
| 105 | 28356.2 | 757.269 | 1.2618 | 86.45 |
| 106 | 28387.8 | 750.328 | 1.2502 | 81.24 |
| 107 | 28464.0 | 733.633 | 1.2224 | 88.26 |
| 108 | 28533.4 | 718.414 | 1.1970 | 73.80 |
| 109 | 28677.9 | 686.739 | 1.1443 | 3.89 |
| 110 | 28745.9 | 671.820 | 1.1194 | 3.59 |
| 111 | 28867.8 | 645.098 | 1.0749 | 74.04 |
| 112 | 28987.7 | 618.804 | 1.0311 | 4.13 |
| 113 | 29051.5 | 604.826 | 1.0078 | 8.69 |
| 114 | 29106.8 | 592.703 | 0.9876 | 4.79 |
| 115 | 29207.1 | 570.711 | 0.9509 | 114.09 |
| 116 | 29320.8 | 545.779 | 0.9094 | 3.45 |

TABLE 8.5-continued

R1-proton-NMR-peaklist

| # | ADDRESS | FREQUENCY [Hz] | [PPM] | INTENSITY |
|---|---|---|---|---|
| 117 | 29410.0 | 526.225 | 0.8768 | 1.79 |
| 118 | 29492.8 | 508.068 | 0.8466 | 1.41 |
| 119 | 29857.9 | 428.030 | 0.7132 | 9.46 |
| 120 | 29911.7 | 416.233 | 0.6935 | 9.30 |

TABLE 8.6

13C NMR of R1 peak list
DU = C:/Bruker/XWIN-NMR, USER = guest,
NAME = chan, EXPNO = F1 = 176.659 ppm,
F2 = 6.843 ppm, MI = 0.06 cm, MAXI = 10000.00 cm,

| # | ADDRESS | FREQUENCY [Hz] | [PPM] | INTENSITY |
|---|---|---|---|---|
| 1 | 5310.9 | 25331.195 | 167.8559 | 0.12 |
| 2 | 8227.3 | 22634.219 | 149.9845 | 1.57 |
| 3 | 8251.8 | 22611.535 | 149.8342 | 11.79 |
| 4 | 8281.1 | 22584.428 | 149.6546 | 12.50 |
| 5 | 8310.4 | 22557.355 | 149.4752 | 12.30 |
| 6 | 9381.7 | 21566.594 | 142.9100 | 0.11 |
| 7 | 10403.1 | 20622.062 | 136.6511 | 0.14 |
| 8 | 10577.3 | 20460.975 | 135.5836 | 1.08 |
| 9 | 10596.8 | 20442.969 | 135.4643 | 5.78 |
| 10 | 10623.6 | 20418.133 | 135.2998 | 6.16 |
| 11 | 10650.4 | 20393.346 | 135.1355 | 6.01 |
| 12 | 11696.9 | 19425.617 | 128.7229 | 0.14 |
| 13 | 12537.9 | 18647.846 | 123.5690 | 2.11 |
| 14 | 12557.4 | 18629.844 | 123.4497 | 10.62 |
| 15 | 12584.3 | 18604.896 | 123.2844 | 11.25 |
| 16 | 12611.3 | 18580.010 | 123.1195 | 10.98 |
| 17 | 13444.2 | 17809.705 | 118.0151 | 0.11 |
| 18 | 14249.2 | 17065.322 | 113.0825 | 0.15 |
| 19 | 15319.0 | 16075.968 | 106.5266 | 0.21 |
| 20 | 15492.3 | 15915.713 | 105.4647 | 0.24 |
| 21 | 15509.0 | 15900.229 | 105.3621 | 0.25 |
| 22 | 15823.2 | 15609.646 | 103.4365 | 0.18 |
| 23 | 16269.0 | 15197.378 | 100.7047 | 0.16 |
| 24 | 18158.1 | 13450.413 | 89.1285 | 0.12 |
| 25 | 19683.7 | 12039.604 | 79.7798 | 0.13 |
| 26 | 19797.3 | 11934.502 | 79.0834 | 0.14 |
| 27 | 19929.2 | 11812.533 | 78.2752 | 0.23 |
| 28 | 19945.5 | 11797.527 | 78.1757 | 0.42 |
| 29 | 20197.3 | 11564.589 | 76.6322 | 0.15 |
| 30 | 20211.9 | 11551.142 | 76.5431 | 0.16 |
| 31 | 20226.2 | 11537.928 | 76.4555 | 0.14 |
| 32 | 20335.9 | 11436.434 | 75.7830 | 0.10 |
| 33 | 20410.2 | 11367.753 | 75.3279 | 0.13 |
| 34 | 20473.6 | 11309.069 | 74.9390 | 0.38 |
| 35 | 20617.2 | 11176.295 | 74.0592 | 0.13 |
| 36 | 20755.1 | 11048.805 | 73.2144 | 0.15 |
| 37 | 20910.0 | 10905.522 | 72.2649 | 0.21 |
| 38 | 21019.3 | 10804.420 | 71.5950 | 0.15 |
| 39 | 21047.5 | 10778.391 | 71.4225 | 0.37 |
| 40 | 21283.2 | 10560.453 | 69.9783 | 0.12 |
| 41 | 21320.7 | 10525.739 | 69.7483 | 0.12 |
| 42 | 21375.2 | 10475.339 | 69.4143 | 0.14 |
| 43 | 21430.8 | 10423.882 | 69.0733 | 0.13 |
| 44 | 22496.2 | 9438.663 | 62.5448 | 0.19 |
| 45 | 22510.2 | 9425.676 | 62.4588 | 0.20 |
| 46 | 23646.3 | 8375.039 | 55.4968 | 0.13 |
| 47 | 24915.8 | 7201.028 | 47.7173 | 0.13 |
| 48 | 25152.5 | 6982.204 | 46.2672 | 0.11 |
| 49 | 25671.3 | 6502.366 | 43.0876 | 0.12 |
| 50 | 25868.3 | 6320.202 | 41.8805 | 0.10 |
| 51 | 25921.2 | 6271.273 | 41.5563 | 0.11 |
| 52 | 26160.1 | 6050.418 | 40.0928 | 0.10 |
| 53 | 26300.3 | 5920.724 | 39.2334 | 0.13 |
| 54 | 26396.6 | 5831.667 | 38.6433 | 0.10 |
| 55 | 26722.2 | 5530.549 | 36.6479 | 0.11 |
| 56 | 26820.5 | 5439.679 | 36.0458 | 0.13 |
| 57 | 27398.1 | 4905.475 | 32.5059 | 0.10 |
| 58 | 27774.8 | 4557.162 | 30.1978 | 0.23 |
| 59 | 28148.7 | 4211.391 | 27.9066 | 0.23 |
| 60 | 28389.5 | 3988.645 | 26.4306 | 0.10 |
| 61 | 28448.2 | 3934.385 | 26.0710 | 0.17 |
| 62 | 28512.9 | 3874.571 | 25.6747 | 0.10 |
| 63 | 28828.2 | 3583.030 | 23.7428 | 0.11 |
| 64 | 29348.8 | 3101.522 | 20.5521 | 0.23 |
| 65 | 29529.3 | 2934.591 | 19.4459 | 0.22 |
| 66 | 29650.2 | 2822.798 | 18.7051 | 0.26 |
| 67 | 29719.5 | 2758.712 | 18.2805 | 0.11 |
| 68 | 29766.2 | 2715.508 | 17.9942 | 0.10 |
| 69 | 29970.4 | 2526.664 | 16.7428 | 0.24 |
| 70 | 29985.5 | 2512.765 | 16.6507 | 0.17 |
| 71 | 30140.7 | 2369.192 | 15.6993 | 0.22 |

TABLE 9.2

2D NMR (HMQC) chemical shift list of O54.

| Assignment | w1 | w2 | Data Height |
|---|---|---|---|
| 1 | 123.540 | 5.337 | 10801059 |
| 2 | 106.679 | 4.875 | 7546160 |
| 3 | 106.701 | 4.860 | 8527622 |
| 4 | 105.189 | 5.129 | 11004760 |
| 5 | 105.382 | 4.997 | 11249292 |
| 6 | 105.173 | 5.114 | 7915383 |
| 7 | 103.375 | 4.725 | 9431190 |
| 8 | 100.663 | 6.513 | 18941426 |
| 9 | 88.873 | 3.329 | 5975702 |
| 10 | 88.850 | 3.307 | 5246604 |
| 11 | 79.767 | 4.210 | 7199634 |
| 12 | 79.708 | 4.184 | 2885672 |
| 13 | 78.203 | 4.213 | 23826162 |
| 14 | 78.196 | 3.907 | 13786228 |
| 15 | 76.818 | 4.148 | 6859174 |
| 16 | 76.490 | 3.944 | 5773632 |
| 17 | 76.642 | 3.749 | 7515808 |
| 18 | 76.628 | 3.730 | 8437212 |
| 19 | 75.842 | 4.089 | 22251034 |
| 20 | 75.318 | 4.241 | 2654032 |
| 21 | 75.330 | 4.213 | 9853961 |
| 22 | 75.103 | 4.299 | 7580958 |
| 23 | 75.169 | 4.279 | 6376272 |
| 24 | 74.986 | 4.025 | 11823145 |
| 25 | 75.168 | 4.003 | 10800605 |
| 26 | 74.084 | 4.330 | 4901724 |
| 27 | 74.098 | 4.309 | 7830222 |
| 28 | 74.228 | 4.291 | 3975150 |
| 29 | 72.281 | 4.711 | 17310028 |
| 30 | 72.230 | 4.625 | 8709239 |
| 31 | 72.206 | 4.606 | 7361591 |
| 32 | 71.479 | 4.220 | 14407576 |
| 33 | 71.481 | 4.208 | 15081282 |
| 34 | 71.581 | 4.169 | 4582404 |
| 35 | 71.613 | 4.150 | 8419769 |
| 36 | 71.628 | 4.121 | 5804582 |
| 37 | 71.637 | 4.099 | 7950110 |
| 38 | 71.667 | 4.080 | 3119152 |
| 39 | 70.305 | 4.890 | 7622650 |
| 40 | 70.298 | 4.868 | 7628303 |
| 41 | 70.265 | 4.314 | 4762902 |
| 42 | 69.983 | 4.676 | 6227999 |
| 43 | 69.918 | 4.649 | 6037791 |
| 44 | 70.105 | 4.341 | 9963877 |
| 45 | 69.129 | 4.783 | 4704838 |

TABLE 9.2-continued

2D NMR (HMQC) chemical shift list of O54.

| Assignment | w1 | w2 | Data Height |
|---|---|---|---|
| 46 | 62.554 | 4.502 | 14998714 |
| 47 | 62.532 | 4.477 | 14154374 |
| 48 | 62.548 | 4.362 | 11342701 |
| 49 | 62.537 | 4.344 | 8091356 |
| 50 | 56.159 | 3.697 | 1838600 |
| 51 | 56.081 | 3.758 | 2144782 |
| 52 | 55.778 | 3.686 | 1783080 |
| 53 | 55.590 | 0.717 | 5572202 |
| 54 | 55.588 | 0.694 | 6671325 |
| 55 | 47.732 | 1.608 | 4217994 |
| 56 | 47.785 | 1.595 | 3965686 |
| 57 | 46.238 | 2.131 | 1734693 |
| 58 | 46.271 | 2.105 | 4919338 |
| 59 | 46.299 | 2.072 | 2490009 |
| 60 | 46.279 | 1.304 | 4826865 |
| 61 | 46.276 | 1.272 | 4573323 |
| 62 | 41.612 | 2.605 | 4436446 |
| 63 | 41.597 | 2.572 | 4591152 |
| 64 | 38.742 | 1.643 | 4256302 |
| 65 | 38.730 | 1.612 | 3985649 |
| 66 | 38.641 | 1.031 | 3538408 |
| 67 | 32.508 | 1.413 | 10863677 |
| 68 | 30.189 | 1.220 | 58134804 |
| 69 | 27.984 | 1.242 | 55524444 |
| 70 | 26.495 | 2.420 | 3113032 |
| 71 | 26.468 | 2.392 | 3183732 |
| 72 | 25.878 | 1.917 | 3435953 |
| 73 | 25.880 | 1.880 | 1979946 |
| 74 | 26.066 | 1.242 | 63345236 |
| 75 | 25.715 | 1.212 | 5054462 |
| 76 | 23.814 | 1.988 | 2104036 |
| 77 | 23.705 | 1.959 | 3237644 |
| 78 | 23.659 | 1.900 | 2754050 |
| 79 | 23.695 | 1.865 | 3108091 |
| 80 | 19.416 | 1.257 | 40949520 |
| 81 | 18.692 | 1.802 | 30867330 |
| 82 | 18.344 | 1.389 | 3540974 |
| 83 | 18.308 | 1.413 | 6204910 |
| 84 | 17.911 | 2.330 | 3260134 |
| 85 | 17.942 | 2.308 | 4212457 |
| 86 | 17.914 | 1.936 | 2468661 |
| 87 | 17.943 | 1.904 | 3914254 |
| 88 | 16.825 | 0.980 | 48392540 |
| 89 | 16.640 | 1.072 | 52924908 |
| 90 | 15.701 | 0.947 | 60375744 |

TABLE 9.3

2D NMR (HMBC) chemical shift list of O54.
DU = C:/Bruker/XWIN-NMR, USER = guest, NAME = chan,
EXPNO = 37, PROCNO = 1
F1PLO = 149.426 ppm, F1PHI = 11.307 ppm, F2PLO = 6.861 ppm,
F2PHI = 0.388 ppm
MI = 2.00 cm, MAXI = 10000.00 cm, PC = 3.000

| # | ADDRESS row/col | FREQUENCY [Hz]F1 / [Hz]F2 | [PPM]F1 / [PPM]F2 | INTENSITY |
|---|---|---|---|---|
| 1 | 294 | 21551.752 | 142.8145 | 3.15 |
|   | 728 | 1553.288 | 2.5881 | |
| 2 | 294 | 21551.752 | 142.8145 | 3.03 |
|   | 791 | 1185.345 | 1.9750 | |
| 3 | 294 | 21551.752 | 142.8145 | 3.00 |
|   | 801 | 1127.853 | 1.8793 | |
| 4 | 294 | 21551.752 | 142.8145 | 41.49 |
|   | 866 | 744.836 | 1.2411 | |
| 5 | 392 | 18639.387 | 123.5154 | 2.70 |
|   | 728 | 1554.313 | 2.5898 | |
| 6 | 392 | 18639.387 | 123.5154 | 2.11 |
|   | 730 | 1540.225 | 2.5664 | |

TABLE 9.3-continued

2D NMR (HMBC) chemical shift list of O54.
DU = C:/Bruker/XWIN-NMR, USER = guest, NAME = chan,
EXPNO = 37, PROCNO = 1
F1PLO = 149.426 ppm, F1PHI = 11.307 ppm, F2PLO = 6.861 ppm,
F2PHI = 0.388 ppm
MI = 2.00 cm, MAXI = 10000.00 cm, PC = 3.000

| # | ADDRESS row/col | FREQUENCY [Hz]F1 / [Hz]F2 | [PPM]F1 / [PPM]F2 | INTENSITY |
|---|---|---|---|---|
| 7 | 392 | 18639.387 | 123.5154 | 2.94 |
|   | 794 | 1164.901 | 1.9410 | |
| 8 | 392 | 18639.387 | 123.5154 | 3.61 |
|   | 801 | 1127.069 | 1.8779 | |
| 9 | 478 | 16106.854 | 106.7334 | 20.41 |
|   | 585 | 2391.723 | 3.9851 | |
| 10 | 478 | 16106.854 | 106.7334 | 3.17 |
|    | 653 | 1992.507 | 3.3200 | |
| 11 | 485 | 15890.850 | 105.3020 | 3.34 |
|    | 494 | 2924.288 | 4.8725 | |
| 12 | 485 | 15890.850 | 105.3020 | 3.27 |
|    | 516 | 2797.792 | 4.6617 | |
| 13 | 485 | 15890.850 | 105.3020 | 5.99 |
|    | 547 | 2614.903 | 4.3570 | |
| 14 | 485 | 15890.850 | 105.3020 | 11.83 |
|    | 583 | 2405.277 | 4.0077 | |
| 15 | 495 | 15600.868 | 103.3804 | 4.55 |
|    | 560 | 2539.046 | 4.2306 | |
| 16 | 495 | 15600.868 | 103.3804 | 3.63 |
|    | 574 | 2456.564 | 4.0932 | |
| 17 | 509 | 15198.148 | 100.7118 | 11.15 |
|    | 312 | 3996.510 | 6.6591 | |
| 18 | 509 | 15198.148 | 100.7118 | 12.11 |
|    | 341 | 3824.267 | 6.3721 | |
| 19 | 509 | 15198.148 | 100.7118 | 2.82 |
|    | 560 | 2539.421 | 4.2312 | |
| 20 | 570 | 13411.609 | 88.8731 | 18.81 |
|    | 495 | 2921.818 | 4.8684 | |
| 21 | 570 | 13411.609 | 88.8731 | 2.73 |
|    | 797 | 1147.142 | 1.9114 | |
| 22 | 570 | 13411.609 | 88.8731 | 6.25 |
|    | 827 | 975.260 | 1.6250 | |
| 23 | 570 | 13411.609 | 88.8731 | 69.46 |
|    | 866 | 746.125 | 1.2432 | |
| 24 | 570 | 13411.609 | 88.8731 | 48.36 |
|    | 892 | 589.846 | 0.9828 | |
| 25 | 616 | 12031.100 | 79.7251 | 10.23 |
|    | 561 | 2533.072 | 4.2207 | |
| 26 | 616 | 12031.100 | 79.7251 | 12.78 |
|    | 568 | 2492.076 | 4.1524 | |
| 27 | 624 | 11792.174 | 78.1418 | 3.71 |
|    | 469 | 3075.630 | 5.1247 | |
| 28 | 624 | 11792.174 | 78.1418 | 2.57 |
|    | 481 | 3002.844 | 5.0034 | |
| 29 | 624 | 11792.174 | 78.1418 | 2.54 |
|    | 534 | 2690.732 | 4.4834 | |
| 30 | 624 | 11792.174 | 78.1418 | 2.56 |
|    | 547 | 2617.207 | 4.3608 | |
| 31 | 624 | 11792.174 | 78.1418 | 29.07 |
|    | 561 | 2532.765 | 4.2201 | |
| 32 | 624 | 11792.174 | 78.1418 | 15.44 |
|    | 573 | 2460.286 | 4.0994 | |
| 33 | 624 | 11792.174 | 78.1418 | 13.41 |
|    | 580 | 2419.846 | 4.0320 | |
| 34 | 624 | 11792.174 | 78.1418 | 8.30 |
|    | 585 | 2390.343 | 3.9828 | |
| 35 | 624 | 11792.174 | 78.1418 | 3.23 |
|    | 868 | 732.442 | 1.2204 | |
| 36 | 632 | 11558.919 | 76.5961 | 11.58 |
|    | 553 | 2577.697 | 4.2950 | |
| 37 | 632 | 11558.919 | 76.5961 | 3.02 |
|    | 563 | 2521.889 | 4.2020 | |
| 38 | 632 | 11558.919 | 76.5961 | 13.81 |
|    | 573 | 2462.246 | 4.1026 | |
| 39 | 632 | 11558.919 | 76.5961 | 9.11 |
|    | 861 | 772.953 | 1.2879 | |
| 40 | 632 | 11558.919 | 76.5961 | 33.06 |
|    | 864 | 755.650 | 1.2591 | |

TABLE 9.3-continued

2D NMR (HMBC) chemical shift list of O54.
DU = C:/Bruker/XWIN-NMR, USER = guest, NAME = chan,
EXPNO = 37, PROCNO = 1
F1PLO = 149.426 ppm, F1PHI = 11.307 ppm, F2PLO = 6.861 ppm,
F2PHI = 0.388 ppm
MI = 2.00 cm, MAXI = 10000.00 cm, PC = 3.000

| # | ADDRESS row col | FREQUENCY [Hz]F1 [Hz]F2 | [PPM]F1 [PPM]F2 | INTENSITY |
|---|---|---|---|---|
| 41 | 632 | 11558.919 | 76.5961 | 53.66 |
|  | 868 | 732.170 | 1.2200 |  |
| 42 | 639 | 11373.424 | 75.3669 | 5.00 |
|  | 326 | 3911.898 | 6.5181 |  |
| 43 | 639 | 11373.424 | 75.3669 | 25.40 |
|  | 563 | 2523.630 | 4.2049 |  |
| 44 | 639 | 11373.424 | 75.3669 | 5.16 |
|  | 574 | 2456.045 | 4.0923 |  |
| 45 | 639 | 11373.424 | 75.3669 | 5.57 |
|  | 611 | 2240.865 | 3.7338 |  |
| 46 | 639 | 11373.424 | 75.3669 | 2.40 |
|  | 808 | 1082.299 | 1.8034 |  |
| 47 | 639 | 11373.424 | 75.3669 | 2.78 |
|  | 864 | 756.608 | 1.2607 |  |
| 48 | 639 | 11373.424 | 75.3669 | 5.47 |
|  | 868 | 732.370 | 1.2203 |  |
| 49 | 646 | 11168.377 | 74.0082 | 8.44 |
|  | 511 | 2828.344 | 4.7127 |  |
| 50 | 646 | 11168.377 | 74.0082 | 6.66 |
|  | 520 | 2772.974 | 4.6204 |  |
| 51 | 646 | 11168.377 | 74.0082 | 5.35 |
|  | 563 | 2524.284 | 4.2060 |  |
| 52 | 646 | 11168.377 | 74.0082 | 49.69 |
|  | 808 | 1082.395 | 1.8035 |  |
| 53 | 655 | 10899.106 | 72.2238 | 25.27 |
|  | 326 | 3911.679 | 6.5177 |  |
| 54 | 655 | 10899.106 | 72.2238 | 2.42 |
|  | 498 | 2902.662 | 4.8365 |  |
| 55 | 655 | 10899.106 | 72.2238 | 5.76 |
|  | 511 | 2829.414 | 4.7144 |  |
| 56 | 655 | 10899.106 | 72.2238 | 2.33 |
|  | 523 | 2756.376 | 4.5927 |  |
| 57 | 655 | 10899.106 | 72.2238 | 2.40 |
|  | 532 | 2703.575 | 4.5048 |  |
| 58 | 655 | 10899.106 | 72.2238 | 9.99 |
|  | 552 | 2588.313 | 4.3127 |  |
| 59 | 655 | 10899.106 | 72.2238 | 7.35 |
|  | 563 | 2523.240 | 4.2043 |  |
| 60 | 655 | 10899.106 | 72.2238 | 2.26 |
|  | 808 | 1083.933 | 1.8061 |  |
| 61 | 659 | 10785.637 | 71.4719 | 2.28 |
|  | 326 | 3912.133 | 6.5185 |  |
| 62 | 659 | 10785.637 | 71.4719 | 2.36 |
|  | 494 | 2925.999 | 4.8754 |  |
| 63 | 659 | 10785.637 | 71.4719 | 3.39 |
|  | 516 | 2800.177 | 4.6657 |  |
| 64 | 659 | 10785.637 | 71.4719 | 7.49 |
|  | 532 | 2702.493 | 4.5030 |  |
| 65 | 659 | 10785.637 | 71.4719 | 7.86 |
|  | 534 | 2691.698 | 4.4850 |  |
| 66 | 659 | 10785.637 | 71.4719 | 2.35 |
|  | 547 | 2614.980 | 4.3571 |  |
| 67 | 659 | 10785.637 | 71.4719 | 46.85 |
|  | 562 | 2525.201 | 4.2075 |  |
| 68 | 659 | 10785.637 | 71.4719 | 2.02 |
|  | 584 | 2398.095 | 3.9958 |  |
| 69 | 665 | 10604.599 | 70.2723 | 2.12 |
|  | 326 | 3911.956 | 6.5182 |  |
| 70 | 665 | 10604.599 | 70.2723 | 18.68 |
|  | 469 | 3075.252 | 5.1241 |  |
| 71 | 665 | 10604.599 | 70.2723 | 3.29 |
|  | 481 | 3002.048 | 5.0021 |  |
| 72 | 665 | 10604.599 | 70.2723 | 3.03 |
|  | 562 | 2525.138 | 4.2074 |  |
| 73 | 665 | 10604.599 | 70.2723 | 6.46 |
|  | 573 | 2460.794 | 4.1002 |  |
| 74 | 665 | 10604.599 | 70.2723 | 3.10 |
|  | 808 | 1081.934 | 1.8027 |  |
| 75 | 666 | 10552.990 | 69.9303 | 2.10 |
|  | 326 | 3912.459 | 6.5190 |  |
| 76 | 666 | 10552.990 | 69.9303 | 13.23 |
|  | 468 | 3077.187 | 5.1273 |  |
| 77 | 666 | 10552.990 | 69.9303 | 10.72 |
|  | 481 | 3002.402 | 5.0027 |  |
| 78 | 666 | 10552.990 | 69.9303 | 3.33 |
|  | 563 | 2522.129 | 4.2024 |  |
| 79 | 666 | 10552.990 | 69.9303 | 4.47 |
|  | 573 | 2461.269 | 4.1010 |  |
| 80 | 666 | 10552.990 | 69.9303 | 2.72 |
|  | 808 | 1081.723 | 1.8024 |  |
| 81 | 671 | 10429.136 | 69.1095 | 38.49 |
|  | 326 | 3911.639 | 6.5177 |  |
| 82 | 671 | 10429.136 | 69.1095 | 8.97 |
|  | 552 | 2589.015 | 4.3139 |  |
| 83 | 671 | 10429.136 | 69.1095 | 63.77 |
|  | 808 | 1081.987 | 1.8028 |  |
| 84 | 705 | 9425.537 | 62.4591 | 3.27 |
|  | 560 | 2542.206 | 4.2359 |  |
| 85 | 705 | 9425.537 | 62.4591 | 2.08 |
|  | 562 | 2526.304 | 4.2094 |  |
| 86 | 740 | 8376.884 | 55.5101 | 3.45 |
|  | 827 | 971.239 | 1.6183 |  |
| 87 | 740 | 8376.884 | 55.5101 | 3.43 |
|  | 849 | 843.561 | 1.4056 |  |
| 88 | 740 | 8376.884 | 55.5101 | 48.00 |
|  | 866 | 746.292 | 1.2435 |  |
| 89 | 740 | 8376.884 | 55.5101 | 31.95 |
|  | 892 | 590.131 | 0.9833 |  |
| 90 | 740 | 8376.884 | 55.5101 | 25.60 |
|  | 896 | 567.050 | 0.9448 |  |
| 91 | 780 | 7196.908 | 47.6909 | 4.85 |
|  | 447 | 3202.461 | 5.3360 |  |
| 92 | 780 | 7196.908 | 47.6909 | 2.83 |
|  | 864 | 756.127 | 1.2599 |  |
| 93 | 780 | 7196.908 | 47.6909 | 3.78 |
|  | 868 | 731.658 | 1.2191 |  |
| 94 | 780 | 7196.908 | 47.6909 | 28.25 |
|  | 883 | 642.229 | 1.0701 |  |
| 95 | 780 | 7196.908 | 47.6909 | 32.38 |
|  | 896 | 567.166 | 0.9450 |  |
| 96 | 780 | 7196.908 | 47.6909 | 2.37 |
|  | 922 | 414.895 | 0.6913 |  |
| 97 | 788 | 6979.996 | 46.2535 | 2.37 |
|  | 730 | 1540.055 | 2.5661 |  |
| 98 | 788 | 6979.996 | 46.2535 | 58.65 |
|  | 864 | 755.679 | 1.2591 |  |
| 99 | 788 | 6979.996 | 46.2535 | 85.12 |
|  | 868 | 731.892 | 1.2195 |  |
| 100 | 804 | 6505.572 | 43.1097 | 4.16 |
|  | 553 | 2577.654 | 4.2949 |  |
| 101 | 804 | 6505.572 | 43.1097 | 4.70 |
|  | 574 | 2455.343 | 4.0911 |  |
| 102 | 804 | 6505.572 | 43.1097 | 3.13 |
|  | 755 | 1393.963 | 2.3227 |  |
| 103 | 804 | 6505.572 | 43.1097 | 3.35 |
|  | 858 | 789.603 | 1.3157 |  |
| 104 | 804 | 6505.572 | 43.1097 | 9.90 |
|  | 861 | 773.435 | 1.2887 |  |
| 105 | 804 | 6505.572 | 43.1097 | 9.41 |
|  | 867 | 737.064 | 1.2281 |  |
| 106 | 804 | 6505.572 | 43.1097 | 2.74 |
|  | 883 | 642.755 | 1.0710 |  |
| 107 | 804 | 6505.572 | 43.1097 | 2.09 |
|  | 892 | 589.037 | 0.9815 |  |
| 108 | 810 | 6311.923 | 41.8265 | 8.24 |
|  | 447 | 3202.295 | 5.3357 |  |

TABLE 9.3-continued

2D NMR (HMBC) chemical shift list of O54.
DU = C:/Bruker/XWIN-NMR, USER = guest, NAME = chan,
EXPNO = 37, PROCNO = 1
F1PLO = 149.426 ppm, F1PHI = 11.307 ppm, F2PLO = 6.861 ppm,
F2PHI = 0.388 ppm
MI = 2.00 cm, MAXI = 10000.00 cm, PC = 3.000

| # | ADDRESS row col | FREQUENCY [Hz]F1 [Hz]F2 | [PPM]F1 [PPM]F2 | INTENSITY |
|---|---|---|---|---|
| 109 | 810 | 6311.923 | 41.8265 | 6.43 |
|  | 755 | 1393.660 | 2.3221 |  |
| 110 | 810 | 6311.923 | 41.8265 | 2.54 |
|  | 830 | 955.929 | 1.5928 |  |
| 111 | 810 | 6311.923 | 41.8265 | 45.72 |
|  | 866 | 744.369 | 1.2403 |  |
| 112 | 810 | 6311.923 | 41.8265 | 3.80 |
|  | 869 | 724.741 | 1.2076 |  |
| 113 | 810 | 6311.923 | 41.8265 | 53.84 |
|  | 883 | 642.271 | 1.0702 |  |
| 114 | 810 | 6311.923 | 41.8265 | 2.36 |
|  | 892 | 589.734 | 0.9826 |  |
| 115 | 814 | 6190.622 | 41.0227 | 2.27 |
|  | 447 | 3204.169 | 5.3389 |  |
| 116 | 814 | 6190.622 | 41.0227 | 4.20 |
|  | 866 | 744.967 | 1.2413 |  |
| 117 | 814 | 6190.622 | 41.0227 | 13.51 |
|  | 883 | 641.291 | 1.0685 |  |
| 118 | 814 | 6190.622 | 41.0227 | 3.54 |
|  | 892 | 590.266 | 0.9835 |  |
| 119 | 817 | 6122.212 | 40.5694 | 2.02 |
|  | 849 | 842.541 | 1.4039 |  |
| 120 | 817 | 6122.212 | 40.5694 | 10.92 |
|  | 866 | 744.098 | 1.2398 |  |
| 121 | 817 | 6122.212 | 40.5694 | 19.65 |
|  | 883 | 641.844 | 1.0695 |  |
| 122 | 817 | 6122.212 | 40.5694 | 4.84 |
|  | 892 | 590.010 | 0.9831 |  |
| 123 | 819 | 6054.448 | 40.1203 | 2.01 |
|  | 800 | 1128.653 | 1.8806 |  |
| 124 | 819 | 6054.448 | 40.1203 | 5.24 |
|  | 830 | 955.874 | 1.5927 |  |
| 125 | 819 | 6054.448 | 40.1203 | 7.20 |
|  | 849 | 842.438 | 1.4037 |  |
| 126 | 819 | 6054.448 | 40.1203 | 39.00 |
|  | 866 | 744.338 | 1.2402 |  |
| 127 | 819 | 6054.448 | 40.1203 | 49.93 |
|  | 883 | 642.047 | 1.0698 |  |
| 128 | 819 | 6054.448 | 40.1203 | 6.64 |
|  | 892 | 589.724 | 0.9826 |  |
| 129 | 819 | 6054.448 | 40.1203 | 2.44 |
|  | 896 | 566.654 | 0.9442 |  |
| 130 | 823 | 5927.002 | 39.2758 | 48.54 |
|  | 866 | 746.066 | 1.2431 |  |
| 131 | 823 | 5927.002 | 39.2758 | 7.22 |
|  | 883 | 642.112 | 1.0699 |  |
| 132 | 823 | 5927.002 | 39.2758 | 60.87 |
|  | 892 | 589.816 | 0.9828 |  |
| 133 | 823 | 5927.002 | 39.2758 | 5.86 |
|  | 896 | 566.631 | 0.9441 |  |
| 134 | 823 | 5927.002 | 39.2758 | 7.24 |
|  | 922 | 415.473 | 0.6923 |  |
| 135 | 827 | 5833.933 | 38.6590 | 3.11 |
|  | 827 | 970.335 | 1.6168 |  |
| 136 | 827 | 5833.933 | 38.6590 | 10.44 |
|  | 865 | 746.825 | 1.2444 |  |
| 137 | 827 | 5833.933 | 38.6590 | 3.42 |
|  | 883 | 642.035 | 1.0698 |  |
| 138 | 827 | 5833.933 | 38.6590 | 11.20 |
|  | 892 | 588.957 | 0.9813 |  |
| 139 | 827 | 5833.933 | 38.6590 | 55.77 |
|  | 896 | 567.124 | 0.9450 |  |
| 140 | 830 | 5737.570 | 38.0205 | 3.79 |
|  | 864 | 753.968 | 1.2563 |  |
| 141 | 830 | 5737.570 | 38.0205 | 4.47 |
|  | 868 | 731.483 | 1.2188 |  |
| 142 | 830 | 5737.570 | 38.0205 | 2.21 |
|  | 883 | 641.875 | 1.0695 |  |
| 143 | 830 | 5737.570 | 38.0205 | 4.70 |
|  | 892 | 589.272 | 0.9819 |  |
| 144 | 830 | 5737.570 | 38.0205 | 11.09 |
|  | 896 | 567.206 | 0.9451 |  |
| 145 | 833 | 5652.819 | 37.4589 | 5.17 |
|  | 865 | 751.942 | 1.2529 |  |
| 146 | 833 | 5652.819 | 37.4589 | 5.78 |
|  | 868 | 732.193 | 1.2200 |  |
| 147 | 833 | 5652.819 | 37.4589 | 2.64 |
|  | 883 | 642.313 | 1.0702 |  |
| 148 | 833 | 5652.819 | 37.4589 | 2.92 |
|  | 892 | 590.189 | 0.9834 |  |
| 149 | 833 | 5652.819 | 37.4589 | 11.22 |
|  | 896 | 567.196 | 0.9451 |  |
| 150 | 837 | 5532.757 | 36.6633 | 2.33 |
|  | 747 | 1441.047 | 2.4011 |  |
| 151 | 837 | 5532.757 | 36.6633 | 6.70 |
|  | 830 | 956.266 | 1.5934 |  |
| 152 | 837 | 5532.757 | 36.6633 | 7.18 |
|  | 849 | 840.791 | 1.4009 |  |
| 153 | 837 | 5532.757 | 36.6633 | 10.60 |
|  | 864 | 754.417 | 1.2570 |  |
| 154 | 837 | 5532.757 | 36.6633 | 10.09 |
|  | 868 | 733.768 | 1.2226 |  |
| 155 | 837 | 5532.757 | 36.6633 | 2.62 |
|  | 883 | 642.220 | 1.0701 |  |
| 156 | 837 | 5532.757 | 36.6633 | 59.49 |
|  | 896 | 567.041 | 0.9448 |  |
| 157 | 837 | 5532.757 | 36.6633 | 7.27 |
|  | 922 | 415.510 | 0.6923 |  |
| 158 | 840 | 5447.502 | 36.0983 | 3.44 |
|  | 611 | 2241.469 | 3.7348 |  |
| 159 | 840 | 5447.502 | 36.0983 | 2.18 |
|  | 775 | 1277.736 | 2.1290 |  |
| 160 | 840 | 5447.502 | 36.0983 | 5.77 |
|  | 778 | 1261.898 | 2.1026 |  |
| 161 | 840 | 5447.502 | 36.0983 | 2.77 |
|  | 780 | 1246.496 | 2.0769 |  |
| 162 | 840 | 5447.502 | 36.0983 | 7.30 |
|  | 861 | 771.393 | 1.2853 |  |
| 163 | 840 | 5447.502 | 36.0983 | 85.50 |
|  | 864 | 755.513 | 1.2589 |  |
| 164 | 840 | 5447.502 | 36.0983 | 94.68 |
|  | 868 | 731.684 | 1.2191 |  |
| 165 | 840 | 5447.502 | 36.0983 | 2.09 |
|  | 883 | 642.211 | 1.0701 |  |
| 166 | 840 | 5447.502 | 36.0983 | 11.25 |
|  | 896 | 566.770 | 0.9444 |  |
| 167 | 858 | 4901.029 | 32.4771 | 2.31 |
|  | 859 | 783.807 | 1.3060 |  |
| 168 | 858 | 4901.029 | 32.4771 | 38.68 |
|  | 883 | 642.014 | 1.0697 |  |
| 169 | 858 | 4901.029 | 32.4771 | 3.35 |
|  | 922 | 416.874 | 0.6946 |  |
| 170 | 870 | 4554.428 | 30.1803 | 9.79 |
|  | 611 | 2241.599 | 3.7350 |  |
| 171 | 870 | 4554.428 | 30.1803 | 3.21 |
|  | 777 | 1263.228 | 2.1048 |  |
| 172 | 870 | 4554.428 | 30.1803 | 18.60 |
|  | 857 | 793.884 | 1.3228 |  |
| 173 | 870 | 4554.428 | 30.1803 | 93.90 |
|  | 864 | 755.200 | 1.2583 |  |
| 174 | 870 | 4554.428 | 30.1803 | 19.16 |
|  | 879 | 668.641 | 1.1141 |  |
| 175 | 870 | 4554.428 | 30.1803 | 3.11 |
|  | 892 | 590.200 | 0.9834 |  |
| 176 | 881 | 4218.921 | 27.9570 | 16.41 |
|  | 855 | 807.262 | 1.3451 |  |

TABLE 9.3-continued

2D NMR (HMBC) chemical shift list of O54.
DU = C:/Bruker/XWIN-NMR, USER = guest, NAME = chan,
EXPNO = 37, PROCNO = 1
F1PLO = 149.426 ppm, F1PHI = 11.307 ppm, F2PLO = 6.861 ppm,
F2PHI = 0.388 ppm
MI = 2.00 cm, MAXI = 10000.00 cm, PC = 3.000

| # | ADDRESS row col | FREQUENCY [Hz]F1 [Hz]F2 | [PPM]F1 [PPM]F2 | INTENSITY |
|---|---|---|---|---|
| 177 | 881 | 4218.921 | 27.9570 | 4.75 |
|  | 864 | 755.803 | 1.2593 |  |
| 178 | 881 | 4218.921 | 27.9570 | 15.67 |
|  | 876 | 683.031 | 1.1381 |  |
| 179 | 881 | 4218.921 | 27.9570 | 73.26 |
|  | 892 | 589.918 | 0.9829 |  |
| 180 | 881 | 4218.921 | 27.9570 | 2.87 |
|  | 922 | 416.446 | 0.6939 |  |
| 181 | 891 | 3935.921 | 26.0817 | 2.34 |
|  | 802 | 1120.176 | 1.8665 |  |
| 182 | 891 | 3935.921 | 26.0817 | 19.11 |
|  | 855 | 806.480 | 1.3438 |  |
| 183 | 891 | 3935.921 | 26.0817 | 8.92 |
|  | 866 | 745.923 | 1.2429 |  |
| 184 | 891 | 3935.921 | 26.0817 | 5.17 |
|  | 868 | 731.989 | 1.2197 |  |
| 185 | 891 | 3935.921 | 26.0817 | 18.56 |
|  | 877 | 680.851 | 1.1344 |  |
| 186 | 891 | 3935.921 | 26.0817 | 4.65 |
|  | 892 | 589.687 | 0.9825 |  |
| 187 | 893 | 3878.913 | 25.7039 | 2.05 |
|  | 791 | 1185.608 | 1.9755 |  |
| 188 | 893 | 3878.913 | 25.7039 | 2.02 |
|  | 810 | 1072.605 | 1.7872 |  |
| 189 | 893 | 3878.913 | 25.7039 | 4.93 |
|  | 855 | 805.970 | 1.3429 |  |
| 190 | 893 | 3878.913 | 25.7039 | 44.75 |
|  | 866 | 744.248 | 1.2401 |  |
| 191 | 893 | 3878.913 | 25.7039 | 4.45 |
|  | 877 | 680.894 | 1.1345 |  |
| 192 | 893 | 3878.913 | 25.7039 | 3.96 |
|  | 892 | 590.170 | 0.9834 |  |
| 193 | 925 | 2932.829 | 19.4346 | 15.68 |
|  | 611 | 2240.954 | 3.7339 |  |
| 194 | 925 | 2932.829 | 19.4346 | 4.57 |
|  | 775 | 1278.753 | 2.1307 |  |
| 195 | 925 | 2932.829 | 19.4346 | 11.84 |
|  | 778 | 1262.372 | 2.1034 |  |
| 196 | 925 | 2932.829 | 19.4346 | 6.85 |
|  | 780 | 1246.392 | 2.0768 |  |
| 197 | 925 | 2932.829 | 19.4346 | 22.66 |
|  | 854 | 816.734 | 1.3609 |  |
| 198 | 925 | 2932.829 | 19.4346 | 93.22 |
|  | 868 | 732.145 | 1.2199 |  |
| 199 | 925 | 2932.829 | 19.4346 | 21.54 |
|  | 875 | 691.416 | 1.1521 |  |
| 200 | 933 | 2709.260 | 17.9531 | 10.65 |
|  | 553 | 2577.918 | 4.2954 |  |
| 201 | 933 | 2709.260 | 17.9531 | 2.40 |
|  | 574 | 2456.969 | 4.0939 |  |
| 202 | 933 | 2709.260 | 17.9531 | 2.47 |
|  | 728 | 1553.812 | 2.5890 |  |
| 203 | 933 | 2709.260 | 17.9531 | 2.44 |
|  | 786 | 1214.060 | 2.0229 |  |
| 204 | 933 | 2709.260 | 17.9531 | 4.64 |
|  | 865 | 746.759 | 1.2443 |  |
| 205 | 933 | 2709.260 | 17.9531 | 5.50 |
|  | 868 | 731.918 | 1.2195 |  |
| 206 | 938 | 2536.520 | 16.8085 | 2.61 |
|  | 653 | 1992.054 | 3.3192 |  |
| 207 | 938 | 2536.520 | 16.8085 | 2.70 |
|  | 829 | 958.476 | 1.5970 |  |
| 208 | 938 | 2536.520 | 16.8085 | 52.11 |
|  | 866 | 745.904 | 1.2428 |  |
| 209 | 938 | 2536.520 | 16.8085 | 17.18 |
|  | 882 | 650.673 | 1.0842 |  |
| 210 | 938 | 2536.520 | 16.8085 | 3.28 |
|  | 895 | 574.736 | 0.9576 |  |
| 211 | 938 | 2536.520 | 16.8085 | 16.84 |
|  | 903 | 526.041 | 0.8765 |  |
| 212 | 938 | 2536.520 | 16.8085 | 8.32 |
|  | 922 | 416.280 | 0.6936 |  |
| 213 | 944 | 2375.487 | 15.7414 | 5.34 |
|  | 830 | 955.713 | 1.5924 |  |
| 214 | 944 | 2375.487 | 15.7414 | 6.94 |
|  | 866 | 745.684 | 1.2425 |  |
| 215 | 944 | 2375.487 | 15.7414 | 21.31 |
|  | 886 | 627.576 | 1.0457 |  |
| 216 | 944 | 2375.487 | 15.7414 | 3.00 |
|  | 892 | 588.774 | 0.9810 |  |
| 217 | 944 | 2375.487 | 15.7414 | 21.33 |
|  | 907 | 503.819 | 0.8395 |  |
| 218 | 944 | 2375.487 | 15.7414 | 10.43 |
|  | 922 | 415.374 | 0.6921 |  |

TABLE 9.5

Proton NMR peak list of O54.
DU = C:/Bruker/XWIN-NMR, USER = guest, NAME = chan,
EXPNO = 35, PROCNO = 1
F1 = 10.000 ppm, F2 = 0.000 ppm, MI = 2.00 cm, MAXI = 10000.00 cm,
PC = 1.000

| # | ADDRESS | FREQUENCY [Hz] | [PPM] | INTENSITY |
|---|---|---|---|---|
| 1 | 7886.3 | 5225.509 | 8.7069 | 180.00 |
| 2 | 11038.4 | 4534.438 | 7.5554 | 72.73 |
| 3 | 12044.3 | 4313.911 | 7.1879 | 160.90 |
| 4 | 13878.4 | 3911.819 | 6.5180 | 14.53 |
| 5 | 17112.8 | 3202.719 | 5.3364 | 9.02 |
| 6 | 17674.0 | 3079.600 | 5.1314 | 10.52 |
| 7 | 17709.4 | 3071.938 | 5.1185 | 10.66 |
| 8 | 18004.6 | 3007.215 | 5.0107 | 10.57 |
| 9 | 18039.9 | 2999.480 | 4.9978 | 10.78 |
| 10 | 18330.8 | 2935.701 | 4.8915 | 6.88 |
| 11 | 18377.3 | 2925.509 | 4.8745 | 16.06 |
| 12 | 18411.1 | 2918.099 | 4.8622 | 10.01 |
| 13 | 18591.4 | 2878.554 | 4.7963 | 3.55 |
| 14 | 18621.6 | 2871.941 | 4.7853 | 4.53 |
| 15 | 18660.9 | 2863.325 | 4.7709 | 3.56 |
| 16 | 18768.9 | 2839.657 | 4.7315 | 8.48 |
| 17 | 18801.9 | 2832.416 | 4.7194 | 15.95 |
| 18 | 18929.2 | 2804.496 | 4.6729 | 5.72 |
| 19 | 18974.3 | 2794.608 | 4.6564 | 6.90 |
| 20 | 19049.2 | 2778.191 | 4.6291 | 5.41 |
| 21 | 19063.7 | 2775.007 | 4.6238 | 4.83 |
| 22 | 19091.3 | 2768.955 | 4.6137 | 5.79 |
| 23 | 19106.0 | 2765.737 | 4.6083 | 5.24 |
| 24 | 19395.7 | 2702.228 | 4.5025 | 11.91 |
| 25 | 19447.9 | 2690.790 | 4.4835 | 16.03 |
| 26 | 19708.9 | 2633.561 | 4.3881 | 6.86 |
| 27 | 19731.8 | 2628.557 | 4.3798 | 8.37 |
| 28 | 19761.7 | 2621.989 | 4.3688 | 16.78 |
| 29 | 19784.1 | 2617.071 | 4.3606 | 18.07 |
| 30 | 19814.8 | 2610.350 | 4.3494 | 12.73 |
| 31 | 19834.7 | 2605.976 | 4.3421 | 13.55 |
| 32 | 19863.8 | 2599.612 | 4.3315 | 9.52 |
| 33 | 19909.8 | 2589.523 | 4.3147 | 13.96 |
| 34 | 19947.5 | 2581.249 | 4.3009 | 10.27 |
| 35 | 19990.6 | 2571.809 | 4.2852 | 7.86 |
| 36 | 20116.2 | 2544.275 | 4.2393 | 6.06 |

TABLE 9.5-continued

Proton NMR peak list of O54.
DU = C:/Bruker/XWIN-NMR, USER = guest, NAME = chan,
EXPNO = 35, PROCNO = 1
F1 = 10.000 ppm, F2 = 0.000 ppm, MI = 2.00 cm, MAXI = 10000.00 cm,
PC = 1.000

| # | ADDRESS | FREQUENCY [Hz] | [PPM] | INTENSITY |
|---|---|---|---|---|
| 37 | 20155.1 | 2535.750 | 4.2251 | 29.53 |
| 38 | 20188.0 | 2528.527 | 4.2131 | 36.53 |
| 39 | 20218.4 | 2521.859 | 4.2020 | 22.79 |
| 40 | 20258.5 | 2513.072 | 4.1873 | 10.10 |
| 41 | 20308.5 | 2502.111 | 4.1691 | 7.17 |
| 42 | 20349.0 | 2493.228 | 4.1543 | 10.94 |
| 43 | 20384.7 | 2485.412 | 4.1412 | 7.98 |
| 44 | 20454.4 | 2470.136 | 4.1158 | 8.00 |
| 45 | 20496.1 | 2460.979 | 4.1005 | 11.54 |
| 46 | 20522.9 | 2455.108 | 4.0908 | 20.70 |
| 47 | 20619.4 | 2433.953 | 4.0555 | 5.10 |
| 48 | 20655.0 | 2426.151 | 4.0425 | 7.46 |
| 49 | 20704.6 | 2415.271 | 4.0244 | 6.32 |
| 50 | 20741.8 | 2407.119 | 4.0108 | 8.93 |
| 51 | 20763.7 | 2402.312 | 4.0028 | 6.78 |
| 52 | 20800.3 | 2394.290 | 3.9894 | 7.59 |
| 53 | 20840.0 | 2385.587 | 3.9749 | 4.23 |
| 54 | 20899.5 | 2372.534 | 3.9532 | 5.04 |
| 55 | 20961.5 | 2358.953 | 3.9305 | 5.93 |
| 56 | 21011.8 | 2347.917 | 3.9122 | 8.88 |
| 57 | 21462.4 | 2249.135 | 3.7476 | 8.28 |
| 58 | 21507.4 | 2239.268 | 3.7311 | 7.60 |
| 59 | 22606.3 | 1998.348 | 3.3297 | 4.57 |
| 60 | 22625.1 | 1994.242 | 3.3228 | 4.57 |
| 61 | 22658.9 | 1986.819 | 3.3105 | 4.74 |
| 62 | 22678.2 | 1982.598 | 3.3034 | 4.55 |
| 63 | 24608.6 | 1559.375 | 2.5983 | 3.63 |
| 64 | 24657.0 | 1548.768 | 2.5806 | 3.98 |
| 65 | 25113.6 | 1448.658 | 2.4138 | 3.70 |
| 66 | 25160.1 | 1438.461 | 2.3968 | 4.03 |
| 67 | 25341.7 | 1398.662 | 2.3305 | 3.88 |
| 68 | 25394.7 | 1387.036 | 2.3111 | 4.43 |
| 69 | 25900.2 | 1276.207 | 2.1264 | 3.15 |
| 70 | 25962.8 | 1262.484 | 2.1036 | 6.25 |
| 71 | 26025.4 | 1248.772 | 2.0807 | 3.23 |
| 72 | 26432.4 | 1159.530 | 1.9320 | 8.83 |
| 73 | 26518.7 | 1140.610 | 1.9005 | 11.87 |
| 74 | 26686.8 | 1103.771 | 1.8391 | 2.00 |
| 75 | 26772.7 | 1084.927 | 1.8077 | 28.83 |
| 76 | 26800.2 | 1078.904 | 1.7977 | 28.10 |
| 77 | 27239.8 | 982.535 | 1.6371 | 4.71 |
| 78 | 27287.4 | 972.099 | 1.6197 | 8.43 |
| 79 | 27366.6 | 954.736 | 1.5908 | 4.35 |
| 80 | 27864.2 | 845.631 | 1.4090 | 14.94 |
| 81 | 28172.8 | 777.969 | 1.2963 | 9.42 |
| 82 | 28216.7 | 768.363 | 1.2803 | 9.50 |
| 83 | 28235.2 | 764.288 | 1.2735 | 9.84 |
| 84 | 28276.7 | 755.206 | 1.2583 | 58.74 |
| 85 | 28321.2 | 745.447 | 1.2421 | 94.67 |
| 86 | 28380.5 | 732.444 | 1.2204 | 58.53 |
| 87 | 28793.1 | 641.978 | 1.0697 | 50.29 |
| 88 | 28906.6 | 617.114 | 1.0282 | 5.31 |
| 89 | 29031.6 | 589.696 | 0.9826 | 56.49 |
| 90 | 29134.1 | 567.228 | 0.9451 | 50.09 |
| 91 | 29765.3 | 428.852 | 0.7146 | 6.67 |
| 92 | 29818.8 | 417.128 | 0.6950 | 6.36 |

REFERENCES (1) Chen, Q. 1995. Methods of study on pharmacology of Chinese medicines. Press of People's Public Health, Beijing. p 892.
(2) Huang, Zh. Sh., Liu, M. P., Chen, Ch. Zh. 1997. Study on effects of Yangshou Dan on improving learning and retention. Chinese Journal of combination of Chinese and west medicine, 9(17): 553.
(3) Zhang, Y., Zhang, H. Y., Li, W. P. 1995. Study on effects of Anjifu on improving intelligence, Chinese Bulletin of Pharmacology, 11(3): 233.
(4) Yang, J., Wang, J., Feng, P. A. 2000. Study on effects of Naokkangtai capsule on improving learning and retention in mice, New Chinese Medicine and Clinical Pharmacology, 1(11): 29.
(5) Yang, J., Wang, J., Zhang, J. Ch. 2000. Study on effects of Crude saponins of peonies on improving learning and retention in mice, Chinese journal of Pharmacology, 2(16): 46.
(6) Xia, W. J., Jin, M. W., Zhang, L. 2000. Study on treatment of senile dementia caused by angio-aging with Didang tang, Pharmacology and Clinical of Chinese Medicines, 16 (4).
(7) Bian, H. M., Yu, J. Z., Gong, J. N. 2000. Study on effects of Tongmai Yizhi capsule on improving learning and retention in mice, Pharmacology and Clinical of Chinese Medicines, 16 (5): 40.
(8) Wei, X. L., Zhang, Y. X. 2000. Study of animal model for studying senile dementia, Chinese journal of Pharmacology, 8(16): 372.
(9) Bureau of Medicinal Police, Department of Public Health. Guide line for study of effect of medicines for treatment of nervous system diseases, in Guidebook of study of new medicine. p 45.
(10) Zhang, D. Sh., Zhang, J. T. 2000. Effects of crude *Ginseng saponins* on improving impairment induced by B-peptide, Chinese journal of Pharmacology, 8(16): 22.

What is claimed is:

1. A method for inhibiting cancer cell growth, comprising contacting the cells with an effective amount of saponins extract from Wenguanguo or *Xanthoceras Sorbifolia*, wherein the cancer is selected from the group consisting of breast cancer, leukocyte cancer, liver cancer, ovary cancer, bladder cancer, prostate cancer, bone cancer, colon cancer, cervix cancer, lung cancer and brain cancer, wherein the saponins effective drug concentration is 65-105 ug/ml for breast cancer, 35-50 ug/ml for leukocyte cancer, 45-60 ug/ml for bladder cancer, 15-20 ug/ml for ovarian cancer, 70-100 ug/ml for brain cancer, 40-70 ug/ml for prostate cancer, 110-130 ug/ml for lung cancer, 68-95 ug/ml for liver cancer, and 145 ug/ml for cervix cancer.

2. The method of claim 1, wherein the cancer is breast cancer.

3. The method of claim 1, wherein the cancer is leukocyte cancer.

4. The method of claim 1, wherein the cancer is liver cancer.

5. The method of claim 1, wherein the cancer is ovary cancer.

6. The method of claim 1, wherein the cancer is prostate cancer.

7. The method of claim 1, wherein the cancer is bone cancer.

8. The method of claim 1, wherein the cancer is brain cancer.

9. The method of claim 1, wherein the cancer is colon cancer.

10. The method of claim 1, wherein the cancer is cervix cancer.

11. The method of claim 1, wherein the cancer is lung cancer.

12. The method of claim 1, wherein the saponins extracts are formulated with a pharmaceutically suitable carrier.

13. A method for inhibiting cancer cell growth, comprising contacting the cells with an effective amount of saponins extract from Wenguanguo or *Xanthoceras Sorbifolia*, wherein the cancer is selected from the group consisting of breast cancer, leukocyte cancer, liver cancer, ovary cancer, bladder cancer, prostate cancer, bone cancer, colon cancer, cervix cancer, lung cancer and brain cancer, wherein the saponins extract effective drug concentration is ug/ml for breast cancer, 45-50 ug/ml for leukocyte cancer, 45-50 ug/ml for bladder cancer, 15 ug/ml for ovarian cancer, 70-85 ug/ml for brain cancer, 40-50 ug/ml for prostate cancer, 110 ug/ml for lung cancer, 45-65 ug/ml for liver cancer, 90 ug/ml for colon cancer and 115 ug/ml for cervix cancer.

14. The method of claim 13, wherein the cancer is breast cancer.

15. The method of claim 13, wherein the cancer is leukocyte cancer.

16. The method of claim 13, wherein the cancer is liver cancer.

17. The method of claim 13, wherein the cancer is ovary cancer.

18. The method of claim 13, wherein the cancer is prostate cancer.

19. The method of claim 13, wherein the cancer is bone cancer.

\* \* \* \* \*